United States Patent
Sampei

(10) Patent No.: US 12,209,121 B2
(45) Date of Patent: Jan. 28, 2025

(54) ANTI-SCLEROSTIN ANTIBODIES AND METHODS OF USE

(71) Applicant: Chugai Seiyaku Kabushiki Kaisha, Tokyo (JP)

(72) Inventor: Zenjiro Sampei, Singapore (SG)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/166,211

(22) Filed: Feb. 8, 2023

(65) Prior Publication Data

US 2023/0250163 A1    Aug. 10, 2023

Related U.S. Application Data

(62) Division of application No. 16/480,765, filed as application No. PCT/JP2018/002611 on Jan. 29, 2018, now Pat. No. 11,608,374.

(30) Foreign Application Priority Data

Jan. 30, 2017   (JP) ................................. 2017-013835

(51) Int. Cl.
| | |
|---|---|
| C07K 16/46 | (2006.01) |
| A61K 39/395 | (2006.01) |
| A61P 19/08 | (2006.01) |
| C07K 16/22 | (2006.01) |
| A61K 38/00 | (2006.01) |

(52) U.S. Cl.
CPC ............ *C07K 16/22* (2013.01); *A61K 39/395* (2013.01); *A61K 39/3955* (2013.01); *A61P 19/08* (2018.01); *C07K 16/46* (2013.01); *C07K 16/461* (2013.01); *A61K 38/00* (2013.01); *C07K 2317/24* (2013.01); *C07K 2317/31* (2013.01); *C07K 2317/515* (2013.01); *C07K 2317/56* (2013.01); *C07K 2317/76* (2013.01); *C07K 2317/77* (2013.01); *C07K 2317/92* (2013.01); *C07K 2317/94* (2013.01)

(58) Field of Classification Search
CPC .... C07K 16/46; C07K 16/461; A61K 39/395; A61K 39/3955
See application file for complete search history.

(56) References Cited

U.S. PATENT DOCUMENTS

| | | |
|---|---|---|
| 4,689,299 A | 8/1987 | Insel et al. |
| 4,801,687 A | 1/1989 | Ngo |
| 5,202,253 A | 4/1993 | Esmon et al. |
| 5,501,854 A | 3/1996 | Raso |
| 5,585,089 A | 12/1996 | Queen et al. |
| 5,830,478 A | 11/1998 | Raso et al. |
| 5,935,935 A | 8/1999 | Connelly et al. |
| 6,737,056 B1 | 5/2004 | Presta |
| 6,821,505 B2 | 11/2004 | Ward |
| 7,138,501 B2 | 11/2006 | Ruben et al. |
| 7,276,585 B2 | 10/2007 | Lazar et al. |
| 7,361,740 B2 | 4/2008 | Hinton et al. |
| 7,592,429 B2 | 9/2009 | Paszty et al. |
| 7,632,924 B2 | 12/2009 | Cho et al. |
| 7,667,004 B2 | 2/2010 | Zhong et al. |
| 7,744,874 B2 | 6/2010 | Korytko et al. |
| 7,820,800 B2 | 10/2010 | Rossi et al. |
| 8,414,893 B2 | 4/2013 | Biere-Citron et al. |
| 8,497,355 B2 | 7/2013 | Igawa et al. |
| 8,562,991 B2 | 10/2013 | Igawa et al. |
| 8,679,490 B2 | 3/2014 | Dennis et al. |
| 9,079,949 B1 | 7/2015 | Andrien, Jr. et al. |
| 9,096,651 B2 | 8/2015 | Igawa et al. |
| 9,315,577 B2 | 4/2016 | Foltz et al. |
| 9,868,948 B2 | 1/2018 | Igawa et al. |
| 9,890,377 B2 | 2/2018 | Igawa et al. |
| 10,233,252 B2 | 3/2019 | Shusta et al. |
| 10,253,100 B2 | 4/2019 | Igawa et al. |
| 10,472,623 B2 | 11/2019 | Igawa et al. |
| 10,598,208 B2 | 3/2020 | Igawa et al. |
| 10,618,965 B2 | 4/2020 | Igawa et al. |
| 11,359,194 B2 | 6/2022 | Igawa et al. |
| 11,371,039 B2 | 6/2022 | Igawa et al. |
| 11,608,374 B2 | 3/2023 | Sampei |
| 11,891,434 B2 | 2/2024 | Igawa et al. |
| 2002/0098193 A1 | 7/2002 | Ward |
| 2003/0059937 A1 | 3/2003 | Ruben et al. |
| 2004/0058393 A1 | 3/2004 | Fukishima et al. |
| 2004/0133357 A1 | 7/2004 | Zhong et al. |
| 2005/0014934 A1 | 1/2005 | Hinton et al. |
| 2005/0244403 A1 | 11/2005 | Lazar et al. |
| 2005/0260711 A1 | 11/2005 | Datta et al. |
| 2006/0014156 A1 | 1/2006 | Rabbani et al. |
| 2006/0141456 A1 | 6/2006 | Edwards et al. |

(Continued)

FOREIGN PATENT DOCUMENTS

| | | |
|---|---|---|
| CA | 2911000 A1 | 10/2007 |
| CN | 1274289 A | 11/2000 |

(Continued)

OTHER PUBLICATIONS

Sampei et al., PLoS One, 2013, vol. 8(2): e57479.*

(Continued)

*Primary Examiner* — Xiaozhen Xie
(74) *Attorney, Agent, or Firm* — Nixon & Vanderhye P.C.

(57) ABSTRACT

The present invention provides anti-sclerostin antibodies and methods of using the same. In some embodiments, an isolated anti-sclerostin antibody of the present invention is a multispecific antibody. The present invention also provides isolated nucleic acids encoding an anti-sclerostin antibody of the present invention. The present invention also provides host cells comprising a nucleic acid of the present invention. The present invention also provides a method of producing an antibody comprising culturing a host cell of the present invention so that the antibody is produced. The present invention also provides a pharmaceutical formulation comprising an anti-sclerostin antibody of the present invention and a pharmaceutically acceptable carrier.

8 Claims, 20 Drawing Sheets

Specification includes a Sequence Listing.

(56) References Cited

U.S. PATENT DOCUMENTS

| | | |
|---|---|---|
| 2006/0153860 A1 | 7/2006 | Cho et al. |
| 2007/0036785 A1 | 2/2007 | Kishimoto et al. |
| 2007/0037734 A1 | 2/2007 | Rossi et al. |
| 2007/0110747 A1 | 5/2007 | Paszty et al. |
| 2007/0135620 A1 | 6/2007 | Chamberlain et al. |
| 2007/0148164 A1 | 6/2007 | Farrington et al. |
| 2007/0160598 A1 | 7/2007 | Dennis et al. |
| 2007/0269371 A1 | 11/2007 | Krummen et al. |
| 2009/0060924 A1 | 3/2009 | Korytko et al. |
| 2010/0216187 A1 | 8/2010 | Lasters et al. |
| 2010/0239577 A1 | 9/2010 | Igawa et al. |
| 2010/0292443 A1 | 11/2010 | Sabbadini et al. |
| 2011/0044986 A1 | 2/2011 | Biere-Citron et al. |
| 2011/0076275 A1 | 3/2011 | Igawa et al. |
| 2011/0098450 A1 | 4/2011 | Igawa et al. |
| 2011/0111406 A1 | 5/2011 | Igawa et al. |
| 2011/0150888 A1 | 6/2011 | Foltz et al. |
| 2011/0245473 A1 | 10/2011 | Igawa et al. |
| 2013/0011866 A1 | 1/2013 | Igawa et al. |
| 2013/0131319 A1 | 5/2013 | Igawa et al. |
| 2013/0303396 A1 | 11/2013 | Igawa et al. |
| 2013/0336963 A1 | 12/2013 | Igawa et al. |
| 2014/0105889 A1 | 4/2014 | Igawa et al. |
| 2014/0234340 A1 | 8/2014 | Igawa et al. |
| 2014/0363428 A1 | 12/2014 | Igawa et al. |
| 2015/0050269 A1 | 2/2015 | Igawa et al. |
| 2015/0056182 A1 | 2/2015 | Igawa et al. |
| 2015/0299313 A1 | 10/2015 | Igawa et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0244526 A1 | 8/2016 | Igawa et al. |
| 2017/0002080 A1 | 1/2017 | Igawa et al. |
| 2017/0022270 A1 | 1/2017 | Igawa et al. |
| 2017/0174778 A1 | 6/2017 | Shusta et al. |
| 2018/0258161 A1 | 9/2018 | Igawa et al. |
| 2018/0282718 A1 | 10/2018 | Igawa et al. |
| 2018/0282719 A1 | 10/2018 | Igawa et al. |
| 2019/0218309 A1 | 7/2019 | Igawa et al. |
| 2019/0352387 A1 | 11/2019 | Sampei |
| 2020/0048627 A1 | 2/2020 | Igawa et al. |
| 2020/0172610 A1 | 6/2020 | Igawa et al. |
| 2021/0079378 A1 | 3/2021 | Igawa et al. |
| 2021/0079379 A1 | 3/2021 | Igawa et al. |
| 2024/0002836 A1 | 1/2024 | Igawa et al. |
| 2024/0158482 A1 | 5/2024 | Igawa et al. |

FOREIGN PATENT DOCUMENTS

| | | | |
|---|---|---|---|
| EP | 0182495 A1 | 5/1986 | |
| EP | 1601697 A1 | 12/2005 | |
| EP | 1601697 B1 | 5/2007 | |
| EP | 2006381 A1 | 12/2008 | |
| EP | 2196541 A1 | 6/2010 | |
| EP | 2275443 A1 | 1/2011 | |
| EP | 2647706 A1 | 10/2013 | |
| EP | 2708558 A2 | 3/2014 | |
| EP | 2275443 B1 | 12/2015 | |
| JP | S61117457 A | 6/1986 | |
| JP | S6352890 A | 3/1988 | |
| JP | H02163085 A | 6/1990 | |
| JP | H03504332 A | 9/1991 | |
| JP | H0441000 B2 | 7/1992 | |
| JP | H0636741 B2 | 5/1994 | |
| JP | H06104071 B2 | 12/1994 | |
| JP | 2559537 B2 | 12/1996 | |
| JP | 2004073210 A | 3/2004 | |
| JP | 2010505436 A | 2/2010 | |
| JP | 2013518131 A | 5/2013 | |
| JP | 2013545734 A | 12/2013 | |
| JP | 2017501706 A | 1/2017 | |
| JP | 6510532 B2 | 5/2019 | |
| KR | 20100074220 A | 7/2010 | |
| KR | 101575914 B1 | 12/2015 | |
| MX | 2013006109 A | 1/2014 | |
| MX | 365235 B | 5/2019 | |
| RU | 2147442 C1 | 4/2000 | |
| RU | 2225721 C2 | 3/2004 | |
| RU | 2430111 C1 | 9/2011 | |
| RU | 2010116152 A | 11/2011 | |
| RU | 2505603 C2 | 1/2014 | |
| WO | WO-8303678 A1 | 10/1983 | |
| WO | WO-9007524 A1 | 7/1990 | |
| WO | WO-9112023 A2 | 8/1991 | |
| WO | WO-9317105 A1 | 9/1993 | |
| WO | WO-9514710 A1 | 6/1995 | |
| WO | WO-9720858 A1 | 6/1997 | |
| WO | WO-9846257 A1 | 10/1998 | |
| WO | WO-0014220 A1 | 3/2000 | |
| WO | WO-03070760 A2 | 8/2003 | |
| WO | WO-03105757 A2 | 12/2003 | |
| WO | WO-03107009 A2 | 12/2003 | |
| WO | WO-2004039826 A1 | 5/2004 | |
| WO | WO-2005080429 A2 | 9/2005 | |
| WO | WO-2006020114 A2 | 2/2006 | |
| WO | WO-2006066598 A2 | 6/2006 | |
| WO | WO-2006082052 A1 | 8/2006 | |
| WO | WO-2006119062 A2 | 11/2006 | |
| WO | WO-2006119107 A2 | 11/2006 | |
| WO | WO-2007076524 A2 | 7/2007 | |
| WO | WO-2007084253 A2 | 7/2007 | |
| WO | WO-2007114319 A1 | 10/2007 | |
| WO | WO-2007142325 A1 | 12/2007 | |
| WO | WO-2008043822 A2 | 4/2008 | |
| WO | WO-2008060785 A2 | 5/2008 | |
| WO | WO-2008115732 A2 | 9/2008 | |
| WO | WO-2009006338 A1 | 1/2009 | |
| WO | WO-2009039175 A2 | 3/2009 | |
| WO | WO-2009041062 A1 | 4/2009 | |
| WO | WO-2009047356 A1 | 4/2009 | |
| WO | WO-2009125825 A1 | 10/2009 | |
| WO | WO-2009139822 A1 | 11/2009 | |
| WO | WO-2011094593 A2 | 8/2011 | |
| WO | WO-2011111007 A2 | 9/2011 | |
| WO | WO2012058393 A2 | 5/2012 | |
| WO | WO-2012073992 A1 | 6/2012 | |
| WO | WO-2012118903 A2 | 9/2012 | |
| WO | WO-2012145417 A1 | 10/2012 | |
| WO | WO-2013138400 A1 | 9/2013 | |
| WO | WO-2013152001 A1 | 10/2013 | |
| WO | WO-2014028354 A1 | 2/2014 | |
| WO | WO-2014144080 A2 | 9/2014 | |
| WO | WO-2014144575 A1 | 9/2014 | |
| WO | WO-2015091738 A1 | 6/2015 | |
| WO | WO-2016000813 A1 | 1/2016 | |
| WO | WO-2016079081 A1 * | 5/2016 | ..... A61K 39/001102 |
| WO | WO-2016098356 A1 | 6/2016 | |
| WO | WO-2016117346 A1 | 7/2016 | |
| WO | WO-2018167322 A1 | 9/2018 | |
| WO | WO-2018169993 A1 | 9/2018 | |

OTHER PUBLICATIONS

U.S. Appl. No. 18/156,138, filed Jan. 18, 2023, Igawa et al., related application.

Sampei, Z., et al., "Identification and Multidimensional Optimization of an Asymmetric Bispecific IgG Antibody Mimicking the Function of Factor VIII Cofactor Activity," PLOS One, 8(2):e57479 (2013).

Khosla, S. and Riggs, L., "Concise Review for Primary-Care Physicians," Mayo Clinic Proc., 70:978-982 (1995).

Avsian-Kretchmer, O. and Hsueh, A. J. W., "Comparative Genomic Analysis of Eight-Membered Ring Cystine Knot-Containing Bone Morphogenetic Protein Antagonists," Mol Endocrinol., 18(1):1-12 (2004).

Balemans, W., et al., "Increased bone density in sclerosteosis is due to the deficiency of a novel secreted protein (SOST)," Hum Mol Genet., 10(5):537-543 (2001).

Brunkow, M. E., et al., "Bone Dysplasia Sclerosteosis Results from Loss of the SOST Gene Product, a Novel Cystine Knot-Containing Protein," Am J Hum Genet., 68:577-589 (2001).

Keller, H. and Kneissel, M., "SOST is a target gene for PTH in bone," Bone, 37:148-158 (2005).

(56) References Cited

OTHER PUBLICATIONS

International Search Report for PCT/JP2018/002611, mailed Apr. 24, 2018.
Abelev, G.I., Monoclonal Antibodies, Sorosovkii Educational Journal, 1998, No. 1, 16-20.
Aboud-Pirak, E., et al., "Binding and Endocytosis of a Monoclonal Antibody to a High Molecular Weight Human Milk Fat Globule Membrane-associated Antigen by Cultured MCF-7 Breast Carcinoma Cells," Cancer Research 48(11):3188-3196 (1988).
Amersham Biosciences, "Affinity Chromatography: Principles and Methods," Edition AD 137:16-18 (2002).
Amersham Biosciences, "Antibody Purification Handbook," Edition 18-1037-1046, accessed at http://www.promix.ru/manuf/ge/chrom/lit/Antibody Purification.pdf [online], accessed on Nov. 5, 2015.
Anchin, J.M., et al., "Recognition of Superpotent Sweetener Ligands by a Library of Monoclonal Antibodies," Journal of Molecular Recognition, 10(5): 235-242 (1997).
Balint, R.F., et al., "Antibody Engineering by Parsimonious Mutagenesis," Gene, 137(1):109-118 (1993).
Bayry, J., et al., "Immuno Affinity Purification of Foot and Mouth Disease Virus Type-Specific Antibodies Using Recombinant Protein Adsorbed to Polystyrene Wells," Journal of Virological Methods 81(1-2):21-30 (1999).
Beck, A., et al., "Strategies and Challenges for the Next Generation of Therapeutic Antibodies," Nature Reviews Immunology 10(5):345-352 (2010).
Brown, N.L., et al., "A Study of the Interactions Between an IgG-Binding Domain Based on the B Domain of Staphylococcal Protein a and Rabbit IgG," Molecular Biotechnology 10(1):9-16 (1998).
Burmeister, W.P., et al., "Crystal Structure of the Complex of Rat Neonatal Fc Receptor With Fc," Nature, 372:379-383 (1994).
Chang, B.S. and Shenson, S., "Practical Approaches to Protein Formulation Development," Pharmaceutical Biotechnology 13:1-25 (2002).
Chaparro-Riggers, J., et al., "Increasing Serum Half-life and Extending Cholesterol Lowering in Vivo by Engineering Antibody With pH-sensitive Binding in PCSK9," The Journal of biological chemistry 287(14):11090-11097 (2012).
Chen, C., et al., "Enhancement and Destruction of Antibody Function by Somatic Mutation: Unequal Occurrence is Controlled by V Gene Combinatorial Associations," 14(12):2784-2794, Jun. 1995).
Chen, Y., et al., "Selection and Analysis of an Optimized Anti-VEGF Antibody: Crystal Structure of an Affinity-Matured Fab in Complex With Antigen," Journal of Molecular Biology 293(4):865-881 (1999).
Colman, P.M., "Effects of Amino Acid Sequence Changes on Antibody-Antigen Interactions," Research in Immunology 145(1):33-36 (1994).
Coloma, M. J., et al., "Design and Production of Novel Tetravalent Bispecific Antibodies," Nature Biotechnology 15(2):159-163 (1997).
Concordance table showing Kabat numbering for antibody 300N, cited by Opponent on Sep. 1, 2016 in EP Opposition in EP2275443.
Concordance table showing Kabat numbering for antibody Hyb C1, cited by Opponent on Sep. 1, 2016 in EP Opposition in EP2275443.
Cuatrecasas, P. and Anfinsen, C.B., "Affinity Chromatography," Methods in Enzymology, 22:345-378 (1971).
Curtiss, F.R., "Selectivity and Specificity are the Keys to Cost-Effective Use of Omalizumab for Allergic Asthma," Journal of Managed Care Pharmacy, 11(9):774-776 (2005).
Dall'acqua, W.F., et al., "Increasing the Affinity of a Human IgG1 for the Neonatal Fc Receptor: Biological Consequences," Journal of Immunology 169(9):5171-5180 (2002).
Datta-Mannan, A., et al., "Monoclonal Antibody Clearance. Impact of Modulating the Interaction of IgG With the Neonatal Fc Receptor," The Journal of Biological Chemistry 282(3):1709-1717 (2007).
Decision of the Opposition Division in EP2275443 dated Apr. 26, 2018, submitted in opposition by Alexion Pharmaceuticals, Inc.
Declaration by Madhusudan Natarajan, Ph. D. dated Dec. 19, 2018 (submitted by the Opponent during EP opposition procedure for EP2708558 and posted by EPO on Jan. 15, 2019), 3 pages.
Declaration of Nimish Gera, Ph.D., CV and Exhibits, dated Sep. 1, 2016, 24 pages.
Devanaboyina, S,C., et al., "The Effect of pH Dependence of Antibody-Antigen Interactions on Subcellular Trafficking Dynamics", mAbs 5:851-859 (2013).
Drake, A.W. and Papalia, G.A., "Chapter 5: Biophysical Considerations for Development of Antibody-Based Therapeutics," Biophysical Considerations for Development of Antibody-Based Therapeutics, 95-97 (2012).
Durkee, K.H., et al., "Immunoaffinity Chromatographic Purification of Russell's Viper Venom Factor X Activator Using Elution in High Concentrations of Magnesium Chloride," Protein Expression and Purification 4(5):405-411 (1993).
Edwards, B.M., et al., "The Remarkable Flexibility of the Human Antibody Repertoire; Isolation of Over One Thousand Different Antibodies to a Single Protein, BLyS," Journal of Molecular Biology 334(1):103-118 (2003).
Ejima, D., et al., "Effective Elution of Antibodies by Arginine and Arginine Derivatives in Affinity Column Chromatography," Analytical Biochemistry, 345(2):250-257 (2005).
European Patent No. 2275443—Opposition proceedings and prosecution, Oct. 15, 2009—Mar. 5, 2018, 4,766 pages.
Ewert, S., et al., "Stability Improvement of Antibodies for Extracellular and Intracellular Applications: CDR Grafting to Stable Frameworks and Structure-based Framework Engineering," Methods, 34(2):184-199 (2004).
Example antibody family tree, attached to the written submission for Opposition against EP 2708559 on Mar. 12, 2020.
Experimental data characterizing the binding of rituximab to its antigen CD20 and to human FcRn (2018), Shire, submitted by opponents in European oppositions in EP2708558 on Dec. 20, 2018 and in EP2708559 on Dec. 21, 2018.
Expert Declaration of Joachim Boucneau, dated Mar. 11, 2020, submitted by opponents in oppositions in European Application Nos. EP2708558 and EP2708559 in Mar. 2020.
Feinberg, H., et al., "Mechanism of pH-dependent N-Acetylgalactosamine Binding by a Functional Mimic of the Hepatocyte Asialoglycoprotein Receptor," The Journal of Biological Chemistry 275(45):35176-35184 (2000).
Ferl, G.Z., et al., "A Predictive Model of Therapeutic Monoclonal Antibody Dynamics and Regulation by the Neonatal Fc Receptor (FcRn)," Annals of Biomedical Engineering 33(11):1640-1652 (2005) (Erratum in: Ann Biomed Eng. Oct. 2011., 39(10):2668).
Fiedler, M., et al., "An Engineered in-1 F(Ab) Fragment With Improved Affinity for the Nogo—a Axonal Growth Inhibitor Permits Immunochemical Detection and Shows Enhanced Neutralizing Activity," Protein Engineering, 15(11): 931-941 (2002).
Finkelman, F.D., et al., "Anti-cytokine Antibodies as Carrier Proteins. Prolongation of in Vivo Effects of Exogenous Cytokines by Injection of Cytokine-Anti-cytokine Antibody Complexes," Journal of Immunology 151:1235-1244 (1993).
Fischer, N. and Léger, O., "Bispecific Antibodies: Molecules That Enable Novel Therapeutic Strategies," Pathobiology: Journal of Immunopathology, Molecular and Cellular Biology, 74(1):3-14 (2007).
Fisher, P.A and Smith, D.E., "Affinity Purification of Antibodies Using Antigens Immobilized on Solid Supports," Biochemical Society Transactions, 16(2):134-138 (1988).
Foote, J. and Winter, G., "Antibody Framework Residues Affecting the Conformation of the Hypervariable Loops," Journal of Molecular Biology 224(2):487-499 (1992).
GE Healthcare. Application note 28-9277-92 AA. "High-throughput screening of elution pH for monoclonal antibodies on MabSelect SuRe using PreDictor plates," General Electric Company (2008).
Biacore GE Healthcare, "Sensor Surface Handbook," pp. 1-100, 2005-2007 (2007).
Gera, N., et al., "Design of pH Sensitive Binding Proteins From the Hyperthermophilic Sso7d Scaffold," PLoS One, 7(11):e48928 (2012).

(56) References Cited

OTHER PUBLICATIONS

Ghetie, V., et al., "Increasing the Serum Persistence of an IgG Fragment by Random Mutagenesis," Nature Biotechnology 15(7):637-640 (1997).
Glick, B. R., et al., "Molecular Biotechnology—Principles and Applications of Recombinant DNA," edited, p. 168, paragraph 5 (2005).
Gopferich, A., et al., "Drug Delivery from Bioerodible Polymers," Chapter 15 in Formulation and Delivery of Proteins and Peptides, 567:242-277 (1994).
Guidance on the use of International Nonproprietary Names (INNs) for Pharmaceutical Substances, World Health Organisation, 2017.
Hamers-Casterman, C., et al., "Naturally Occurring Antibodies Devoid of Light Chains," Nature, 363(6428):446-448 (1993).
Hanson, C.V., et al., "Catalytic Antibodies and Their Applications," Biotechnology Letters, 16:631-636 (2005).
Hinton, P.R., et al., "An Engineered Human IgG1 Antibody With Longer Serum Half-life," Journal of Immunology, 176(1):346-356 (2006).
Hinton, P.R., et al., "Engineered Human IgG Antibodies With Longer Serum Half-lives in Primates," The Journal of Biological Chemistry 279(8):6213-6216 (2004).
Hironiwa, N., et al., "Calcium-dependent antigen binding as a novel modality for antibody recycling by endosomal antigen dissociation," mAbs 8(1):65-73 (2016).
Hoogenboom, H.R., "Selecting and Screening Recombinant Antibody Libraries," Nature Biotechnology 23(9):1105-1116 (2005).
Sigma-Aldrich®, Product Information, Monoclonal ANTI-FLAG® M1, Clone M1, accessed at http://www.sigmaaldrich.com/content/dam/sigmaaldrich/does/Sigma/Datasheet/f3040dat.pdf, 1 page (2008).
Hughes-Jones, N.C., et al., "The Effect of pH and Ionic Strength on the Reaction between Anti-D and Erythrocytes," Immunology, 7:72-81 (1964).
Huse, K., et al., "Purification of Antibodies by Affinity Chromatography," Journal of Biochemical and Biophysical Methods 51(3):217-231 (2002).
Igawa, et al., "Antibody Optimization Technologies for Developing Next Generation Antibody Therapeutics", Bio Industry 28:15-21 (2011).
Igawa, T., et al., "Engineering the Variable Region of Therapeutic IgG Antibodies," MAbs, 3(3):243-52 (2011).
Igawa, T., et al., "Reduced Elimination of IgG Antibodies by Engineering the Variable Region," Protein engineering, design & selection, 23(5):385-92 (2010).
Igawa, T., et al., "Antibody Recycling by Engineered pH-Dependent Antigen Binding Improves the Duration of Antigen Neutralization," Nature Biotechnology 28(11):1203-1207 (2010).
Igawa, T., et al., "Engineered Monoclonal Antibody With Novel Antigen-sweeping Activity in Vivo," PLoS One 8(5):e63236 (2013).
Ishii-Watabe, A., et al., "FcRn, a Critical Regulator of Antibody Pharmacokinetics," Nihon Yakurigaku Zasshi. Folia Pharmacologica Japonica 136(5):280-284, Nippon Yakuri Gakkai, Japan (2010.
Ito, W., et al., "The His-probe Method: Effects of Histidine Residues Introduced Into the Complementarity-Determining Regions of Antibodies on Antigen-antibody Interactions at Different Ph Values," FEBS letters, 309(1):85-88 (1992).
Jain, M., et al., "Engineering Antibodies for Clinical Applications," Trends in Biotechnology, 25(7):307-316 (2007).
Junghans, R.P. and Anderson, C.L., "The Protection Receptor for IgG Catabolismis the Beta2-Microglobulin-Containing Neonatal Intestinal Transport Receptor," Proceedings of the National Academy of Sciences of the United States of America 93(11):5512-5516 (1996).
Kakita, M., et al., "Isolation of a Human Monoclonal Antibody With Strong Neutralizing Activity Against Diphtheria Toxin", Infection and Immunity, 74:3682-3683 (2006).
Kamata, N., et al., "Comparison of Ph and Ionic Strength Dependence of Interactions Between Monoclonal Antibodies and Bovine Beta-lactoglobulin," Bioscience, Biotechnology, and Biochemistry, 60(1):25-29 (1996).

Kim, S.J., et al., "Antibody Engineering for the Development of Therapeutic Antibodies," Molecules and Cells 20(1):17-29 (2005).
King, "Applications and Engineering of Monoclonal Antibodies" Taylor & Francis, ISBN 0-203-21169-3, 1-236 (2005).
King, D., "Antibody Engineering: Design for Specific Applications," Applications and Engineering of Monoclonal Antibodies, 27-75, Chapter 2, (1998).
Knappik et al., "Fully Synthetic Human Combinatorial Antibody Libraries (HuCAL) Based on Modular Consensus Frameworks and CDRs Randomized with Trinucleotides," Journal of Molecular Biology, 296(1):57-86 (2000).
Kobayashi et al., "A Monoclonal Antibody Specific for a Distinct Region of Hen Egg-white Lysozyme," Molecular Immunology, 19:619-30 (1982).
Kranz, D.M., et al., "Mechanisms of Ligand Binding by Monoclonal Anti-fluorescyl Antibodies," The Journal of Biological Chemistry, 257(12):6987-6995 (1982).
Kroetsch, A., et al., "Engineered pH-dependent recycling antibodies enhance elimination of Staphylococcal enterotoxin B superantigen in mice," MABS, 11(2):411-421 (2019).
Kuroda, D., et al., "Computer-Aided Antibody Design," Protein Engineering, Design & Selection 25:507-521 (2012).
Kussie, P., et al., "A Single Engineered Amino Acid Substitution Changes Antibody Fine Specificity," Journal of Immunology, 152(1):146-152 (1994).
Laitinen, O. H., et al., "Brave New (Strept)Avidins in Biotechnology," Trends Biotechnol., 25(6):269-77 (2007).
Lee, C.V., et al., "High-Affinity Human Antibodies From Phage-displayed Synthetic Fab Libraries With a Single Framework Scaffold," Journal of Molecular Biology 340(5):1073-1093 (2004).
Linder, M., et al., "Design of a pH-dependent Cellulose-Binding Domain," FEBS Letters, 447(1):13-16 (1999).
Lloyd, C., et al., "Modelling the Human Immune Response: Performance of a 1011 Human Antibody Repertoire Against a Broad Panel of Therapeutically Relevant Antigens," Protein Engineering, Design & Selection 22(3):159-168 (2009).
Maeda, K., et al., "pH-Dependent Receptor/Ligand Dissociation as a Determining Factor for Intracellular Sorting of Ligands for Epidermal Growth Factor Receptors in Rat Hepatocytes," Journal of Controlled Release, 82(1):71-82 (2002).
Maier, J.K.X. and Labute, P., "Assessment of Fully Automated Antibody Homology Modeling Protocols in Molecular Operating Environment," Proteins 82(8):1599-1610 (2014).
Marshall, S.A, et al., "Rational Design and Engineering of Therapeutic Proteins," Drug Discovery Today, 8(5):212-221 (2003).
Martin, W.L., et al., "Crystal Structure at 2.8 a of an Forn/heterodimeric Fc Complex: Mechanism of Ph-dependent Binding," Molecular Cell, 7(4):867-877 (2001).
Maxfield, F.R. and McGraw, T.E., "Endocytic Recycling," Nature Reviews Molecular Cell Biology 5(2):121-132 (2004).
Mellman, I., "The Importance of Being Acid: The Role of Acidification in Intracellular Membrane Traffic," The Journal of Experimental Biology 172:39-45 (1992).
Merchant, A.M., et al., "An Efficient Route to Human Bispecific IgG," Nature Biotechnology, 16(7):677-681, Nature America Publishing, United States (Jul. 1998).
Montero-Julian, F.A., et al., "Pharmacokinetic Study of Anti-interleukin-6 (II-6) Therapy With Monoclonal Antibodies: Enhancement Ofil-6 Clearance by Cocktails of Anti-il-6 Antibodies," Blood, 85(4):917-24 (1995).
Muller, Y.A., et al., "VEGF and the Fab Fragment of a Humanized Neutralizing Antibody: Crystal Structure of the Complex at 2.4 a Resolution and Mutational Analysis of the Interface," Structure, 6(9):1153-1167 (1998).
Müller, D. and Kontermann, R.E., "Bispecific Antibodies: Handbook of Therapeutic Antibodies" (ed. by S. Dübel), 2:345-378 (2007).
Murtaugh, M.L., et al., "A Combinatorial Histidine Scanning Library Approach to EngineerHighly pH-Dependent Protein Switches," Protein Science 20(9):1619-1631 (2011).
Nair, D. T., et al., "Epitope Recognition by Diverse Antibodies Suggests Conformational Convergence in an Antibody Response," J Immunol., 168:2371-2382 (2002).

(56) References Cited

OTHER PUBLICATIONS

Narhi, L.O., et al., "Effect of Three Elution Buffers on the Recovery and Structure of Monoclonal Antibodies," Analytical Biochemistry 253(2):236-245 (1997).
Nordlund, H.R., et al., "Introduction of Histidine Residues Into Avidin Subunit Interfaces Allows Ph-dependent Regulation of Quaternary Structure and Biotin Binding," FEBS Letters, 555(3):449-454 (2003).
Ober, R.J., et al., "Visualizing the Site and Dynamics of IgG Salvage by the MHC Class I-related Receptor, FcRn," Journal of Immunology 172(4):2021-2029 (2004).
Originally filed claims of European Application No. 13195713.6, European Publication No. 2708558, submitted by opponent in European opposition in EP2708558 on Dec. 20, 2018.
Originally filed description of European Application No. 13195713.6, European Publication No. 2708558, submitted by opponent in European opposition in EP2708558 on Dec. 20, 2018.
Osbourn, J.K., et al., "Generation of a Panel of Related Human scFv Antibodies With High Affinities for Human CEA," Immunotechnology, 2(3):181-196 (1996).
Pakula, A.A., et al., "Genetic Analysis of Protein Stability and Function," Annual Review of Genetics, 23:289-310 (1989).
Palladino, M. A., et al., "Anti-TNF-Alpha Therapies: the Next Generation," Nature Reviews Drug Discovery, 2(9):736-746 (2003).
Pancook, J.D., et al., "In Vitro Affinity Maturation of Human IgM Antibodies Reactive with Tumor-Associated Antigens," Hybridoma and Hybridomics, 20(5-6):383-396 (2001).
Patel, T. V., et al., "A Forgotten Cause of Kidney Injury in Chronic Myelomonocytic Leukemia," Am J Kidney Dis, 54(1):159-64 (2009).
Patentee's explanation in the submission of Apr. 28, 2020 in Annex A made in the appeal case for EP 2552955.
Patentee's response to Article 94(3) EPC communication on EP 3521311 filed on Oct. 20, 2020.
Pavlou, A.K. and Belsey, M.J., "The Therapeutic Antibodies Market to 2008," European Journal of Pharmaceutics and Biopharmaceutics, 59(3):389-396 (2005).
Product Information Sheet from SIGMA—H-Y Medium (1998) and document establishing that it was published in 1998, 4 pages (submitted by the Opponent during EP opposition procedure for EP2708558 and posted by EPO on Jan. 15, 2019).
Product labelling information for Rituxan (Rituximab), dated Nov. 1997.
Promega Protocols and Applications Guide, 1991, 2nd Edition (submitted by the Opponent during EP opposition procedure for EP2708558 and posted by EPO on Jan. 14, 2019), 3 pages.
Rabia, L. A., et al., "Understanding and overcoming trade-offs between antibody affinity, specificity, stability and solubility," Biochem Eng J., 137:365-374 (2018).
Rachner, T.D., et al., "Osteoporosis: Now and the Future," Lancet 377(9773):1276-1287 (2011).
Rajpal, A., et al., "A General Method for Greatly Improving the Affinity of Antibodies by Using Combinatorial Libraries," Proceedings of the National Academy of Sciences of the United States of America 102(24):8466-8471 (2005).
Raso, V., "Intracellular Targeting Using Bispecific Antibodies," Methods in Molecular Medicine, vol. 25: Drug Targeting: Strategies, Principles, and Applications, 37-50 (2000).
Raso, V., et al., "Antibodies Capable of Releasing Diphtheria Toxin in Response to the Low pH Found in Endosomes," Journal of Biological Chemistry 272:27618-27622 (1997).
Raso, V., et al., "Intracellular Targeting with Low pH-Triggered Bispecific Antibodies," The Journal of Biological Chemistry 272(44):27623-27628 (1997).
Rathanaswami, P., et al., "Demonstration of an in Vivo Generated Sub-picomolar Affinity Fully Human Monoclonal Antibody to Interleukin-8," Biochemical and Biophysical Research Communications, 334:1004-1013 (2005).
Reichert, J.M., et al., "Monoclonal Antibody Successes in the Clinic," Nature Biotechnology, 23(9):1073-1078 (2005).
Reverberi, R., et al., "Factors Affecting the Antigen-Antibody reaction," Blood Transfusion 5:227-240 (2007).
Rich, R.L. and Myszka D.G., "Grading the Commercial Optical Biosensor Literature-Class of 2008: 'The Mighty Binders'," Journal of Molecular Recognition 23(1):1-64 (2010).
Rich, R.L., et al., "A global benchmark study using affinity-based biosensors," Analytical Biochemistry, 386(2):194-216 (2009).
Rituximab biologic license application approval, dated Nov. 26, 1997 (submitted by the Opponent during EP opposition procedure for EP2708558 and posted by EPO on Jan. 15, 2019), 7 pages.
Rituximab product information, IDEC Pharmaceuticals Corporation, Nov. 1997, (submitted by the Opponent during EP opposition procedure for EP2708558 and posted by EPO on Jan. 15, 2019, 2 pages Japanese Patent office, Tokyo mailed on Jan. 15, 2019), 2 pages.
Rituximab, Wikipedia (https://de.wikipedia.org/wiki /Rituximab), accessed on Oct. 24, 2018, (submitted by the Opponent during EP opposition procedure for EP 2708558 and posted by EPO on Jan. 15, 2019).
Roche Media Release, "FDA grants supplemental approval for ACTEMRA," Jan. 5, 2011, 4 pages, submitted by opponents in oppositions in European Application Nos. EP2708558 and EP2708559 in Mar. 2020.
Rojas, J.R., et al., "Formation, Distribution, and Elimination of Infliximab and Anti-Infliximab Immune Complexes in Cynomolgus Monkeys," The Journal of Pharmacology and Experimental Therapeutics 313(2):578-585 (2005).
Roopenian, D. C. and Akilesh, S., "FcRn: the neonatal Fc receptor comes of age," Nat Rev Immunol., 7:715-725 (2007).
Rudikoff, S., et al., "Single Amino Acid Substitution Altering Antigen-binding Specificity," Proceedings of the National Academy of Sciences of the United States of America 79(6):1979-1983 (1982).
Sada, E., et al., "Effect of Histidine Residues in Antigenic Sites on pH Dependence of Immuno-Adsorption Equilibrium," Applied Microbiology and Biotechnology 27:528-532 (1988).
Sarkar, C.A., et al., "Rational Cytokine Design for Increased Lifetime and Enhanced Potency Using Ph-activated "Histidine Switching"," Nature Biotechnology, 20(9):908-913 (2002).
Sato, K., et al., "Reshaping a Human Antibody to Inhibit the Interleukin 6-dependent Tumor Cell Growth," Cancer Research, 53(4):851-856 (1993).
Schier, R., et al., "Isolation of Picomolar Affinity Anti-c-erbB-2 Single-chain Fv by Molecular Evolution of the Complementarity Determining Regions in the Center of the Antibody Binding Site," Journal of Molecular Biology 263:551-567 (1996).
Schrama, D., et al., "Antibody Targeted Drugs as Cancer Therapeutics," Nature Reviews Drug Discovery, 5(2):147-159 (2006).
Schroeder, H.W., Jr., "Similarity and Divergence in the Development and Expression of the Mouse and Human Antibody Repertoires," Developmental and Comparative Immunology 30(1-2):119-135 (2006).
Schröter, C., et al., "A Generic Approach to Engineer Antibody Ph-switches Using Combinatorial Histidine Scanning Libraries and Yeast Display," mAbs 7(1):138-151 (2015).
Shadduck, R.K., et al., "Fractionation of Antibodies to L-cell Colony-Stimulating Factor by Affinity Chromatography," Blood 53(6):1182-1190 (1979).
Shields, R. L., et al., "High Resolution Mapping of the Binding Site on Human IgG1 for Fc Gamma RI, Fc Gamma RIII, Fc Gamma RIII, and FcRn and Design of Igg1 Variants With Improved Binding to the Fc Gamma R," The Journal of Biological Chemistry, 276(9):6591-6604 (2001).
Singer, M. and Berg, P., Genes & Genomes, Structure of Proteins, 67-69 (1991).
Stearns, D.J., et al., "The Interaction of a Ca2+-Dependent Monoclonal Antibody with the Protein C Activation Peptide Region. Evidence for Obligatory Ca2+ Binding to Both Antigen and Antibody," Journal of Biological Chemistry 263:826-832 (1988).
Stewart, J.D., et al., "Site-directed Mutagenesis of a Catalytic Antibody: an Arginine and a Histidine Residue Play Key Roles," Biochemistry 33:1994-2003 (1994).

(56) References Cited

OTHER PUBLICATIONS

Tabrizi, M.A., et al., "Elimination Mechanisms of Therapeutic Monoclonal Antibodies," Drug Discovery Today, 11(1-2):81-88 (2006).
Third Party Submission under 37 C.F.R.1.290 submitted Apr. 3, 2019 in U.S. Appl. No. 15/952,951.
Third Party Submission under 37 C.F.R.1.290 submitted Jan. 17, 2019 in U.S. Appl. No. 15/952,951.
Tsuchiya, M., "Therapeutic Antibody," Credit Suisse Seminar at Fuji-Gotemba Research Laboratories, p. 21, Shizuoka, Japan (2006).
Van Assche, G., et al., "Adalimumab in Crohn's disease," Biologics Target and Therapy, 1(4):355-365 (2007).
Vaughn, D.E., et al., "Structural Basis of pH-Dependent Antibody Binding by the Neonatal Fc Receptor," Structure 6:63-73 (1998).
Venturi, M., et al., "The Monoclonal Antibody 1f6 Identifies a pH-dependent Conformational Change in the Hydrophilic NH(2) terminus of NhaA Na(+)/H(+) Antiporter of *Escherichia coli*," The Journal of Biological Chemistry 275(7):4734-4742 (2000).
Wang, W., "Instability, Stabilization, and Formulation of Liquid Protein Pharmaceuticals," International Journal of Pharmaceutics 185(2):129-188 (1999).
Ward, S.L. and Ingham, K.C., "A Calcium-binding Monoclonal Antibody That Recognizes a Non-calcium-binding Epitope in the Short Consensus Repeat Units (Scrs) of Complement C1r," Molecular Immunology, 29(1):83-93 (1992).
Wikipedia, "Chaotropic agent," [online], [retrieved on Nov. 2, 2015]. Retrieved from the Internet: https://en.wikipedia.org/wiki/Chaotropicagent.
Wojciak, J.M., et al., "The Crystal Structure of Sphingosine-1-Phosphate in Complex With a Fab Fragment Reveals Metal Bridging of an Antibody and Its Antigen," Proceedings of the National Academy of Sciences of the United States of America, 106(42):17717-17722 (2009).
Wu, H., et al., "Stepwise in vitro Affinity Maturation Ofvitaxin, an Av-33-specific Humanized Mab," Proceedings of the National Academy of Sciences USA, 95(11):6037-6042 (1998).
Wu, H., et al., "Development of Motavizumab, an Ultra-potent Antibody for the Prevention of Respiratory Syncytial Virus Infection in the Upper and Lower Respiratory Tract," Journal of Molecular Biology 368:652-665 (2007).
Wu, H., et al., "Humanization of a Murine Monoclonal Antibody by Simultaneous Optimization of Framework and CDR Residues," Journal of Molecular Biology 294(1):151-162 (1999).
Yamamoto, T., et al., "Molecular Studies of PH-dependent Ligand Interactions With the Low-density Lipoprotein Receptor," Biochemistry, 47(44):11647-11652 (2008).
Yang, M., et al., "Effect of anti CD20 antibody Fab' fragment on apoptosis of B lymphoma cells and intracellular calcium," Tumor, 26(2):116-119 (2006).
Yang, W.P., et al., "CDR Walking Mutagenesis for the Affinity Maturation of a Potent Human Anti-HIV-1 Antibody Into the Picomolar Range," Journal of Molecular Biology, 254(3):392-403 (1995).
Yeung, Y.A., et al., "Engineering Human IgG1 Affinity to Human Neonatal Fc Receptor: Impact of Affinity Improvement on Pharmacokinetics in Primates," Journal of Immunology 182(12):7663-7671 (2009).
Yoon, S.O., et al., "Construction, Affinity Maturation, and Biological Characterization of an Anti-tumor-associated Glycoprotein-72 Humanized Antibody," The Journal of Biological Chemistry 281(11):6985-6992 (2006).
Yu, X., et al., "Development and Validation of a Cell-Based Fluorescent Method for Measuring Antibody Affinity," Journal of Immunological Methods, 442:49-53 (2017).
Zalevsky, J., et al., "Enhanced Antibody Half-life Improves in Vivo Activity," Nature Biotechnology 28(2):157-159 (2010).
Zhang, Q., et al., "Monoclonal Antibodies as Therapeutic Agents in Oncology and Antibody Gene Therapy," Cell Research, 17(2):89-99 (2007).
Zhou, T., et al., "Interfacial Metal and Antibody Recognition," Proceedings of the National Academy of Sciences of the United States of America, 102(41):14575-14580 (2005).
Zhu, X., et al., "MHC Class I-Related Neonatal Fc Receptor for IgG Is Functionally Expressed in Monocytes, Intestinal Macrophages, and Dendritic Cells", Journal of Immunology 166:3266-3276 (2001).
U.S. Appl. No. 06/534,658, filed Sep. 22, 1983, Insel et al.
U.S. Appl. No. 07/139,504, filed Dec. 30, 1987, That.
U.S. Appl. No. 07/730,040, filed Jul. 12, 1991, Esmon et al.
U.S. Appl. No. 07/998,754, filed Dec. 28, 1992, Raso.
U.S. Appl. No. 08/472,523, filed Jun. 7, 1995, Raso et al.
U.S. Appl. No. 08/477,728, filed Jun. 7, 1995, Queen et al.
U.S. Appl. No. 08/484,891, filed Jun. 7, 1995, Connelly et al.
U.S. Appl. No. 09/483,588, filed Jan. 14, 2000, Presta.
U.S. Appl. No. 09/880,748, filed Jun. 15, 2001, Ruben et al.
U.S. Appl. No. 09/933,497, filed Aug. 20, 2001, Ward.
U.S. Appl. No. 10/257,864, filed Jun. 24, 2003, Fukishima et al.
U.S. Appl. No. 10/514,516, filed Oct. 28, 2005, Edwards et al.
U.S. Appl. No. 10/576,372, filed Apr. 19, 2006, Rossi et al.
U.S. Appl. No. 10/723,434, filed Nov. 26, 2003, Zhong et al.
U.S. Appl. No. 10/822,300, filed Apr. 9, 2004, Hinton et al.
U.S. Appl. No. 10/902,682, filed Jul. 29, 2004, Rabbani et al.
U.S. Appl. No. 11/090,981, filed Mar. 24, 2005, Lazar et al.
U.S. Appl. No. 11/094,625, filed Mar. 30, 2005, Datta et al.
U.S. Appl. No. 11/155,909, filed Jun. 17, 2005, Cho et al.
U.S. Appl. No. 11/411,003, filed Apr. 25, 2006, Paszty et al.
U.S. Appl. No. 11/432,872, filed May 12, 2006, Farrington et al.
U.S. Appl. No. 11/436,266, filed May 17, 2006, Chamberlain et al.
U.S. Appl. No. 11/557,466, filed Nov. 7, 2006, Dennis et al.
U.S. Appl. No. 11/585,172, filed Oct. 24, 2006, Kishimoto et al.
U.S. Appl. No. 11/713,577, filed Feb. 28, 2007, Krummen et al.
U.S. Appl. No. 12/160,472, 371 (c) date Jul. 10, 2008, Korytko et al.
U.S. Appl. No. 12/311,768, filed Feb. 22, 2010, Lasters et al.
U.S. Appl. No. 12/660,528, filed Feb. 26, 2010, Sabbadini et al.
U.S. Appl. No. 12/679,922, filed Oct. 1, 2010, Igawa et al.
U.S. Appl. No. 12/680,087, filed Jan. 3, 2011, Igawa et al.
U.S. Appl. No. 12/680,112, filed Jun. 23, 2010, Igawa et al.
U.S. Appl. No. 12/733,933, filed Jun. 3, 2010, Igawa et al.
U.S. Appl. No. 12/809,563, filed Jun. 18, 2010, Biere-Citron et al.
U.S. Appl. No. 12/936,587, filed Jan. 3, 2011, Igawa et al., related application.
U.S. Appl. No. 12/990,137, filed Feb. 11, 2011, Foltz et al.
U.S. Appl. No. 13/595,139, filed Aug. 27, 2012, Igawa et al., related application.
U.S. Appl. No. 13/889,484, filed May 8, 2013, Igawa et al., related application.
U.S. Appl. No. 13/889,512, filed May 8, 2013, Igawa et al., related application.
U.S. Appl. No. 13/990,158, filed Mar. 28, 2014, Igawa et al., related application.
U.S. Appl. No. 14/007,947, filed Dec. 30, 2013, Igawa et al.
U.S. Appl. No. 14/347,034, filed Mar. 25, 2014, Igawa et al.
U.S. Appl. No. 14/347,187, filed Jul. 25, 2014, Igawa et al.
U.S. Appl. No. 14/349,884, filed Apr. 4, 2014, Igawa et al.
U.S. Appl. No. 14/361,013, filed May 28, 2014, Igawa et al.
U.S. Appl. No. 14/379,825, filed Aug. 20, 2014, Igawa et al.
U.S. Appl. No. 14/404,051, filed Nov. 26, 2014, Igawa et al.
U.S. Appl. No. 14/641,026, filed Mar. 6, 2015, Andrien et al.
U.S. Appl. No. 14/781,069, filed Sep. 29, 2015, Mimoto et al.
U.S. Appl. No. 15/050,145, filed Feb. 22, 2016, Igawa et al.
U.S. Appl. No. 15/210,360, filed Jul. 14, 2016, Igawa et al.
U.S. Appl. No. 15/230,904, filed Aug. 8, 2016, Igawa et al.
U.S. Appl. No. 15/952,945, filed Apr. 13, 2018, Igawa et al., related application.
U.S. Appl. No. 15/952,951, filed Apr. 13, 2018, Igawa et al., related application.
U.S. Appl. No. 15/988,348, filed May 24, 2018, Igawa et al., related application.
U.S. Appl. No. 16/108,897, filed Aug. 22, 2018, Igawa et al.
U.S. Appl. No. 16/361,498, filed Mar. 22, 2019, Igawa et al., related application.
U.S. Appl. No. 16/697,310, filed Nov. 27, 2019, Igawa et al.

(56) References Cited

OTHER PUBLICATIONS

U.S. Appl. No. 17/020,497, filed Sep. 14, 2020, Igawa et al., related application.
U.S. Appl. No. 17/020,543, filed Sep. 14, 2020, Igawa et al., related application.
Almagro, J.C., et al., "Design and Validation of a Synthetic VH Repertoire with Tailored Diversity for Protein Recognition," Journal of Molecular Recognition, 19(5):413-422 (2006).
Anderson, C.L., et al., "Perspective—FcRn Transports Albumin: Relevance to Immunology and Medicine," Trends in Immunology, 27(7):343-348 (2006).
Bazin, R., et al., "Use of hu-IgG-SCID Mice to Evaluate the in Vivo Stability of Human Monoclonal IgG Antibodies," Journal of Immunological Methods, 172(2):209-217 (1994).
Birn, H., et al., "Renal Albumin Absorption in Physiology and Pathology," Kidney International, 69(3):440-449 (2006).
Chaudhury, C., et al., "The Major Histocompatibility Complex-related Fc Receptor for Igg (FcRn) Binds Albumin and Prolongs Its Lifespan," The Journal of Experimental Medicine, 197(3):315-322 (2003).
Chilukuri, N., et al., "Polyethylene Glycosylation Prolongs the Circulatory Stability of Recombinant Human Butyrylcholinesterase," Chemico-Biological Interactions, 157-158:115-21 (2005).
Chuang, V.T.G., et al., "Pharmaceutical Strategies Utilizing Recombinant Human Serum Albumin," Pharmaceutical Research, 19(5):569-577 (2002).
Dall'acqua, W.F., et al., "Properties of Human IgG1s Engineered for Enhanced Binding to the Neonatal Fc Receptor (FcRn)," The Journal of Biological Chemistry 281(33):23514-23524 (Aug. 2006).
Dennis, M.S., et al., "Albumin Binding as a General Strategy for Improving the Pharmacokinetics of Proteins," The Journal of Biological Chemistry, 277(38):35035-35043 (2002).
Dirnberger, D., et al., "Secretion of Biologically Active Glycoforms of Bovine Follicle Stimulating Hormone in Plants," European Journal of Biochemistry, 268(16):4570-4579 (2001).
Franks, F., "Conformational Stability of Proteins," Chapter 11 in Protein Biotechnology, 395-436 (1993).
Gekle, M., "Renal Tubule Albumin Transport," Annual Review of Physiology, 67:573-594 (2005).
Guasch, A., et al., "Charge Selectivity of the Glomerular Filtration Barrier in Healthy and Nephrotic Humans," The Journal of Clinical Investigation, 92(5):2274-2282 (1993).
Holt, L.J., et al., "Anti-Serum Albumin Domain Antibodies for Extending the Half-Lives of Short Lived Drugs," Protein Engineering, Design & Selection, 21(5):283-288 (2008).
Huang, Y.J., et al., "Recombinant Human Butyrylcholinesterase From Milk of Transgenic Animals to Protect Against Organophosphate Poisoning," Proceedings of the National Academy of Sciences, 104(34):13603-13608 (2007).
Inoue, M., et al., "Synthesis of a Superoxide Dismutase Derivative That Circulates Bound to Albumin and Accumulates in Tissues Whose pH Is Decreased," Biochemistry, 28(16):6619-6624 (1989).
Janeway, C.A., et al., "The Immune System in Health and Disease," Immunobiology, 5th edition, 122 (2001).

Kawamoto, M., "Circulatory Stability and Plasma Lidocaine Levels During Continuous and Intermittent Thoracic Epidural Analgesia," Journal of Anesthesia, 5(2):166-171 (1991).
Kim, H.J., et al., "The Glycosylation and Pharmacokinetics of CTLA4Ig Produced in Rice Cells," Biological & Pharmaceutical Bulletin, 30(10):1913-1917 (2007).
Knudsen, L.B., et al., "Potent Derivatives of Glucagon-Like Peptide-1 with Pharmacokinetic Properties Suitable for Once Daily Administration," Journal of Medicinal Chemistry, 43(9):1664-1669 (2000).
Kratz, J., "Albumin as a Drug Carrier: Design of Prodrugs, Drug Conjugates and Nanoparticles," Journal of Controlled Release, 132(3):171-183 (2008).
Kurtzhals, P., et al., "Albumin Binding and Time Action of Acylated Insulins in Various Species," Journal of Pharmaceutical Sciences, 85(3):304-308 (1996).
Kurtzhals, P., et al., "Effect of Fatty Acids and Selected Drugs on the Albumin Binding of a Long-Acting, Acylated Insulin Analogue," Journal of Pharmaceutical Sciences, 86(12):1365-1368 (1997).
Makrides, S.C., et al., "Extended in Vivo Half-Life of Human Soluble Complement Receptor Type 1 Fused to a Serum Albumin-Binding Receptor," The Journal of Pharmacology and Experimental Therapeutics, 277(1):534-542 (1996).
Manning, M.C., et al., "Stability of Protein Pharmaceuticals," Pharmaceutical Research, 6(11):903-918 (1989).
O'Hear, C. and Foote, J., "Antibody buffering of a ligand in vivo," PNAS, 102(1):40-44 (2005).
Peters, Jr., T., Albumin—Biochemistry, Genetics, and Medical Applications, Academic Press, 76-79 (1996).
Petkova, S.B., et al., "Enhanced Half-life of Genetically Engineered Human IgG1 Antibodies in a Humanized FcRn Mouse Model: Potential Application in Humorally Mediated Autoimmune Disease," International Immunology, 18(12):1759-1769 (2006).
Rehlaender, B.N., et al., "Antibodies as Carrier Proteins," Pharmaceutical Research, 15(11):1652-1656 (1998).
Saxena, A., et al., "Role of Oligosaccharides in the Pharmacokinetics of Tissue-Derived and Genetically Engineered Cholinesterases," Molecular Pharmacology, 53(1):112-122 (1998).
Schultze, H.E., et al., "Turnover of Plasma Proteins", Molecular Biology of Human Proteins with Special Reference to Plasma Proteins, Nature and Metabolism of Extracellular Proteins, 1:476-477 (1996).
Smith, B.J., et al., "Prolonged in Vivo Residence Times of Antibody Fragments Associated With Albumin," Bioconjugate Chemistry, 12(5):750-756 (2001).
Stork, R., et al., "A Novel Tri-Functional Antibody Fusion Protein With Improved Pharmacokinetic Properties Generated by Fusing a Bispecific Single-chain Diabody With an Albumin-binding Domain From Streptococcal Protein G," Protein Engineering, Design & Selection, 20(11):569-576 (2007).
U.S. Appl. No. 13/637,415, filed Mar. 30, 2011, Igawa et al.
U.S. Appl. No. 15/379,597, filed Dec. 15, 2016, Shusta et al.
U.S. Appl. No. 18/390,581, filed Dec. 20, 2023, Igawa et al., related application.

* cited by examiner

Examples of each residue shuffling variants

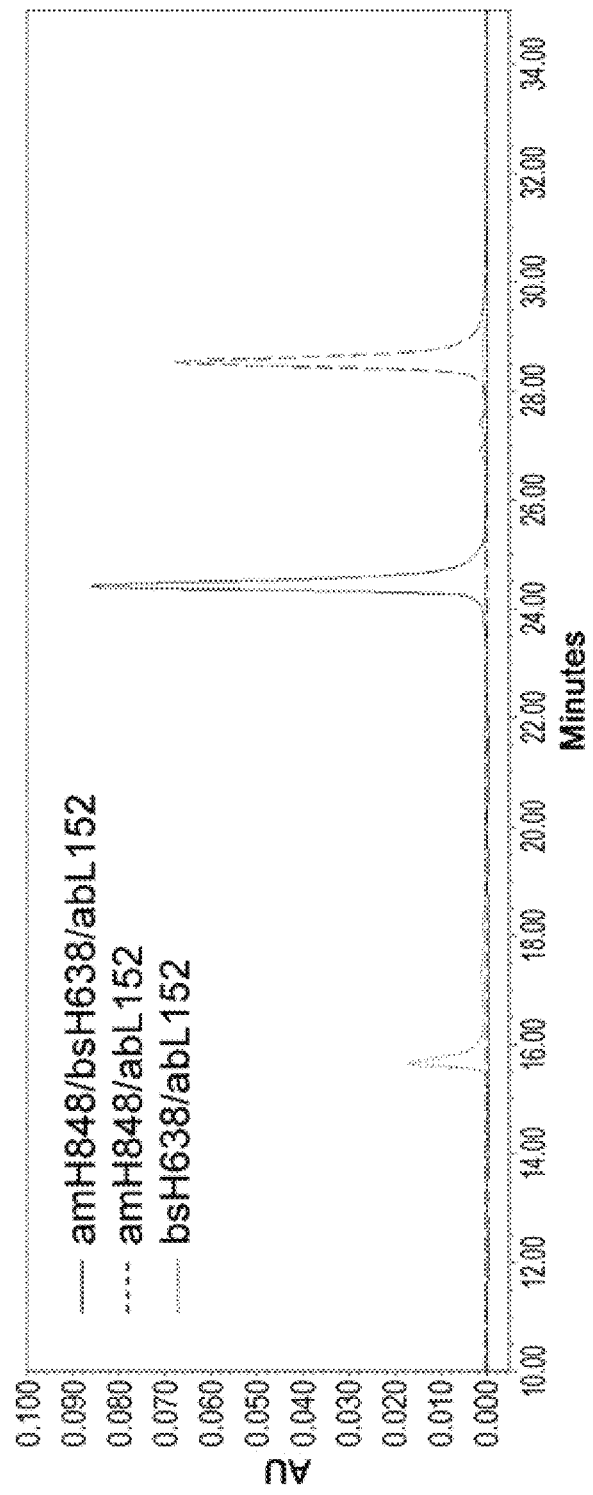

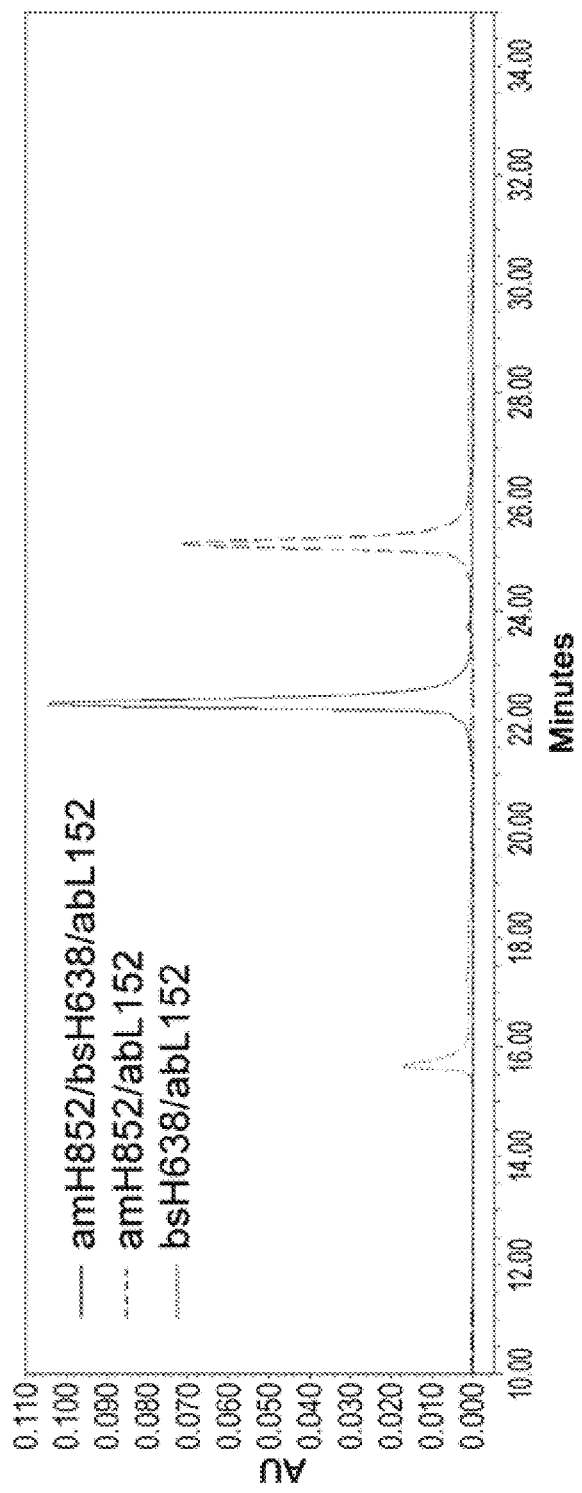

ANTI-SCLEROSTIN ANTIBODIES AND METHODS OF USE

CROSS-REFERENCE TO RELATED APPLICATIONS

This application is a divisional of U.S. patent application Ser. No. 16/480,765, filed Jul. 25, 2019, now U.S. Pat. No. 11,608,374, which is the U.S. National Phase of PCT Application No. PCT/JP2018/002611, filed Jan. 29, 2018, which claims priority to Japanese Patent Application No. 2017-013835, filed Jan. 30, 2017, each of which, including its corresponding Sequence Listing, is incorporated herein by reference in its entirety.

REFERENCE TO SEQUENCE LISTING SUBMITTED ELECTRONICALLY

The content of the electronically submitted sequence listing (Name: 6663_0233_Sequence_Listing.xml; Size: 179 kilobytes; and Date of Creation: Jan. 31, 2023) filed with the application is incorporated herein by reference in its entirety.

TECHNICAL FIELD

The present invention relates to anti-sclerostin antibodies and methods of using the same.

BACKGROUND ART

Loss of bone mineral content can be caused by a wide variety of conditions and may result in significant medical problems. For example, osteoporosis is a debilitating disease in humans and is characterized by marked decreases in skeletal bone mass and bone mineral density (BMD), structural deterioration of bone, including degradation of bone microarchitecture and corresponding increases in bone fragility (i.e., decreases in bone strength), and susceptibility to fracture in afflicted individuals. Osteoporosis in humans is generally preceded by clinical osteopenia, a condition found in approximately 25 million people in the United States. Another 7-8 million patients in the United States have been diagnosed with clinical osteoporosis. The frequency of osteoporosis in the human population increases with age. Among Caucasians, osteoporosis is predominant in women who, in the United States, comprise 80% of the osteoporosis patient pool. The increased fragility and susceptibility to fracture of skeletal bone in the aged is aggravated by the greater risk of accidental falls in this population. Fractured hips, wrists, and vertebrae are among the most common injuries associated with osteoporosis. Hip fractures in particular are extremely uncomfortable and expensive for the patient, and for women, correlate with high rates of mortality and morbidity.

While treatments for osteoporosis exist in the form of lifestyle modification and pharmacotherapy, the currently available therapies are limited in number and efficacy, are often associated with undesirable side effects and are not universally acceptable to patients (See, e.g., NPL 1). A number of antiresorptive agents including calcitonin, bisphosphonates, estrogen replacement and selective estrogen receptor modulators (SERMs) prevent further bone loss, but they do not rebuild bone once it has been lost. An anabolic agent which increases bone mass and bone mineral density and restores bone architecture is available in the form of human PTH (1-34). However, this therapeutic agent requires daily subcutaneous injection, often for a year or more, resulting in less than complete patient compliance.

Sclerostin, the product of the SOST gene, is a 213-amino-acid secreted glycoprotein. Sclerostin is a member of the super-family of cystine-knot containing factors. Sclerostin is related to the DAN/Cerberus protein family, which interferes directly with BMP signaling by inhibiting the binding of BMP to the receptors and thus the BMP signaling cascade (See, e.g., NPL 2). Sclerostin mRNA expression is detected in adult humans predominantly in bone and kidney. Sclerostin protein is detectable predominantly in bone. Within bone, its expression is restricted to the mature and terminally differentiated bone forming cells, the osteocytes.

Sclerostin is a potent negative regulator of bone formation in human and mice. Lack of SOST expression gives rise to sclerosteosis (See, e.g., NPL 3; NPL 4). Patients suffer from life-long bone overgrowth resulting in increased bone mineral density and strength. This phenotype can be recapitulated in SOST deficient mice and its overexpression results in osteopenia. SOST is down-regulated by PTH during bone formation suggesting that part of the anabolic action of PTH might be mediated via SOST (See, e.g., NPL 5).

Due to its role as a potent negative regulator of bone formation, sclerostin is a desirable target for therapeutic intervention for disorders or conditions which would benefit from an increase in at least one of bone mass, bone mineral density, bone mineral content and bone strength, e.g., osteoporosis. Anti-sclerostin antibodies described in, e.g., PTL 1, PTL 2, PTL 3, PTL 4, PTL 5, and PTL 6 have been shown to bind to sclerostin and inhibit sclerostin activity in vitro and in vivo, including sclerostin activity associated with the negative regulation of bone formation. However, there is a further need for improvements in efficacy and convenience of agents that bind to sclerostin and antagonize its activity in the art.

CITATION LIST

Patent Literature

[PTL 1] WO2006/119062
[PTL 2] WO2006/119107
[PTL 3] WO2008/115732
[PTL 4] WO2009/039175
[PTL 5] WO2009/047356
[PTL 6] WO2012/145417

Non-Patent Literature

[NPL 1] Khosla and Riggs (1995) Mayo Clin Proc 70(10): 978-982
[NPL 2] Avsian-Kretchmer and Hsueh (2004) Mol Endocrinol 18(1): 1-12
[NPL 3] Balemans et al (2001) Hum Mol Genet 10(5): 537-543
[NPL 4] Brunkow et al (2001) Am J Hum Genet 68(3): 577-589
[NPL 5] Keller and Kneissel (2005) Bone 37(2): 148-158

SUMMARY OF INVENTION

Technical Problem

The invention provides anti-sclerostin antibodies and methods of using the same.

Solution to Problem

In some embodiments, an isolated anti-sclerostin antibody of the present invention is a multispecific antibody. In some embodiments, an isolated anti-sclerostin antibody of the present invention comprises at least two different variable regions. In some embodiments, an isolated anti-sclerostin antibody of the present invention binds to at least two different epitopes of sclerostin. In some embodiments, an isolated anti-sclerostin antibody of the present invention binds to sclerostin with a higher affinity at neutral pH than at acidic pH.

In some embodiments, an isolated anti-sclerostin antibody of the present invention forms an immune complex with sclerostin. In some embodiments, the immune complex comprises at least two antibody molecules of the present invention and at least two sclerostin molecules.

In some embodiments, an isolated anti-sclerostin antibody of the present invention binds to the same epitope as an anti-sclerostin antibody comprising a VH (heavy-chain variable region) sequence of SEQ ID NO: 7 and a VL (light-chain variable region) sequence of SEQ ID NO: 15. In further embodiments, an isolated anti-sclerostin antibody of the present invention binds to the same epitope as an anti-sclerostin antibody comprising a VH sequence of SEQ ID NO: 23 and a VL sequence of SEQ ID NO: 27.

In some embodiments, an isolated anti-sclerostin antibody of the present invention comprises a VH comprising the amino acid sequence of SEQ ID NO: 7 and a VL comprising the amino acid sequence of SEQ ID NO: 15, wherein at least one amino acid is substituted at the following positions: (a) in HVR-H1 (SEQ ID NO: 31), at position 1; (b) in HVR-H2 (SEQ ID NO: 34), at positions 3, 5, 8, 9, 11, and 12; (c) in HVR-H3 (SEQ ID NO: 38), at positions 2, 4, 5, 7, and 13; (d) in HVR-L1 (SEQ ID NO: 52), at positions 1, 4, 5, 6, 7, 8, 9, 10, and 11; (e) in HVR-L2 (SEQ ID NO: 56), at positions 1, 2, 4, 5, 6, and 7; and (f) in HVR-L3 (SEQ ID NO: 60), at positions 1, 2, 3, 4, 5, 6, 7, and 8. In further embodiments, an isolated anti-sclerostin antibody of the present invention comprises a VH comprising the amino acid sequence of SEQ ID NO: 23 and a VL comprising the amino acid sequence of SEQ ID NO: 27, wherein at least one amino acid is substituted at the following hypervariable region (HVR) positions: (a) in HVR-H1 (SEQ ID NO: 32), at positions 1, 2, and 4; (b) in HVR-H2 (SEQ ID NO: 37), at position 9; (c) in HVR-H3 (SEQ ID NO: 43), at positions 2 and 9; (d) in HVR-L1 (SEQ ID NO: 55), at positions 1, 4, 5, 6, 7, 8, 9, 10, and 11; (e) in HVR-L2 (SEQ ID NO: 59), at positions 1, 2, 4, 5, 6, and 7; and (f) in HVR-L3 (SEQ ID NO: 62), at positions 1, 3, 4, 5, 6, 7, and 8.

In some embodiments, an isolated anti-sclerostin antibody of the present invention has an inhibitory activity against sclerostin.

In some embodiments, an isolated anti-sclerostin antibody of the present invention comprises a common light chain.

In some embodiments, an isolated anti-sclerostin antibody of the present invention is a monoclonal antibody. In some embodiments, an isolated anti-sclerostin antibody of the present invention is a human, humanized, or chimeric antibody. In further embodiments, an isolated anti-sclerostin antibody of the present invention is a full length IgG1 antibody. In further embodiments, an isolated anti-sclerostin antibody of the present invention is an antibody fragment that binds to sclerostin. In further embodiments, an isolated anti-sclerostin antibody of the present invention is a bispecific antibody.

In some embodiments, an isolated anti-sclerostin antibody of the present invention comprises a first variable region comprising a VH sequence of SEQ ID NO: 101 or 102 and a VL sequence of any one of SEQ ID NOs: 98-100, 105, and a second variable region comprising a VH sequence of SEQ ID NO: 103 or 104 and a VL sequence of any one of SEQ ID NOs: 98-100, 105. In further embodiments, the VL sequences of the first and second variable regions are identical.

In some embodiments, an isolated anti-sclerostin antibody of the present invention comprises a VH comprising the amino acid sequence of SEQ ID NO: 7 and a VL comprising the amino acid sequence of SEQ ID NO: 15, wherein at least one amino acid is substituted at the following HVR positions: (a) in HVR-H2 (SEQ ID NO: 34), at positions 5 and 8; (b) in HVR-H3 (SEQ ID NO: 38), at positions 2, 5, 7, and 13; (c) in HVR-L1 (SEQ ID NO: 52), at positions 4 and 7; (d) in HVR-L2 (SEQ ID NO: 56), at positions 1 and 2; and (e) in HVR-L3 (SEQ ID NO: 60), at position 1.

The invention also provides isolated nucleic acids encoding an anti-sclerostin antibody of the present invention. The invention also provides host cells comprising a nucleic acid of the present invention. The invention also provides a method of producing an antibody comprising culturing a host cell of the present invention so that the antibody is produced.

The invention also provides a pharmaceutical formulation comprising an anti-sclerostin antibody of the present invention and a pharmaceutically acceptable carrier.

The invention also provides a method of treating an individual having a bone-related disease. In some embodiments, the method comprises administering to the individual an effective amount of an anti-sclerostin antibody of the present invention. The invention also provides a method of treating a disease or condition which is associated with an increased level of sclerostin in an individual. In some embodiments, the method comprises administering to the individual an effective amount of an anti-sclerostin antibody of the present invention. The invention also provides a method of increasing bone formation and/or inhibiting bone resorption in an individual. In some embodiments, the method comprises administering to the individual an effective amount of an anti-sclerostin antibody of the present invention to increase bone formation and/or inhibit bone resorption. The invention also provides a method of increasing bone mineral density in an individual. In some embodiments, the method comprises administering to the individual an effective amount of an anti-sclerostin antibody of the present invention to increase bone mineral density.

More specifically, the present invention provides the following:

[1] An isolated multispecific antibody that binds to sclerostin, wherein the antibody comprises at least two different variable regions through which the antibody binds to at least two different epitopes of sclerostin, and wherein the antibody binds to sclerostin with a higher affinity at neutral pH than at acidic pH.

[2] The multispecific antibody of [1], which forms an immune complex with sclerostin, wherein the immune complex comprises at least two antibody molecules and at least two sclerostin molecules.

[3] The multispecific antibody of [1] or [2], wherein one of the at least two variable regions binds to the same epitope as an anti-sclerostin antibody comprising a VH sequence of SEQ ID NO: 7 and a VL sequence of SEQ ID NO: 15.

[4] The multispecific antibody of any one of [1] to [3], wherein one of the at least two variable regions binds to the same epitope as an anti-sclerostin antibody comprising a VH sequence of SEQ ID NO: 23 and a VL sequence of SEQ ID NO: 27.

[5] The multispecific antibody of any one of [1] to [4], wherein one of the at least two variable regions comprises a VH comprising the amino acid sequence of SEQ ID NO: 7 and a VL comprising the amino acid sequence of SEQ ID NO: 15, wherein at least one amino acid is substituted at the following positions: (a) in HVR-H1 (SEQ ID NO: 31), at position 1; (b) in HVR-H2 (SEQ ID NO: 34), at positions 3, 5, 8, 9, 11, and 12; (c) in HVR-H3 (SEQ ID NO: 38), at positions 2, 4, 5, 7, and 13; (d) in HVR-L1 (SEQ ID NO: 52), at positions 1, 4, 5, 6, 7, 8, 9, 10, and 11; (e) in HVR-L2 (SEQ ID NO: 56), at positions 1, 2, 4, 5, 6, and 7; and (f) in HVR-L3 (SEQ ID NO: 60), at positions 1, 3, 4, 5, 6, 7, and 8.

[6] The multispecific antibody of any one of [1] to [5], wherein one of the at least two variable regions comprises a VH comprising the amino acid sequence of SEQ ID NO: 23 and a VL comprising the amino acid sequence of SEQ ID NO: 27, wherein at least one amino acid is substituted at the following positions: (a) in HVR-H1 (SEQ ID NO: 32), at positions 1, 2, and 4; (b) in HVR-H2 (SEQ ID NO: 37), at position 9; (c) in HVR-H3 (SEQ ID NO: 43), at positions 2 and 9; (d) in HVR-L1 (SEQ ID NO: 55), at positions 1, 4, 5, 6, 7, 8, 9, 10, and 11; (e) in HVR-L2 (SEQ ID NO: 59), at positions 1, 2, 4, 5, 6, and 7; and (f) in HVR-L3 (SEQ ID NO: 62), at positions 1, 3, 4, 5, 6, 7, and 8.

[7] The multispecific antibody of any one of [1] to [6], which has an inhibitory activity against sclerostin.

[8] The multispecific antibody of any one of [1] to [7], wherein the at least two different variable regions comprise a common light chain.

[9] A bispecific antibody comprising a first variable region comprising a VH sequence of SEQ ID NO: 101 or 102 and a VL sequence of any one of SEQ ID NOs: 98-100, and 105, and a second variable region comprising a VH sequence of SEQ ID NO: 103 or 104 and a VL sequence of any one of SEQ ID NOs: 98-100, and 105.

[10] The bispecific antibody of [9], wherein the VL sequences of the first and second variable regions are identical.

[11] A pharmaceutical formulation comprising the antibody of any one of [1] to [10] and a pharmaceutically acceptable carrier.

[12] A method of treating an individual having a bone-related disease comprising administering to the individual an effective amount of the antibody of any one of [1] to [10].

[13] A method of treating a disease or condition which is associated with an increased level of sclerostin in an individual comprising administering to the individual an effective amount of the antibody of any one of [1] to [10].

[14] A method of increasing bone formation and/or inhibiting bone resorption in an individual comprising administering to the individual an effective amount of the antibody of any one of [1] to [10] to increase bone formation and/or inhibit bone resorption.

[15] A method of increasing bone mineral density in an individual comprising administering to the individual an effective amount of the antibody of any one of [1] to [10] to increase bone mineral density.

The present invention also provides the following:

[16] An isolated anti-sclerostin antibody that comprises a VH comprising the amino acid sequence of SEQ ID NO: 7 and a VL comprising the amino acid sequence of SEQ ID NO: 15, wherein at least one amino acid is substituted at the following positions: (a) in HVR-H1 (SEQ ID NO: 31), at position 1; (b) in HVR-H2 (SEQ ID NO: 34), at positions 3, 5, 8, 9, 11, and 12; (c) in HVR-H3 (SEQ ID NO: 38), at positions 2, 4, 5, 7, and 13; (d) in HVR-L1 (SEQ ID NO: 52), at positions 1, 4, 5, 6, 7, 8, 9, 10, and 11; (e) in HVR-L2 (SEQ ID NO: 56), at positions 1, 2, 4, 5, 6, and 7; and (f) in HVR-L3 (SEQ ID NO: 60), at positions 1, 3, 4, 5, 6, 7, and 8.

[17] An isolated anti-sclerostin antibody that comprises a VH comprising the amino acid sequence of SEQ ID NO: 23 and a VL comprising the amino acid sequence of SEQ ID NO: 27, wherein at least one amino acid is substituted at the following hypervariable region (HVR) positions: (a) in HVR-H1 (SEQ ID NO: 32), at positions 1, 2, and 4; (b) in HVR-H2 (SEQ ID NO: 37), at position 9; (c) in HVR-H3 (SEQ ID NO: 43), at positions 2 and 9; (d) in HVR-L1 (SEQ ID NO: 55), at positions 1, 4, 5, 6, 7, 8, 9, 10, and 11; (e) in HVR-L2 (SEQ ID NO: 59), at positions 1, 2, 4, 5, 6, and 7; and (f) in HVR-L3 (SEQ ID NO: 62), at positions 1, 3, 4, 5, 6, 7, and 8.

[18] The antibody of [16] or [17], which binds to sclerostin with a higher affinity at neutral pH than at acidic pH.

[19] The antibody of any one of [16] to [18], which has an inhibitory activity against sclerostin.

[20] A pharmaceutical formulation comprising the antibody of any one of [16] to [19] and a pharmaceutically acceptable carrier.

[21] A method of treating an individual having a bone-related disease comprising administering to the individual an effective amount of the antibody of any one of [16] to [19].

[22] A method of treating a disease or condition which is associated with an increased level of sclerostin in an individual comprising administering to the individual an effective amount of the antibody of any one of [16] to [19].

[23] A method of increasing bone formation and/or inhibiting bone resorption in an individual comprising administering to the individual an effective amount of the antibody of any one of [16] to [19] to increase bone formation and/or inhibit bone resorption.

[24] A method of increasing bone mineral density in an individual comprising administering to the individual an effective amount of the antibody of any one of [16] to [19] to increase bone mineral density.

The present invention also provides the following:

[25] A method of producing a common VL shared between two different VHs, the method comprising the steps of:

(1) providing a first variable region (V1) comprising a first VH (VH1) and a first VL (VL1), and a second variable region (V2) comprising a second VH (VH2) and a second VL (VL2), wherein V1 has a binding activity to a first antigen (Ag1) and V2 has a binding activity to a second antigen (Ag2); and (2) constructing a modified VL (mVL) by replacing an amino acid residue at a position in HVR-L1, HVR-L2, or HVR-L3 of VL1 with an amino acid residue at the corresponding position in HVR-L1, HVR-L2, or HVR-L3 of VL2, according to Kabat numbering.

[26] The method of [25], further comprising the step of:

(3) repeating the step (2) for amino acids at different positions, until the amino acids at all positions in HVR-L1, HVR-L2, and HVR-L3 of VL1 are replaced.

[27] The method of [26], further comprising the steps of:
(2') constructing a modified VL (mVL) by replacing an amino acid residue at a position in HVR-L1, HVR-L2, or HVR-L3 of VL2 with an amino acid residue at the corresponding position in HVR-L1, HVR-L2, or HVR-L3 of VL1, according to Kabat numbering; and
(3') repeating the step (2') for amino acids at different positions, until the amino acids at all positions in HVR-L1, HVR-L2, and HVR-L3 of VL2 are replaced.
[28] The method of any one of [25] to [27], further comprising the step of:
(4) measuring binding activities of the mVLs constructed in the aforementioned steps to Ag1 or Ag2 when combined with VH1 or VH2, respectively.
[29] The method of [28], further comprising the steps of:
(5) selecting a preferable amino acid residue at a position in HVR-L1, HVR-L2, and HVR-L3 from the two amino acid residues, one of which is the amino acid residue located at the corresponding position in VL1 (AA1) and the other of which is the amino acid residue located at the corresponding position in VL2 (AA2), based on the binding activities of the mVLs measured in the step (4);
(6) repeating the step (5) for at least two different positions in HVR-L1, HVR-L2, and HVR-L3; and
(7) constructing a novel VL (nVL) comprising the amino acid residues selected in the steps (5) and (6) at their positions in HVR-L1, HVR-L2, and HVR-L3.
[30] The method of [29], wherein the step (5) is repeated until the preferable amino acid residues at all positions in HVR-L1, HVR-L2, and HVR-L3 are selected.
[31] The method of [29] or [30], wherein the amino acid sequence of any one of FRs selected from FR-L1, FR-L2, FR-L3, and FR-L4 of nVL is selected from the two amino acid sequences, one of which is the amino acid sequence of the corresponding FR of VL1 and the other of which is the amino acid sequence of the corresponding FR of VL2.
[32] The method of any one of [25] to [31], wherein both VL1 and VL2 are variable regions derived from kappa light chain.
[33] The method of any one of [25] to [31], wherein both VL1 and VL2 are variable regions derived from lambda light chain.
[34] The method of any one of [25] to [33], wherein the amino acid length of any one of HVRs selected from HVR-L1, HVR-L2, and HVR-L3 of VL1 is the same as that of the corresponding HVR of VL2.
[35] The method of any one of [25] to [34], wherein the amino acid length of any one of FRs selected from FR-L1, FR-L2, FR-L3, and FR-L4 of VL1 is the same as that of the corresponding FR of VL2.
[36] The method of any one of [25] to [35], wherein the amino acid sequence of any one of FRs selected from FR-L1, FR-L2, FR-L3, and FR-L4 of VL1 has an identity of 50% or more, compared with that of the corresponding FR of VL2.

p<0.01, $$$: p<0.001 vs vehicle by t-test analysis. ++: p<0.01, +++: p<0.001 vs same dosage of mabA_NpH3-SG2 by t-test analysis.

Figure 12:
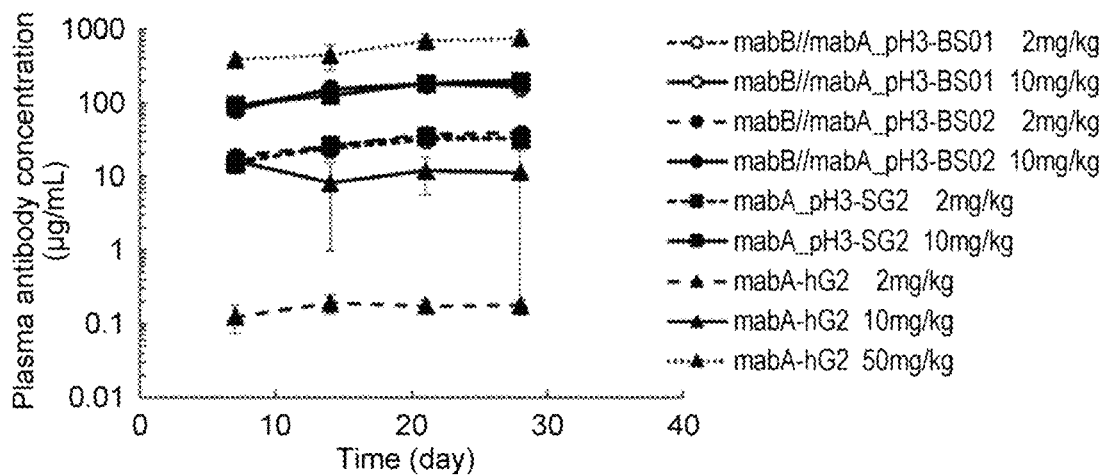

FIG. 12 illustrates a time course of plasma concentration of anti-sclerostin antibodies (mabB//mabA_pH3-BS01, mabB//mabA_pH3-BSO2, mabA_pH3-SG2, and mabA-hG2) intravenously administered in SCID mice, as described in Example 9.

Figure 13:
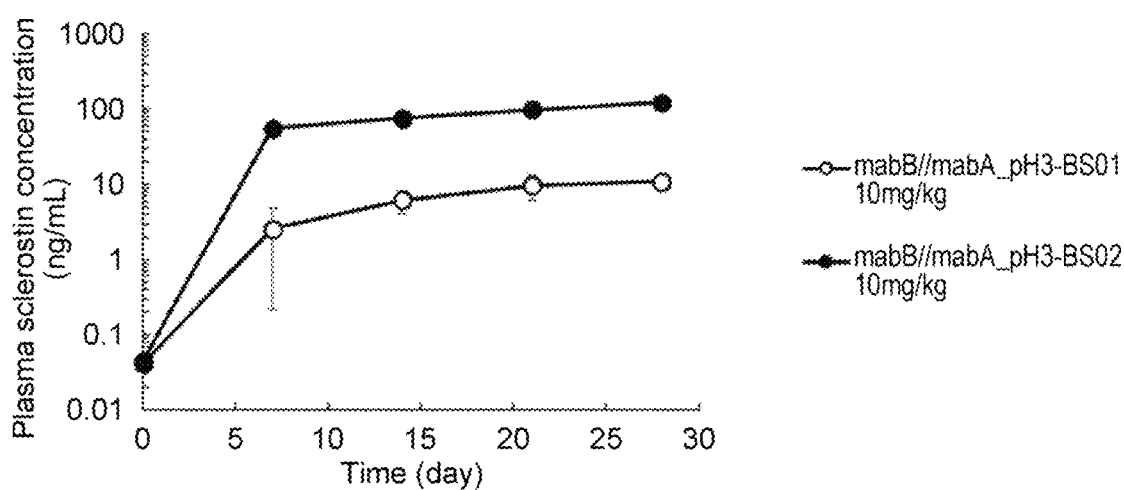

FIG. 13 illustrates a time course of plasma concentration of sclerostin after intravenous administration of anti-sclerostin antibodies (mabB//mabA_pH3-BSO1 and mabB//mabA_pH3-BSO2) in SCID mice, as described in Example 9.

Figure 14:
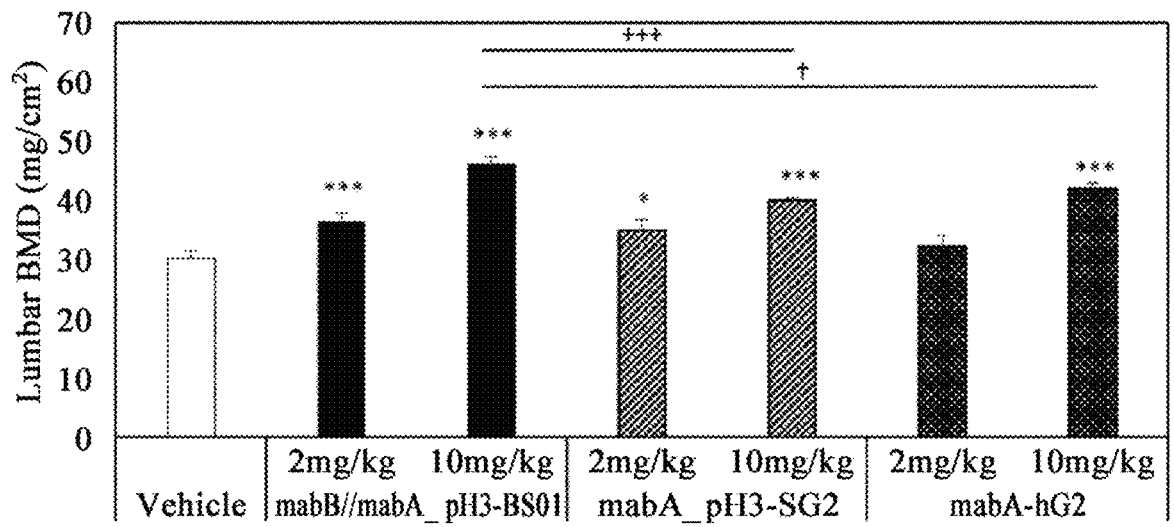

FIG. 14 illustrates in vivo efficacy of anti-sclerostin antibodies (mabB//mabA_pH3-BSO1, mabA_pH3-SG2, and mabA-hG2) on bone mineral density (BMD) of lumbar spine in SCID mice, as described in Example 9. Data represent mean+SE. *: $p<0.05$, : $p<0.01$, *: $p<0.001$ vs vehicle by Wlliams analysis. +: $p<0.5$, ++: $p<0.01$, +++: $p<0.001$ vs same dosage of mabA_pH3-SG2 or mabA-hG2 by t-test analysis.

Figure 15:
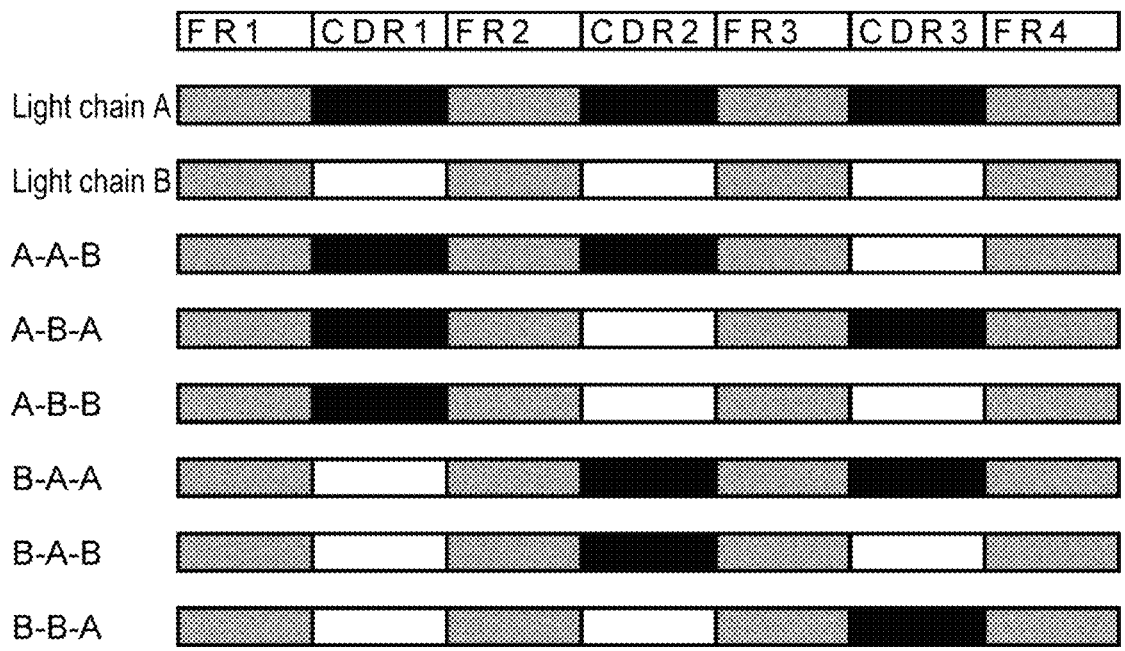

FIG. 15 illustrates a schematic diagram of the CDR Shuffling method, as described in Example 10. CDRs at the same position of the light chains of mabA and mabB were mutually exchanged (shuffled) and subsequently the variant light chains of A-A-B, A-B-A, A-B-B, B-A-A, B-A-B, and B-B-A were constructed.

Figure 16:
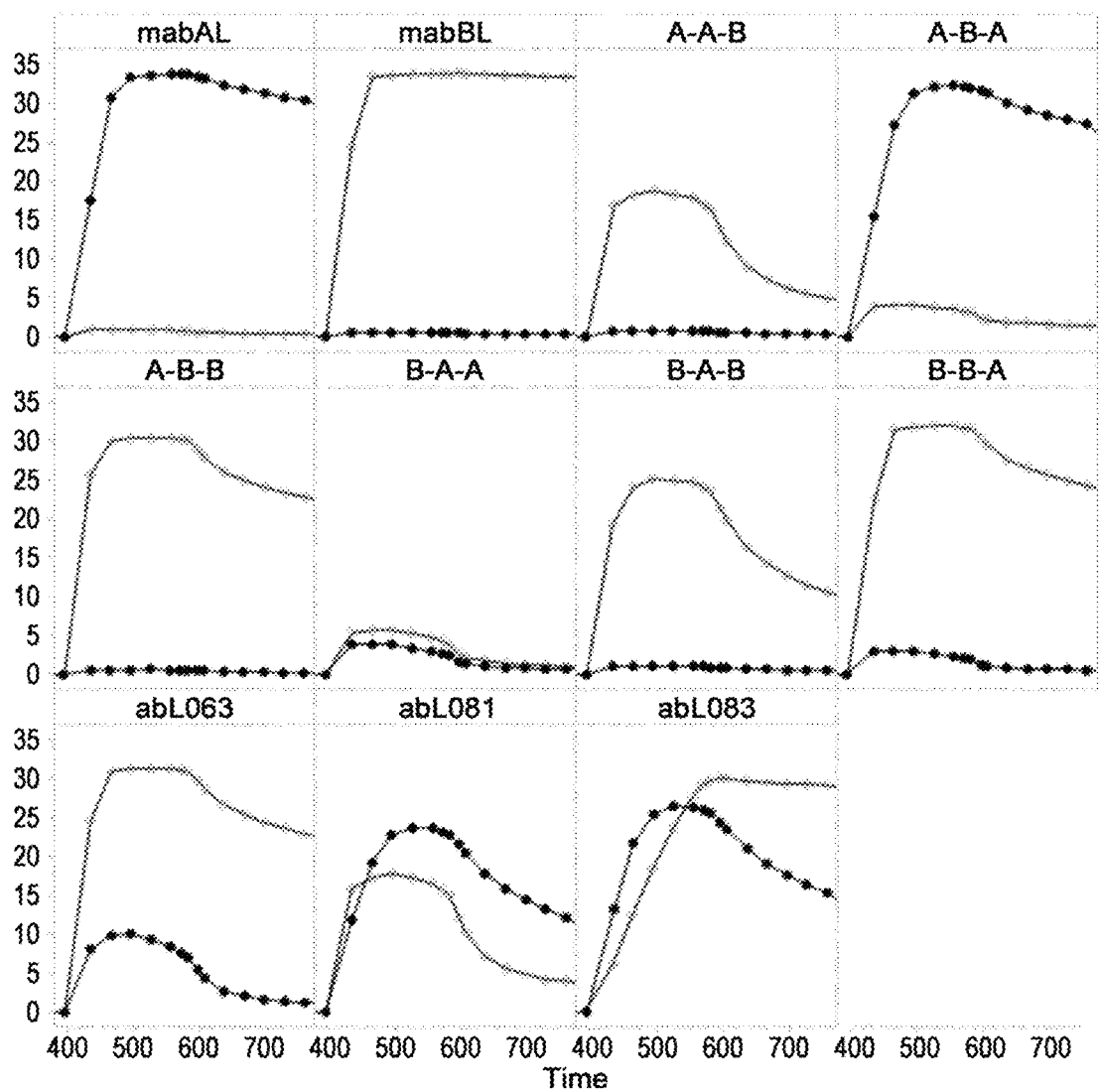

FIG. 16 illustrates the binding of CDR-shuffled anti-sclerostin antibody variants to human sclerostin, as described in Example 10. Each of the light chains of mabA, mabB, A-A-B, A-B-A, A-B-B, B-A-A, B-A-B, B-B-A, abL063, abL081, and abL083 were combined with either the heavy chain of mabA (closed circles) or the heavy chain of mabB (open circles), and the binding activity of the resultant antibodies to human sclerostin were measured by SPR analysis. Each plot is normalized by the capture level of the antibodies.

Figure 17:
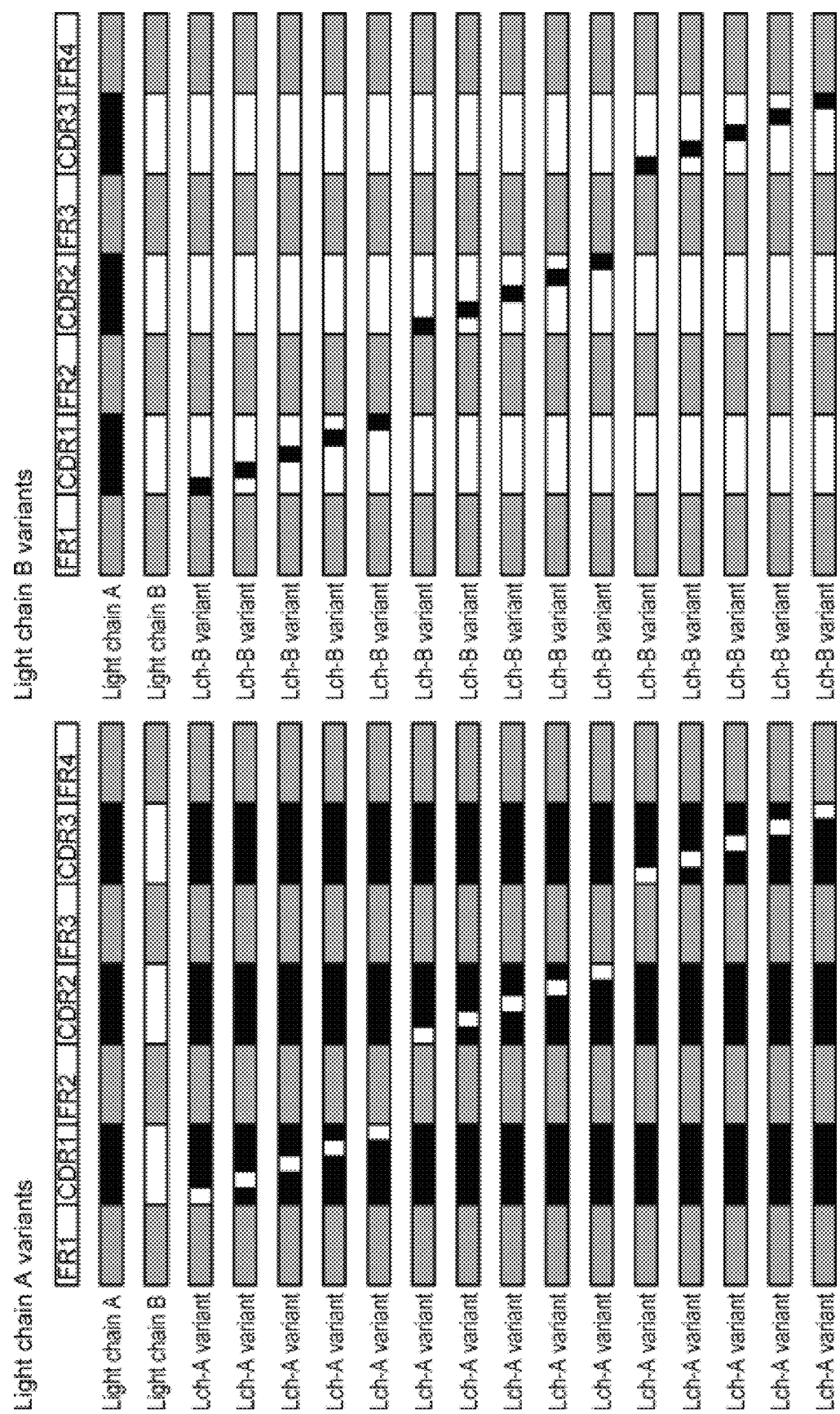

FIG. 17 illustrates a schematic diagram of the first step of the Each Residue Shuffling method, as described in Example 10. Amino acid residues at the same position in the CDRs of the mabA and mabB light chains were mutually exchanged (shuffled) and subsequently the variant mabA light chain and mabB light chain were constructed.

Figure 18:

FIG. 18 illustrates a schematic diagram of the later step of the Each Residue Shuffling method, as described in Example 10. A pair of the mabA and mabB light chain variants having a single mutation at the same position were evaluated and compared each other. By selecting better amino acid residues at each position and combining the selected ones, the "each residue-shuffling" light chain variants were designed.

Figure 19:
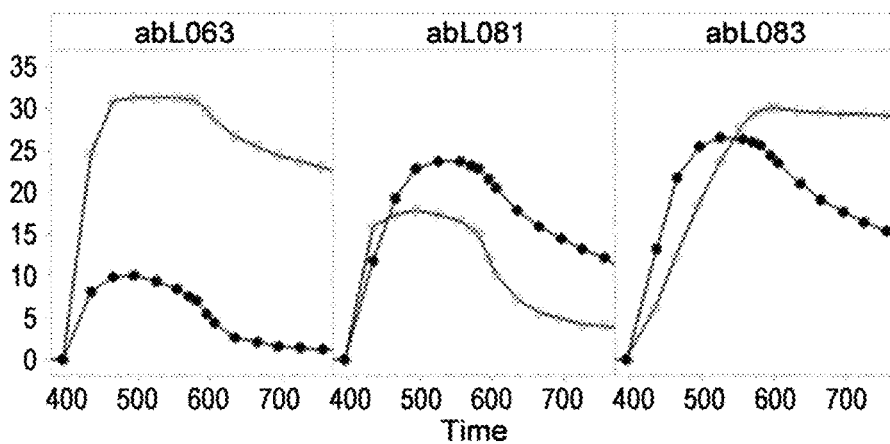

FIG. 19 illustrates the binding of Each Residue-shuffled anti-sclerostin antibody variants to human sclerostin, as described in Example 10. Each of the light chains of abL063, abL081, and abL083 were combined with either of the mabA heavy chain (closed circles) or the mabB heavy chain (open circles), and the binding activity of the resultant antibodies to human sclerostin were measured by SPR analysis. Each plot is normalized by the capture level of the antibodies.

FIG. 20a illustrates a chromatogram obtained by applying a pI-engineered biparatopic anti-sclerostin antibodies and homodimeric antibodies to cation exchange chromatography, as described in Example 11. The chromatogram includes (i) a biparatopic antibody containing a mabA heavy chain variant, a mabB heavy chain variant, and a common light chain variant, (ii) a homodimeric antibody containing the mabA heavy chain variant and the common light chain variant, and (iii) a homodimeric antibody containing the mabB heavy chain variant and the common light chain variant. The biparatopic antibody used in FIG. 20a was amH848/bsH638/abL152.

Figure 20B:
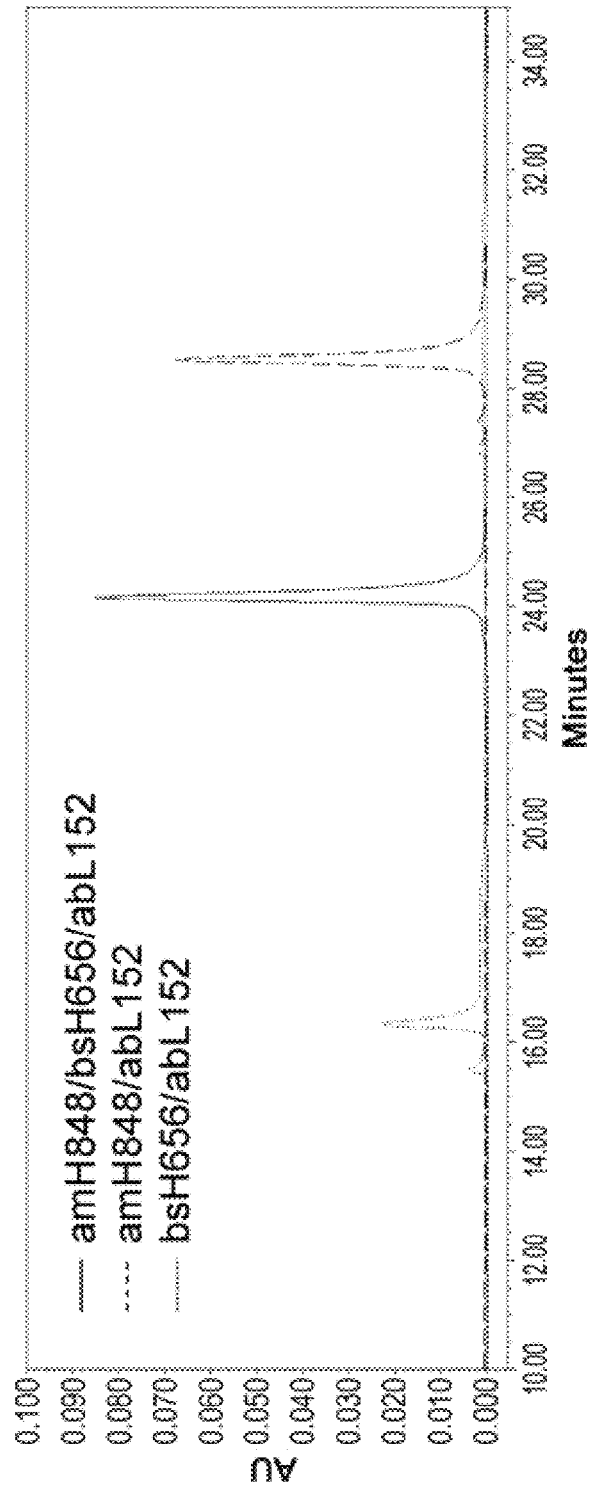

FIG. 20b illustrates a chromatogram obtained by applying a pI-engineered biparatopic anti-sclerostin antibodies and homodimeric antibodies to cation exchange chromatography, as described in Example 11. The chromatogram includes (i) a biparatopic antibody containing a mabA heavy chain variant, a mabB heavy chain variant, and a common light chain variant, (ii) a homodimeric antibody containing the mabA heavy chain variant and the common light chain variant, and (iii) a homodimeric antibody containing the mabB heavy chain variant and the common light chain variant. The biparatopic antibody used in FIG. 20b was amH848/bsH656/abL152.

FIG. 20c illustrates a chromatogram obtained by applying a pI-engineered biparatopic anti-sclerostin antibodies and homodimeric antibodies to cation exchange chromatography, as described in Example 11. The chromatogram includes (i) a biparatopic antibody containing a mabA heavy chain variant, a mabB heavy chain variant, and a common light chain variant, (ii) a homodimeric antibody containing the mabA heavy chain variant and the common light chain variant, and (iii) a homodimeric antibody containing the mabB heavy chain variant and the common light chain variant. The biparatopic antibody used in FIG. 20c was amH852/bsH638/abL152.

Figure 20D:
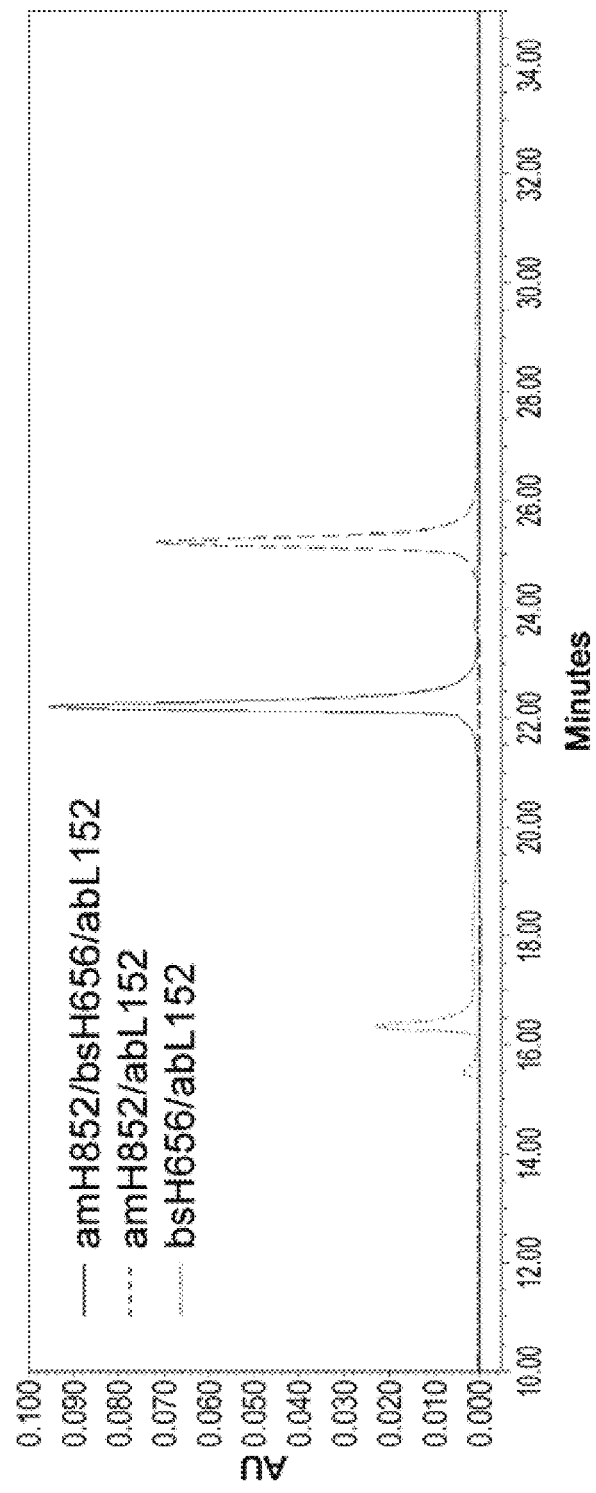

FIG. 20d illustrates a chromatogram obtained by applying a pI-engineered biparatopic anti-sclerostin antibodies and homodimeric antibodies to cation exchange chromatography, as described in Example 11. The chromatogram includes (i) a biparatopic antibody containing a mabA heavy chain variant, a mabB heavy chain variant, and a common light chain variant, (ii) a homodimeric antibody containing the mabA heavy chain variant and the common light chain variant, and (iii) a homodimeric antibody containing the mabB heavy chain variant and the common light chain variant. The biparatopic antibody used in FIG. 20d was amH852/bsH656/abL152.

Figure 21:
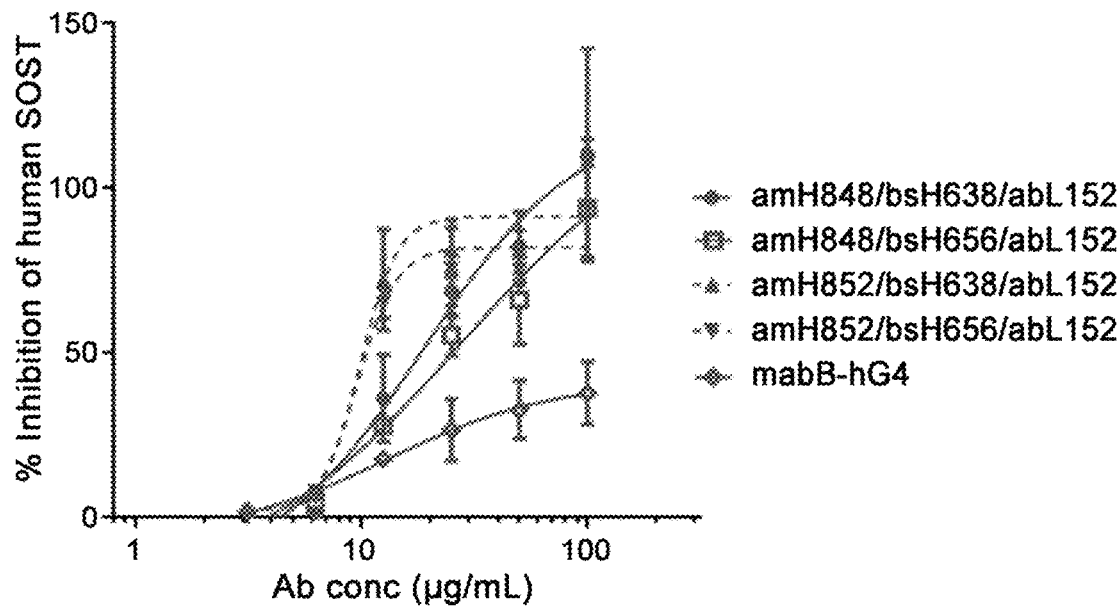

FIG. 21 illustrates in vitro neutralizing activity of pI-engineered biparatopic anti-sclerostin antibodies (amH848/bsH638/abL152, amH848/bsH656/abL152, amH852/bsH638/abL152, and amH852/bsH656/abL152) and an anti-sclerostin antibody mabB, as described in Example 11.

Figure 22A:
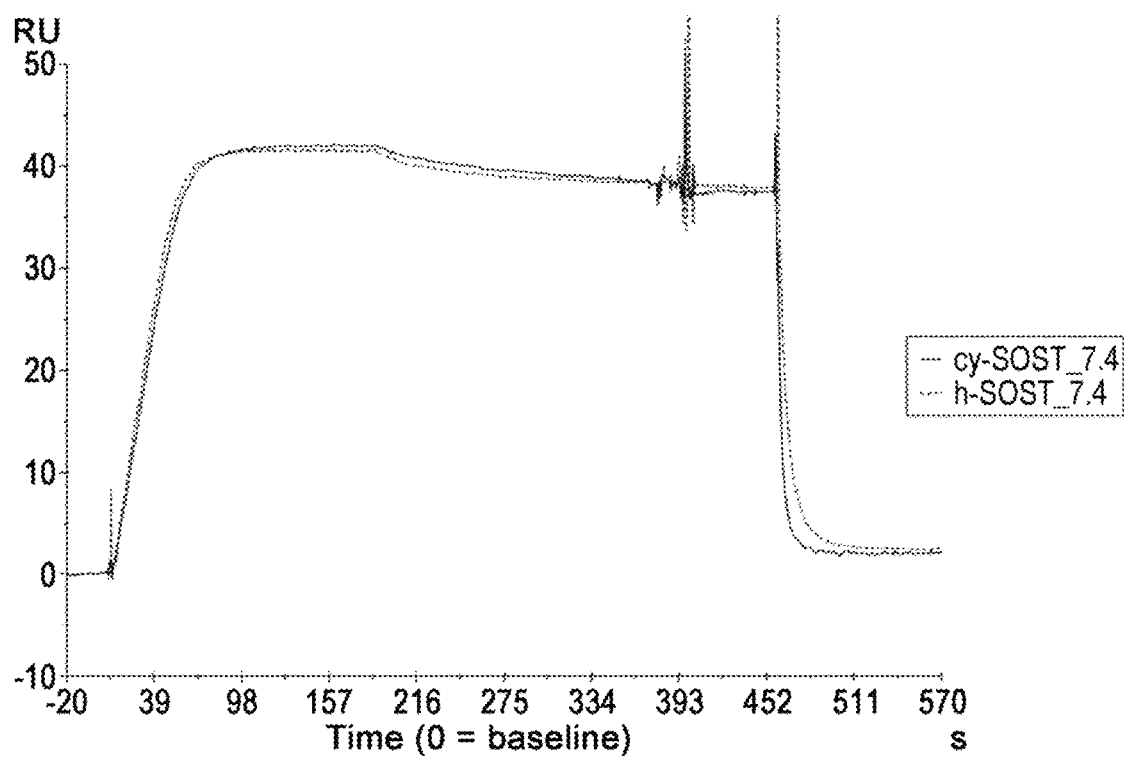

FIG. 22a illustrates a Biacore sensorgram of anti-sclerostin biparatopic antibodies towards human sclerostin (h-SOST) and cynomolgus monkey sclerostin (cy-SOST) at pH 7.4, as described in Example 12. As a biparatopic antibody, amH848/bsH638/abL152 is used.

Figure 22B:
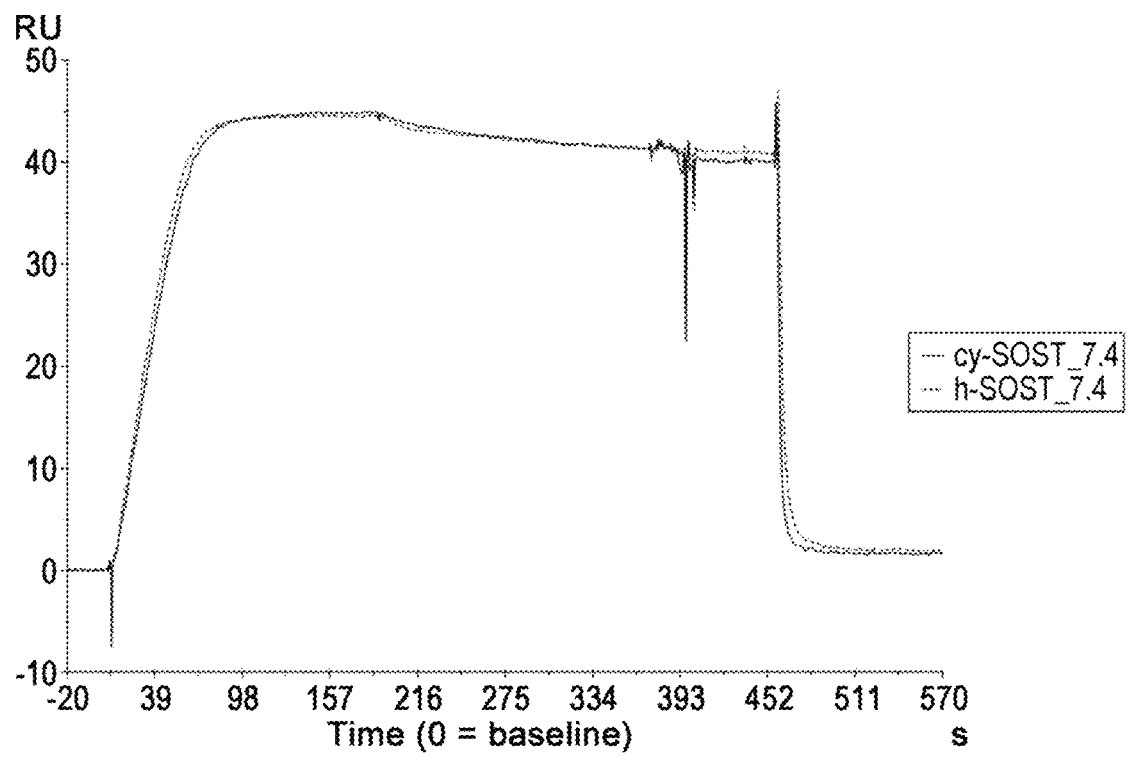

FIG. 22b illustrates a Biacore sensorgram of anti-sclerostin biparatopic antibodies towards human sclerostin (h-SOST) and cynomolgus monkey sclerostin (cy-SOST) at pH 7.4, as described in Example 12. As a biparatopic antibody, amH848/bsH656/abL152 is used.

Figure 22C:
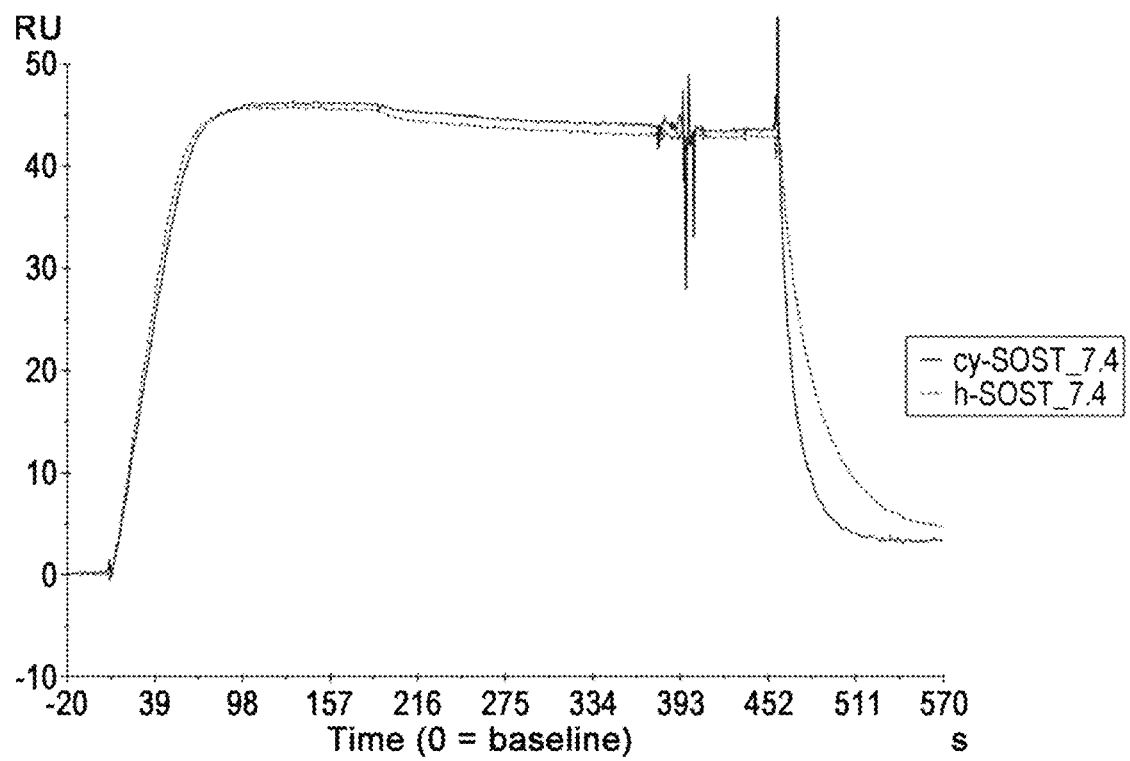

FIG. 22c illustrates a Biacore sensorgram of anti-sclerostin biparatopic antibodies towards human sclerostin (h-SOST) and cynomolgus monkey sclerostin (cy-SOST) at pH 7.4, as described in Example 12. As a biparatopic antibody, amH852/bsH638/abL152 is used.

Figure 22D:
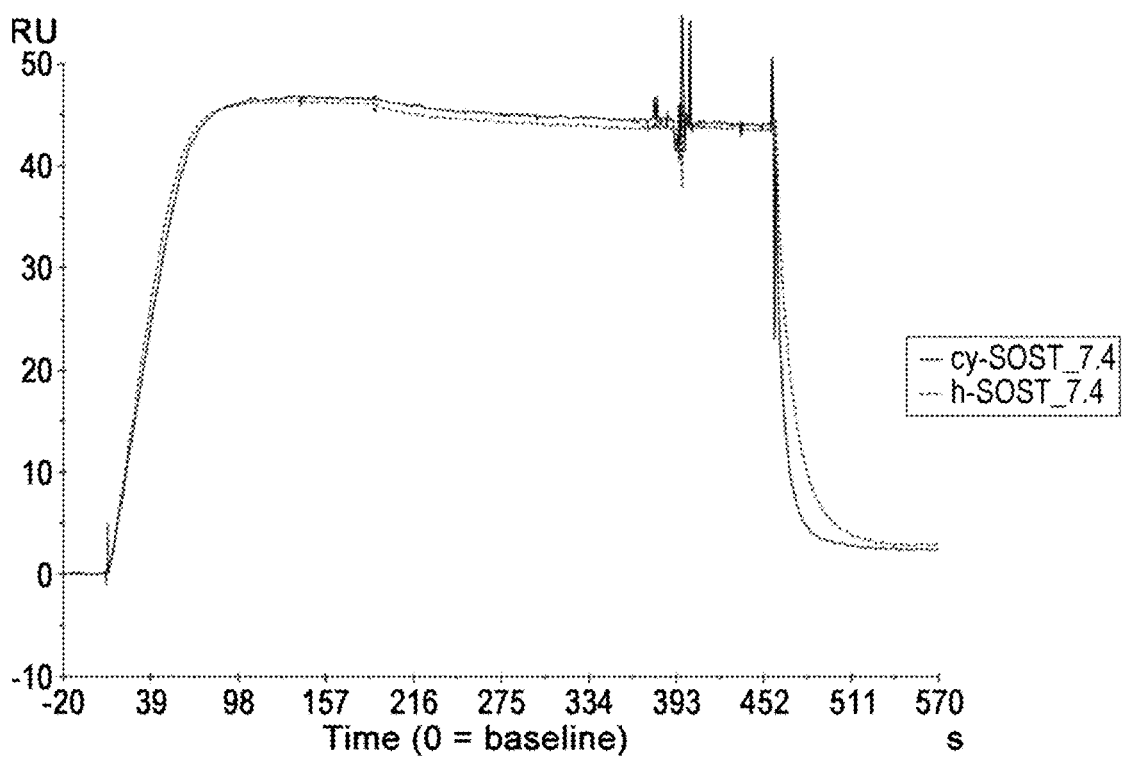

FIG. 22d illustrates a Biacore sensorgram of anti-sclerostin biparatopic antibodies towards human sclerostin (h-SOST) and cynomolgus monkey sclerostin (cy-SOST) at pH 7.4, as described in Example 12. As a biparatopic antibody, amH852/bsH656/abL152 is used.

DESCRIPTION OF EMBODIMENTS

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3d edition (2001) Cold Spring Harbor Laboratory Press, Cold Spring Harbor, N.Y.; Current Protocols in Molecular Biology (F. M. Ausubel, et al. eds., (2003)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, A Laboratory Manual, and Animal Cell Culture (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

I. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application. All references cited herein, including patent applications and publications, are incorporated by reference in their entirety.

For purposes of interpreting this specification, the following definitions will apply and whenever appropriate, terms used in the singular will also include the plural and vice versa. It is to be understood that the terminology used herein is for the purpose of describing particular embodiments only, and is not intended to be limiting. In the event that any definition set forth below conflicts with any document incorporated herein by reference, the definition set forth below shall control.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-sclerostin antibody" and "an antibody that binds to sclerostin" refer to an antibody that is capable of binding sclerostin with sufficient affinity such that the antibody is useful as a diagnostic and/or therapeutic agent in targeting sclerostin. In one embodiment, the extent of binding of an anti-sclerostin antibody to an unrelated, non-sclerostin protein is less than about 10% of the binding of the antibody to sclerostin as measured, e.g., by a radioimmunoassay (RIA). In certain embodiments, an antibody that binds to sclerostin has a dissociation constant (Kd) of 1micro M or less, 100 nM or less, 10 nM or less, 1 nM or less, 0.1 nM or less, 0.01 nM or less, or 0.001 nM or less (e.g. $10^{-8}$ M or less, e.g. from $10^{-8}$ M to $10^{-13}$ M, e.g., from $10^{-9}$ M to $10^{-13}$ M). In certain embodiments, an anti-sclerostin antibody binds to an epitope of sclerostin that is conserved among sclerostin from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called alpha, delta, epsilon, gamma, and mu, respectively.

The term "cytotoxic agent" as used herein refers to a substance that inhibits or prevents a cellular function and/or causes cell death or destruction. Cytotoxic agents include, but are not limited to, radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu); chemotherapeutic agents or drugs (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" includes any determinant capable of being bound by an antibody. An epitope is a region of an antigen that is bound by an antibody that targets that antigen, and includes specific amino acids that directly contact the antibody. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) or glycine-lysine (residues 446-447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-sclerostin antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies composing the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa and lambda, based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

The term "sclerostin," as used herein, refers to any native sclerostin from any vertebrate source, including mammals such as primates (e.g. humans) and rodents (e.g., mice and rats), unless otherwise indicated. The term encompasses "full-length" unprocessed sclerostin as well as any form of sclerostin that results from processing in the cell. The term also encompasses naturally occurring variants of sclerostin, e.g., splice variants or allelic variants. The amino acid sequence of an exemplary human sclerostin is shown in SEQ ID NO: 1. The amino acid sequences of an exemplary cynomolgus monkey, rat, and mouse sclerostin are shown in SEQ ID NOs: 2, 3, and 4, respectively.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on anti-sclerostin antibodies and uses thereof. In certain embodiments, antibodies that bind to sclerostin are provided. Antibodies of the invention are useful, e.g., for the diagnosis or treatment of a bone-related disease. In another aspect, the invention is based, in part, on methods of producing a common VL. Such methods are useful, e.g., for the production of a multispecific antibody such as a bispecific antibody.

A. Exemplary Anti-Sclerostin Antibodies

In one aspect, the invention provides isolated antibodies that bind to sclerostin. In certain embodiments, anti-sclerostin antibody variants which are prepared by introducing amino acid modifications into an antibody comprising a VH sequence of SEQ ID NO: 7 and a VL sequence of SEQ ID NO: 15 are provided (mabA variants). In certain embodiments, anti-sclerostin antibody variants which are prepared by introducing amino acid modifications into an antibody comprising a VH sequence of SEQ ID NO: 23 and a VL sequence of SEQ ID NO: 27 are also provided (mabB variants). In certain embodiments, an anti-sclerostin antibody of the present invention is a multispecific antibody which comprises at least two different variable regions. In certain embodiments, an anti-sclerostin antibody of the present invention is a multiparatopic antibody which comprises at least two different variable regions through which the antibody binds to at least two different epitopes on a sclerostin molecule.

In some embodiments, one of the two different variable regions of the multispecific antibody of the present invention can be selected from the variable regions of the mabA variants. In some embodiments, one of the two different variable regions of the multispecific antibody of the present invention can be selected from the variable regions of the mabB variants. In certain embodiment, one of the two different variable regions of the multispecific antibody binds to the same epitope of the antibody comprising a VH sequence of SEQ ID NO: 7 and a VL sequence of SEQ ID NO: 15 (mabA). In certain embodiment, one of the two different variable regions of the multispecific antibody binds to the same epitope of the antibody comprising a VH sequence of SEQ ID NO: 23 and a VL sequence of SEQ ID NO: 27 (mabB). In further embodiments, the multispecific antibody of the present invention comprises a variable region derived from any one of the mabA variants and a variable region derived from any one of the mabB variants. In particular embodiments, the anti-sclerostin antibody is bispecific antibody or a biparatopic antibody.

In some embodiments, an anti-sclerostin antibody of the present invention forms a complex with the antigen, sclerostin (also described herein as an antigen-antibody complex or an immune complex). In some embodiments, the complex comprises at least two antibody molecules of the present invention. In further embodiments, the complex comprises at least two antigen molecules. In particular embodiments, the complex comprises two antibody molecules of the present invention and two antigen molecules, wherein each antibody molecule binds to two antigen molecule and each antigen molecule binds to two antibody molecule.

In some embodiments, an anti-sclerostin antibody of the present invention is taken up into cells. In particular embodiments, uptake of the antibody into cells is enhanced when the antibody is forming a complex with the antigen compared with when the antibody is not forming a complex with the antigen. Enhanced uptake of the antigen-antibody complex into cells can lead to enhanced clearance of the antigen from plasma when the antibody is administered in a subject. In another embodiment, clearance of sclerostin from plasma is enhanced when an anti-sclerostin antibody of the present invention is administered in a subject.

In some embodiments, an anti-sclerostin antibody of the present invention is taken up into cells through the interaction between an Fc region of the antibody and an Fc receptor on the surface of the cells. In particular embodiments, the Fc receptor can be Fc gamma receptor (Fc gamma R), which includes, for example, Fc gamma RI including isoforms Fc gamma RIa, Fc gamma RIb, and Fc gamma RIc; Fc gamma RII including isoforms Fc gamma RIIa (including allotypes H131 (type H) and R131 (type R)), Fc gamma RIIb (including Fc gamma RIIb-1 and Fc gamma RIIb-2), and Fc gamma RIIc; and Fc gamma RIII including isoforms Fc gamma RIIIa (including allotypes V158 and F158), and Fc gamma RIIIb (including allotypes Fc gamma RIIIb-NA1 and Fc gamma RIIIb-NA2).

An immune complex comprising two or more antibody molecules can more strongly bind to Fc receptors on a cell surface and more efficiently be taken up into cells, due to the avidity effect through the multiple Fc regions in the complex, compared with an immune complex comprising only one antibody molecule. In some embodiments, an anti-sclerostin antibody of the present invention comprises at least two different variable regions, which bind to epitopes on a sclerostin molecule different from each other, and two or more of the antibody molecules and two or more sclerostin molecules bind to each other and form an immune complex. In particular embodiments, an anti-sclerostin antibody of the present invention comprises two different variable regions, which bind to epitopes on a sclerostin molecule different from each other, and two of the antibody molecules and two sclerostin molecules bind to each other and form an immune complex.

In some embodiments, an anti-sclerostin antibody of the present invention binds to sclerostin with a higher affinity at neutral pH than at acidic pH. In another aspect, the invention provides anti-sclerostin antibodies that exhibit pH-dependent binding to sclerostin. As used herein, the expression "pH-dependent binding" means "reduced binding at acidic pH as compared to at neutral pH", and both expressions may be interchangeable. For example, anti-sclerostin antibodies "with pH-dependent binding characteristics" include antibodies that bind to sclerostin with higher affinity at neutral pH than at acidic pH. In particular embodiments, the antibodies of the present invention bind to sclerostin with at least 2, 3, 5, 10, 15, 20, 25, 30, 35, 40, 45, 50, 55, 60, 65, 70, 75, 80, 85, 90, 95, 100, 200, 400, 1000, 10000, or more times higher affinity at neutral pH than at acidic pH.

When an antigen is a soluble protein, the binding of an antibody to the antigen can result in an extended half-life of the antigen in plasma (i.e., reduced clearance of the antigen from plasma), since the antibody can have a longer half-life in plasma than the antigen itself and may serve as a carrier for the antigen. This is due to the recycling of the antigen-antibody complex by FcRn through the endosomal pathway in cell (Roopenian and Akilesh (2007) Nat Rev Immunol 7(9): 715-725). However, an antibody with pH-dependent binding characteristics, which binds to its antigen in neutral extracellular environment while releasing the antigen into acidic endosomal compartments following its entry into cells, is expected to have superior properties in terms of antigen neutralization and clearance relative to its counterpart that binds in a pH-independent manner (Igawa et al (2010) Nature Biotechnol 28(11); 1203-1207; Devanaboyina et al (2013) mAbs 5(6): 851-859; International Patent Application Publication No: WO 2009/125825).

An antibody having both properties mentioned above, that is, an antibody which binds to an antigen in a pH-dependent manner and forms an immune complex comprising two or more antibody molecules, is expected to have even more superior properties for highly accelerated elimination of antigens from plasma.

The "affinity" of an antibody for sclerostin, for purposes of the present disclosure, is expressed in terms of the KD of the antibody. The KD of an antibody refers to the equilibrium dissociation constant of an antibody-antigen interaction. The greater the KD value is for an antibody binding to its antigen, the weaker its binding affinity is for that particular antigen. Accordingly, as used herein, the expression "higher affinity at neutral pH than at acidic pH" (or the equivalent expression "pH-dependent binding") means that the KD of the antibody at acidic pH is greater than the KD of the antibody at neutral pH. For example, in the context of the present invention, an antibody is considered to bind to sclerostin with higher affinity at neutral pH than at acidic pH if the KD of the antibody binding to sclerostin at acidic pH is at least 2 times greater than the KD of the antibody binding to sclerostin at neutral pH. Thus, the present invention includes antibodies that bind to sclerostin at acidic pH with a KD that is at least 2, 3, 5, 10, 15, 20, 25, 30, 35, 40, 45, 50, 55, 60, 65, 70, 75, 80, 85, 90, 95, 100, 200, 400, 1000, 10000, or more times greater than the KD of the antibody binding to sclerostin at neutral pH. In another embodiment, the KD value of the antibody at neutral pH can b-e $10^{-7}$ M, $10^{-8}$ M, $10^{-9}$ M, $10^{-10}$ M, $10^{-11}$ M, $10^{-12}$ M, or less. In another embodiment, the KD value of the antibody at acidic pH can be $10^{-9}$ M, $10^{-8}$ M, $10^{-7}$ M, $10^{-6}$ M, or greater.

The binding properties of an antibody for a particular antigen may also be expressed in terms of the kd of the antibody. The kd of an antibody refers to the dissociation rate constant of the antibody with respect to a particular antigen and is expressed in terms of reciprocal seconds (i.e., $sec^{-1}$). An increase in kd value signifies weaker binding of an antibody to its antigen. The present invention therefore includes antibodies that bind to sclerostin with a higher kd value at acidic pH than at neutral pH. The present invention includes antibodies that bind to sclerostin at acidic pH with a kd that is at least 2, 3, 5, 10, 15, 20, 25, 30, 35, 40, 45, 50, 55, 60, 65, 70, 75, 80, 85, 90, 95, 100, 200, 400, 1000, 10000, or more times greater than the kd of the antibody binding to sclerostin at neutral pH. In another embodiment, the kd value of the antibody at neutral pH can be $10^{-2}$ 1/s, $10^{-3}$ 1/s, $10^{-4}$ 1/s, 10–5 1/s, $10^{-6}$ 1/s, or less. In another embodiment, the kd value of the antibody at acidic pH can be $10^{-3}$ 1/s, $10^{-2}$ 1/s, $10^{-1}$ 1/s, or greater.

In certain instances, a "reduced binding at acidic pH as compared to at neutral pH" is expressed in terms of the ratio of the KD value of the antibody at acidic pH to the KD value of the antibody at neutral pH (or vice versa). For example, an antibody may be regarded as exhibiting "reduced binding to sclerostin at acidic pH as compared to its binding at neutral pH", for purposes of the present invention, if the antibody exhibits an acidic/neutral KD ratio of 2 or greater. In certain exemplary embodiments, the acidic/neutral KD ratio for an antibody of the present invention can be 2, 3, 5, 10, 15, 20, 25, 30, 35, 40, 45, 50, 55, 60, 65, 70, 75, 80, 85, 90, 95, 100, 200, 400, 1000, 10000, or greater. In another embodiment, the KD value of the antibody at neutral pH can be $10^{-7}$ M, $10^{-8}$ M, $10^{-9}$ M, $10^{-10}$ M, $10^{-11}$ M, $10^{-12}$ M, or less. In another embodiment, the KD value of the antibody at acidic pH can be $10^{-9}$ M, $10^{-8}$ M, $10^{-7}$ M, $10^{-6}$ M, or greater.

In certain instances, a "reduced binding at acidic pH as compared to at neutral pH" is expressed in terms of the ratio of the kd value of the antibody at acidic pH to the kd value of the antibody at neutral pH (or vice versa). For example, an antibody may be regarded as exhibiting "reduced binding to sclerostin at acidic pH as compared to its binding at neutral pH", for purposes of the present invention, if the antibody exhibits an acidic/neutral kd ratio of 2 or greater. In certain exemplary embodiments, the acidic/neutral kd ratio for an antibody of the present invention can be 2, 3, 5, 10, 15, 20, 25, 30, 35, 40, 45, 50, 55, 60, 65, 70, 75, 80, 85, 90, 95, 100, 200, 400, 1000, 10000, or greater. In another embodiment, the kd value of the antibody at neutral pH can be $10^{-2}$ 1/s, $10^{-3}$ 1/s, $10^{-4}$ 1/s, 10–5 1/s, $10^{-6}$ 1/s, or less. In another embodiment, the kd value of the antibody at acidic pH can be $10^{-3}$ 1/s, $10^{-2}$ 1/s, 10–1 1/s, or greater.

As used herein, the expression "acidic pH" means a pH of 4.0 to 6.5. The expression "acidic pH" includes pH values of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, and 6.5. In particular aspects, the "acidic pH" is 5.8.

As used herein, the expression "neutral pH" means a pH of 6.7 to about 10.0. The expression "neutral pH" includes pH values of 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0. In particular aspects, the "neutral pH" is 7.4.

KD values, and kd values, as expressed herein, may be determined using a surface plasmon resonance-based biosensor to characterize antibody-antigen interactions. (See, e.g., Example 3, herein). KD values, and kd values can be determined at 25 degrees C. or 37 degrees C.

In certain embodiments, an anti-sclerostin antibody of the present invention has an inhibitory activity against sclerostin. In another embodiment, an anti-sclerostin antibody of the present invention blocks sclerostin signaling through a cell surface receptor such as low density lipoprotein receptor-related protein 5 and 6 (LRP5 and LRP6).

In certain embodiments, an anti-sclerostin antibody of the present invention binds to sclerostin from more than one species. In particular embodiments, the anti-sclerostin antibody binds to sclerostin from a human and non-human animal. In particular embodiments, the anti-sclerostin antibody binds to sclerostin from human, mouse, rat, and monkey (e.g. cynomolgus, rhesus macaque, marmoset, chimpanzee, and baboon).

MabA Variants

In one aspect, the invention provides an anti-sclerostin antibody comprising at least one, two, three, four, five, or six HVRs selected from (a) HVR-H1 comprising the amino acid sequence of SEQ ID NO: 124; (b) HVR-H2 comprising the amino acid sequence of SEQ ID NO: 126; (c) HVR-H3 comprising the amino acid sequence of SEQ ID NO: 127; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132.

In one aspect, the invention provides an antibody comprising at least one, at least two, or all three VH HVR sequences selected from (a) HVR-H1 comprising the amino acid sequence of SEQ ID NO: 124; (b) HVR-H2 comprising the amino acid sequence of SEQ ID NO: 126; and (c) HVR-H3 comprising the amino acid sequence of SEQ ID NO: 127. In one embodiment, the antibody comprises HVR-H3 comprising the amino acid sequence of SEQ ID NO: 127. In another embodiment, the antibody comprises HVR-H3 comprising the amino acid sequence of SEQ ID NO: 127 and HVR-L3 comprising the amino acid sequence of SEQ ID NO: 132. In a further embodiment, the antibody comprises HVR-H3 comprising the amino acid sequence of SEQ ID NO: 127, HVR-L3 comprising the amino acid sequence of SEQ ID NO: 132, and HVR-H2 comprising the amino acid sequence of SEQ ID NO: 126. In a further embodiment, the antibody comprises (a) HVR-H1 comprising the amino acid sequence of SEQ ID NO: 124; (b) HVR-H2 comprising the amino acid sequence of SEQ ID NO: 126; and (c) HVR-H3 comprising the amino acid sequence of SEQ ID NO: 127. In a further embodiment, the antibody comprises (a) HVR-H1 comprising the amino acid sequence of SEQ ID NO: 31; (b) HVR-H2 comprising the amino acid sequence of SEQ ID NO: 69; and (c) HVR-H3 comprising the amino acid sequence of SEQ ID NO: 70. In a further embodiment, the antibody comprises (a) HVR-H1 comprising the amino acid sequence of SEQ ID NO: 124; (b) HVR-H2 comprising the amino acid sequence of SEQ ID NO: 118; and (c) HVR-H3 comprising the amino acid sequence of SEQ ID NOs: 120. In a further embodiment, the antibody comprises (a) HVR-H1 comprising the amino acid sequence of SEQ ID NO: 31; (b) HVR-H2 comprising the amino acid sequence of SEQ ID NO: 36; and (c) HVR-H3 comprising the amino acid sequence of SEQ ID NO: 41. In a further embodiment, the antibody comprises (a) HVR-H1 comprising the amino acid sequence of SEQ ID NO: 116; (b) HVR-H2 comprising the amino acid sequence of SEQ ID NO: 118; and (c) HVR-H3 comprising the amino acid sequence of SEQ ID NO: 120. In a further embodiment, the antibody comprises (a) HVR-H1 comprising the amino acid sequence of SEQ ID NO: 31; (b) HVR-H2 comprising the amino acid sequence of SEQ ID NO: 118; and (c) HVR-H3 comprising the amino acid sequence of SEQ ID NO: 120.

In a further embodiment, the antibody comprises (a) HVR-H1 from the VH sequence of SEQ ID NO: 8-14, 101, or 102; (b) HVR-H2 from the VH sequence of SEQ ID NO: 8-14, 101, or 102; and (c) HVR-H3 from the VH sequence of SEQ ID NO: 8-14, 101, or 102. In a further embodiment, the antibody comprises (a) HVR-H1 from the VH sequence of SEQ ID NO: 10; (b) HVR-H2 from the VH sequence of SEQ ID NO: 10; and (c) HVR-H3 from the VH sequence of SEQ ID NO: 10. In a further embodiment, the antibody comprises (a) HVR-H1 from the VH sequence of SEQ ID NO: 101; (b) HVR-H2 from the VH sequence of SEQ ID NO: 101; and (c) HVR-H3 from the VH sequence of SEQ ID NO: 101. In a further embodiment, the antibody comprises (a) HVR-H1 from the VH sequence of SEQ ID NO: 102; (b) HVR-H2 from the VH sequence of SEQ ID NO: 102; and (c) HVR-H3 from the VH sequence of SEQ ID NO: 102.

In another aspect, the invention provides an antibody comprising at least one, at least two, or all three VL HVR sequences selected from (a) HVR-L1 comprising the amino acid sequence of SEQ ID NO: 130; (b) HVR-L2 comprising the amino acid sequence of SEQ ID NO: 131; and (c) HVR-L3 comprising the amino acid sequence of SEQ ID NO: 132. In one embodiment, the antibody comprises (a) HVR-L1 comprising the amino acid sequence of SEQ ID NO: 130; (b) HVR-L2 comprising the amino acid sequence of SEQ ID NO: 131; and (c) HVR-L3 comprising the amino acid sequence of SEQ ID NO: 132. In one embodiment, the antibody comprises (a) HVR-L1 comprising the amino acid sequence of SEQ ID NO: 71; (b) HVR-L2 comprising the amino acid sequence of SEQ ID NO: 72; and (c) HVR-L3 comprising the amino acid sequence of SEQ ID NO: 73. In one embodiment, the antibody comprises (a) HVR-L1 comprising the amino acid sequence of SEQ ID NO: 122; (b) HVR-L2 comprising the amino acid sequence of SEQ ID NO: 123; and (c) HVR-L3 comprising the amino acid sequence of SEQ ID NO: 60. In one embodiment, the antibody comprises (a) HVR-L1 comprising the amino acid sequence of SEQ ID NO: 53; (b) HVR-L2 comprising the amino acid sequence of SEQ ID NO: 56; and (c) HVR-L3 comprising an amino acid sequence selected from SEQ ID NO: 60. In one embodiment, the antibody comprises (a) HVR-L1 comprising the amino acid sequence of SEQ ID NO: 109; (b) HVR-L2 comprising the amino acid sequence of SEQ ID NO: 112; and (c) HVR-L3 comprising an amino acid sequence selected from SEQ ID NO: 60. In one embodiment, the antibody comprises (a) HVR-L1 comprising the amino acid sequence of SEQ ID NO: 110; (b) HVR-L2 comprising the amino acid sequence of SEQ ID NO: 113; and (c) HVR-L3 comprising an amino acid sequence selected from SEQ ID NO: 60. In one embodiment, the antibody comprises (a) HVR-L1 comprising the amino acid sequence of SEQ ID NO: 110; (b) HVR-L2 comprising the amino acid sequence of SEQ ID NO: 114; and (c) HVR-L3 comprising an amino acid sequence selected from SEQ ID NO: 60. In one embodiment, the antibody comprises (a) HVR-L1 comprising the amino acid sequence of SEQ ID NO: 111; (b) HVR-L2 comprising the amino acid sequence of SEQ ID NO: 115; and (c) HVR-L3 comprising an amino acid sequence selected from SEQ ID NO: 60.

In one embodiment, the antibody comprises (a) HVR-L1 from the VL sequence of SEQ ID NO: 16-22, 98-100, or 105; (b) HVR-L2 from the VL sequence of SEQ ID NO: 16-22, 98-100, or 105; and (c) HVR-L3 from the VL sequence of SEQ ID NO: 16-22, 98-100, or 105. In one embodiment, the antibody comprises (a) HVR-L1 from the VL sequence of SEQ ID NO: 18; (b) HVR-L2 from the VL sequence of SEQ ID NO: 18; and (c) HVR-L3 from the VL sequence of SEQ ID NO: 18. In one embodiment, the antibody comprises (a) HVR-L1 from the VL sequence of SEQ ID NO: 98; (b) HVR-L2 from the VL sequence of SEQ ID NO: 98; and (c) HVR-L3 from the VL sequence of SEQ ID NO: 98. In one embodiment, the antibody comprises (a) HVR-L1 from the VL sequence of SEQ ID NO: 99; (b) HVR-L2 from the VL sequence of SEQ ID NO: 99; and (c) HVR-L3 from the VL sequence of SEQ ID NO: 99. In one embodiment, the antibody comprises (a) HVR-L1 from the VL sequence of SEQ ID NO: 100; (b) HVR-L2 from the VL sequence of SEQ ID NO: 100; and (c) HVR-L3 from the VL sequence of SEQ ID NO: 100. In one embodiment, the antibody comprises (a) HVR-L1 from the VL sequence of SEQ ID NO: 105; (b) HVR-L2 from the VL sequence of SEQ ID NO: 105; and (c) HVR-L3 from the VL sequence of SEQ ID NO: 105.

In another aspect, an antibody of the invention comprises (a) a VH domain comprising at least one, at least two, or all three VH HVR sequences selected from (i) HVR-H1 comprising the amino acid sequence of SEQ ID NO: 124, (ii) HVR-H2 comprising the amino acid sequence of SEQ ID NO: 126, and (iii) HVR-H3 comprising an amino acid sequence selected from SEQ ID NO: 127; and (b) a VL domain comprising at least one, at least two, or all three VL HVR sequences selected from (i) HVR-L1 comprising the amino acid sequence of SEQ ID NO: 130, (ii) HVR-L2 comprising the amino acid sequence of SEQ ID NO: 131, and (c) HVR-L3 comprising the amino acid sequence of SEQ ID NO: 132.

In another aspect, the invention provides an antibody comprising (a) HVR-H1 comprising the amino acid sequence of SEQ ID NO: 124; (b) HVR-H2 comprising the amino acid sequence of SEQ ID NO: 126; (c) HVR-H3 comprising the amino acid sequence of SEQ ID NO: 127; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132. In another aspect, the invention provides an antibody comprising (a) HVR-H1 comprising the amino acid sequence of SEQ ID NO: 31; (b) HVR-H2 comprising the amino acid sequence of SEQ ID NO: 69; (c) HVR-H3 comprising the amino acid sequence of SEQ ID NO: 70; (d) HVR-L1 comprising the amino acid sequence of SEQ ID NO: 71; (e) HVR-L2 comprising the amino acid sequence of SEQ ID NO: 72; and (f) HVR-L3 comprising the amino acid sequence of SEQ ID NO: 73. In another aspect, the invention provides an antibody comprising (a) HVR-H1 comprising the amino acid sequence of SEQ ID NO: 124; (b) HVR-H2 comprising the amino acid sequence of SEQ ID NO: 118; (c) HVR-H3 comprising the amino acid sequence of SEQ ID NO: 120; (d) HVR-L1 comprising the amino acid sequence of SEQ ID NO: 122; (e) HVR-L2 comprising the amino acid sequence of SEQ ID NO: 123; and (f) HVR-L3 comprising the amino acid sequence of SEQ ID NO: 60. In another aspect, the invention provides an antibody comprising (a) HVR-H1 comprising the amino acid sequence of SEQ ID NO: 31; (b) HVR-H2 comprising the amino acid sequence of SEQ ID NO: 36; (c) HVR-H3 comprising the amino acid sequence of SEQ ID NO: 41; (d) HVR-L1 comprising the amino acid sequence of SEQ ID NO: 53; (e) HVR-L2 comprising the amino acid sequence of SEQ ID NO: 56; and (f) HVR-L3 comprising the amino acid sequence of SEQ ID NO: 60. In another aspect, the invention provides an antibody comprising (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 120; (d) HVR-L1 comprising the amino acid sequence of SEQ ID NO: 111; (e) HVR-L2 comprising the amino acid sequence of SEQ ID NO: 115; and (f) HVR-L3 comprising the amino acid sequence of SEQ ID NO: 60. In another aspect, the invention provides an antibody comprising (a) HVR-H1 comprising the amino acid sequence of SEQ ID NO: 31; (b) HVR-H2 comprising the amino acid sequence of SEQ ID NO: 118; (c) HVR-H3 comprising the amino acid sequence of SEQ ID NO: 120; (d) HVR-L1 comprising the amino acid sequence of SEQ ID NO: 111; (e) HVR-L2 comprising the amino acid sequence of SEQ ID NO: 115; and (f) HVR-L3 comprising the amino acid sequence of SEQ ID NO: 60.

In another aspect, the invention provides an antibody comprising (a) HVR-H1 from the VH sequence of SEQ ID NO: 8-14, 101, or 102; (b) HVR-H2 from the VH sequence of SEQ ID NO: 8-14, 101, or 102; (c) HVR-H3 from the VH sequence of SEQ ID NO: 8-14, 101, or 102; (d) HVR-L1 from the VL sequence of SEQ ID NO: 16-22, 98-100, or 105; (e) HVR-L2 from the VL sequence of SEQ ID NO: 16-22, 98-100, or 105; and (f) HVR-L3 from the VL sequence of SEQ ID NO: 16-22, 98-100, or 105. In another aspect, the invention provides an antibody comprising (a) HVR-H1 from the VH sequence of SEQ ID NO: 10; (b) HVR-H2 from the VH sequence of SEQ ID NO: 10; (c) HVR-H3 from the VH sequence of SEQ ID NO: 10; (d)

HVR-L1 from the VL sequence of SEQ ID NO: 18; (e) HVR-L2 from the VL sequence of SEQ ID NO: 18; and (f) HVR-L3 from the VL sequence of SEQ ID NO: 18. In another aspect, the invention provides an antibody comprising (a) HVR-H1 from the VH sequence of SEQ ID NO: 101; (b) HVR-H2 from the VH sequence of SEQ ID NO: 101; (c) HVR-H3 from the VH sequence of SEQ ID NO: 101; (d) HVR-L1 from the VL sequence of SEQ ID NO: 105; (e) HVR-L2 from the VL sequence of SEQ ID NO: 105; and (f) HVR-L3 from the VL sequence of SEQ ID NO: 105. In another aspect, the invention provides an antibody comprising (a) HVR-H1 from the VH sequence of SEQ ID NO: 102; (b) HVR-H2 from the VH sequence of SEQ ID NO: 102; (c) HVR-H3 from the VH sequence of SEQ ID NO: 102; (d) HVR-L1 from the VL sequence of SEQ ID NO: 105; (e) HVR-L2 from the VL sequence of SEQ ID NO: 105; and (f) HVR-L3 from the VL sequence of SEQ ID NO: 105.

In certain embodiments, any one or more amino acids of an anti-sclerostin antibody as provided above are substituted at the following HVR positions: (a) in HVR-H1 (SEQ ID NO: 31), at position 1; (b) in HVR-H2 (SEQ ID NO: 34), at positions 3, 5, 8, 9, 11, and 12; (c) in HVR-H3 (SEQ ID NO: 38), at positions 2, 4, 5, 7, and 13; (d) in HVR-L1 (SEQ ID NO: 52), at positions 1, 4, 5, 6, 7, 8, 9, 10, and 11; (e) in HVR-L2 (SEQ ID NO: 56), at positions 1, 2, 4, 5, 6, and 7; and (f) in HVR-L3 (SEQ ID NO: 60), at positions 1, 3, 4, 5, 6, 7, and 8. In one embodiment, an antibody of the present invention comprises a VH comprising the amino acid sequence of SEQ ID NO: 7 and a VL comprising the amino acid sequence of SEQ ID NO: 15, wherein at least one amino acid is substituted at the following HVR positions: (a) in HVR-H1 (SEQ ID NO: 31), at position 1; (b) in HVR-H2 (SEQ ID NO: 34), at positions 3, 5, 8, 9, 11, and 12; (c) in HVR-H3 (SEQ ID NO: 38), at positions 2, 4, 5, 7, and 13; (d) in HVR-L1 (SEQ ID NO: 52), at positions 1, 4, 5, 6, 7, 8, 9, 10, and 11; (e) in HVR-L2 (SEQ ID NO: 56), at positions 1, 2, 4, 5, 6, and 7; and (f) in HVR-L3 (SEQ ID NO: 60), at positions 1, 3, 4, 5, 6, 7, and 8. In a further embodiment, an antibody of the present invention comprises a VH comprising the amino acid sequence of SEQ ID NO: 7 and a VL comprising the amino acid sequence of SEQ ID NO: 15, wherein at least one amino acid is substituted at the following HVR positions: (a) in HVR-H2 (SEQ ID NO: 34), at positions 5 and 8; (c) in HVR-H3 (SEQ ID NO: 38), at positions 2, 5, 7, and 13; (d) in HVR-L1 (SEQ ID NO: 52), at positions 4 and 7; (e) in HVR-L2 (SEQ ID NO: 56), at positions 1 and 2; and (f) in HVR-L3 (SEQ ID NO: 60), at position 1. In a further embodiment, an antibody of the present invention comprises a VH comprising the amino acid sequence of SEQ ID NO: 7 and a VL comprising the amino acid sequence of SEQ ID NO: 15, wherein at least one amino acid is substituted at the following HVR positions: (a) in HVR-H1 (SEQ ID NO: 31), at position 1; (b) in HVR-H2 (SEQ ID NO: 34), at positions 3, 5, 8, 9, 11, and 12; (c) in HVR-H3 (SEQ ID NO: 38), at positions 2, 4, and 5; (d) in HVR-L1 (SEQ ID NO: 52), at positions 4, 5, 7, 8, 9, and 11; and (e) in HVR-L2 (SEQ ID NO: 56), at positions 1, 2, 4, 5, and 6.

In certain embodiments, the one or more amino acid substitutions of an anti-sclerostin antibody are conservative substitutions, as provided herein. In certain embodiments, any one or more of the following substitutions may be made in any combination (note: the below-mentioned abbreviation "AxB" means that amino acid A at position (number) x is substituted with amino acid B, where A and B are one-letter amino acid abbreviations used in the art):

(a) in HVR-H1 (SEQ ID NO: 31): D1S; (b) in HVR-H2 (SEQ ID NO: 34): N3M; N5H; G8H or R; A9Y; Y11L; N12K; (c) in HVR-H3 (SEQ ID NO: 38): G2H or E; D4S; D5H or E; Y7H; D13H; (d) in HVR-L1 (SEQ ID NO: 52): R1K; Q4H or E; D5G; I6V; S7H; N8T or D; Y9A; L10V; N11A; (e) in HVR-L2 (SEQ ID NO: 56): Y1H or W; T2H or A; R4T; L5R; L6W or E; S7T; and (f) in HVR-L3 (SEQ ID NO: 60): Q1H; G3Y; D4S or H; T5D; L6Y; P7H; Y8W. In one embodiment, an antibody of the present invention comprises a VH comprising the amino acid sequence of SEQ ID NO: 7 and a VL comprising the amino acid sequence of SEQ ID NO: 15, wherein any one or more of the following substitutions may be made in any combination: (a) in HVR-H1 (SEQ ID NO: 31): D1S; (b) in HVR-H2 (SEQ ID NO: 34): N3M; N5H; G8H or R; A9Y; Y11L; N12K; (c) in HVR-H3 (SEQ ID NO: 38): G2H or E; D4S; D5H or E; Y7H; D13H; (d) in HVR-L1 (SEQ ID NO: 52): R1K; Q4H or E; D5G; I6V; S7H; N8T or D; Y9A; L10V; N11A; (e) in HVR-L2 (SEQ ID NO: 56): Y1H or W; T2H or A; R4T; L5R; L6W or E; S7T; and (f) in HVR-L3 (SEQ ID NO: 60): Q1H; G3Y; D4S or H; T5D; L6Y; P7H; Y8W. In a further embodiment, an antibody of the present invention comprises a VH comprising the amino acid sequence of SEQ ID NO: 7 and a VL comprising the amino acid sequence of SEQ ID NO: 15, wherein any one or more of the following substitutions may be made in any combination: (a) in HVR-H2 (SEQ ID NO: 34): N5H; G8H; (c) in HVR-H3 (SEQ ID NO: 38): G2H; D5H; Y7H; D13H; (d) in HVR-L1 (SEQ ID NO: 52): Q4H; S7H; (e) in HVR-L2 (SEQ ID NO: 56): Y1H; T2H; and (f) in HVR-L3 (SEQ ID NO: 60): Q1H. In a further embodiment, an antibody of the present invention comprises a VH comprising the amino acid sequence of SEQ ID NO: 7 and a VL comprising the amino acid sequence of SEQ ID NO: 15, wherein any one or more of the following substitutions may be made in any combination: (a) in HVR-H1 (SEQ ID NO: 31): D1S; (b) in HVR-H2 (SEQ ID NO: 34): N3M; N5H; G8R; A9Y; Y11L; N12K; (c) in HVR-H3 (SEQ ID NO: 38): G2E; D4S; D5E; (d) in HVR-L1 (SEQ ID NO: 52): Q4E; D5G; S7H; N8T or D; Y9A; N11A; and (e) in HVR-L2 (SEQ ID NO: 56): Y1W; T2A; R4T; L5R; L6W or E.

All possible combinations of the above substitutions are encompassed by the consensus sequences of SEQ ID NOs: 124, 126, 127, 130, 131, and 132 for HVR-H1, HVR-H2, HVR-H3, HVR-L1, HVR-L2, and HVR-L3, respectively.

In any of the above embodiments, an anti-sclerostin antibody is humanized. In one embodiment, an anti-sclerostin antibody comprises HVRs as in any of the above embodiments, and further comprises an acceptor human framework, e.g. a human immunoglobulin framework or a human consensus framework. In another embodiment, an anti-sclerostin antibody comprises HVRs as in any of the above embodiments, and further comprises a VH or VL comprising an FR sequence. In a further embodiment, the anti-sclerostin antibody comprises the following heavy chain or light chain variable domain FR sequences: For the heavy chain variable domain, FR1 comprises the amino acid sequence of SEQ ID NO: 45, FR2 comprises the amino acid sequence of SEQ ID NO: 47 or 48, FR3 comprises the amino acid sequence of SEQ ID NO: 49 or 134, FR4 comprises the amino acid sequence of SEQ ID NO: 51. For the light chain variable domain, FR1 comprises the amino acid sequence of SEQ ID NO: 65, FR2 comprises the amino acid sequence of SEQ ID NO: 66, FR3 comprises the amino acid sequence of SEQ ID NO: 67, FR4 comprises the amino acid sequence of SEQ ID NO: 68.

In another aspect, an anti-sclerostin antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 10. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-sclerostin antibody comprising that sequence retains the ability to bind to sclerostin. In certain embodiments, a total of 1 to 10 amino acids have been substituted, inserted and/or deleted in SEQ ID NO: 10. In certain embodiments, substitutions, insertions, or deletions occur in regions outside the HVRs (i.e., in the FRs). Optionally, the anti-sclerostin antibody comprises the VH sequence in SEQ ID NO: 10, including post-translational modifications of that sequence. In a particular embodiment, the VH comprises one, two or three HVRs selected from: (a) HVR-H1 comprising the amino acid sequence of SEQ ID NO: 31, (b) HVR-H2 comprising the amino acid sequence of SEQ ID NO: 36, and (c) HVR-H3 comprising the amino acid sequence of SEQ ID NO: 41.

In another aspect, an anti-sclerostin antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 101. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-sclerostin antibody comprising that sequence retains the ability to bind to sclerostin. In certain embodiments, a total of 1 to 10 amino acids have been substituted, inserted and/or deleted in SEQ ID NO: 101. In certain embodiments, substitutions, insertions, or deletions occur in regions outside the HVRs (i.e., in the FRs). Optionally, the anti-sclerostin antibody comprises the VH sequence in SEQ ID NO: 101, including post-translational modifications of that sequence. In a particular embodiment, the VH comprises one, two or three HVRs selected from: (a) HVR-H1 comprising the amino acid sequence of SEQ ID NO: 116, (b) HVR-H2 comprising the amino acid sequence of SEQ ID NO: 118, and (c) HVR-H3 comprising the amino acid sequence of SEQ ID NO: 120.

In another aspect, an anti-sclerostin antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 102. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-sclerostin antibody comprising that sequence retains the ability to bind to sclerostin. In certain embodiments, a total of 1 to 10 amino acids have been substituted, inserted and/or deleted in SEQ ID NO: 102. In certain embodiments, substitutions, insertions, or deletions occur in regions outside the HVRs (i.e., in the FRs). Optionally, the anti-sclerostin antibody comprises the VH sequence in SEQ ID NO: 102, including post-translational modifications of that sequence. In a particular embodiment, the VH comprises one, two or three HVRs selected from: (a) HVR-H1 comprising the amino acid sequence of SEQ ID NO: 31, (b) HVR-H2 comprising the amino acid sequence of SEQ ID NO: 118, and (c) HVR-H3 comprising the amino acid sequence of SEQ ID NO: 120.

In another aspect, an anti-sclerostin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 18. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-sclerostin antibody comprising that sequence retains the ability to bind to sclerostin. In certain embodiments, a total of 1 to 10 amino acids have been substituted, inserted and/or deleted in SEQ ID NO: 18. In certain embodiments, the substitutions, insertions, or deletions occur in regions outside the HVRs (i.e., in the FRs). Optionally, the anti-sclerostin antibody comprises the VL sequence in SEQ ID NO: 18, including post-translational modifications of that sequence. In a particular embodiment, the VL comprises one, two or three HVRs selected from (a) HVR-L1 comprising the amino acid sequence of SEQ ID NO: 53; (b) HVR-L2 comprising the amino acid sequence of SEQ ID NO: 56; and (c) HVR-L3 comprising the amino acid sequence of SEQ ID NO: 60.

In another aspect, an anti-sclerostin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 105. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-sclerostin antibody comprising that sequence retains the ability to bind to sclerostin. In certain embodiments, a total of 1 to 10 amino acids have been substituted, inserted and/or deleted in SEQ ID NO: 105. In certain embodiments, the substitutions, insertions, or deletions occur in regions outside the HVRs (i.e., in the FRs). Optionally, the anti-sclerostin antibody comprises the VL sequence in SEQ ID NO: 105, including post-translational modifications of that sequence. In a particular embodiment, the VL comprises one, two or three HVRs selected from (a) HVR-L1 comprising the amino acid sequence of SEQ ID NO: 111; (b) HVR-L2 comprising the amino acid sequence of SEQ ID NO: 115; and (c) HVR-L3 comprising the amino acid sequence of SEQ ID NO: 60.

In another aspect, an anti-sclerostin antibody is provided, wherein the antibody comprises a VH as in any of the embodiments provided above, and a VL as in any of the embodiments provided above. In one embodiment, the antibody comprises the VH and VL sequences in any one of SEQ ID NOs: 7-14, 101, and 102 and any one of SEQ ID NOs: 15-22, 98-100, and 105, respectively, including post-translational modifications of those sequences. In one embodiment, the antibody comprises the VH and VL sequences in SEQ ID NO: 10 and SEQ ID NO: 18, respectively, including post-translational modifications of those sequences. In one embodiment, the antibody comprises the VH and VL sequences in SEQ ID NO: 101 and SEQ ID NO: 105, respectively, including post-translational modifications of those sequences. In one embodiment, the antibody comprises the VH and VL sequences in SEQ ID NO: 102 and SEQ ID NO: 105, respectively, including post-translational modifications of those sequences.

In a particular embodiment, an anti-sclerostin antibody of the present invention is not an antibody comprising the VH and VL sequences in SEQ ID NO: 7 and SEQ ID NO: 15, respectively.

MabB Variants

In one aspect, the invention provides an anti-sclerostin antibody comprising at least one, two, three, four, five, or six HVRs selected from (a) HVR-H1 comprising the amino acid sequence of SEQ ID NO: 128; (b) HVR-H2 comprising the amino acid sequence of SEQ ID NO: 125; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132.

In one aspect, the invention provides an antibody comprising at least one, at least two, or all three VH HVR sequences selected from (a) HVR-H1 comprising the amino acid sequence of SEQ ID NO: 128; (b) HVR-H2 comprising the amino acid sequence of SEQ ID NO: 125; and (c) HVR-H3 comprising the amino acid sequence of SEQ ID NO: 129. In one embodiment, the antibody comprises HVR-H3 comprising the amino acid sequence of SEQ ID NO: 129. In another embodiment, the antibody comprises HVR-H3 comprising the amino acid sequence of SEQ ID NO: 129 and HVR-L3 comprising the amino acid sequence of SEQ ID NO: 132. In a further embodiment, the antibody comprises HVR-H3 comprising the amino acid sequence of SEQ ID NO: 129, HVR-L3 comprising the amino acid sequence of SEQ ID NO: 132, and HVR-H2 comprising the amino acid sequence of SEQ ID NO: 125. In a further embodiment, the antibody comprises (a) HVR-H1 comprising the amino acid sequence of SEQ ID NO: 128; (b) HVR-H2 comprising the amino acid sequence of SEQ ID NO: 125; and (c) HVR-H3 comprising the amino acid sequence of SEQ ID NO: 129. In a further embodiment, the antibody comprises (a) HVR-H1 comprising the amino acid sequence of SEQ ID NO: 74; (b) HVR-H2 comprising the amino acid sequence of SEQ ID NO: 37; and (c) HVR-H3 comprising the amino acid sequence of SEQ ID NO: 75. In a further embodiment, the antibody comprises (a) HVR-H1 comprising the amino acid sequence of SEQ ID NO: 117; (b) HVR-H2 comprising the amino acid sequence of SEQ ID NO: 125; and (c) HVR-H3 comprising the amino acid sequence of SEQ ID NOs: 121. In a further embodiment, the antibody comprises (a) HVR-H1 comprising the amino acid sequence of SEQ ID NO: 33; (b) HVR-H2 comprising the amino acid sequence of SEQ ID NO: 37; and (c) HVR-H3 comprising the amino acid sequence of SEQ ID NO: 43. In a further embodiment, the antibody comprises (a) HVR-H1 comprising the amino acid sequence of SEQ ID NO: 117; (b) HVR-H2 comprising the amino acid sequence of SEQ ID NO: 119; and (c) HVR-H3 comprising the amino acid sequence of SEQ ID NO: 121. In a further embodiment, the antibody comprises (a) HVR-H1 comprising the amino acid sequence of SEQ ID NO: 117; (b) HVR-H2 comprising the amino acid sequence of SEQ ID NO: 37; and (c) HVR-H3 comprising the amino acid sequence of SEQ ID NO: 121.

In a further embodiment, the antibody comprises (a) HVR-H1 from the VH sequence of SEQ ID NO: 24-26, 103, or 104; (b) HVR-H2 from the VH sequence of SEQ ID NO: 24-26, 103, or 104; and (c) HVR-H3 from the VH sequence of SEQ ID NO: 24-26, 103, or 104. In a further embodiment, the antibody comprises (a) HVR-H1 from the VH sequence of SEQ ID NO: 24; (b) HVR-H2 from the VH sequence of SEQ ID NO: 24; and (c) HVR-H3 from the VH sequence of SEQ ID NO: 24. In a further embodiment, the antibody comprises (a) HVR-H1 from the VH sequence of SEQ ID NO: 103; (b) HVR-H2 from the VH sequence of SEQ ID NO: 103; and (c) HVR-H3 from the VH sequence of SEQ ID NO: 103. In a further embodiment, the antibody comprises (a) HVR-H1 from the VH sequence of SEQ ID NO: 104; (b) HVR-H2 from the VH sequence of SEQ ID NO: 104; and (c) HVR-H3 from the VH sequence of SEQ ID NO: 104.

In another aspect, the invention provides an antibody comprising at least one, at least two, or all three VL HVR sequences selected from (a) HVR-L1 comprising the amino acid sequence of SEQ ID NO: 130; (b) HVR-L2 comprising the amino acid sequence of SEQ ID NO: 131; and (c) HVR-L3 comprising the amino acid sequence of SEQ ID NO: 132. In one embodiment, the antibody comprises (a) HVR-L1 comprising the amino acid sequence of SEQ ID NO: 130; (b) HVR-L2 comprising the amino acid sequence of SEQ ID NO: 131; and (c) HVR-L3 comprising the amino acid sequence of SEQ ID NO: 132. In one embodiment, the antibody comprises (a) HVR-L1 comprising the amino acid sequence of SEQ ID NO: 55; (b) HVR-L2 comprising the amino acid sequence of SEQ ID NO: 59; and (c) HVR-L3 comprising the amino acid sequence of SEQ ID NO: 76. In one embodiment, the antibody comprises (a) HVR-L1 comprising the amino acid sequence of SEQ ID NO: 122; (b) HVR-L2 comprising the amino acid sequence of SEQ ID NO: 123; and (c) HVR-L3 comprising the amino acid sequence of SEQ ID NO: 60. In one embodiment, the antibody comprises (a) HVR-L1 comprising the amino acid sequence of SEQ ID NO: 55; (b) HVR-L2 comprising the amino acid sequence of SEQ ID NO: 59; and (c) HVR-L3 comprising an amino acid sequence selected from SEQ ID NO: 63. In one embodiment, the antibody comprises (a) HVR-L1 comprising the amino acid sequence of SEQ ID NO: 109; (b) HVR-L2 comprising the amino acid sequence of SEQ ID NO: 112; and (c) HVR-L3 comprising an amino acid sequence selected from SEQ ID NO: 60. In one embodiment, the antibody comprises (a) HVR-L1 comprising the amino acid sequence of SEQ ID NO: 110; (b) HVR-L2 comprising the amino acid sequence of SEQ ID NO: 113; and (c) HVR-L3 comprising an amino acid sequence selected from SEQ ID NO: 60. In one embodiment, the antibody comprises (a) HVR-L1 comprising the amino acid sequence of SEQ ID NO: 110; (b) HVR-L2 comprising the amino acid sequence of SEQ ID NO: 114; and (c) HVR-L3 comprising an amino acid sequence selected from SEQ ID NO: 60. In one embodiment, the antibody comprises (a) HVR-L1 comprising the amino acid sequence of SEQ ID NO: 111; (b) HVR-L2 comprising the amino acid sequence of SEQ ID NO: 115; and (c) HVR-L3 comprising an amino acid sequence selected from SEQ ID NO: 60.

In one embodiment, the antibody comprises (a) HVR-L1 from the VL sequence of SEQ ID NO: 28-30, 98-100, or 105; (b) HVR-L2 from the VL sequence of SEQ ID NO: 28-30, 98-100, or 105; and (c) HVR-L3 from the VL sequence of SEQ ID NO: 28-30, 98-100, or 105. In one embodiment, the antibody comprises (a) HVR-L1 from the VL sequence of SEQ ID NO: 28; (b) HVR-L2 from the VL sequence of SEQ ID NO: 28; and (c) HVR-L3 from the VL sequence of SEQ ID NO: 28. In one embodiment, the antibody comprises (a) HVR-L1 from the VL sequence of SEQ ID NO: 98; (b) HVR-L2 from the VL sequence of SEQ ID NO: 98; and (c) HVR-L3 from the VL sequence of SEQ ID NO: 98. In one embodiment, the antibody comprises (a) HVR-L1 from the VL sequence of SEQ ID NO: 99; (b) HVR-L2 from the VL sequence of SEQ ID NO: 99; and (c)

HVR-L3 from the VL sequence of SEQ ID NO: 99. In one embodiment, the antibody comprises (a) HVR-L1 from the VL sequence of SEQ ID NO: 100; (b) HVR-L2 from the VL sequence of SEQ ID NO: 100; and (c) HVR-L3 from the VL sequence of SEQ ID NO: 100. In one embodiment, the antibody comprises (a) HVR-L1 from the VL sequence of SEQ ID NO: 105; (b) HVR-L2 from the VL sequence of SEQ ID NO: 105; and (c) HVR-L3 from the VL sequence of SEQ ID NO: 105.

In another aspect, an antibody of the invention comprises (a) a VH domain comprising at least one, at least two, or all three VH HVR sequences selected from (i) HVR-H1 comprising the amino acid sequence of SEQ ID NO: 128, (ii) HVR-H2 comprising the amino acid sequence of SEQ ID NO: 125, and (iii) HVR-H3 comprising an amino acid sequence selected from SEQ ID NO: 129; and (b) a VL domain comprising at least one, at least two, or all three VL HVR sequences selected from (i) HVR-L1 comprising the amino acid sequence of SEQ ID NO: 130, (ii) HVR-L2 comprising the amino acid sequence of SEQ ID NO: 131, and (c) HVR-L3 comprising the amino acid sequence of SEQ ID NO: 132.

In another aspect, the invention provides an antibody comprising (a) HVR-H1 comprising the amino acid sequence of SEQ ID NO: 128; (b) HVR-H2 comprising the amino acid sequence of SEQ ID NO: 125; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132. In another aspect, the invention provides an antibody comprising (a) HVR-H1 comprising the amino acid sequence of SEQ ID NO: 74; (b) HVR-H2 comprising the amino acid sequence of SEQ ID NO: 37; (c) HVR-H3 comprising the amino acid sequence of SEQ ID NO: 75; (d) HVR-L1 comprising the amino acid sequence of SEQ ID NO: 55; (e) HVR-L2 comprising the amino acid sequence of SEQ ID NO: 59; and (f) HVR-L3 comprising the amino acid sequence of SEQ ID NO: 76. In another aspect, the invention provides an antibody comprising (a) HVR-H1 comprising the amino acid sequence of SEQ ID NO: 117; (b) HVR-H2 comprising the amino acid sequence of SEQ ID NO: 125; (c) HVR-H3 comprising the amino acid sequence of SEQ ID NO: 121; (d) HVR-L1 comprising the amino acid sequence of SEQ ID NO: 122; (e) HVR-L2 comprising the amino acid sequence of SEQ ID NO: 123; and (f) HVR-L3 comprising the amino acid sequence of SEQ ID NO: 60. In another aspect, the invention provides an antibody comprising (a) HVR-H1 comprising the amino acid sequence of SEQ ID NO: 33; (b) HVR-H2 comprising the amino acid sequence of SEQ ID NO: 37; (c) HVR-H3 comprising the amino acid sequence of SEQ ID NO: 43; (d) HVR-L1 comprising the amino acid sequence of SEQ ID NO: 55; (e) HVR-L2 comprising the amino acid sequence of SEQ ID NO: 59; and (f) HVR-L3 comprising the amino acid sequence of SEQ ID NO: 63. In another aspect, the invention provides an antibody comprising (a) HVR-H1 comprising the amino acid sequence of SEQ ID NO: 117; (b) HVR-H2 comprising the amino acid sequence of SEQ ID NO: 119; (c) HVR-H3 comprising the amino acid sequence of SEQ ID NO: 121; (d) HVR-L1 comprising the amino acid sequence of SEQ ID NO: 111; (e) HVR-L2 comprising the amino acid sequence of SEQ ID NO: 115; and (f) HVR-L3 comprising the amino acid sequence of SEQ ID NO: 60. In another aspect, the invention provides an antibody comprising (a) HVR-H1 comprising the amino acid sequence of SEQ ID NO: 117; (b) HVR-H2 comprising the amino acid sequence of SEQ ID NO: 37; (c) HVR-H3 comprising the amino acid sequence of SEQ ID NO: 121; (d) HVR-L1 comprising the amino acid sequence of SEQ ID NO: 111; (e) HVR-L2 comprising the amino acid sequence of SEQ ID NO: 115; and (f) HVR-L3 comprising the amino acid sequence of SEQ ID NO: 60.

In another aspect, the invention provides an antibody comprising (a) HVR-H1 from the VH sequence of SEQ ID NO: 24-26, 103, or 104; (b) HVR-H2 from the VH sequence of SEQ ID NO: 24-26, 103, or 104; (c) HVR-H3 from the VH sequence of SEQ ID NO: 24-26, 103, or 104; (d) HVR-L1 from the VL sequence of SEQ ID NO: 28-30, 98-100, or 105; (e) HVR-L2 from the VL sequence of SEQ ID NO: 28-30, 98-100, or 105; and (f) HVR-L3 from the VL sequence of SEQ ID NO: 28-30, 98-100, or 105. In another aspect, the invention provides an antibody comprising (a) HVR-H1 from the VH sequence of SEQ ID NO: 24; (b) HVR-H2 from the VH sequence of SEQ ID NO: 24; (c) HVR-H3 from the VH sequence of SEQ ID NO: 24; (d) HVR-L1 from the VL sequence of SEQ ID NO: 28; (e) HVR-L2 from the VL sequence of SEQ ID NO: 28; and (f) HVR-L3 from the VL sequence of SEQ ID NO: 28. In another aspect, the invention provides an antibody comprising (a) HVR-H1 from the VH sequence of SEQ ID NO: 103; (b) HVR-H2 from the VH sequence of SEQ ID NO: 103; (c) HVR-H3 from the VH sequence of SEQ ID NO: 103; (d) HVR-L1 from the VL sequence of SEQ ID NO: 105; (e) HVR-L2 from the VL sequence of SEQ ID NO: 105; and (f) HVR-L3 from the VL sequence of SEQ ID NO: 105. In another aspect, the invention provides an antibody comprising (a) HVR-H1 from the VH sequence of SEQ ID NO: 104; (b) HVR-H2 from the VH sequence of SEQ ID NO: 104; (c) HVR-H3 from the VH sequence of SEQ ID NO: 104; (d) HVR-L1 from the VL sequence of SEQ ID NO: 105; (e) HVR-L2 from the VL sequence of SEQ ID NO: 105; and (f) HVR-L3 from the VL sequence of SEQ ID NO: 105.

In certain embodiments, any one or more amino acids of an anti-sclerostin antibody as provided above are substituted at the following HVR positions: (a) in HVR-H1 (SEQ ID NO: 32), at positions 1, 2, and 4; (b) in HVR-H2 (SEQ ID NO: 37), at position 9; (c) in HVR-H3 (SEQ ID NO: 43), at positions 2 and 9; (d) in HVR-L1 (SEQ ID NO: 55), at positions 1, 4, 5, 6, 7, 8, 9, 10, and 11; (e) in HVR-L2 (SEQ ID NO: 59), at positions 1, 2, 4, 5, 6, and 7; and (f) in HVR-L3 (SEQ ID NO: 62), at positions 1, 3, 4, 5, 6, 7, and 8. In one embodiment, an antibody of the present invention comprises a VH comprising the amino acid sequence of SEQ ID NO: 23 and a VL comprising the amino acid sequence of SEQ ID NO: 27, wherein at least one amino acid is substituted at the following HVR positions: (a) in HVR-H1 (SEQ ID NO: 32), at positions 1, 2, and 4; (b) in HVR-H2 (SEQ ID NO: 37), at position 9; (c) in HVR-H3 (SEQ ID NO: 43), at positions 2 and 9; (d) in HVR-L1 (SEQ ID NO: 55), at positions 1, 4, 5, 6, 7, 8, 9, 10, and 11; (e) in HVR-L2 (SEQ ID NO: 59), at positions 1, 2, 4, 5, 6, and 7; and (f) in HVR-L3 (SEQ ID NO: 62), at positions 1, 3, 4, 5, 6, 7, and 8. In a further embodiment, an antibody of the present invention comprises a VH comprising the amino acid sequence of SEQ ID NO: 23 and a VL comprising the amino acid sequence of SEQ ID NO: 27, wherein at least one amino acid is substituted at the following HVR positions: (a) in HVR-H1 (SEQ ID NO: 32), at positions 1 and 2; (b) in HVR-H3 (SEQ ID NO: 43), at position 2; and (c) in HVR-L3 (SEQ ID NO: 62), at positions 4 and 7. In a further embodiment, an antibody of the present invention comprises a VH comprising the amino acid sequence of SEQ ID NO: 23 and a VL comprising the amino acid sequence of SEQ ID NO: 27, wherein at least one amino acid is substituted at the following HVR positions: (a) in HVR-H1 (SEQ ID NO: 32), at positions 1 and 4; (b) in HVR-H2 (SEQ ID NO: 37), at position 9; (c) in HVR-H3 (SEQ ID NO: 43), at position 9; (d) in HVR-L1 (SEQ ID NO: 55), at positions 1, 4, 5, 6, 7, 8, 9, and 10; (e) in HVR-L2 (SEQ ID NO: 59), at positions 5, 6, and 7; and (f) in HVR-L3 (SEQ ID NO: 62), at positions 3, 4, 5, 6, and 8.

In certain embodiments, the one or more amino acid substitutions of an anti-sclerostin antibody are conservative substitutions, as provided herein. In certain embodiments, any one or more of the following substitutions may be made in any combination: (a) in HVR-H1 (SEQ ID NO: 32): D1H; T2H; Q4M; (b) in HVR-H2 (SEQ ID NO: 37): T9H; (c) in HVR-H3 (SEQ ID NO: 43): D2H; F9Y; (d) in HVR-L1 (SEQ ID NO: 55): K1R; Q4H or E; D5G; V6I; H7S; T8N or D; A9Y; ViOL; AliN; (e) in HVR-L2 (SEQ ID NO: 59): W1H or Y; A2H or T; T4R; R5L; W6L or E; T7S; and (f) in HVR-L3 (SEQ ID NO: 62): Q1H; Y3G; S4D or H; D5T; Y6L; P7H; W8Y. In one embodiment, an antibody of the present invention comprises a VH comprising the amino acid sequence of SEQ ID NO: 23 and a VL comprising the amino acid sequence of SEQ ID NO: 27, wherein any one or more of the following substitutions may be made in any combination: (a) in HVR-H1 (SEQ ID NO: 32): D1H; T2H; Q4M; (b) in HVR-H2 (SEQ ID NO: 37): T9H; (c) in HVR-H3 (SEQ ID NO: 43): D2H; F9Y; (d) in HVR-L1 (SEQ ID NO: 55): K1R; Q4H or E; D5G; V6I; H7S; T8N or D; A9Y; ViOL; AliN; (e) in HVR-L2 (SEQ ID NO: 59): W1H or Y; A2H or T; T4R; R5L; W6L or E; T7S; and (f) in HVR-L3 (SEQ ID NO: 62): Q1H; Y3G; S4D or H; D5T; Y6L; P7H; W8Y. In a further embodiment, an antibody of the present invention comprises a VH comprising the amino acid sequence of SEQ ID NO: 23 and a VL comprising the amino acid sequence of SEQ ID NO: 27, wherein any one or more of the following substitutions may be made in any combination: (a) in HVR-H1 (SEQ ID NO: 32): D1H; T2H; (b) in HVR-H3 (SEQ ID NO: 43): D2H; and (c) in HVR-L3 (SEQ ID NO: 62): S4H; P7H. In a further embodiment, an antibody of the present invention comprises a VH comprising the amino acid sequence of SEQ ID NO: 23 and a VL comprising the amino acid sequence of SEQ ID NO: 27, wherein any one or more of the following substitutions may be made in any combination: (a) in HVR-H1 (SEQ ID NO: 32): D1H; Q4M; (b) in HVR-H2 (SEQ ID NO: 37): T9H; (c) in HVR-H3 (SEQ ID NO: 43): F9Y; (d) in HVR-L1 (SEQ ID NO: 55): K1R; Q4E; D5G; V6I; H7S; T8D; A9Y; ViOL; (e) in HVR-L2 (SEQ ID NO: 59): R5L; W6L or E; T7S; and (f) in HVR-L3 (SEQ ID NO: 62): Y3G; S4D; D5T; Y6L; W8Y.

All possible combinations of the above substitutions are encompassed by the consensus sequences of SEQ ID NOs: 128, 125, 129, 130, 131, and 132 for HVR-H1, HVR-H2, HVR-H3, HVR-L1, HVR-L2, and HVR-L3, respectively.

In any of the above embodiments, an anti-sclerostin antibody is humanized. In one embodiment, an anti-sclerostin antibody comprises HVRs as in any of the above embodiments, and further comprises an acceptor human framework, e.g. a human immunoglobulin framework or a human consensus framework. In another embodiment, an anti-sclerostin antibody comprises HVRs as in any of the above embodiments, and further comprises a VH or VL comprising an FR sequence. In a further embodiment, the anti-sclerostin antibody comprises the following heavy chain or light chain variable domain FR sequences: For the heavy chain variable domain, FR1 comprises the amino acid sequence of SEQ ID NO: 46, or 133, FR2 comprises the amino acid sequence of SEQ ID NO: 48, FR3 comprises the amino acid sequence of SEQ ID NO: 50, FR4 comprises the amino acid sequence of SEQ ID NO: 51 or 135. For the light chain variable domain, FR1 comprises the amino acid sequence of SEQ ID NO: 65, FR2 comprises the amino acid sequence of SEQ ID NO: 66, FR3 comprises the amino acid sequence of SEQ ID NO: 67, FR4 comprises the amino acid sequence of SEQ ID NO: 68.

In another aspect, an anti-sclerostin antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 24. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-sclerostin antibody comprising that sequence retains the ability to bind to sclerostin. In certain embodiments, a total of 1 to 10 amino acids have been substituted, inserted and/or deleted in SEQ ID NO: 24. In certain embodiments, substitutions, insertions, or deletions occur in regions outside the HVRs (i.e., in the FRs). Optionally, the anti-sclerostin antibody comprises the VH sequence in SEQ ID NO: 24, including post-translational modifications of that sequence. In a particular embodiment, the VH comprises one, two or three HVRs selected from: (a) HVR-H1 comprising the amino acid sequence of SEQ ID NO: 33, (b) HVR-H2 comprising the amino acid sequence of SEQ ID NO: 37, and (c) HVR-H3 comprising the amino acid sequence of SEQ ID NO: 43.

In another aspect, an anti-sclerostin antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 103. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-sclerostin antibody comprising that sequence retains the ability to bind to sclerostin. In certain embodiments, a total of 1 to 10 amino acids have been substituted, inserted and/or deleted in SEQ ID NO: 103. In certain embodiments, substitutions, insertions, or deletions occur in regions outside the HVRs (i.e., in the FRs). Optionally, the anti-sclerostin antibody comprises the VH sequence in SEQ ID NO: 103, including post-translational modifications of that sequence. In a particular embodiment, the VH comprises one, two or three HVRs selected from: (a) HVR-H1 comprising the amino acid sequence of SEQ ID NO: 117, (b) HVR-H2 comprising the amino acid sequence of SEQ ID NO: 119, and (c) HVR-H3 comprising the amino acid sequence of SEQ ID NO: 121.

In another aspect, an anti-sclerostin antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 104. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-sclerostin antibody comprising that sequence retains the ability to bind to sclerostin. In certain embodiments, a total of 1 to 10 amino acids have been substituted, inserted and/or deleted in SEQ ID NO: 104. In certain embodiments, substitutions, insertions, or deletions occur in regions outside the HVRs (i.e., in the FRs). Optionally, the anti-sclerostin antibody comprises the VH sequence in SEQ ID NO: 104, including post-translational modifications of that sequence. In a particular embodiment, the VH comprises one, two or three HVRs selected from: (a) HVR-H1 comprising the amino acid sequence of SEQ ID NO: 117, (b) HVR-H2 comprising the amino acid sequence of SEQ ID NO: 37, and (c) HVR-H3 comprising the amino acid sequence of SEQ ID NO: 121.

In another aspect, an anti-sclerostin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 28. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-sclerostin antibody comprising that sequence retains the ability to bind to sclerostin. In certain embodiments, a total of 1 to 10 amino acids have been substituted, inserted and/or deleted in SEQ ID NO: 28. In certain embodiments, the substitutions, insertions, or deletions occur in regions outside the HVRs (i.e., in the FRs). Optionally, the anti-sclerostin antibody comprises the VL sequence in SEQ ID NO: 28, including post-translational modifications of that sequence. In a particular embodiment, the VL comprises one, two or three HVRs selected from (a) HVR-L1 comprising the amino acid sequence of SEQ ID NO: 55; (b) HVR-L2 comprising the amino acid sequence of SEQ ID NO: 59; and (c) HVR-L3 comprising the amino acid sequence of SEQ ID NO: 63.

In another aspect, an anti-sclerostin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 105. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-sclerostin antibody comprising that sequence retains the ability to bind to sclerostin. In certain embodiments, a total of 1 to 10 amino acids have been substituted, inserted and/or deleted in SEQ ID NO: 105. In certain embodiments, the substitutions, insertions, or deletions occur in regions outside the HVRs (i.e., in the FRs). Optionally, the anti-sclerostin antibody comprises the VL sequence in SEQ ID NO: 105, including post-translational modifications of that sequence. In a particular embodiment, the VL comprises one, two or three HVRs selected from (a) HVR-L1 comprising the amino acid sequence of SEQ ID NO: 111; (b) HVR-L2 comprising the amino acid sequence of SEQ ID NO: 115; and (c) HVR-L3 comprising the amino acid sequence of SEQ ID NO: 60.

In another aspect, an anti-sclerostin antibody is provided, wherein the antibody comprises a VH as in any of the embodiments provided above, and a VL as in any of the embodiments provided above. In one embodiment, the antibody comprises the VH and VL sequences in any one of SEQ ID NOs: 23-26, 103, and 104 and any one of SEQ ID NOs: 27-30, 98-100, and 105, respectively, including post-translational modifications of those sequences. In one embodiment, the antibody comprises the VH and VL sequences in SEQ ID NO: 24 and SEQ ID NO: 28, respectively, including post-translational modifications of those sequences. In one embodiment, the antibody comprises the VH and VL sequences in SEQ ID NO: 103 and SEQ ID NO: 105, respectively, including post-translational modifications of those sequences. In one embodiment, the antibody comprises the VH and VL sequences in SEQ ID NO: 104 and SEQ ID NO: 105, respectively, including post-translational modifications of those sequences.

In a particular embodiment, an anti-sclerostin antibody of the present invention is not an antibody comprising the VH and VL sequences in SEQ ID NO: 23 and SEQ ID NO: 27, respectively.

In a further aspect, the invention provides an antibody that binds to the same epitope as an anti-sclerostin antibody provided herein. In another aspect, the invention provides an antibody that competes for binding sclerostin with an anti-sclerostin antibody provided herein. For example, in certain embodiments, an antibody is provided that binds to the same epitope as and/or competes for binding sclerostin with an anti-sclerostin antibody comprising a VH sequence of SEQ ID NO: 7 and a VL sequence of SEQ ID NO: 15. For example, in certain embodiments, an antibody is provided that binds to the same epitope as and/or competes for binding sclerostin with an anti-sclerostin antibody comprising a VH sequence of SEQ ID NO: 23 and a VL sequence of SEQ ID NO: 27. In certain embodiments, an antibody is provided that binds to a loop structure of sclerostin which comprises amino acids 109-134 (CGPARLLPNAIGRGKWWRPSGPDFRC) of SEQ ID NO: 1. In certain embodiments, an antibody is provided that binds to a cystine-knot structure of sclerostin which comprises four polypeptides of amino acids 74-87 (DVSEYSCRELHFTR), amino acids 96-113 (SAKPVTELVCSGQCGPAR), amino acids 124-140 (WWRPSGPDFRCIPDRYR), amino acids 161-172 (LVASCKCKRLTR) of SEQ ID NO: 1, disulfide-bonded each other.

In one aspect, an anti-sclerostin antibody of the present invention is a multispecific antibody or a multiparatopic antibody comprising at least two different variable regions. In particular embodiments, the anti-sclerostin antibody is bispecific antibody or a biparatopic antibody. Any variable regions of an anti-sclerostin antibody as provided herein, or any combination of them can be used in the multispecific or multiparatopic antibody. In some embodiments, the multispecific or multiparatopic antibody of the present invention comprises a variable region derived from any one of the mabA variants and a variable region derived from any one of the mabB variants.

In one embodiment, the multispecific antibody of the present invention is an antibody wherein a first variable region comprises (a) HVR-H1 comprising the amino acid sequence of SEQ ID NO: 124; (b) HVR-H2 comprising the amino acid sequence of SEQ ID NO: 126; (c) HVR-H3 comprising the amino acid sequence of SEQ ID NO: 127; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132, and a second variable region comprises (a) HVR-H1 comprising the amino acid sequence of SEQ ID NO: 128; (b) HVR-H2 comprising the amino acid sequence of SEQ ID NO: 125; (c) HVR-H3 comprising the amino acid sequence of SEQ ID NO: 129; (d) HVR-L1 comprising the amino acid sequence of SEQ ID NO: 130; (e) HVR-L2 comprising the amino acid sequence of SEQ ID NO: 131; and (f) HVR-L3 comprising the amino acid sequence of SEQ ID NO: 132. In a further embodiment, the multispecific antibody of the present invention is an antibody wherein a first variable region comprises (a) HVR-H1 comprising the amino acid sequence of SEQ ID NO: 31; (b) HVR-H2 comprising the amino acid sequence of SEQ ID NO: 69; (c) HVR-H3 comprising the amino acid sequence of SEQ ID NO: 70; (d) HVR-L1 comprising the amino acid sequence of SEQ ID NO: 71; (e) HVR-L2 comprising the amino acid sequence of SEQ ID NO: 72; and (f) HVR-L3 comprising the amino acid sequence of SEQ ID NO: 73, and a second variable region comprises (a) HVR-H1 comprising the amino acid sequence of SEQ ID NO: 74; (b) HVR-H2 comprising the amino acid sequence of SEQ ID NO: 37; (c) HVR-H3 comprising the amino acid sequence of SEQ ID NO: 75; (d) HVR-L1 comprising the amino acid sequence of SEQ ID NO: 55; (e) HVR-L2 comprising the amino acid sequence of SEQ ID NO: 59; and (f) HVR-L3 comprising the amino acid sequence of SEQ ID NO: 76. In a further embodiment, the multispecific antibody of the present invention is an antibody wherein a first variable region comprises (a) HVR-H1 comprising the amino acid sequence of SEQ ID NO: 124; (b) HVR-H2 comprising the amino acid sequence of SEQ ID NO: 118; (c) HVR-H3 comprising the amino acid sequence of SEQ ID NO: 120; (d) HVR-L1 comprising the amino acid sequence of SEQ ID NO: 122; (e) HVR-L2 comprising the amino acid sequence of SEQ ID NO: 123; and (f) HVR-L3 comprising the amino acid sequence of SEQ ID NO: 60, and a second variable region comprises (a) HVR-H1 comprising the amino acid sequence of SEQ ID NO: 117; (b) HVR-H2 comprising the amino acid sequence of SEQ ID NO: 125; (c) HVR-H3 comprising the amino acid sequence of SEQ ID NO: 121; (d) HVR-L1 comprising the amino acid sequence of SEQ ID NO: 122; (e) HVR-L2 comprising the amino acid sequence of SEQ ID NO: 123; and (f) HVR-L3 comprising the amino acid sequence of SEQ ID NO: 60.

In one embodiment, the multispecific antibody of the present invention is an antibody wherein a first variable region comprises (a) HVR-H1 from the VH sequence of any one of SEQ ID NOs: 8-14, 101, 102; (b) HVR-H2 from the VH sequence of any one of SEQ ID NOs: 8-14, 101, 102; (c) HVR-H3 from the VH sequence of any one of SEQ ID NOs: 8-14, 101, 102; (d) HVR-L1 from the VL sequence of any one of SEQ ID NOs: 16-22, 98-100, 105; (e) HVR-L2 from the VL sequence of any one of SEQ ID NOs: 16-22, 98-100, 105; and (f) HVR-L3 from the VL sequence of any one of SEQ ID NOs: 16-22, 98-100, 105, and a second variable region comprises (a) HVR-H1 from the VH sequence of any one of SEQ ID NOs: 24-26, 103, 104; (b) HVR-H2 from the VH sequence of any one of SEQ ID NOs: 24-26, 103, 104; (c) HVR-H3 from the VH sequence of any one of SEQ ID NOs: 24-26, 103, 104; (d) HVR-L1 from the VL sequence of any one of SEQ ID NOs: 28-30, 98-100, 105; (e) HVR-L2 from the VL sequence of any one of SEQ ID NOs: 28-30, 98-100, 105; and (f) HVR-L3 from the VL sequence of any one of SEQ ID NOs: 28-30, 98-100, 105. In a further embodiments, the multispecific antibody of the present invention is an antibody wherein a first variable region comprises (a) HVR-H1 from the VH sequence of any one of SEQ ID NOs: 8-14; (b) HVR-H2 from the VH sequence of any one of SEQ ID NOs: 8-14; (c) HVR-H3 from the VH sequence of any one of SEQ ID NOs: 8-14; (d) HVR-L1 from the VL sequence of any one of SEQ ID NOs: 16-22; (e) HVR-L2 from the VL sequence of any one of SEQ ID NOs: 16-22; and (f) HVR-L3 from the VL sequence of any one of SEQ ID NOs: 16-22, and a second variable region comprises (a) HVR-H1 from the VH sequence of any one of SEQ ID NOs: 24-26; (b) HVR-H2 from the VH sequence of any one of SEQ ID NOs: 24-26; (c) HVR-H3 from the VH sequence of any one of SEQ ID NOs: 24-26; (d) HVR-L1 from the VL sequence of any one of SEQ ID NOs: 28-30; (e) HVR-L2 from the VL sequence of any one of SEQ ID NOs: 28-30; and (f) HVR-L3 from the VL sequence of any one of SEQ ID NOs: 28-30. In a further embodiments, the multispecific antibody of the present invention is an antibody wherein a first variable region comprises (a) HVR-H1 from the VH sequence of any one of SEQ ID NOs: 101, 102; (b) HVR-H2 from the VH sequence of any one of SEQ ID NOs: 101, 102; (c) HVR-H3 from the VH sequence of any one of SEQ ID NOs: 101, 102; (d) HVR-L1 from the VL sequence of any one of SEQ ID NOs: 98-100, 105; (e) HVR-L2 from the VL sequence of any one of SEQ ID NOs: 98-100, 105; and (f) HVR-L3 from the VL sequence of any one of SEQ ID NOs: 98-100, 105, and a second variable region comprises (a) HVR-H1 from the VH sequence of any one of SEQ ID NOs: 103, 104; (b) HVR-H2 from the VH sequence of any one of SEQ ID NOs: 103, 104; (c) HVR-H3 from the VH sequence of any one of SEQ ID NOs: 103, 104; (d) HVR-L1 from the VL sequence of any one of SEQ ID NOs: 98-100, 105; (e) HVR-L2 from the VL sequence of any one of SEQ ID NOs: 98-100, 105; and (f) HVR-L3 from the VL sequence of any one of SEQ ID NOs: 98-100, 105.

In one embodiment, the multispecific antibody of the present invention is an antibody wherein a first variable region comprises a VH comprising the amino acid sequence of SEQ ID NO: 7 and a VL comprising the amino acid sequence of SEQ ID NO: 15, wherein at least one amino acid is substituted at the following HVR positions: (a) in HVR-H1 (SEQ ID NO: 31), at position 1; (b) in HVR-H2 (SEQ ID NO: 34), at positions 3, 5, 8, 9, 11, and 12; (c) in HVR-H3 (SEQ ID NO: 38), at positions 2, 4, 5, 7, and 13; (d) in HVR-L1 (SEQ ID NO: 52), at positions 1, 4, 5, 6, 7, 8, 9, 10, and 11; (e) in HVR-L2 (SEQ ID NO: 56), at positions 1, 2, 4, 5, 6, and 7; and (f) in HVR-L3 (SEQ ID NO: 60), at positions 1, 3, 4, 5, 6, 7, and 8, and a second variable region comprises a VH comprising the amino acid sequence of SEQ ID NO: 23 and a VL comprising the amino acid sequence of SEQ ID NO: 27, wherein at least one amino acid is substituted at the following HVR positions: (a) in HVR-H1 (SEQ ID NO: 32), at positions 1, 2, and 4; (b) in HVR-H2 (SEQ ID NO: 37), at position 9; (c) in HVR-H3 (SEQ ID NO: 43), at positions 2 and 9; (d) in HVR-L1 (SEQ ID NO: 55), at positions 1, 4, 5, 6, 7, 8, 9, 10, and 11; (e) in HVR-L2 (SEQ ID NO: 59), at positions 1, 2, 4, 5, 6, and 7; and (f) in HVR-L3 (SEQ ID NO: 62), at positions 1, 3, 4, 5, 6, 7, and 8. In a further embodiment, the multispecific antibody of the present invention is an antibody wherein a first variable region comprises a VH comprising the amino acid sequence of SEQ ID NO: 7 and a VL comprising the amino acid sequence of SEQ ID NO: 15, wherein at least one amino acid is substituted at the following HVR positions: (a) in HVR-H2 (SEQ ID NO: 34), at positions 5 and 8; (b) in HVR-H3 (SEQ ID NO: 38), at positions 2, 5, 7, and 13; (c) in HVR-L1 (SEQ ID NO: 52), at positions 4 and 7; (d) in HVR-L2 (SEQ ID NO: 56), at positions 1 and 2; and (e) in HVR-L3 (SEQ ID NO: 60), at position 1, and a second variable region comprises a VH comprising the amino acid sequence of SEQ ID NO: 23 and a VL comprising the amino acid sequence of SEQ ID NO: 27, wherein at least one amino acid is substituted at the following HVR positions: (a) in HVR-H1 (SEQ ID NO: 32), at positions 1 and 2; (b) in HVR-H3 (SEQ ID NO: 43), at position 2; and (c) in HVR-L3 (SEQ ID NO: 62), at positions 4 and 7. In a further embodiment, the multispecific antibody of the present invention is an antibody wherein a first variable region comprises a VH comprising the amino acid sequence of SEQ ID NO: 7 and a VL comprising the amino acid sequence of SEQ ID NO: 15, wherein at least one amino acid is substituted at the following HVR positions: (a) in HVR-H1 (SEQ ID NO: 31), at position 1; (b) in HVR-H2 (SEQ ID NO: 34), at positions 3, 5, 8, 9, 11, and 12; (c) in HVR-H3 (SEQ ID NO: 38), at positions 2, 4, and 5; (d) in HVR-L1 (SEQ ID NO: 52), at positions 4, 5, 7, 8, 9, and 11; and (e) in HVR-L2 (SEQ ID NO: 56), at positions 1, 2, 4, 5, and 6, and a second variable region comprises a VH comprising the amino acid sequence of SEQ ID NO: 23 and a VL comprising the amino acid sequence of SEQ ID NO: 27, wherein at least one amino acid is substituted at the following HVR positions: (a) in HVR-H1 (SEQ ID NO: 32), at positions 1 and 4; (b) in HVR-H2 (SEQ ID NO: 37), at position 9; (c) in HVR-H3 (SEQ ID NO: 43), at position 9; (d) in HVR-L1 (SEQ ID NO: 55), at positions 1, 4, 5, 6, 7, 8, 9, and 10; (e) in HVR-L2 (SEQ ID NO: 59), at positions 5, 6, and 7; and (f) in HVR-L3 (SEQ ID NO: 62), at positions 3, 4, 5, 6, and 8.

In one embodiment, the multispecific antibody of the present invention is an antibody wherein a first variable region comprises a VH comprising the amino acid sequence of SEQ ID NO: 7 and a VL comprising the amino acid sequence of SEQ ID NO: 15, wherein any one or more of the following substitutions may be made in any combination: (a) in HVR-H1 (SEQ ID NO: 31): D1S; (b) in HVR-H2 (SEQ ID NO: 34): N3M; N5H; G8H or R; A9Y; Y11L; N12K; (c) in HVR-H3 (SEQ ID NO: 38): G2H or E; D4S; D5H or E; Y7H; D13H; (d) in HVR-L1 (SEQ ID NO: 52): R1K; Q4H or E; D5G; I6V; S7H; N8T or D; Y9A; L10V; N11A; (e) in HVR-L2 (SEQ ID NO: 56): Y1H or W; T2H or A; R4T; L5R; L6W or E; S7T; and (f) in HVR-L3 (SEQ ID NO: 60): Q1H; G3Y; D4S or H; T5D; L6Y; P7H; Y8W, and a second variable region comprises a VH comprising the amino acid sequence of SEQ ID NO: 23 and a VL comprising the amino acid sequence of SEQ ID NO: 27, wherein any one or more of the following substitutions may be made in any combination: (a) in HVR-H1 (SEQ ID NO: 32): D1H; T2H; Q4M; (b) in HVR-H2 (SEQ ID NO: 37): T9H; (c) in HVR-H3 (SEQ ID NO: 43): D2H; F9Y; (d) in HVR-L1 (SEQ ID NO: 55): K1R; Q4H or E; D5G; V6I; H7S; T8N or D; A9Y; ViOL; AliN; (e) in HVR-L2 (SEQ ID NO: 59): W1H or Y; A2H or T; T4R; R5L; W6L or E; T7S; and (f) in HVR-L3 (SEQ ID NO: 62): Q1H; Y3G; S4D or H; D5T; Y6L; P7H; W8Y. In a further embodiment, the multispecific antibody of the present invention is an antibody wherein a first variable region comprises a VH comprising the amino acid sequence of SEQ ID NO: 7 and a VL comprising the amino acid sequence of SEQ ID NO: 15, wherein any one or more of the following substitutions may be made in any combination: (a) in HVR-H2 (SEQ ID NO: 34): N5H; G8H; (c) in HVR-H3 (SEQ ID NO: 38): G2H; D5H; Y7H; D13H; (d) in HVR-L1 (SEQ ID NO: 52): Q4H; S7H; (e) in HVR-L2 (SEQ ID NO: 56): Y1H; T2H; and (f) in HVR-L3 (SEQ ID NO: 60): Q1H, and a second variable region comprises a VH comprising the amino acid sequence of SEQ ID NO: 23 and a VL comprising the amino acid sequence of SEQ ID NO: 27, wherein any one or more of the following substitutions may be made in any combination: (a) in HVR-H1 (SEQ ID NO: 32): D1H; T2H; (b) in HVR-H3 (SEQ ID NO: 43): D2H; and (c) in HVR-L3 (SEQ ID NO: 62): S4H; P7H. In a further embodiment, the multispecific antibody of the present invention is an antibody wherein a first variable region comprises a VH comprising the amino acid sequence of SEQ ID NO: 7 and a VL comprising the amino acid sequence of SEQ ID NO: 15, wherein any one or more of the following substitutions may be made in any combination: (a) in HVR-H1 (SEQ ID NO: 31): D1S; (b) in HVR-H2 (SEQ ID NO: 34): N3M; N5H; G8R; A9Y; Y11L; N12K; (c) in HVR-H3 (SEQ ID NO: 38): G2E; D4S; D5E; (d) in HVR-L1 (SEQ ID NO: 52): Q4E; D5G; S7H; N8T or D; Y9A; N11A; and (e) in HVR-L2 (SEQ ID NO: 56): Y1W; T2A; R4T; L5R; L6W or E, and a second variable region comprises a VH comprising the amino acid sequence of SEQ ID NO: 23 and a VL comprising the amino acid sequence of SEQ ID NO: 27, wherein any one or more of the following substitutions may be made in any combination: (a) in HVR-H1 (SEQ ID NO: 32): D1H; Q4M; (b) in HVR-H2 (SEQ ID NO: 37): T9H; (c) in HVR-H3 (SEQ ID NO: 43): F9Y; (d) in HVR-L1 (SEQ ID NO: 55): K1R; Q4E; D5G; V6I; H7S; T8D; A9Y; ViOL; (e) in HVR-L2 (SEQ ID NO: 59): R5L; W6L or E; T7S; and (f) in HVR-L3 (SEQ ID NO: 62): Y3G; S4D; D5T; Y6L; W8Y.

In one embodiment, the multispecific antibody of the present invention is an antibody wherein a first variable region comprises the VH and VL sequences in any one of SEQ ID NOs: 7-14, 101, 102, and any one of SEQ ID NOs: 15-22, 98-100, 105, respectively, and a second variable region comprises the VH and VL sequences in any one of SEQ ID NOs: 23-26, 103, 104, and any one of SEQ ID NOs: 27-30, 98-100, 105, respectively. In a further embodiment, the multispecific antibody of the present invention is an antibody wherein a first variable region comprises the VH and VL sequences in any one of SEQ ID NOs: 7-14, and any one of SEQ ID NOs: 15-22, respectively, and a second variable region comprises the VH and VL sequences in any one of SEQ ID NOs: 23-26, and any one of SEQ ID NOs: 27-30, respectively. In a further embodiment, the multispecific antibody of the present invention is an antibody wherein a first variable region comprises the VH and VL sequences in any one of SEQ ID NOs: 101, 102, and any one of SEQ ID NOs: 98-100, 105, respectively, and a second variable region comprises the VH and VL sequences in any one of SEQ ID NOs: 103, 104, and any one of SEQ ID NOs: 98-100, 105, respectively.

In one embodiment, the multispecific antibody of the present invention is an antibody wherein a first variable region binds to the same epitope as, or competes for binding sclerostin with, an anti-sclerostin antibody comprising a VH sequence of SEQ ID NO: 7 and a VL sequence of SEQ ID NO: 15, and a second variable region binds to the same epitope as, or competes for binding sclerostin with, an anti-sclerostin antibody comprising a VH sequence of SEQ ID NO: 23 and a VL sequence of SEQ ID NO: 27.

In one aspect, the multispecific antibody of the present invention is an antibody wherein the at least two different variable regions comprise a common light chain. A common light chain is able to bind to each of at least two different heavy chains, and consequently at least two different variable regions are formed. In some embodiments, a common light chain is shared between mabA and mabB. Such a light chain is able to bind to both the heavy chain of mabA and the heavy chain of mabB, and consequently two different variable regions like mab A and mabB are formd, respectively.

Common Light Chain Between mabA and mabB

In one embodiment, the invention provides a common light chain comprising at least one, at least two, or all three VL HVR sequences selected from (a) HVR-L1 comprising the amino acid sequence of SEQ ID NO: 122; (b) HVR-L2 comprising the amino acid sequence of SEQ ID NO: 123; and (c) HVR-L3 comprising the amino acid sequence of SEQ ID NO: 60. In another embodiment, the common light chain comprises (a) HVR-L1 comprising the amino acid sequence of SEQ ID NO: 122; (b) HVR-L2 comprising the amino acid sequence of SEQ ID NO: 123; and (c) HVR-L3 comprising the amino acid sequence of SEQ ID NO: 60. In a particular embodiment, the common light chain comprises (a) HVR-L1 comprising the amino acid sequence of SEQ ID NO: 109; (b) HVR-L2 comprising the amino acid sequence of SEQ ID NO: 112; and (c) HVR-L3 comprising the amino acid sequence of SEQ ID NO: 60. In a particular embodiment, the common light chain comprises (a) HVR-L1 comprising the amino acid sequence of SEQ ID NO: 110; (b) HVR-L2 comprising the amino acid sequence of SEQ ID NO: 113; and (c) HVR-L3 comprising the amino acid sequence of SEQ ID NO: 60. In a particular embodiment, the common light chain comprises (a) HVR-L1 comprising the amino acid sequence of SEQ ID NO: 110; (b) HVR-L2 comprising the amino acid sequence of SEQ ID NO: 114; and (c) HVR-L3 comprising the amino acid sequence of SEQ ID NO: 60. In a particular embodiment, the common light chain comprises (a) HVR-L1 comprising the amino acid sequence of SEQ ID NO: 111; (b) HVR-L2 comprising the amino acid sequence of SEQ ID NO: 115; and (c) HVR-L3 comprising the amino acid sequence of SEQ ID NO: 60. In one embodiment, the common light chain comprises (a) HVR-L1 from the VL sequence of SEQ ID NO: 98; (b) HVR-L2 from the VL sequence of SEQ ID NO: 98; and (c) HVR-L3 from the VL sequence of SEQ ID NO: 98. In one embodiment, the common light chain comprises (a) HVR-L1 from the VL sequence of SEQ ID NO: 99; (b) HVR-L2 from the VL sequence of SEQ ID NO: 99; and (c) HVR-L3 from the VL sequence of SEQ ID NO: 99. In one embodiment, the common light chain comprises (a) HVR-L1 from the VL sequence of SEQ ID NO: 100; (b) HVR-L2 from the VL sequence of SEQ ID NO: 100; and (c) HVR-L3 from the VL sequence of SEQ ID NO: 100. In one embodiment, the common light chain comprises (a) HVR-L1 from the VL sequence of SEQ ID NO: 105; (b) HVR-L2 from the VL sequence of SEQ ID NO: 105; and (c) HVR-L3 from the VL sequence of SEQ ID NO: 105.

In certain embodiments, any one or more amino acids of a common light chain as provided above are substituted at the following HVR positions: (a) in HVR-L1 (SEQ ID NO: 52), at positions 4, 5, 7, 8, 9, and 11; and (b) in HVR-L2 (SEQ ID NO: 56), at positions 1, 2, 4, 5, and 6. In one embodiment, a common light chain of the present invention comprises a VL comprising the amino acid sequence of SEQ ID NO: 15, wherein at least one amino acid is substituted at the following HVR positions: (a) in HVR-L1 (SEQ ID NO: 52), at positions 4, 5, 7, 8, 9, and 11; and (b) in HVR-L2 (SEQ ID NO: 56), at positions 1, 2, 4, 5, and 6.

In certain embodiments, any one or more amino acids of a common light chain as provided above are substituted at the following HVR positions: (a) in HVR-L1 (SEQ ID NO: 55), at positions 1, 4, 5, 6, 7, 8, 9, and 10; (b) in HVR-L2 (SEQ ID NO: 59), at positions 5, 6, and 7; and (c) in HVR-L3 (SEQ ID NO: 62), at positions 3, 4, 5, 6, and 8. In one embodiment, a common light chain of the present invention comprises a VL comprising the amino acid sequence of SEQ ID NO: 27, wherein at least one amino acid is substituted at the following HVR positions: (a) in HVR-L1 (SEQ ID NO: 55), at positions 1, 4, 5, 6, 7, 8, 9, and 10; (b) in HVR-L2 (SEQ ID NO: 59), at positions 5, 6, and 7; and (c) in HVR-L3 (SEQ ID NO: 62), at positions 3, 4, 5, 6, and 8.

In certain embodiments, the one or more amino acid substitutions of a common light chain are conservative substitutions, as provided herein. In certain embodiments, any one or more of the following substitutions may be made in any combination: (a) in HVR-L1 (SEQ ID NO: 52): Q4E; DSG; S7H; N8T or D; Y9A; N11A; and (b) in HVR-L2 (SEQ ID NO: 56): Y1W; T2A; R4T; LSR; L6W or E. In one embodiment, a common light chain of the present invention comprises a VL comprising the amino acid sequence of SEQ ID NO: 15, wherein any one or more of the following substitutions may be made in any combination: (a) in HVR-L1 (SEQ ID NO: 52): Q4E; DSG; S7H; N8T or D; Y9A; N11A; and (b) in HVR-L2 (SEQ ID NO: 56): Y1W; T2A; R4T; LSR; L6W or E.

In certain embodiments, the one or more amino acid substitutions of a common light chain are conservative substitutions, as provided herein. In certain embodiments, any one or more of the following substitutions may be made in any combination: (a) in HVR-L1 (SEQ ID NO: 55): K1R; Q4E; DSG; V6I; H7S; T8D; A9Y; ViOL; (b) in HVR-L2 (SEQ ID NO: 59): RSL; W6L or E; T7S; and (c) in HVR-L3 (SEQ ID NO: 62): Y3G; S4D; DST; Y6L; W8Y. In one embodiment, a common light chain of the present invention comprises a VL comprising the amino acid sequence of SEQ ID NO: 27, wherein any one or more of the following substitutions may be made in any combination: (a) in HVR-L1 (SEQ ID NO: 55): K1R; Q4E; DSG; V6I; H7S; T8D; A9Y; ViOL; (b) in HVR-L2 (SEQ ID NO: 59): RSL; W6L or E; T7S; and (c) in HVR-L3 (SEQ ID NO: 62): Y3G; S4D; DST; Y6L; W8Y.

All possible combinations of the above substitutions are encompassed by the consensus sequences of SEQ ID NOs: 122, 123, and 60 for HVR-L1, HVR-L2, and HVR-L3, respectively.

In any of the above embodiments, a common light chain is humanized. In one embodiment, a common light chain comprises HVRs as in any of the above embodiments, and further comprises an acceptor human framework, e.g. a human immunoglobulin framework or a human consensus framework. In another embodiment, a common light chain comprises HVRs as in any of the above embodiments, and further comprises a VL comprising an FR sequence. In a further embodiment, the common light chain comprises the following light chain variable domain FR sequences: FR1 comprises the amino acid sequence of SEQ ID NO: 65, FR2 comprises the amino acid sequence of SEQ ID NO: 66, FR3 comprises the amino acid sequence of SEQ ID NO: 67, FR4 comprises the amino acid sequence of SEQ ID NO: 68.

In another aspect, a common light chain is provided, wherein the light chain comprises a light chain variable domain (VL) having at least 90%, 91%, 92%, 93%, 94%, 95%, 96%, 97%, 98%, 99%, or 100% sequence identity to the amino acid sequence of SEQ ID NO: 105. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence. In certain embodiments, a total of 1 to 10 amino acids have been substituted, inserted and/or deleted in SEQ ID NO: 105. In certain embodiments, the substitutions, insertions, or deletions occur in regions outside the HVRs (i.e., in the FRs). Optionally, the common light chain comprises the VL sequence in SEQ ID NO: 105, including post-translational modifications of that sequence. In a particular embodiment, the VL comprises one, two or three HVRs selected from (a) HVR-L1 comprising the amino acid sequence of SEQ ID NO: 111; (b) HVR-L2 comprising the amino acid sequence of SEQ ID NO: 115; and (c) HVR-L3 comprising the amino acid sequence of SEQ ID NO: 60.

In a particular embodiment, a common light chain of the present invention is not a light chain comprising the VL sequences in SEQ ID NO: 15 or SEQ ID NO: 27.

In one embodiment, the multispecific antibody of the present invention is an antibody wherein a first variable region comprises (a) HVR-H1 comprising the amino acid sequence of SEQ ID NO: 124; (b) HVR-H2 comprising the amino acid sequence of SEQ ID NO: 118; (c) HVR-H3 comprising the amino acid sequence of SEQ ID NO: 120; (d) HVR-L1 comprising the amino acid sequence of SEQ ID NO: 122; (e) HVR-L2 comprising the amino acid sequence of SEQ ID NO: 123; and (f) HVR-L3 comprising the amino acid sequence of SEQ ID NO: 60, and a second variable region comprises (a) HVR-H1 comprising the amino acid sequence of SEQ ID NO: 117; (b) HVR-H2 comprising the amino acid sequence of SEQ ID NO: 125; (c) HVR-H3 comprising the amino acid sequence of SEQ ID NO: 121; (d) HVR-L1 comprising the amino acid sequence of SEQ ID NO: 122; (e) HVR-L2 comprising the amino acid sequence of SEQ ID NO: 123; and (f) HVR-L3 comprising the amino acid sequence of SEQ ID NO: 60, and wherein the VL sequences of the first and second variable regions are identical.

In one embodiment, the multispecific antibody of the present invention is an antibody wherein a first variable region comprises (a) HVR-H1 from the VH sequence of SEQ ID NO: 101 or 102; (b) HVR-H2 from the VH sequence of SEQ ID NO: 101 or 102; (c) HVR-H3 from the VH sequence of SEQ ID NO: 101 or 102; (d) HVR-L1 from the VL sequence of any one of SEQ ID NOs: 98-100, 105; (e) HVR-L2 from the VL sequence of any one of SEQ ID NOs: 98-100, 105; and (f) HVR-L3 from the VL sequence of any one of SEQ ID NOs: 98-100, 105, and a second variable region comprises (a) HVR-H1 from the VH sequence of SEQ ID NO: 103 or 104; (b) HVR-H2 from the VH sequence of SEQ ID NO: 103 or 104; (c) HVR-H3 from the VH sequence of SEQ ID NO: 103 or 104; (d) HVR-L1 from the VL sequence of any one of SEQ ID NOs: 98-100, 105; (e) HVR-L2 from the VL sequence of any one of SEQ ID NOs: 98-100, 105; and (f) HVR-L3 from the VL sequence of any one of SEQ ID NOs: 98-100, 105, and wherein the VL sequences of the first and second variable regions are identical.

In one embodiment, the multispecific antibody of the present invention is an antibody wherein a first variable region comprises a VH comprising the amino acid sequence of SEQ ID NO: 7 and a VL comprising the amino acid sequence of SEQ ID NO: 15, wherein at least one amino acid is substituted at the following HVR positions: (a) in HVR-H1 (SEQ ID NO: 31), at position 1; (b) in HVR-H2 (SEQ ID NO: 34), at positions 3, 5, 8, 9, 11, and 12; (c) in HVR-H3 (SEQ ID NO: 38), at positions 2, 4, and 5; (d) in HVR-L1 (SEQ ID NO: 52), at positions 4, 5, 7, 8, 9, and 11; and (e) in HVR-L2 (SEQ ID NO: 56), at positions 1, 2, 4, 5, and 6, and a second variable region comprises a VH comprising the amino acid sequence of SEQ ID NO: 23 and a VL comprising the amino acid sequence of SEQ ID NO: 27, wherein at least one amino acid is substituted at the following HVR positions: (a) in HVR-H1 (SEQ ID NO: 32), at positions 1 and 4; (b) in HVR-H2 (SEQ ID NO: 37), at position 9; (c) in HVR-H3 (SEQ ID NO: 43), at position 9; (d) in HVR-L1 (SEQ ID NO: 55), at positions 1, 4, 5, 6, 7, 8, 9, and 10; (e) in HVR-L2 (SEQ ID NO: 59), at positions 5, 6, and 7; and (f) in HVR-L3 (SEQ ID NO: 62), at positions 3, 4, 5, 6, and 8, and wherein the VL sequences of the first and second variable regions are identical.

In one embodiment, the multispecific antibody of the present invention is an antibody wherein a first variable region comprises a VH comprising the amino acid sequence of SEQ ID NO: 7 and a VL comprising the amino acid sequence of SEQ ID NO: 15, wherein any one or more of the following substitutions may be made in any combination: (a) in HVR-H1 (SEQ ID NO: 31): D1S; (b) in HVR-H2 (SEQ ID NO: 34): N3M, N5H, G8R, A9Y, Y11L, N12K; (c) in HVR-H3 (SEQ ID NO: 38): G2E, D4S, D5E; (d) in HVR-L1 (SEQ ID NO: 52): Q4E, D5G, S7H, N8T or D, Y9A, N11A; and (e) in HVR-L2 (SEQ ID NO: 56): Y1W, T2A, R4T, L5R, L6W or E, and a second variable region comprises a VH comprising the amino acid sequence of SEQ ID NO: 23 and a VL comprising the amino acid sequence of SEQ ID NO: 27, wherein any one or more of the following substitutions may be made in any combination: (a) in HVR-H1 (SEQ ID NO: 32): D1H; Q4M; (b) in HVR-H2 (SEQ ID NO: 37): T9H; (c) in HVR-H3 (SEQ ID NO: 43): F9Y; (d) in HVR-L1 (SEQ ID NO: 55): K1R, Q4E, D5G, V6I, H7S, T8D, A9Y, ViOL; (e) in HVR-L2 (SEQ ID NO: 59): R5L, W6L or E, T7S; and (f) in HVR-L3 (SEQ ID NO: 62): Y3G, S4D, D5T, Y6L, W8Y, and wherein the VL sequences of the first and second variable regions are identical.

In one embodiment, the multispecific antibody of the present invention is an antibody wherein a first variable region comprises the VH and VL sequences in SEQ ID NO: 101 or 102 and any one of SEQ ID NOs: 98-100, 105, respectively, and a second variable region comprises the VH and VL sequences in SEQ ID NO: 103 or 104 and any one of SEQ ID NOs: 98-100, 105, respectively, and wherein the VL sequences of the first and second variable regions are identical. In a further embodiment, the multispecific antibody of the present invention is an antibody wherein a first variable region comprises the VH and VL sequences in SEQ ID NO: 101 and SEQ ID NO: 105, respectively, and a second variable region comprises the VH and VL sequences in SEQ ID NO: 103 and SEQ ID NO: 105, respectively. In a further embodiment, the multispecific antibody of the present invention is an antibody wherein a first variable region comprises the VH and VL sequences in SEQ ID NO: 101 and SEQ ID NO: 105, respectively, and a second variable region comprises the VH and VL sequences in SEQ ID NO: 104 and SEQ ID NO: 105, respectively. In a further embodiment, the multispecific antibody of the present invention is an antibody wherein a first variable region comprises the VH and VL sequences in SEQ ID NO: 102 and SEQ ID NO: 105, respectively, and a second variable region comprises the VH and VL sequences in SEQ ID NO: 103 and SEQ ID NO: 105, respectively. In a further embodiment, the multispecific antibody of the present invention is an antibody wherein a first variable region comprises the VH and VL sequences in SEQ ID NO: 102 and SEQ ID NO: 105, respectively, and a second variable region comprises the VH and VL sequences in SEQ ID NO: 104 and SEQ ID NO: 105, respectively.

In a further aspect of the invention, an anti-sclerostin antibody according to any of the above embodiments is a monoclonal antibody, including a chimeric, humanized or human antibody. In one embodiment, an anti-sclerostin antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an anti-sclerostin antibody according to any of the above embodiments may incorporate any of the features, singly or in combination, as described in Sections 1-7 below:

1. Antibody Affinity

In certain embodiments, an antibody provided herein has a dissociation constant (Kd) of 1micro M or less, 100 nM or less, 10 nM or less, 1 nM or less, 0.1 nM or less, 0.01 nM or less, or 0.001 nM or Less (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER (registered trademark) multi-well plates (Thermo Scientific) are coated overnight with 5 micro g/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23 degrees C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20 (registered trademark)) in PBS. When the plates have dried, 150 micro l/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE (registered trademark) surface plasmon resonance assay. For example, an assay using a BIACORE (registered trademark)-2000 or a BIACORE (registered trademark)-3000 (BIAcore, Inc., Piscataway, NJ) is performed at 25 degrees C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 micro g/ml (~0.2 micro M) before injection at a flow rate of 5 micro l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25 degrees C. at a flow rate of approximately 25 micro l/min. Association rates ($k_{on}$) and dissociation rates ($k_{off}$) are calculated using a simple one-to-one Langmuir binding model (BIACORE (registered trademark) Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25 degrees C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409;

Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB (registered trademark) technology; U.S. Pat. No. 7,041,870 describing K-M MOUSE (registered trademark) technology, and U.S. Patent Application Publication No. US 2007/0061900, describing VELOCIMOUSE (registered trademark) technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, NJ, 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naïve repertoire can be cloned (e.g., from human) to provide a single source of antibodies to a wide range of non-self and also self antigens without any immunization as described by Griffiths et al., EMBO J, 12: 725-734 (1993). Finally, naïve libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for sclerostin and the other is for any other antigen. In certain embodiments, bispecific antibodies may bind to two different epitopes of sclerostin. Bispecific antibodies may also be used to localize cytotoxic agents to cells which express sclerostin. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bispecific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting Fab" or "DAF" comprising an antigen binding site that binds to sclerostin as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |

TABLE 1-continued

| Original Residue | Exemplary Substitutions | Preferred Substitutions |
|---|---|---|
| His (H) | Aso; Gla; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, le;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or residues that contact antigen, with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be analyzed to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion of an enzyme (e.g. for ADEPT) or a polypeptide which increases the plasma half-life of the antibody to the N- or C-terminus of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about +/−3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG$_2$, IgG$_3$ or IgG$_4$ Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks Fc gamma R binding (hence likely lacking ADCC activity), but retains FcRn binding ability. The primary cells for mediating ADCC, NK cells, express Fc gamma RIII only, whereas monocytes express Fc gamma RI, Fc gamma RII and Fc gamma RIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I.

et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACT1™ non-radioactive cytotoxicity assay for flow cytometry (CellTechnology, Inc. Mountain View, CA; and Cyto-Tox 96 (registered trademark) non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). Clq binding assays may also be carried out to confirm that the antibody is unable to bind Clq and hence lacks CDC activity. See, e.g., Clq and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) Clq binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-sclerostin antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, SP20 cell). In one embodiment, a method of making an anti-sclerostin antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-sclerostin antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B.K.C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and SP20p2/0. For a review of certain mammalian host cell lines suitable for antibody production, see, e.g., Yazaki and Wu, Methods in Molecular Biology, Vol. 248 (B.K.C. Lo, ed., Humana Press, Totowa, NJ), pp. 255-268 (2003).

Antibodies with pH-dependent characteristics may be obtained by using screening methods and/or mutagenesis methods e.g., as described in WO 2009/125825. The screening methods may comprise any process by which an antibody having pH-dependent binding characteristics is identified within a population of antibodies specific for a particular antigen. In certain embodiments, the screening methods may comprise measuring one or more binding parameters (e.g., KD or kd) of individual antibodies within an initial population of antibodies both at acidic and neutral pH. The binding parameters of the antibodies may be measured using, e.g., surface plasmon resonance, or any other analytic method that allows for the quantitative or qualitative assessment of the binding characteristics of an antibody to a particular antigen. In certain embodiments, the screening methods may comprise identifying an antibody that binds to an antigen with an acidic/neutral KD ratio of 2 or greater. Alternatively, the screening methods may comprise identifying an antibody that binds to an antigen with an acidic/neutral kd ratio of 2 or greater.

In another embodiment, the mutagenesis methods may comprise incorporating a deletion, substitution, or addition of an amino acid within the heavy and/or light chain of the antibody to enhance the pH-dependent binding of the antibody to an antigen. In certain embodiments, the mutagenesis may be carried out within one or more variable domains of the antibody, e.g., within one or more HVRs (e.g., CDRs). For example, the mutagenesis may comprise substituting an amino acid within one or more HVRs (e.g., CDRs) of the antibody with another amino acid. In certain embodiments, the mutagenesis may comprise substituting one or more amino acids in at least one HVR (e.g., CDR) of the antibody with a histidine. In certain embodiments, "enhanced pH-dependent binding" means that the mutated version of the antibody exhibits a greater acidic/neutral KD ratio, or a greater acidic/neutral kd ratio, than the original "parent" (i.e., the less pH-dependent) version of the antibody prior to mutagenesis. In certain embodiments, the mutated version of the antibody has an acidic/neutral KD ratio of 2 or greater. Alternatively, the mutated version of the antibody has an acidic/neutral kd ratio of 2 or greater.

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals (usually non-human mammals) are immunized against the antigen, immunogenic conjugates, or derivatives by combining, e.g., 100 micro g or 5 micro g of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature 256(5517):495-497 (1975). In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro.

The immunizing agent will typically include the antigenic protein or a fusion variant thereof. Generally either peripheral blood lymphocytes (PBLs) are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press (1986), pp. 59-103).

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, California USA, and SP-2 cells (and derivatives thereof, e.g., X63-Ag8-653) available from the American Type Culture Collection, Manassas, Virginia USA. Human myeloma and mouse-human heteromyeloma cell lines also have been described for the production of human monoclonal antibodies (Kozbor et al. J. Immunol. 133(6):3001-3005 (1984); Brodeur et al., Monoclonal Antibody Production Techniques and Applications, Marcel Dekker, Inc., New York, pp. 51-63 (1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA). Such techniques and assays are known in the art. For example, binding affinity may be determined by the Scatchard analysis of Munson, Anal. Biochem. 107(1):220-239 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography.

Multispecific antibodies can be suitably prepared, for example, by substituting an amino acid side chain present in one of the Fc regions with a larger side chain (knob; which means "bulge"), and substituting an amino acid side chain present in the Fc region with a smaller side chain (hole; which means "void"), to place the knob within the hole. This can promote efficient association between Fc regions having different amino acid sequences from each other (WO 1996/027011; Ridgway et al., Prot. Eng. 9:617-621 (1996); Merchant et al., Nat.Biotech. 16, 677-681 (1998)).

For promoting association between heterologous Fc regions, other known techniques can also be used. Specifically, it can be achieved by introducing electrostatic repulsion into the interface of the CH2 or CH3 domain of the Fc regions to suppress unintended homologous association between the Fc regions (WO 2006/106905). In addition, association between heterologous Fc regions can be efficiently induced using strand-exchange engineered domain (SEED) CH3 heterodimers (Davis et al., Prot. Eng. Des. & Sel., 23:195-202 (2010)). In addition, heterodimerized antibody production techniques that use association of antibody CH1 and CL, and association of VH and VL can also be used (WO 2011/028952). As with the method described in WO 2008/119353 and WO 2011/131746, it is also possible to use the technique of producing heterodimerized antibodies by producing two types of homodimerized antibodies in advance, incubating the antibodies under reducing conditions to dissociate them, and allowing them to associate again. As with the method described in Strop (J. Mol. Biol. 420: 204-219 (2012)), it is also possible to use the technique of producing heterodimerized antibodies by introducing charged residues such as Lys, Arg, Glu, and Asp so that electrostatic repulsion is introduced into CH3 domains. Furthermore, as with the method described in WO 2012/058768, it is also possible to use the technique of producing heterodimerized antibodies by adding alterations to the CH2 and CH3 domains.

A method has been reported to efficiently separate and purify heterodimerized antibodies from a homodimerized antibodies using ion exchange chromatography, by introducing amino acid alterations into the variable regions of the two types of antibody heavy chains to create a difference in isoelectric points between the homodimerized antibodies and the heterodimerized antibodies (WO 2007/114325).

Another method has been reported to purify heterodimerized antibodies using Protein A chromatography, by constructing a heterodimerized antibody comprising two types of heavy chains derived from mouse IgG2a that binds to Protein A and rat IgG2b that does not bind to Protein A (WO 1998/050431 and WO 1995/033844). Furthermore, a heterodimerized antibody can be efficiently purified using Protein A chromatography, by substituting amino acid residues at positions 435 and 436 (EU numbering), which are located in the Protein A binding site of an antibody heavy chain, with amino acids such as Tyr or His, to yield different Protein A binding affinities.

In one aspect, the present invention provides a method for producing a common VL. In general, one VL specifically binds to only one VH to form an antibody variable region, while a common VL can bind to at least two different VHs to form at least two different variable regions. A common VL can be used, e.g., when constructing a multispecific antibody such as a bispecific antibody. The present invention also provides a method for producing a multispecific antibody comprising a common VL.

In one embodiment, the present invention provides a method for producing a common VL shared between two different VHs. The method can comprise the steps of:
(1) providing a first variable region (V1) comprising a first VH (VH1) and a first VL (VL1), and a second variable region (V2) comprising a second VH (VH2) and a second VL (VL2), wherein V1 has a binding activity to a first antigen (Ag1) and V2 has a binding activity to a second antigen (Ag2); and
(2) constructing a modified VL (mVL) by replacing an amino acid residue at a position in HVR-L1, HVR-L2, or HVR-L3 of VL1 with an amino acid residue at the corresponding position in HVR-L1, HVR-L2, or HVR-L3 of VL2, according to Kabat numbering. Ag1 and Ag2 may be antigens that are identical to or different from each other. Additionally, V1 and V2 may bind to epitopes that are identical to or different from each other. For example, Ag1 and Ag2 may be the same antigen but V1 and V2 may bind to different epitopes on the same antigen.

The construction of mVL can be conducted, for example, using a recombinant method such as providing nucleic acids encoding VL1 and VL2, and mutating the nucleic acid encoding VL1 by replacing a codon for an amino acid residue at a position in HVR-L1, HVR-L2, or HVR-L3 of VL1 with a codon for an amino acid residue at the corresponding position in HVR-L1, HVR-L2, or HVR-L3 of VL2, according to Kabat numbering. The mVL can be obtained by introducing the mutated nucleic acid into a host cell and culturing the host cell so that the mVL is produced.

In one embodiment, the method further comprises the step of:
(3) repeating the step (2) for amino acids at different positions, until the amino acids at all positions in HVR-L1, HVR-L2, and HVR-L3 of VL1 are replaced.

In the steps (2) and (3), the amino acid replacement can be conducted at a position where both VL1 and VL2 have amino acid residues but the types of the amino acid residues in VL1 and VL2 are different from each other. When the amino acid residue at a position in VL1 is identical to the residue at the corresponding position in VL2, the replacement at the position may be skipped. When there is no position in VL2 corresponding to the position in VL1, the replacement at the position may be skipped.

In one embodiment, the method further comprises the steps of: (2') constructing a modified VL (mVL) by replacing an amino acid residue at a position in HVR-L1, HVR-L2, or HVR-L3 of VL2 with an amino acid residue at the corresponding position in HVR-L1, HVR-L2, or HVR-L3 of VL1, according to Kabat numbering; and (3') repeating the step (2') for amino acids at different positions, until the amino acids at all positions in HVR-L1, HVR-L2, and HVR-L3 of VL2 are replaced.

The construction of mVL can be conducted, for example, using a recombinant method such as providing nucleic acids encoding VL1 and VL2, and mutating the nucleic acid encoding VL2 by replacing a codon for an amino acid residue at a position in HVR-L1, HVR-L2, or HVR-L3 of VL2 with a codon for an amino acid residue at the corresponding position in HVR-L1, HVR-L2, or HVR-L3 of VL1, according to Kabat numbering. The mVL can be obtained by introducing the mutated nucleic acid into a host cell and culturing the host cell so that the mVL is produced.

In the steps (2') and (3'), the amino acid replacement can be conducted at a position where both VL1 and VL2 have amino acid residues but the types of the amino acid residues in VL1 and VL2 are different from each other. When the amino acid residue at a position in VL2 is identical to the residue at the corresponding position in VL1, the replacement at the position may be skipped. When there is no position in VL1 corresponding to the position in VL2, the replacement at the position may be skipped.

In one embodiment, the method further comprises the step of:
(4) measuring binding activities of the mVLs constructed in the aforementioned steps to Ag1 or Ag2 when combined with VH1 or VH2, respectively.

The binding activity of mVL when combined with VH1 or VH2 can be measured, for example, by conducting binding assays for a modified variable region comprising mVL and either VH1 or VH2. The modified variable region (mV1) comprising mVL and VH1 can be obtained by providing nucleic acids encoding mVL and VH1, introducing the nucleic acids into a host cell, and culturing the host cell so that mV1 is produced. The modified variable region (mV2) comprising mVL and VH2 can be obtained by providing nucleic acids encoding mVL and VH2, introducing the nucleic acids into a host cell, and culturing the host cell so that mV2 is produced. Binding assays for mV1 or mV2 can be conducted, e.g., by known methods such as ELISA and Biacore methods.

In one embodiment, the method further comprises the steps of:
(5) selecting a preferable amino acid residue at a position in HVR-L1, HVR-L2, and HVR-L3 from the two amino acid residues, one of which is the amino acid residue located at the corresponding position in VL1 (AA1) and the other of which is the amino acid residue located at the corresponding position in VL2 (AA2), based on the binding activities of the mVLs measured in the step (4);
(6) repeating the step (5) for at least two different positions in HVR-L1, HVR-L2, and HVR-L3; and
(7) constructing a novel VL (nVL) comprising the amino acid residues selected in the steps (5) and (6) at their positions in HVR-L1, HVR-L2, and HVR-L3.

A preferable amino acid residue at a position in HVR-L1, HVR-L2, and HVR-L3 can be selected by evaluating whether the presence of the amino acid residue at the position is indispensable for the antigen binding or not. Under an exemplary situation where mVL is constructed by replacing an amino acid residue (AA1) at a position in VL1 with another amino acid residue (AA2) at the corresponding position in VL2, and if such mVL loses a binding activity to Ag1 when combined with VH1, it can be estimated that AA1 would be indispensable for the antigen binding, and selecting AA1 as an amino acid residue at the position would be preferable. On the contrary, if the mVL described above still keeps a binding activity to Ag1 when combined with VH1, it can be estimated that AA1 would be dispensable for the antigen binding, and replaceable with AA2. In that case, selecting AA2 as an amino acid residue at the position would be preferable because that would almost certainly increase the binding activity of mVL to Ag2 when combined with VH2. Alternatively, if the mVL described above has an intermediate binding activity to Ag1 when combined with VH1, it can be estimated that both AA1 and AA2 could be a candidate, and either of AA1 or AA2 could be selected as an amino acid residue at the position, depending on the situation. In the steps (5) and (6), the amino acid selection can be conducted at a position where both VL1 and VL2 have amino acid residues but the types of the amino acid residues in VL1 and VL2 are different from each other. When the amino acid residue at a position in VL1 is identical to the residue at the corresponding position in VL2, that amino acid residue is automatically selected as a preferable amino acid residue at the position. When there is no position in VL1 corresponding to the position in VL2, or no position in VL2 corresponding to the position in VL1, the selection at the position may be skipped, or alternatively, the new position may be created in nVL, into which the amino acid residue existing only in VL1 or VL2 is incorporated. Furthermore, the step (5) may be repeated until the preferable amino acid residues at all positions in HVR-L1, HVR-L2, and HVR-L3 are selected.

The amino acid sequence of nVL can be designed by connecting the amino acid sequences of HVRs (HVR-L1, HVR-L2, and HVR-L3) and FRs (FR-L1, FR-L2, FR-L3, and FR-L4) together. The amino acid sequences of HVR-L1, HVR-L2, and HVR-L3 can be determined so that they comprise the amino acid residues selected in the steps (5) and (6) at their positions. The amino acid sequence of any one of FRs selected from FR-L1, FR-L2, FR-L3, and FR-L4 can be selected from the two amino acid sequences, one of which is the amino acid sequence of the corresponding FR of VL1 and the other of which is the amino acid sequence of the corresponding FR of VL2. Such a methodology to build an engineered antibody having FRs derived from different antibodies (called "FR shuffling") is already known in the art (see, e.g, US2004/0044187).

The construction of nVL can be conducted, for example, using a recombinant method such as providing nucleic acids encoding the HVRs (HVR-L1, HVR-L2, and HVR-L3) and FRs (FR-L1, FR-L2, FR-L3, and FR-L4), and ligating them to build a nucleic acid encoding nVL. The nVL can be obtained by introducing the nucleic acid into a host cell and culturing the host cell so that the nVL is produced.

In one embodiment, both VL1 and VL2 are variable regions derived from kappa light chain. In a further embodiment, both VL1 and VL2 belong to the same subgroup of kappa light chain such as human VK1, VK2, VK3, VK4, VK5, VK6, and VK7. In another embodiment, both VL1 and VL2 are variable regions derived from lambda light chain. In a further embodiment, both VL1 and VL2 belong to the same subgroup of lambda light chain such as human VL1, VL2, VL3, VL4, VL5, VL6, VL7, VL8, and VL9.

In one embodiment, the amino acid length of any one of HVRs selected from HVR-L1, HVR-L2, and HVR-L3 of VL1 is the same as that of the corresponding HVR of VL2. In a further embodiment, the amino acid length of HVR-L1, HVR-L2, and HVR-L3 of VL1 is the same as that of HVR-L1, HVR-L2, and HVR-L3 of VL2, respectively.

In one embodiment, the amino acid sequence of any one of HVRs selected from HVR-L1, HVR-L2, and HVR-L3 of VL1 has an identity of 10% or more, 20% or more, 30% or more, 40% or more, 50% or more, 60% or more, 70% or more, 80% or more, 90% or more, 95% or more, or 100%, compared with that of the corresponding HVR of VL2.

In one embodiment, the amino acid length of any one of FRs selected from FR-L1, FR-L2, FR-L3, and FR-L4 of VL1 is the same as that of the corresponding FR of VL2. In a further embodiment, the amino acid length of FR-L1, FR-L2, FR-L3, and FR-L4 of VL1 is the same as that of FR-L1, FR-L2, FR-L3, and FR-L4 of VL2, respectively.

In one embodiments, the amino acid sequence of any one of FRs selected from FR-L1, FR-L2, FR-L3, and FR-L4 of VL1 has an identity of 50% or more, 55% or more, 60% or more, 65% or more, 70% or more, 75% or more, 80% or more, 85% or more, 90% or more, 95% or more, or 100%, compared with that of the corresponding FR of VL2.

In one embodiment, the method further comprises the steps of:
(8) producing a multispecific antibody comprising at least two variable regions, one of which comprises VH1 and nVL and binds to Ag1, and the other of which comprises VH2 and nVL and binds to Ag2.

Such a multispecific antibody can be produced, for example, using a recombinant method such as providing nucleic acids encoding VH1, VH2, and nVL, introducing the nucleic acids into a host cell and culturing the host cell so that the multispecific antibody is produced. Each of VH1 and VH2 may be connected to a heavy chain constant region. nVL may be connected to a light chain constant region.

Assays

Anti-sclerostin antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes for binding to sclerostin with any anti-sclerostin antibody described herein. In certain embodiments, when such a competing antibody is present in excess, it blocks (e.g., reduces) the binding of a reference antibody to sclerostin by at least 10%, 15%, 20%, 25%, 30%, 35%, 40%, 45%, 50%, 55%, 60%, 65%, 70%, 75% or more. In some instances, binding is inhibited by at least 80%, 85%, 90%, 95%, or more. In certain embodiments, such a competing antibody binds to the same epitope (e.g., a linear or a conformational epitope) that is bound by an anti-sclerostin antibody described herein. Detailed exemplary methods for mapping an epitope to which an antibody binds are provided in Morris (1996) "Epitope Mapping Protocols," in Methods in Molecular Biology vol. 66 (Humana Press, Totowa, NJ).

In an exemplary competition assay, immobilized sclerostin is incubated in a solution comprising a first labeled antibody that binds to sclerostin and a second unlabeled antibody that is being tested for its ability to compete with the first antibody for binding to sclerostin. The second antibody may be present in a hybridoma supernatant. As a control, immobilized sclerostin is incubated in a solution comprising the first labeled antibody but not the second unlabeled antibody. After incubation under conditions permissive for binding of the first antibody to sclerostin, excess unbound antibody is removed, and the amount of label associated with immobilized sclerostin is measured. If the amount of label associated with immobilized sclerostin is substantially reduced in the test sample relative to the control sample, then that indicates that the second antibody is competing with the first antibody for binding to sclerostin. See Harlow and Lane (1988) Antibodies: A Laboratory Manual ch.14 (Cold Spring Harbor Laboratory, Cold Spring Harbor, NY).

In another aspect, an antibody that binds to the same epitope as an anti-sclerostin antibody provided herein or that competes for binding sclerostin with an anti-sclerostin antibody provided herein may be identified using sandwich assays. Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. See David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme. An antibody which simultaneously binds to sclerostin with an anti-sclerostin antibody provided herein can be determined to be an antibody that binds to a different epitope from the anti-sclerostin antibody. Therefore, an antibody which does not simultaneously bind to sclerostin with an anti-sclerostin antibody provided herein can be determined to be an antibody that binds to the same epitope as the anti-sclerostin antibody or that competes for binding sclerostin with the anti-sclerostin antibody.

2. Activity Assays

In one aspect, assays are provided for identifying anti-sclerostin antibodies having biological activity. Biological activity may include, e.g., an inhibitory activity against sclerostin. Antibodies having such biological activity in vivo and/or in vitro are also provided.

In certain embodiments, an antibody of the invention is tested for such biological activity. In various aspects, the anti-sclerostin antibody is capable of neutralizing sclerostin in a MC3T3 cell-based mineralization assay. Mineralization by osteoblast-lineage cells in culture, either primary cells or cell lines, is used as an in vitro model of bone formation. An exemplary cell-based mineralization assay is described in U.S. Patent Publication No. 20070110747. MC3T3-E1 cells (Sudo et al., J. Cell Biol., 96: 191-198 (1983)) and subclones of the original cell line can form mineral in culture upon growth in the presence of differentiating agents. For the MC3T3-E1 cells, sclerostin can inhibit one or more of the sequence of events leading up to and including mineral deposition (i.e., sclerostin inhibits mineralization). Anti-sclerostin antibodies that are able to neutralize sclerostin's inhibitory activity allow for mineralization of the culture in the presence of sclerostin such that there is a statistically significant increase in, e.g., deposition of calcium phosphate (measured as calcium) as compared to the amount of calcium measured in the sclerostin-only (i.e., no antibody) treatment group.

In another aspect, the anti-sclerostin antibody is capable of neutralizing sclerostin in a cell-based assay, such as a bone specific alkaline phosphatase assay, described in International Patent Publication No. WO 2008/115732. The bone specific alkaline phosphatase assay is predicated on the ability of sclerostin to decrease BMP-4 and Wnt3a-stimulated alkaline phosphatase levels in the multipotential murine cell line, C2C12. A neutralizing anti-sclerostin antibody mediates a dose-dependent increase of alkaline phosphatase activity in this assay.

In another aspect, the anti-sclerostin antibody is capable of neutralizing sclerostin in a cell-based Wnt signaling assay in HEK293 cell lines, such as the Wnt assay involving Wnt1-mediated induction of STF reporter gene described in International Patent Publication No. WO 2009/047356. Alternatively or in addition, the anti-sclerostin antibody is capable of neutralizing sclerostin in a BMP2-induced mineralization assay in MC3T3 cells, such as the mineralization assay described in International Patent Publication No. WO 2009/047356.

In certain embodiments, inhibition of sclerostin activity includes at least a 5%, 10%, 15%, 20%, 25%, 30%, 35%, or 40% or greater decrease of sclerostin activity in the assay as compared to a negative control under similar conditions. In some embodiments, it refers to the inhibition of sclerostin activity of at least 45%, 50%, 55%, 60%, 65%, 70%, 75%, 80%, 85%, 90%, or 95% or greater.

In certain aspects, the anti-sclerostin antibody of the present invention is taken up into cells, and especially the uptake of the antibody is enhanced when it binds to the antigen to form an immune complex. The uptake of the antibody into cells can be observed by cell imaging analysis. A fluorescence-labeled antibody is contacted with cells expressing an Fc receptor (e.g., Fc gamma R) in the absence and presence of antigen, and the resulting fluorescence intensity of the cells is measured using an image analyser. Cells useful for such an assay can be those that express an endogenous Fc receptor, or can be those that are genetically modified, transiently or stably, to express a transgene encoding an Fc receptor. Where an increased fluorescence intensity is detected in the presence of the antigen compared with in the absence of the antigen, it is determined that uptake of the test antibody into cells is enhanced when the test antibody is complexed with the antigen.

In another aspect, whether an antibody can form an immune complex with an antigen, especially an immune complex containing two or more antibody molecules, can be evaluated, for example by a method such as size exclusion (gel filtration) chromatography, ultracentrifugation, light scattering, electron microscope, or mass spectrometry (Mol Immunol (2002) 39: 77-84, Mol Immunol (2009) 47: 357-364). These methods can estimate the molecular size of the immune complex formed in the presence of the antigen. When the molecular size of an immune complex is larger than supposed from one antibody molecule, it is determined that the antibody can form an immune complex containing two or more antibody molecules. In another aspect, formation of an immune complex can be detected by a binding assay to an Fc receptor (e.g., Fc gamma R) using such as ELISA, FACS, or SPR (surface plasmon resonance assay; for example, using Biacore) (J Biol Chem (2001) 276 (9): 6591-6604; J Immunol Methods (1982) 50: 109-114; J Immunol (2010) 184 (4): 1968-1976; mAbs (2009) 1(5): 491-504). These methods make use of the property that an immune complex containing two or more antibody molecules can bind to an Fc receptor more strongly than an antibody molecule alone or an immune complex containing one antibody molecule. When an antibody binds to an Fc receptor with a higher affinity in the presence of the antigen compared with in the absence of the antigen, it is determined that the antibody can form an immune complex containing two or more antibody molecules.

C. Immunoconjugates

The invention also provides immunoconjugates comprising an anti-sclerostin antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $^{211}$At, $^{131}$I $^{125}$I $^{90}$Y $^{186}$Re, $^{188}$Re, $^{153}$Sm, $^{212}$Bi, $^{32}$P, $^{212}$Pb and radioactive isotopes of Lu. When the radioconjugate is used for detection, it may comprise a radioactive atom for scintigraphic studies, for example Tc-99m or $^{123}$I, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

D. Methods and Compositions for Diagnostics and Detection

In certain embodiments, any of the anti-sclerostin antibodies provided herein is useful for detecting the presence of sclerostin in a biological sample. The term "detecting" as used herein encompasses quantitative or qualitative detection. In certain embodiments, a biological sample comprises a cell or tissue, such as serum, whole blood, plasma, biopsy sample, tissue sample, cell suspension, saliva, sputum, oral fluid, cerebrospinal fluid, amniotic fluid, ascites fluid, milk, colostrum, mammary gland secretion, lymph, urine, sweat, lacrimal fluid, gastric fluid, synovial fluid, peritoneal fluid, ocular lens fluid or mucus.

In one embodiment, an anti-sclerostin antibody for use in a method of diagnosis or detection is provided. In a further aspect, a method of detecting the presence of sclerostin in a biological sample is provided. In certain embodiments, the method comprises contacting the biological sample with an anti-sclerostin antibody as described herein under conditions permissive for binding of the anti-sclerostin antibody to sclerostin, and detecting whether a complex is formed between the anti-sclerostin antibody and sclerostin. Such method may be an in vitro or in vivo method. In one embodiment, an anti-sclerostin antibody is used to select subjects eligible for therapy with an anti-sclerostin antibody, e.g. where sclerostin is a biomarker for selection of patients.

Exemplary disorders that may be diagnosed using an antibody of the invention include bone-related diseases, such as achondroplasia, cleidocranial dysostosis, enchondromatosis, fibrous dysplasia, Gaucher's Disease, hypophosphatemic rickets, Marfan's syndrome, multiple hereditary exostoses, neurofibromatosis, osteogenesis imperfecta, osteopetrosis, osteopoikilosis, sclerotic lesions, pseudoarthrosis, pyogenic osteomyelitis, periodontal disease, antiepileptic drug-induced bone loss, primary and secondary hyperparathyroidism, familial hyperparathyroidism syndromes, weightlessness-induced bone loss, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthe's Disease, adolescent idiopathic scoliosis, infantile onset multisystem inflammatory disease, Winchester Syndrome, Menkes Disease, Wilson's Disease, ischemic bone disease (such as Legg-Calve-Perthes disease and regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy-related bone loss, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV-associated bone loss, bone loss associated with loss of growth hormone, bone loss associated with cystic fibrosis, chemotherapy-associated bone loss, tumor-induced bone loss, cancer-related bone loss, hormone ablative bone loss, multiple myeloma, drug-induced bone loss, anorexia nervosa, disease-associated facial bone loss, disease-associated cranial bone loss, disease-associated bone loss of the jaw, disease-associated bone loss of the skull, bone loss associated with aging, facial bone loss associated with aging, cranial bone loss associated with aging, jaw bone loss associated with aging, skull bone loss associated with aging, and bone loss associated with space travel.

In certain embodiments, labeled anti-sclerostin antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, those coupled with an enzyme that employs hydrogen peroxide to oxidize a dye precursor such as HRP, lactoperoxidase, or microperoxidase, biotin/avidin, spin labels, bacteriophage labels, stable free radicals, and the like.

E. Pharmaceutical Formulations

Pharmaceutical formulations of an anti-sclerostin antibody as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX (registered trademark), Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a second bone-enhancing agent selected from the group consisting of an antiresorptive agent, a bone-forming agent (i.e., anabolic), an estrogen receptor modulator (including, but not limited to, raloxifene, bazedoxifene and lasofoxifene), a drug that has an inhibitory effect on osteoclasts, a bisphosphonate (including, but not limited to, alendronate sodium (FOSAMAX (registered trademark)), risedronate, ibandronate sodium (BONIVA (registered trademark)) and zoledronic acid (RECLAST (registered trademark))); an estrogen or estrogen analogue; an anti-RANK ligand (RANKL) inhibitor, such as an anti-RANKL antibody (e.g., PROLIA (registered trademark)); vitamin D, or a vitamin D derivative or mimic thereof; a calcium source, a cathepsin-K (cat-K) inhibitor (e.g. odanacatib), Tibolone, calcitonin or a calcitriol; hormone replacement therapy, parathyroid hormone (PTH) or a peptide fragment thereof, PTH-related protein (PTHrp), bone morphogenetic protein (e.g., BMP-1, BMP-2, BMP-3, BMP-4, BMP-5, BMP-6, BMP-7, BMP-8, BMP-9, BMP-10, BMP-11, BMP-12, BMP-13, BMP-14 and/or BMP-15), osteogenin, NaF, a PGE2 agonist, a statin, strontium ranelate, a sclerostin inhibitor (e.g., an anti-sclerostin antibody described in, for example, U.S. Pat. No. 7,592,429 or U.S. Pat. No. 7,872,106), an anti-DKK1 antibody or inhibitor, Forteo (registered trademark) (Teriparatide), Preotact (registered trademark), or Protelos (registered trademark). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

F. Therapeutic Methods and Compositions

Any of the anti-sclerostin antibodies provided herein may be used in therapeutic methods.

In one aspect, an anti-sclerostin antibody for use as a medicament is provided. In further aspects, an anti-sclerostin antibody for use in treating a bone-related disease and/or a disease or condition which is associated with an increased level of sclerostin is provided. In certain embodiments, an anti-sclerostin antibody for use in a method of treatment is provided. In certain embodiments, the invention provides an anti-sclerostin antibody for use in a method of treating an individual having a bone-related disease and/or a disease or condition which is associated with an increased level of sclerostin comprising administering to the individual an effective amount of the anti-sclerostin antibody. In one such embodiment, the method further comprises administering to the individual an effective amount of at least one additional therapeutic agent, e.g., as described below. In further embodiments, the invention provides an anti-sclerostin antibody for use in (i) increasing bone formation, (ii) inhibiting bone resorption, and/or (iii) increasing bone mineral density. In certain embodiments, the invention provides an anti-sclerostin antibody for use in a method of (i) increasing bone formation, (ii) inhibiting bone resorption, and/or (iii) increasing bone mineral density in an individual comprising administering to the individual an effective amount of the anti-sclerostin antibody to (i) increase bone formation, (ii) inhibit bone resorption, and/or (iii) increase bone mineral density, respectively. In further embodiments, the invention provides an anti-sclerostin antibody for use in enhancing the clearance of sclerostin from plasma. In certain embodiments, the invention provides an anti-sclerostin antibody for use in a method of enhancing the clearance of sclerostin from plasma in an individual comprising administering to the individual an effective amount of the anti-sclerostin antibody to enhance the clearance of sclerostin from plasma. An anti-sclerostin antibody according to any of the above embodiments may form an immune complex containing at least two antibody molecules. An anti-sclerostin antibody according to any of the above embodiments may also bind to sclerostin with a higher affinity at neutral pH (e.g., pH7.4) than at acidic pH (e.g., pH5.8). An "individual" according to any of the above embodiments is preferably a human.

In a further aspect, the invention provides for the use of an anti-sclerostin antibody in the manufacture or preparation of a medicament. In one embodiment, the medicament is for treatment of a bone-related disease and/or a disease or condition which is associated with an increased level of sclerostin. In a further embodiment, the medicament is for use in a method of treating an individual having a bone-related disease and/or a disease or condition which is associated with an increased level of sclerostin comprising administering to the individual an effective amount of the medicament. In one such embodiment, the method further comprises administering to the individual an effective amount of at least one additional therapeutic agent, e.g., as described below. In a further embodiment, the medicament is for (i) increasing bone formation, (ii) inhibiting bone resorption, and/or (iii) increasing bone mineral density. In a further embodiment, the medicament is for use in a method of (i) increasing bone formation, (ii) inhibiting bone resorption, and/or (iii) increasing bone mineral density in an individual comprising administering to the individual an effective amount of the medicament to (i) increase bone formation, (ii) inhibit bone resorption, and/or (iii) increase bone mineral density, respectively. In a further embodiment, the medicament is for enhancing the clearance of sclerostin from plasma. In a further embodiment, the medicament is for use in a method of enhancing the clearance of sclerostin from plasma in an individual comprising administering to the individual an effective amount of the medicament to enhance the clearance of sclerostin from plasma. An anti-sclerostin antibody according to any of the above embodiments may form an immune complex containing at least two antibody molecules. An anti-sclerostin antibody according to any of the above embodiments may also bind to sclerostin with a higher affinity at neutral pH (e.g., pH7.4) than at acidic pH (e.g., pH5.8). An "individual" according to any of the above embodiments may be a human.

In a further aspect, the invention provides a method for treating a bone-related disease and/or a disease or condition which is associated with an increased level of sclerostin. In one embodiment, the method comprises administering to an individual having such a bone-related disease and/or a disease or condition which is associated with an increased level of sclerostin an effective amount of an anti-sclerostin antibody. In one such embodiment, the method further comprises administering to the individual an effective amount of at least one additional therapeutic agent, as described below. An "individual" according to any of the above embodiments may be a human.

In a further aspect, the invention provides a method for (i) increasing bone formation, (ii) inhibiting bone resorption, and/or (iii) increasing bone mineral density in an individual. In one embodiment, the method comprises administering to the individual an effective amount of an anti-sclerostin antibody to (i) increase bone formation, (ii) inhibit bone resorption, and/or (iii) increase bone mineral density, respectively. In one embodiment, an "individual" is a human.

In a further aspect, the invention provides a method for enhancing the clearance of sclerostin from plasma in an individual. In one embodiment, the method comprises administering to the individual an effective amount of an anti-sclerostin antibody to enhance the clearance of sclerostin from plasma. An anti-sclerostin antibody according to any of the above embodiments may form an immune complex containing at least two antibody molecules. An anti-sclerostin antibody according to any of the above embodiments may also bind to sclerostin with a higher affinity at neutral pH (e.g., pH7.4) than at acidic pH (e.g., pH5.8). In one embodiment, an "individual" is a human.

In a further aspect, the invention provides pharmaceutical formulations comprising any of the anti-sclerostin antibodies provided herein, e.g., for use in any of the above therapeutic methods. In one embodiment, a pharmaceutical formulation comprises any of the anti-sclerostin antibodies provided herein and a pharmaceutically acceptable carrier. In a further embodiment, the pharmaceutical formulation is for treatment of a bone-related disease and/or a disease or condition which is associated with an increased level of sclerostin. In one embodiment, the pharmaceutical formulation is administered to an individual having a bone-related disease and/or a disease or condition which is associated with an increased level of sclerostin. In another embodiment, a pharmaceutical formulation comprises any of the anti-sclerostin antibodies provided herein and at least one additional therapeutic agent, e.g., as described below. In a further embodiment, the pharmaceutical formulation is for (i) increasing bone formation, (ii) inhibiting bone resorption, and/or (iii) increasing bone mineral density. In a further embodiment, the pharmaceutical formulation is for enhancing the clearance of sclerostin from plasma. An anti-sclerostin antibody according to any of the above embodiments may form an immune complex containing at least two antibody molecules. An anti-sclerostin antibody according to any of the above embodiments may also bind to sclerostin with a higher affinity at neutral pH (e.g., pH7.4) than at acidic pH (e.g., pH5.8). An "individual" according to any of the above embodiments is preferably a human.

In certain embodiments, a bone-related disease is selected from the group consisting of achondroplasia, cleidocranial dysostosis, enchondromatosis, fibrous dysplasia, Gaucher's Disease, hypophosphatemic rickets, Marfan's syndrome, multiple hereditary exostoses, neurofibromatosis, osteogenesis imperfecta, osteopetrosis, osteopoikilosis, sclerotic lesions, pseudoarthrosis, pyogenic osteomyelitis, periodontal disease, antiepileptic drug-induced bone loss, primary and secondary hyperparathyroidism, familial hyperparathyroidism syndromes, weightlessness-induced bone loss, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthe's Disease, adolescent idiopathic scoliosis, infantile onset multisystem inflammatory disease, Winchester Syndrome, Menkes Disease, Wilson's Disease, ischemic bone disease (such as Legg-Calve-Perthes disease and regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy-related bone loss, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV-associated bone loss, bone loss associated with loss of growth hormone, bone loss associated with cystic fibrosis, chemotherapy-associated bone loss, tumor-induced bone loss, cancer-related bone loss, hormone ablative bone loss, multiple myeloma, drug-induced bone loss, anorexia nervosa, disease-associated facial bone loss, disease-associated cranial bone loss, disease-associated bone loss of the jaw, disease-associated bone loss of the skull, bone loss associated with aging, facial bone loss associated with aging, cranial bone loss associated with aging, jaw bone loss associated with aging, skull bone loss associated with aging, and bone loss associated with space travel.

In some embodiments, a medicament for increasing bone formation, inhibiting bone resorption, and/or increasing bone mineral density are useful for improving outcomes in orthopedic procedures, dental procedures, implant surgery, joint replacement, bone grafting, bone cosmetic surgery and bone repair such as fracture healing, nonunion healing, delayed union healing and facial reconstruction. Such a medicament may be administered before, during and/or after the procedure, replacement, graft, surgery or repair.

In some embodiments, a medicament for increasing bone formation, inhibiting bone resorption, and/or increasing bone mineral density are also useful for the treatment of any fracture comprising a gap between two segments of bone. Exemplary bone gap defects include, but are not limited to, a comminuted fracture, a non-union fracture, a segmental skeletal defect, surgically created bone defects, surgically treated bone defects, and bone defects created from traumatic injury to the bone or disease (including, but not limited to, arthritis, tumor removal (resection) or infection removal). In some embodiments, the bone gap defect is produced by removal of infected sections of bone or the removal of cancer from the bone due to bone cancers including, but not limited to, osteosarcoma, Ewing's sarcoma, chondrosarcoma, malignant fibrous histiocytoma, fibrosarcoma, and chordoma. In some embodiments, the bone gap defect is a developmental deformity, e.g., due to a genetic defect. In some embodiments, the bone gap defect is produced by removal of sections of bone containing a benign tumor. Exemplary benign bone tumors include, but are not limited to, osteoma, osteoid osteoma, osteoblastoma, osteochondroma, enchondroma, chondromyxoid fibroma, aneurysmal bone cyst, unicameral bone cyst, fibrous dysplasia of bone and giant cell tumor of the bone.

Bone formation and/or bone mineral density may be measured using radiography (e.g., radiographic absorptiometry), single- and/or dual-energy X-ray absorptiometry, quantitative computed tomography (QCT), ultrasonography, and magnetic resonance imaging. The amount of bone mass may also be calculated from body weights or by using other methods (see Gunness—Hey, Metab. Bone Dis. Relat. Res., 5: 177-181 (1984)). Animal models are used in the art for testing the effect of the pharmaceutical compositions and methods on, for example, parameters of bone loss, bone resorption, bone formation, bone strength, or bone mineralization that mimic conditions of human disease such as osteoporosis and osteopenia. Examples of such models include the ovariectomized rat model (Kalu, Bone and Mineral, 15: 175-191 (1991); Frost and Jee, Bone and Mineral, 18: 227-236 (1992); and Jee and Yao, J. Musculoskelet. Neuronal Interact., 1: 193-207 (2001)).

Alternatively, a physiological response to one or more sclerostin binding agents can be gauged by monitoring bone marker levels. Bone markers are products created during the bone remodeling process and are released by bone, osteoblasts, and/or osteoclasts. Fluctuations in bone marker levels imply changes in bone remodeling. Markers indicative of bone resorption (or osteoclast activity) include, for example, C-telopeptide (e.g., C-terminal telopeptide of type 1 collagen (CTX) or serum cross-linked C-telopeptide), N-telopeptide (N-terminal telopeptide of type 1 collagen (NTX)), deoxypyridinoline (DPD), pyridinoline, urinary hydroxyproline, galactosyl hydroxylysine, and tartrate-resistant acid phosphatase (e.g., serum tartrate-resistant acid phosphatase isoform 5b). Bone formation/mineralization markers include, but are not limited to, bone-specific alkaline phosphatase (BSAP), peptides released from N- and C-terminal extension of type I procollagen (P1NP, P1CP), and osteocalcin.

In a further aspect, the invention provides methods for preparing a medicament or a pharmaceutical formulation, comprising mixing any of the anti-sclerostin antibodies provided herein with a pharmaceutically acceptable carrier, e.g. for use in any of the above therapeutic methods. In one embodiment, the methods for preparing a medicament or a pharmaceutical formulation further comprise adding at least one additional therapeutic agent to the medicament or pharmaceutical formulation.

Antibodies of the invention can be used either alone or in combination with other agents in a therapy. For instance, an antibody of the invention may be co-administered with at least one additional therapeutic agent. In certain embodiments, an additional therapeutic agent is a second bone-enhancing agent selected from the group consisting of an antiresorptive agent, a bone-forming agent (i.e., anabolic), an estrogen receptor modulator (including, but not limited to, raloxifene, bazedoxifene and lasofoxifene), a drug that has an inhibitory effect on osteoclasts, a bisphosphonate (including, but not limited to, alendronate sodium (FOSAMAX (registered trademark)), risedronate, ibandronate sodium (BONIVA (registered trademark)) and zoledronic acid (RECLAST (registered trademark))); an estrogen or estrogen analogue; an anti-RANK ligand (RANKL) inhibitor, such as an anti-RANKL antibody (e.g., PROLIA (registered trademark)); vitamin D, or a vitamin D derivative or mimic thereof; a calcium source, a cathepsin-K (cat-K) inhibitor (e.g. odanacatib), Tibolone, calcitonin or a calcitriol; hormone replacement therapy, parathyroid hormone (PTH) or a peptide fragment thereof, PTH-related protein (PTHrp), bone morphogenetic protein (e.g., BMP-1, BMP-2, BMP-3, BMP-4, BMP-5, BMP-6, BMP-7, BMP-8, BMP-9, BMP-10, BMP-11, BMP-12, BMP-13, BMP-14 and/or BMP-15), osteogenin, NaF, a PGE2 agonist, a statin, strontium ranelate, a sclerostin inhibitor (e.g., an anti-sclerostin antibody described in, for example, U.S. Pat. No. 7,592,429 or U.S. Pat. No. 7,872,106), an anti-DKKI antibody or inhibitor, Forteo (registered trademark) (Teriparatide), Preotact (registered trademark), or Protelos (registered trademark).

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-sclerostin antibody and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 micro g/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 micro g/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

It is understood that any of the above formulations or therapeutic methods may be carried out using an immunoconjugate of the invention in place of or in addition to an anti-sclerostin antibody.

G. Articles of Manufacture

In another aspect of the invention, an article of manufacture containing materials useful for the treatment, prevention and/or diagnosis of the disorders described above is provided. The article of manufacture comprises a container and a label on or a package insert associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active ingredient in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-sclerostin antibody.

All patent and non-patent documents cited in this specification are incorporated herein by reference.

EXAMPLES

The following are examples of methods and compositions of the invention. It is understood that various other embodiments may be practiced, given the general description provided above.

Example 1: Expression and Purification of Recombinant Human, Cynomolgus Monkey, Rat, and Mouse Sclerostin Recombinant human sclerostin (NCBI GenBank accession number: NP_079513, SEQ ID NO: 1) was expressed transiently using FreeStyle293-F cell line (Thermo Fisher, Carlsbad, CA, USA). Conditioned media expressing human sclerostin was applied to a Heparin sepharose HP column (GE healthcare, Uppsala, Sweden), followed by elution with NaCl gradient. Fractions containing human sclerostin were pooled, and salt concentration was adjusted to 100 mM NaCl. The resulting sample was applied to a SP-sepharose HP cation exchange column (GE healthcare, Uppsala, Sweden) and eluted with a NaCl gradient. Fractions containing human sclerostin were pooled and subjected to a Superdex 200 or Superdex 75 gel filtration column (GE healthcare, Uppsala, Sweden). Fractions containing human sclerostin were pooled and stored at −150 degrees C.

Expression and purification of recombinant cynomolgus monkey sclerostin (SEQ ID NO: 2), rat sclerostin (NCBI GenBank accession number: NP_085073.1, SEQ ID NO: 3), and mouse sclerostin (NCBI GenBank accession number: NP_077769.4, SEQ ID NO: 4) was done exactly the same way as the human counterpart.

Example 2: Generation of pH-Dependent Anti-Sclerostin Antibodies, and Biparatopic Antibodies Anti-sclerostin antibodies mabA (VH; SEQ ID NO: 7 and VL; SEQ ID NO: 15) and mabB (VH; SEQ ID NO: 23 and VL; SEQ ID NO: 27), both of which are known in the art, were modified in the amino acid sequences so that the pH-dependent antigen binding activities were given to the antibodies. Antibody variants of mabA and mabB were generated as follows: A vast number of mutations and their combinations were examined and some mutations were introduced to the variable region of mabA or mabB to improve its antigen-binding properties, and the optimized variable regions mabA_pH1 (VH; SEQ ID NO: 8 and VL; SEQ ID NO: 16), mabA_pH2 (VH; SEQ ID NO: 9 and VL; SEQ ID NO: 17), mabA_pH3 (VH; SEQ ID NO: 10 and VL; SEQ ID NO: 18), mabA_pH4 (VH; SEQ ID NO: 11 and VL; SEQ ID NO: 19), mabA_NpH1 (VH; SEQ ID NO: 12 and VL; SEQ ID NO: 20), mabA_NpH2 (VH; SEQ ID NO: 13 and VL; SEQ ID NO: 21), mabA_NpH3 (VH; SEQ ID NO: 14 and VL; SEQ ID NO: 22), mabB_pH1 (VH; SEQ ID NO: 24 and VL; SEQ ID NO: 28), mabB_pH4 (VH; SEQ ID NO: 25 and VL; SEQ ID NO: 29), and mabB_pH5 (VH; SEQ ID NO: 26 and VL; SEQ ID NO: 30) were generated. The amino acid sequences of the antibody variants are summarized in Table 2. The genes encoding the VH were combined with the wild-type human IgG2 CH, hG2 (SEQ ID NO: 77), human IgG4 CH, hG4 (SEQ ID NO: 108), or modified human IgG CH variants SG1 (SEQ ID NO: 78), SG2 (SEQ ID NO: 79), BS01b (SEQ ID NO: 80), and BS01a (SEQ ID NO: 81), and the genes encoding the VL were combined with the wild-type human CL, SK1 (SEQ ID NO: 82), each of them was cloned into an expression vector.

TABLE 2

Amino acid sequences of mabA and mabB variants

| | SEQ ID NO: | | | | | | | |
|---|---|---|---|---|---|---|---|---|
| | Variable region | | Hyper Variable region (HVR) | | | | | |
| Antibody name | VH | VL | H1 | H2 | H3 | L1 | L2 | L3 |
| mabA | 7 | 15 | 31 | 34 | 38 | 52 | 56 | 60 |
| mabA-pH1 | 8 | 16 | 31 | 35 | 39 | 53 | 56 | 60 |
| mabA-pH2 | 9 | 17 | 31 | 35 | 40 | 53 | 56 | 60 |
| mabA-pH3 | 10 | 18 | 31 | 36 | 41 | 53 | 56 | 60 |
| mabA-pH4 | 1 | 19 | 31 | 36 | 41 | 54 | 56 | 60 |
| mabA-NpH1 | 12 | 20 | 31 | 34 | 42 | 52 | 57 | 60 |
| mabA-NpH2 | 13 | 21 | 21 | 34 | 38 | 52 | 57 | 60 |
| mabA-NpH3 | 14 | 22 | 31 | 34 | 38 | 52 | 58 | 61 |
| mabB | 23 | 27 | 32 | 37 | 43 | 55 | 59 | 62 |
| mabB-pH1 | 24 | 28 | 33 | 37 | 43 | 55 | 59 | 63 |
| mabB-pH4 | 25 | 29 | 33 | 37 | 43 | 55 | 59 | 64 |
| mabB-pH5 | 26 | 30 | 33 | 37 | 44 | 55 | 59 | 64 |

An anti-sclerostin antibody SCL0099-rbIgG (VH; SEQ ID NO: 83 and VL; SEQ ID NO: 84) for the pharmacokinetic analyses was prepared as follows: Twelve to sixteen week old NZW rabbits were immunized intradermally with human sclerostin and/or monkey sclerostin (50-100 micro g/dose/rabbit). This dose was repeated 4-5 times over 2 months period. One week after the final immunization, the spleen and blood from immunized rabbits were collected. Antigen-specific B-cells were stained with labelled antigen, sorted with FCM cell sorter (FACS aria III, BD), and plated in 96-well plates at one cell/well density together with 25,000 cells/well of EL4 cells (European Collection of Cell Cultures) and activated rabbit T-cell conditioned medium diluted 20 times, and were cultured for 7-12 days. EL4 cells were treated with mitomycin C (Sigma, Cat No. M4287) for 2 hours and washed 3 times in advance before use. The activated rabbit T-cell conditioned medium was prepared by culturing rabbit thymocytes in RPMI-1640 medium containing Phytohemagglutinin-M (Roche, Cat No. 1 1082132-001), phorbol 12-myristate 13-acetate (Sigma, Cat No. P1585) and 2% FBS. After cultivation, B-cell culture supernatants were collected for further analysis and pellets were cryopreserved. Some anti-sclerostin antibodies were selected and the heavy and light chain variable regions were cloned with the rabbit IgG constant region (rbIgG) (SEQ ID NO: 85) and rabbit Igk constant region (rbIgk) (SEQ ID NO: 86), respectively. SCL0099-rbIgG was then chosen for the pharmacokinetic analyses. An anti-sclerostin antibody SCL0122-SG110 (VH; SEQ ID NO: 87 and VL; SEQ ID NO: 88) was also prepared for the pharmacokinetic analyses. The VH and VL were combined with a modified human IgG CH variants SG110 (SEQ ID NO: 89), and the wild-type human CL, SK1 (SEQ ID NO: 82), respectively. An anti-sclerostin antibody SCL0800-rbIgG (VH; SEQ ID NO: 90 and VL; SEQ ID NO: 91) was also prepared for the pharmacokinetic analyses. The VH and VL were combined with the rabbit IgG constant region (rbIgG) (SEQ ID NO: 85) and rabbit Igk constant region (rbIgk) (SEQ ID NO: 86), respectively.

Recombinant antibodies were expressed transiently using FreeStyle293-F cell line (Thermo Fisher, Carlsbad, CA, USA). Purification from the conditioned media expressing antibodies was done with a conventional method using protein A. Gel filtration was further conducted if necessary.

A pair of parental antibodies (Ab-A and Ab-B, listed in Table 3) was mixed in 1×PBS at 1:1 molar ratio in the presence of 25 mM 2-mercaptoethylamine-HCl (2-MEA) and incubated at 37 degrees C. for 90 minutes to generate bispecific antibodies. The bispecific antibody product was purified by using Protein A under a standard condition in order to remove 2-MEA.

TABLE 3

Construction of biparatopic antibodies

| Biparatopic Ab | Ab-A | Ab-B |
|---|---|---|
| mabB//mabA_pH1-BS01 | mabB_pH4-BS01a | mabA_pH4-BS01b |
| mabB//mabA_pH2-BS01 | mabB_pH5-BS01a | mabA_pH3-BS01b |
| mabB//mabA_pH3-BS01 | mabB_pH5-BS01a | mabA_pH4-BS01b |
| mabB//mabA-BS01 | mabB-BS01a | mabA-BS01b |
| mabB//mabA_pH1-BS02 | mabB_pH4-BS01a | mabA_pH4-BS01b |
| mabB//mabA_pH2-BS02 | mabB_pHS-BS01a | mabA_pH3-BS01b |

TABLE 3-continued

Construction of biparatopic antibodies

| Biparatopic Ab | Ab-A | Ab-B |
|---|---|---|
| mabB//mabA_pH3-BS02 | mabB_pHS-BS01a | mabA_pH4-BS01b |
| mabB//mabA_NpH3-BS01 | mabB_pH1-BS01a | mabA_NpH3-BS01b |

Example 3: Evaluation of pH-Dependency in Biacore

The affinity of anti-sclerostin variants binding to human, cynomolgus monkey (cyno), rat, or mouse sclerostin at pH 7.4 and pH 5.8 were determined at 37 degrees C. using Biacore T200 instrument (GE Healthcare). Anti-human Fc (GE Healthcare) was immobilized onto all flow cells of a CM4 sensor chip using amine coupling kit (GE Healthcare). All antibodies and analytes were prepared in ACES pH7.4 or pH 5.8 buffer containing 20 mM ACES, 150 mM NaCl, 1.2 mM $CaCl_2$, 0.05% Tween 20, 0.005% $NaN_3$. Each antibody was captured onto the sensor surface by anti-human Fce. Human, cyno, rat, or mouse sclerostin was injected at 1.25 nM and snM or 0.5 nM and 2 nM for pH7.4 assay condition, and SnM or 2 nM for pH5.8 assay condition. Sensor surface was regenerated each cycle with 3M $MgCl_2$. Binding affinity were determined by processing and fitting the data to 1:1 binding model using Biacore T200 Evaluation software, version 2.0 (GE Healthcare).

The pH dependent interaction assessment was determined by a modified Biacore assay. Briefly, an additional dissociation phase at pH5.8 was integrated into the Biacore assay immediately after dissociation phase at pH7.4. This is to assess the pH-dependent dissociation between antibody and antigen from the complexes formed at pH7.4. The dissociation rate at pH5.8 buffer was determined by processing and fitting data using Scrubber 2.0 (BioLogic Software) curve fitting software.

The affinity (KD) of anti-sclerostin variants binding to human, cynomolgus monkey (cyno), rat, or mouse sclerostin at pH 7.4 and pH 5.8 are shown in Table 4. $k_{off}7.4 \gg 5.8$ refers to dissociation rate at pH5.8 for antibody/antigen complexes that was formed at pH7.4.

TABLE 4

Kinetic parameters of anti-sclerostin (SOST) antibodies at pH 7.4 and pH 5.8

| | human-SOST | | | cyno-SOST | | |
|---|---|---|---|---|---|---|
| Antibody name | KD7.4 | KD5.8 | koff7.4>>5.8 | KD7.4 | KD5.8 | koff7.4>>5.8 |
| mabA | 8.00E−11 | 1.44E−09 | 6.31E−03 | 7.53E−11 | 1.40E−09 | 6.97E−03 |
| mabA_pH1 | 2.13E−10 | n.d. | 1.31E−02 | 2.02E−10 | n.d. | 1.56E−02 |
| mabA_pH2 | 2.58E−10 | n.d. | 1.39E−02 | 2.52E−10 | n.d. | 1.65E−02 |
| mabA_NpH2 | 3.23E−10 | 6.90E−10 | 2.30E−03 | 2.80E−10 | 6.27E−10 | 1.80E−03 |
| mabA_NpH1 | 1.93E−10 | 4.35E−10 | 2.14E−03 | 1.89E−10 | 4.59E−10 | 1.82E−03 |
| mabA_pH3 | | | | | | |
| mabA_NpH3 | | | | | | |
| mabA_pH4 | | | | | | |
| mabB | | | | | | |
| mabB_pH1 | | | | | | |
| mabB_pH4 | | | | | | |
| mabB_pH5 | | | | | | |
| mabB//mabA_pH1 | | | | | | |
| mabB//mabA_pH2 | | | | | | |
| mabB//mabA_pH3 | | | | | | |

| | mouse-SOST | | | rat-SOST | | |
|---|---|---|---|---|---|---|
| Antibody name | KD7.4 | KD5.8 | koff7.4>>5.8 | KD7.4 | KD5.8 | koff7.4>>5.8 |
| mabA | 3.02E−15 | 5.00E−16 | # | 9.38E−14 | 3.07E−15 | # |
| mabA_pH1 | 6.32E−11 | 5.21E−09 | 1.07E−02 | 2.52E−11 | 4.20E−09 | 5.90E−03 |

TABLE 4-continued

Kinetic parameters of anti-sclerostin (SOST) antibodies at pH 7.4 and pH 5.8

| | | | | | | |
|---|---|---|---|---|---|---|
| mabA_pH2 | 8.07E−11 | 5.43E−09 | 8.05E−03 | 3.12E−11 | 4.45E−09 | 4.86E−03 |
| mabA_NpH2 | 5.57E−12 | 1.68E−14 | # | 6.61E−12 | 7.36E−14 | # |
| mabA_NpH1 | 2.04E−10 | 5.03E−10 | 1.91E−03 | 8.26E−11 | 2.92E−10 | 8.05E−04 |
| mabA_pH3 | 2.87E−10 | 1.05E−09 | 9.32E−04 | 1.84E−10 | n.d. | 1.82E−02 |
| mabA_NpH3 | | | | 4.26E−11 | 4.54E−11 | # |
| mabA_pH4 | 1.73E−09 | n.d. | 4.18E−02 | | | |
| mabB | 1.41E−11 | 2.60E−10 | 2.65E−03 | | | |
| mabB_pH1 | 1.38E−10 | n.d. | 2.06E−02 | | | |
| mabB_pH4 | 7.82E−10 | n.d. | * | | | |
| mabB_pH5 | 5.89E−10 | n.d. | * | | | |
| mabB//mabA_pH1 | | | 3.47E−02 | | | |
| mabB//mabA_pH2 | | | 1.86E−02 | | | |
| mabB//mabA_pH3 | | | 5.16E−02 | | | |

Remarks:
n.d. refers to weak binding,
KD cannot be determined
* refers to fast koff at pH 7.4, koff at pH 5.8 cannot be determined
# refers to slow dissociation, koff at pH 5.8 cannot be determined

Example 4: Evaluation of In Vitro Neutralizing Efficacy

Wnt1 Induced Reporter Gene Assay

Complete medium was prepared as follows: 50 mL of fetal bovine serum (Bovogen, Cat. SFBS-D), 5 mL of Penicillin/Streptomycin (Gibco, Cat.15140-122) and 5 mL of MEM Non-essential amino acid (Gibco, Cat.11140-050) were added to 500 mL of DMEM (Gibco, Cat.11965-092).

HEK293T cells (ATCC CRL11268) were seeded on the day before transfection at a density of $2 \times 10^4$ cells per well (in 0.05 mL volume) of a 96-well plate (PerkinElmer Cat. 600568) in complete medium.

On the next day, a series of three-fold dilution of antibodies in PBS were prepared, starting at 400 micro g/mL. 4 micro g/ml of sclerostin (monkey, rat, or mouse) were prepared in complete medium. 60 micro L of serially diluted antibodies and 60 micro L of 4 micro g/ml of sclerostin were mixed and incubated for 1 hour at 37 degrees C. in a polypropylene plate. 50 micro L of mixture of antibody and antigen was added to the culture plate and incubated for 30 minutes at 37 degrees C. Final concentrations of the antibody and sclerostin in culture medium were 100 micro g/ml and 1 micro g/ml, respectively.

The following plasmids were used in this assay: phWnt1, which is a CAG promoter-driven human Wnt1 (nucleotide sequence of SEQ ID NO: 5, amino acid sequence of SEQ ID NO: 6) plasmid; pCXND3, which is an empty CAG vector; pTCF-Fluc (Promega pGL4.49), which is a TCF/LEF response element-driven Firefly luciferase plasmid; pTK-Rluc (Promega pGL4.74), which is a TK promoter-driven Renilla luciferase plasmid.

Transfection of plasmids was performed as follows: The fixed amount of plasmids were added to a final volume of 5 mL per well of OptiMEM (Invitrogen, Cat. 31985-070), specifically 0.1 ng of pCXND3, 50 ng of pTCF-Fluc, and 50 ng of pTK-Rluc for controls wells and 0.1 ng of phWnt1, 50 ng of pTCF-Fluc, and 50 ng of pTK-Rluc for Wnt1 treatment wells. 0.3 mL per well of FuGENE (Promega, Cat. E231A) was added to diluted plasmids and mixed well. The DNA-lipid complex was then added to cells and incubated for more than 16 hours at 37 degrees C. in 5% $CO_2$ incubator. Each condition was tested in duplicates.

On the next day, luciferase activity was measured with Dual-Glo Luciferase assay system (Promega, Cat. E2940). Measurement of luciferase activity was done by a microplate reader, SpectraMax Paradigm (Molecular Devices).

Figure 1:
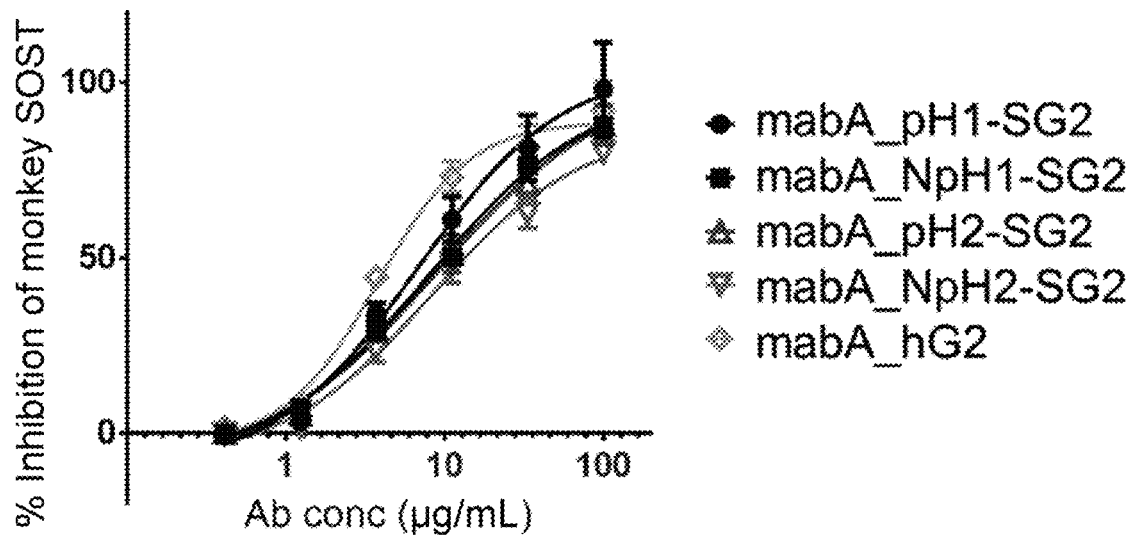
FIG. 1 illustrates in vitro neutralizing activity of anti-sclerostin antibodies mabA and its variants (mabA_pH1, mabA_NpH1, mabA_pH2, and mabA_NpH2), as described in Example 4.
Figure 2:
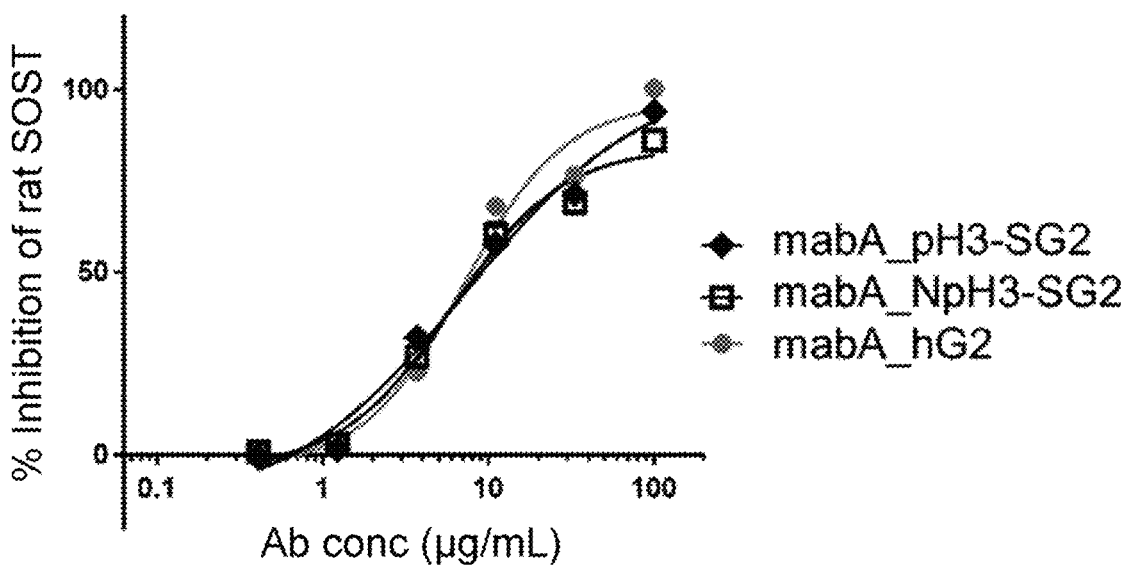
FIG. 2 illustrates in vitro neutralizing activity of anti-sclerostin antibodies mabA and its variants (mabA_pH3 and mabA_NpH3), as described in Example 4.
Figure 3:
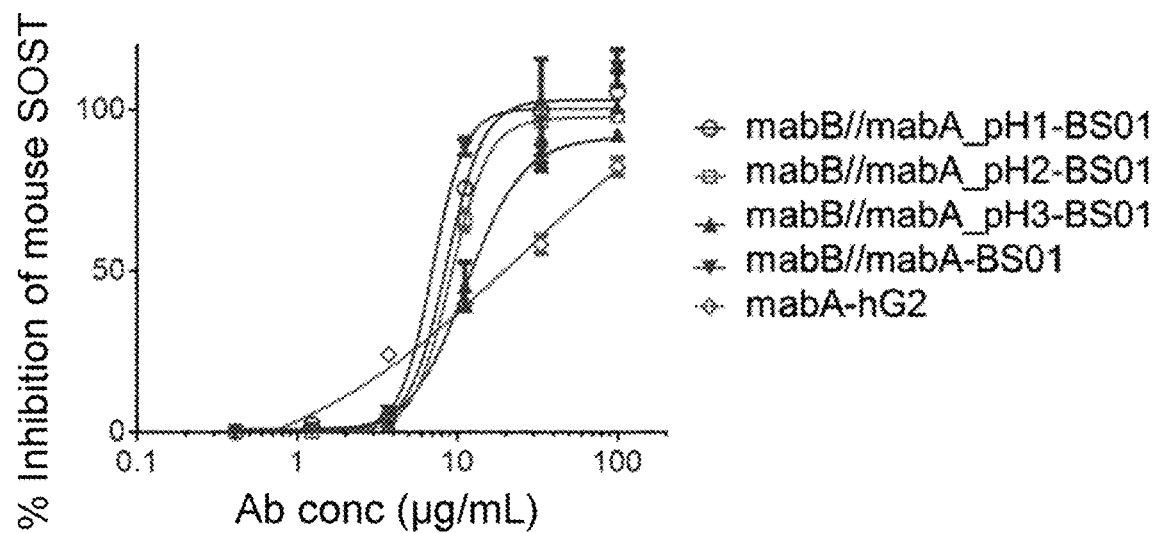
FIG. 3 illustrates in vitro neutralizing activity of an anti-sclerostin antibody mabA and biparatopic anti-sclerostin antibodies (mabB//mabA_pH1, mabB//mabA_pH2, mabB//mabA_pH3, and mabB//mabA), as described in Example 4.

The ratio of firefly to renilla luciferase (F/R) was calculated in each well. The percent of sclerostin inhibition was defined as $100 \times [(F/R_{MAb} - F/R_{Wnt(+)sosT(+)})/(F/R_{Wnt(+)SOST(-)} - F/R_{Wnt(+)sosT(+)})]$. Herein, F/R $_{Wnt(+)sosT(-)}$ Represents the F/R Value in the presence of Wnt1 alone, which indicates the assumed maximum inhibition of sclerostin. F/R $M_{ab}$ represents the F/R value in the presence of the anti-sclerostin monoclonal antibody to be evaluated, Wnt1 and sclerostin. F/R$_{Wnt(+)sosT(+)}$ represents the F/R value in the presence of Wnt1 and sclerostin, which indicates no inhibition of sclerostin.

pH dependent antibodies (mabA_pH1-SG2, mabA_pH2-SG2, and mabA_pH3-SG2) showed comparable neutralizing activity compared to parent mabA-hG2 (FIGS. 1 and 2).

pH dependent biparatopic antibodies (mabB//mabA_pH1-BSO1, mabB//mabA_pH2-BSO1, and mabB//mabA_pH3-BSO1) showed superior specific activity to mabA-hG2 in Wnt1 reporter gene assay (FIG. 3).

Example 5 Immune Complex Formation of Biparatopic Anti-Sclerostin Antibodies

Antigen Uptake Assay

Ability of antigen uptake by antibody was assessed by in vitro cell-based assay. MDCK cell expressing human Fc gamma receptor IIB and human FcRn was established and cultured in EMEM (Sigma, Cat. M5650) with 10% fetal bovine serum (Bovogen, Cat. SFBS-D), 2 mM GlutaMAX-1 (Invitrogen, Cat. 35050-061) and 1% Penicillin/Streptomycin (Invitrogen Cat. 15140).

MDCK cells were seeded at a density of $5 \times 10^4$ cells per well in a 48-well plate. Mouse sclerostin was labelled with a pH-sensitive fluorescent dye, pHrodo-Red, (Molecular Probes, Cat. P36600) by following manufacturer's instruction. Antibodies and labelled sclerostin were mixed at 1:1 molar ratio in culture medium and incubated at 37 degrees C. for one hour. Immediately after incubation, culture medium of the cells was aspirated and replaced with the antibody-antigen mixture, thereafter the cell culture was incubated at 37 degrees C. for 1.5 hours. MDCK cells were washed and detached by trypsin. MDCK cells were washed with culture medium and suspended with 0.2% FBS in PBS. Amount of internalized antigen was measured based on fluorescent intensity detected by flow cytometry. Mean fluorescent intensity (MFI) in a live cell was calculated by FlowJo software. mabB//mabA_pH1-BSO1, mabB//mabA_pH2-BSO1, and mabB//mabA_pH3-BSO1 showed enhanced antigen uptake compared to non-pH-dependent antibodies (mabB//mabA_NpH3-BSO1 and mabA_NpH3-SG2) (Table 5). It is convinced that these results would be due to an ability of the antibodies to form a large immune complex with the antigens which would lead to accelerated uptake of the complex into the cells and a pH-dependent antigen binding activity of the antibodies which would lead to accelerated release of the antigens in the cells.

TABLE 5

Amounts of fluorescence-labeled sclerostin taken up into cells

| | MFI |
|---|---|
| mabB//mabA_pH1-BS01 | 2429 |
| mabB//mabA_pH2-BS01 | 1956 |
| mabB//mabA_pH3-BS01 | 2130 |
| mabB//mabA_NpH3-BS01 | 653 |
| mabA_NpH3-SG2 | 561 |
| Sclerostin only | 181 |

Transmission Electron Microscopy

Figure 4:
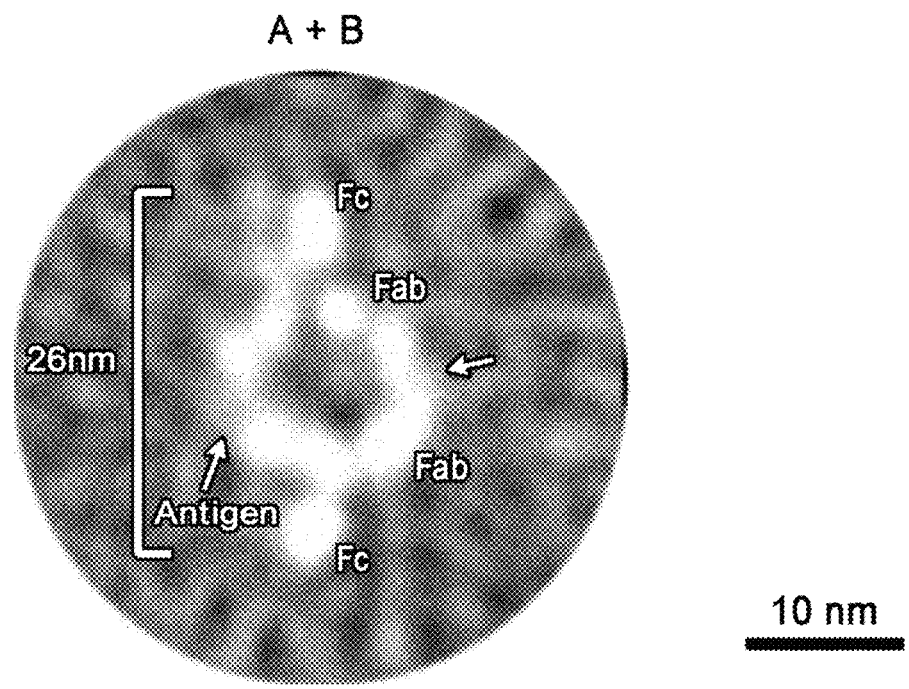
FIG. 4 illustrates a representative image of an immune complex between a biparatopic anti-sclerostin antibody (mabB//mabA) and a sclerostin antigen observed by transmission electron microscopy, as described in Example 5.

Immune complex formation was confirmed by transmission electron microscopy. mabB//mabA-BS01 and human sclerostin were mixed at 1:1 molar ratio and incubated at 37 degrees C. for one hour. Immediately after incubation, the mixture was diluted 1:1000 for imaging. Electron microscopy analysis was performed using FEI Tecnai T12 electron microscope equipped with CCD camera. Images of each grid were acquired at multiple scales to assess the overall distribution of the specimen. Microscopy observation and analysis were performed in Nanoimaging Services, Inc. A representative image is shown in FIG. 4. The complex composed of two molecules of antibody and two molecules of antigen was observed.

Size Exclusion Chromatography

Figure 5A:
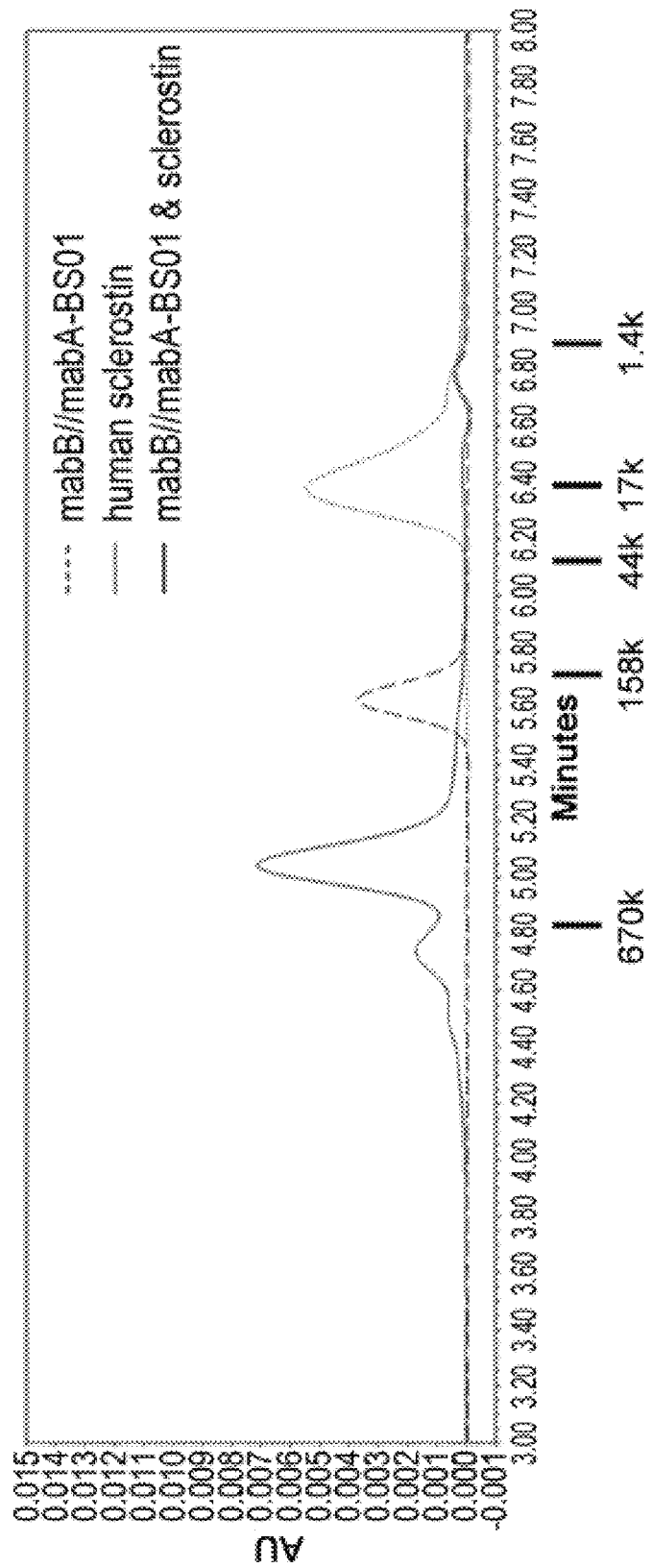
FIG. 5a illustrates a chromatogram obtained by applying a biparatopic anti-sclerostin antibody alone, a sclerostin antigen alone, and an immune complex between the biparatopic anti-sclerostin antibody and the sclerostin antigen, to size exclusion chromatography, as described in Example 5. For the biparatopic antibody, mabB//mabA is used.
Figure 5B:
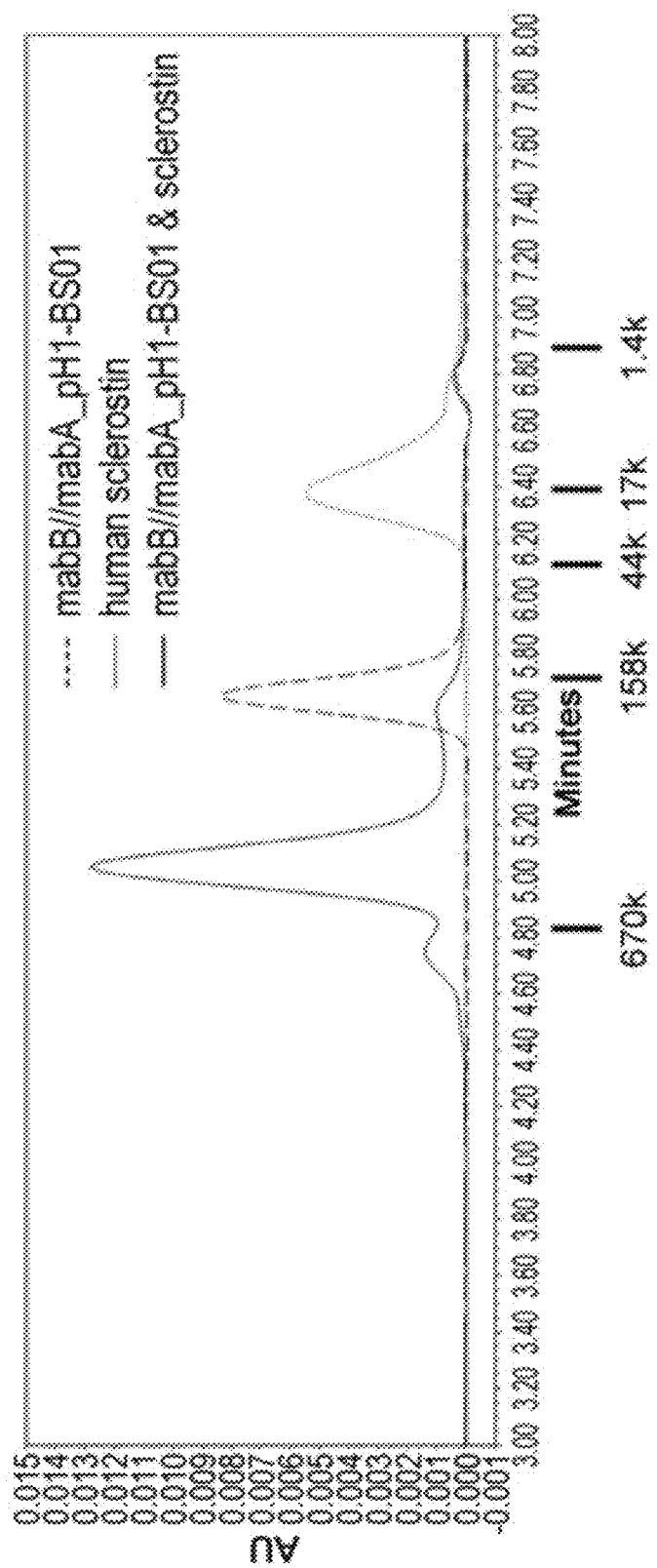
FIG. 5b illustrates a chromatogram obtained by applying a biparatopic anti-sclerostin antibody alone, a sclerostin antigen alone, and an immune complex between the biparatopic anti-sclerostin antibody and the sclerostin antigen, to size exclusion chromatography, as described in Example 5. For the biparatopic antibody, mabB//mabA_pH1 is used.
Figure 5C:
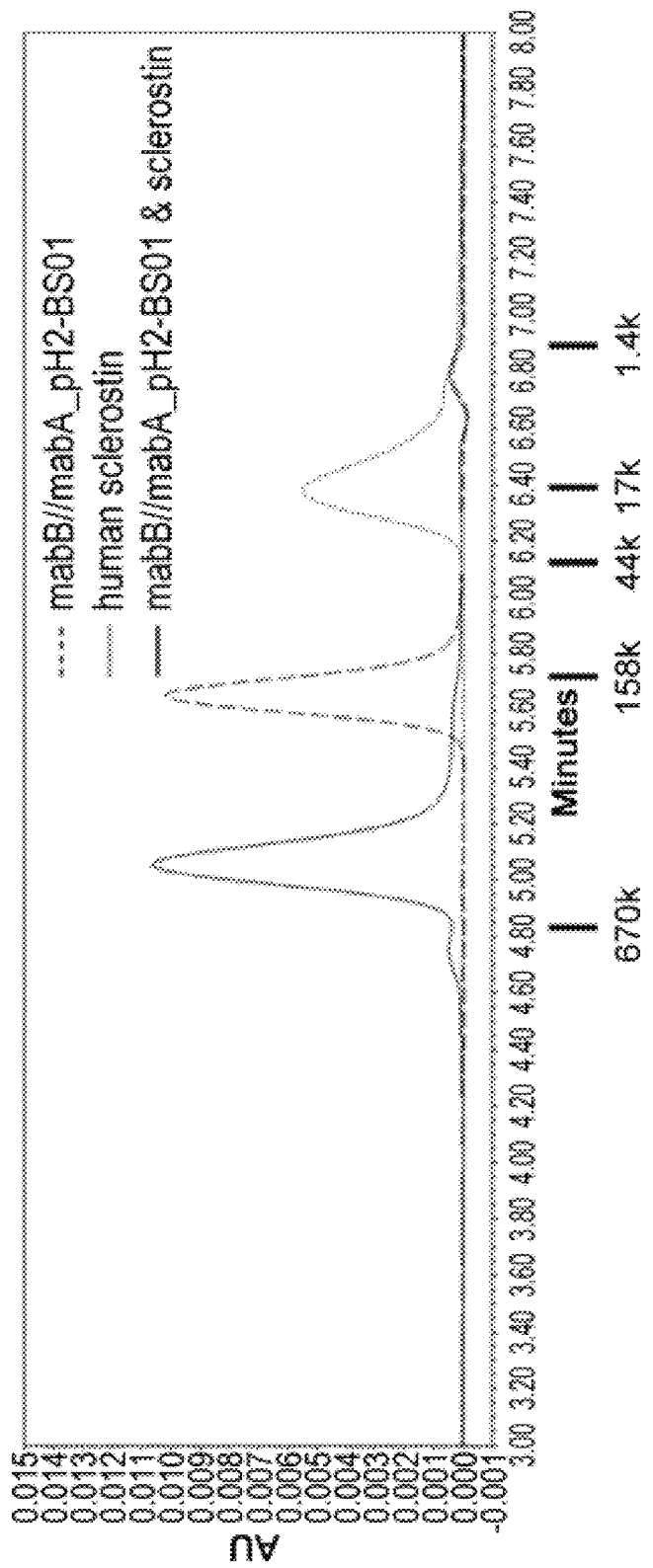
FIG. 5c illustrates a chromatogram obtained by applying a biparatopic anti-sclerostin antibody alone, a sclerostin antigen alone, and an immune complex between the biparatopic anti-sclerostin antibody and the sclerostin antigen, to size exclusion chromatography, as described in Example 5. For the biparatopic antibody, mabB//mabA-pH2 is used.

Size exclusion chromatography (SEC) was carried out on an ACQUITY UPLC Protein BEH SEC Column, 450 angstrom, 1.7 micro m, 4.6 mm×150 mm (Waters) in 50 mM $Na_2HPO_4$, 300 mM NaCl, pH 7.0 at a flow rate of 0.3 ml/min on an ACQUITY UPLC H-Class system (Waters). Detection was done by a UV detector (280 nm). For sample preparation of immune complex, each antibody (1 micro M) was mixed with human sclerostin (1 micro M) in 1:1 molar ratio and incubated for 1 hour at 25 degrees C. in PBS. The chromatograms for mabB//mabA-BSO1, mabB//mabA_pH1-BS01, and mabB//mabA_pH2-BS01 are shown in FIGS. 5a, 5b, and 5c, respectively. It is speculated from the chromatograms that these biparatopic antibodies, when mixed with antigens, would form a large immune complex which would contain more than one antibody molecule.

5.4. Biacore Analysis of Fc Gamma RIIB Binding

The binding of anti-sclerostin antibodies/sclerostin immune complex towards mouse Fc gamma RIIB at pH 7.4 were determined at 25 degrees C. using Biacore T200 instrument (GE Healthcare). All antibodies and mouse Fc gamma RIIB were prepared in ACES pH 7.4 containing 20 mM ACES, 250 mM NaCl, 1.2 mM $CaCl_2$, 0.05% Tween 20, 1 mg/ml BSA, 1 mg/ml carboxymethyl dextran (CMD), 0.005% $NaN_3$. Anti-Histidine antibody (GE Healthcare) was immobilized onto all flow cells of a CM4 sensor chip using amine coupling kit (GE Healthcare). Mouse Fc gamma RIIB was captured on flow cell 2 by anti-Histidine antibody with flow cell 1 as reference flow cell. Mouse Fc gamma RIIB capture levels were aimed at 400 resonance unit (RU). All antibodies were injected at 100 nM over all flow cells. Immune complexes were prepared by mixing 1:1 molar ratio of antibody and human sclerostin and incubated at room temperature for one hour. Sensor surface was regenerated each cycle with 10 mM Glycine-HCl, pH1.5.

Figure 6:
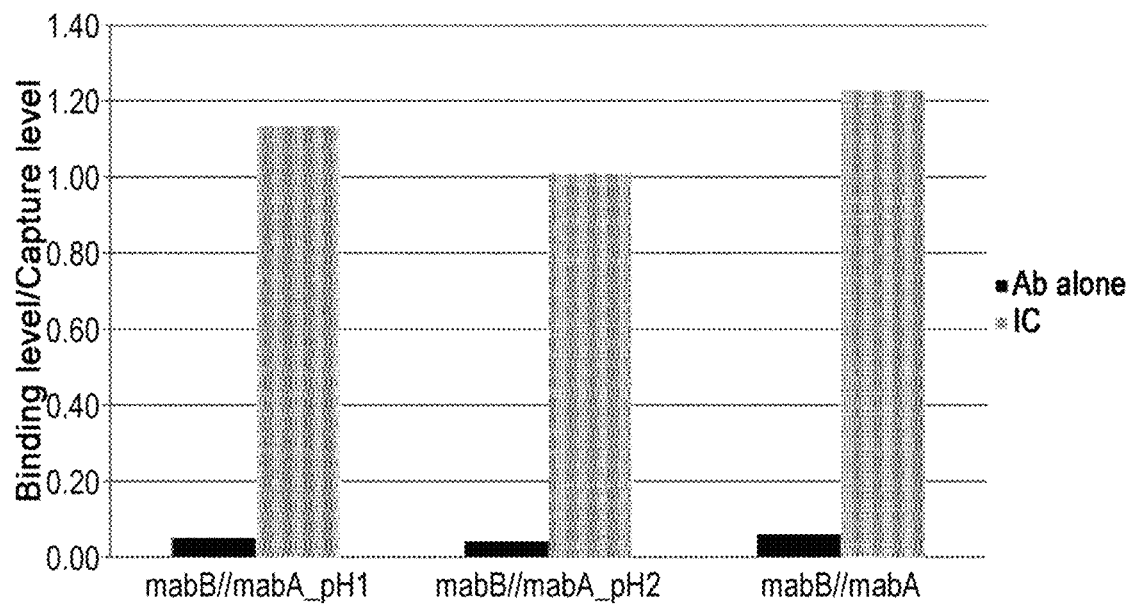
FIG. 6 illustrates Biacore analysis of biparatopic antibodies (mabB//mabA_pH1, mabB//mabA_pH2, mabB//mabA), as described in Example 5. Their binding activities to Fc gamma RIIB are measured in the absence (referred to as Ab alone) and presence (referred to as IC) of the antigen.

The binding levels of anti-sclerostin antibodies or immune complex towards mouse Fc gamma RIIB were monitored from the binding response. Binding levels were normalized to the capture level of corresponding mouse Fc gamma RIIB. The results show that the binding of the antibodies to Fc gamma RIIB was largely enhanced when they formed an immune complex with the antigen (FIG. 6).

Example 6 In Vivo Pharmacokinetics and Sweeping Effects of pH-Dependent Anti-Sclerostin Antibodies (Monkey)

In Vivo Test Using Cynomolgus Monkey

The in vivo pharmacokinetics of anti-sclerostin antibody was assessed upon administration of anti-sclerostin antibody in cynomolgus monkey (Primetrics or Biological Resource Centre, Singapore). A dose level of 10 mg/kg was injected into the cephalic vein or saphenous vein using a disposable syringe. Blood was collected before the start of dosing and either 5 minutes, 7 hours and 1, 2, 3, 7, 14, 21, 28, 35, 42, 49 and 56 days after the end of dosing. The blood was immediately cooled on ice, and the plasma was obtained by centrifugation at 4 degrees C., 2500×g for 10 minutes. The plasma samples were stored in a −80 degrees C. freezer until measurement. The anti-sclerostin antibodies used were mabA-hG2, mabA_pH1-SG2, mabA_pH2-SG2, mabA_NpH1-SG2, and mabA_NpH2-SG2.

Measurement of Anti-Sclerostin Antibody Concentration in Plasma by ELISA

Figure 7:
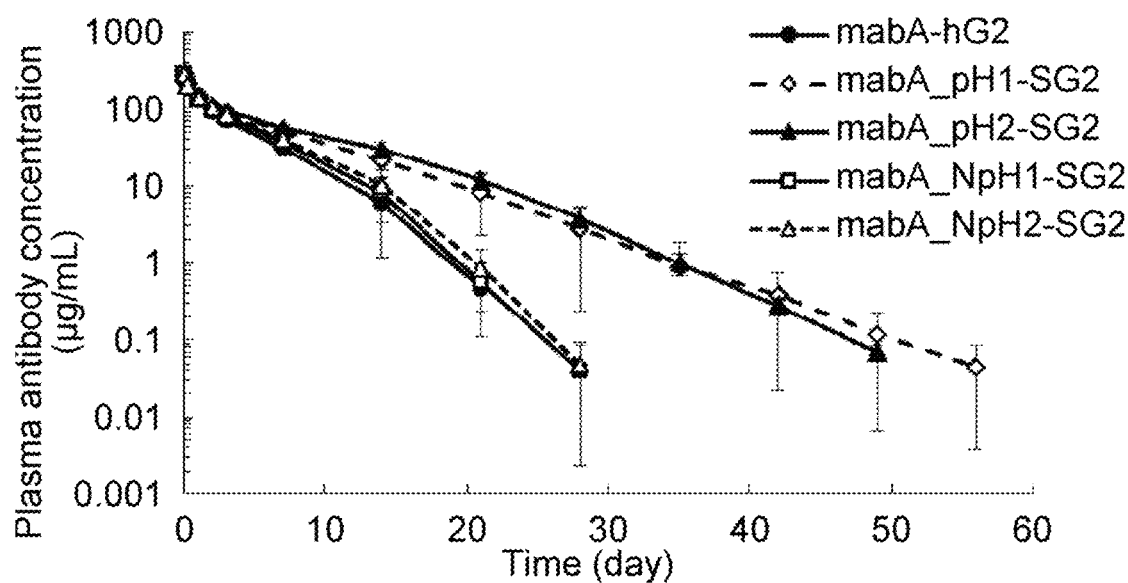
FIG. 7 illustrates a time course of plasma concentration of anti-sclerostin antibodies (mabA, mabA_pH1, mabA_pH2, mabA_NpH1, and mabA_NpH2) intravenously administered in cynomolgus monkey, as described in Example 6.

The concentration of anti-sclerostin antibody in cynomolgus monkey plasma was measured by ELISA. Anti-human IgG k chain antibody (Antibody Solutions) was dispensed onto Nunc-ImmunoPlate MaxiSorp (Nalge Nunc International) and allowed to stand overnight at 4 degrees C. to prepare anti-human IgG-immobilized plates. Calibration curve samples and cynomolgus monkey plasma samples diluted 100-fold or more were prepared. Subsequently, the samples were dispensed onto the anti-human IgG-immobilized plates, and allowed to stand for 1 hour at room temperature. Then, HRP-labelled anti-human IgG Antibody (SouthernBiotech) was added to react for 30 minutes at room temperature, and washing was performed. Subsequently, ABTS ELISA HRP Substrate (KPL) was added. The signal was measured by a plate reader at a wavelength of 405 nm. The anti-sclerostin antibody concentration was calculated based on the response of the calibration curve using the analytical software SOFTmax PRO (Molecular Devices). The time course of plasma anti-sclerostin antibody concentration as measured by this method is shown in FIG. 7. The results indicate that the pH-dependent anti-sclerostin antibodies, mabA_pH1-SG2 and mabA_pH2-SG2, have prolonged PK profiles compared with the non-pH-dependent anti-sclerostin antibodies, mabA_NpH1-SG2 and mabA_NpH2-SG2, respectively.

Measurement of Total Sclerostin Concentration in Plasma by Electrochemiluminescence (ECL)

Figure 8:
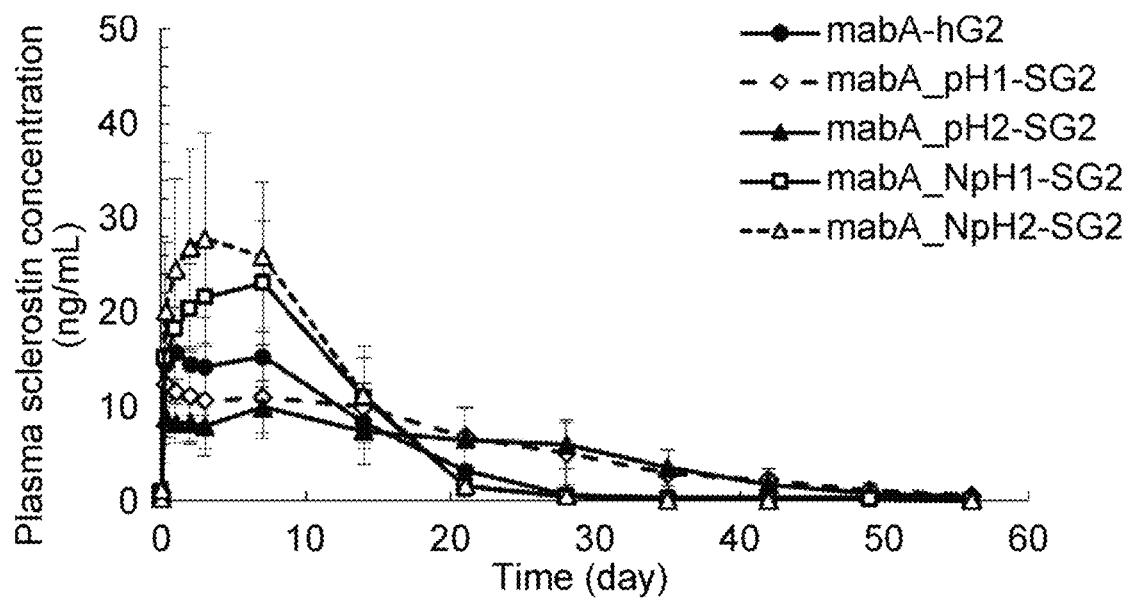
FIG. 8 illustrates a time course of plasma concentration of sclerostin after intravenous administration of anti-sclerostin antibodies (mabA, mabA_pH1, mabA_pH2, mabA_NpH1, and mabA_NpH2) in cynomolgus monkey, as described in Example 6.

The concentration of total sclerostin in cynomolgus monkey plasma was measured by ECL. Anti-sclerostin-immobilized plates were prepared by dispensing anti-sclerostin antibody SCL0099-rbIgG onto a MULTI-ARRAY 96-well bare plate (Meso Scale Discovery) and allowed to stand overnight at 4 degrees C. Calibration curve samples and cynomolgus monkey plasma samples diluted 16.7-fold or more were prepared. The samples were mixed in mabA-hG2 solution (20 micro g/mL) to make all sclerostin form a complex with the antibody and incubated at 37 degrees C. for 1 hour. Subsequently, the samples were added onto an anti-sclerostin-immobilized plate, and incubated at 30 degrees C. for 1 hour. Next, SULFO TAG labelled anti-human IgG antibody (SouthernBiotech) was added and the plate was incubated for 1 hour at room temperature. Read Buffer T (×2) (Meso Scale Discovery) was immediately added to the plate and signal was detected by SECTOR Imager 2400 (Meso Scale Discovery). The total sclerostin concentration was calculated based on the response of the calibration curve using the analytical software SOFTmax PRO (Molecular Devices). The time course of total sclerostin concentration in plasma measured by this method is shown in FIG. 8. The results indicate that the pH-dependent anti-sclerostin antibodies, mabA_pH1-SG2 and mabA_pH2-SG2, have an ability to reduce sclerostin accumulation in plasma 2-3 fold compared with non-pH-dependent anti-sclerostin antibodies, mabA_NpH1-SG2 and mabA_NpH2-SG2, respectively.

Example 7 In Vivo PD Efficacy of pH-Dependent Anti-Sclerostin Antibodies (Monkey)

Evaluation of Serum Bone Marker in Monkey

Figure 9:
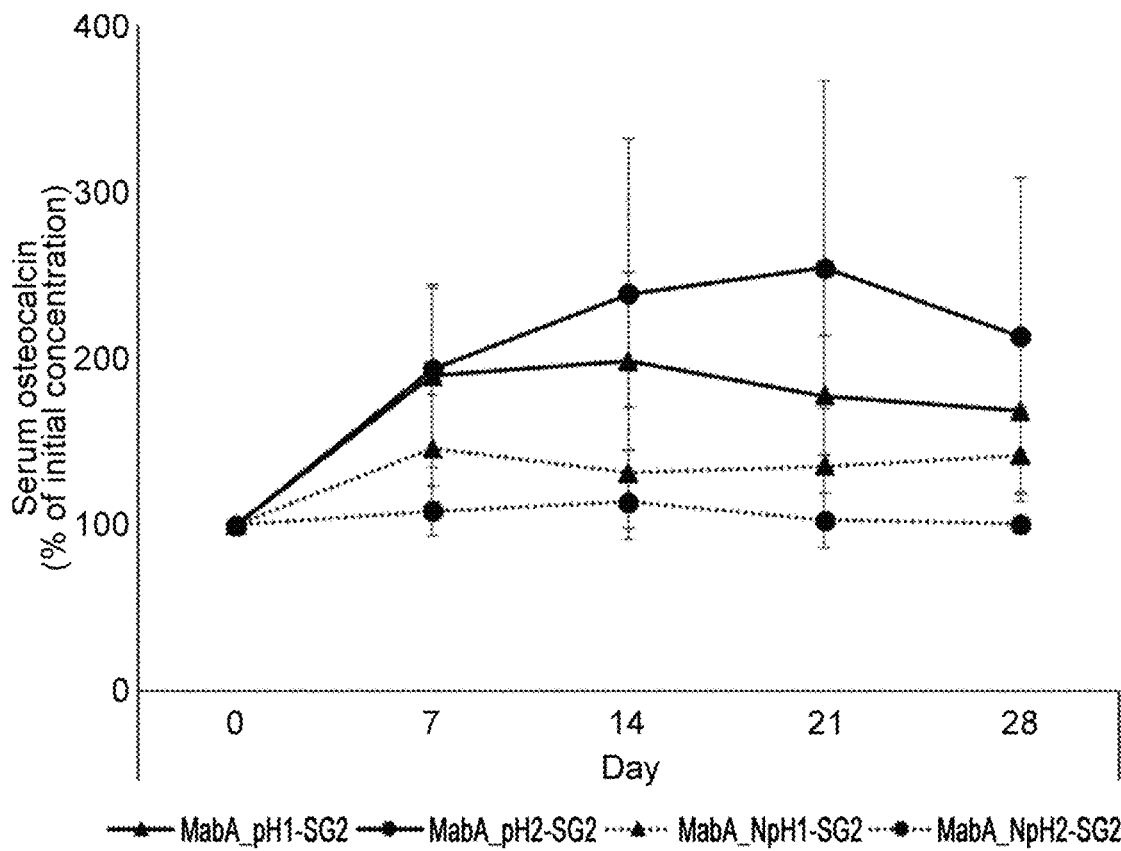
FIG. 9 illustrates a time course of serum concentration of a bone formation marker osteocalcin after intravenous administration of anti-sclerostin antibodies (mabA_pH1, mabA_pH2, mabA_NpH1, and mabA_NpH2) in cynomolgus monkey, as described in Example 7.

Osteocalcin, clinically used bone formation marker, was measured in monkey described in EXAMPLE 6. Serum was collected every week, and measurement was done using a commercial ELISA kit (Biomedical Technologies Inc., Cat. J64816). Each serum was diluted by 10-fold with the designated sample buffer prior to the measurement. The concentration of osteocalcin was shown as % change from baseline (the concentration prior to antibody administration is denoted by 100%). ADA positive animals were omitted in analysis. The time course of serum osteocalcin concentration measured by this method is shown in FIG. 9. Mean (n=3 to 4) is shown with error bars indicating standard deviation. The pH-dependent anti-sclerostin antibodies, mabA_pH1-SG2 and mabA_pH2-SG2, showed higher osteocalcin level compared to the non-pH-dependent anti-sclerostin antibodies, mabA_NpH1-SG2 and mabA_NpH2-SG2, respectively.

Example 8: In Vivo Efficacy of pH-Dependent Sclerostin Antibody in Normal Rats

In Vivo Test Using Normail Rats

Efficacy of pH dependent anti-sclerostin antibody was evaluated in normal rats. Conventional antibody mabA-hG2 at 10 mg/kg, non-pH dependent antibody mabA_NpH3-SG2 at 3 and 10 mg/kg, and pH-dependent antibody mabA_pH3-SG2 at 1, 3 and 10 mg/kg, were administered intravenously (IV) into 8-week-old female normal rats (Charles River Laboratories Japan, Inc.) by once weekly for 4 weeks. Plasma samples were obtained by collecting blood from the jugular vein once weekly before antibody administrations, and plasma levels of antibodies were measured by ELISA. After 4 weeks of administrations, rats were sacrificed, and lumbar spine and right femurs were obtained. Bone mineral density (BMD) of lumbar spine and right femur were assessed by dual-energy X-ray absorptiometry (DXA) using a DCS-600EX (Aloka). Data are represented as the mean+/−SE and statistical significance was determined using JMP (Ver.11.2.1, SAS Institute Inc.). The Williams test or student t-test was performed to detect the significant differences in the antibody-treated groups compared with the vehicle group or other antibody group at same dosage.

Measurement of Anti-Sclerostin Antibody Concentration in Plasma by ELISA

Figure 10:
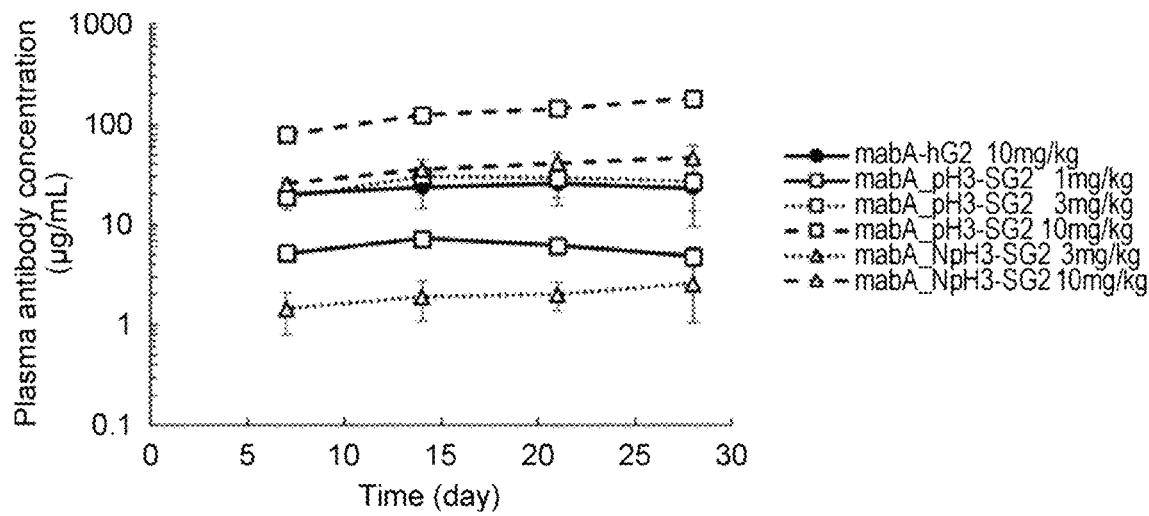
FIG. 10 illustrates a time course of plasma concentration of anti-sclerostin antibodies (mabA, mabA_pH3, and mabA_NpH3) intravenously administered in normal rats, as described in Example 8.

The concentration of anti-sclerostin antibody in rat plasma was measured by ELISA as described in Example 6. Plasma rat samples were diluted 100 fold or more. The time course of plasma anti-sclerostin antibody concentration as measured by this method is shown in FIG. 10. Plasma levels of antibodies were increased in a dose-dependent manner.

Figure 11A:
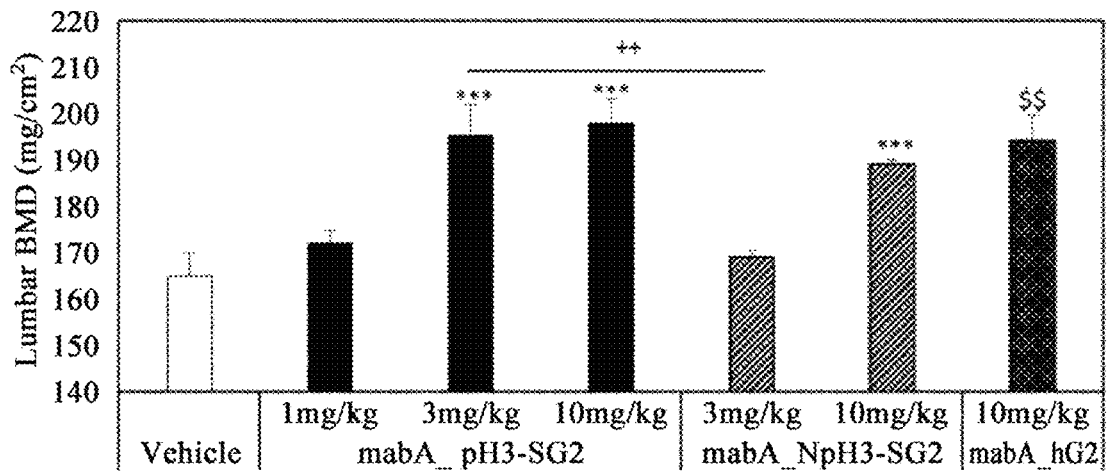
FIG. 11a illustrates in vivo efficacy of anti-sclerostin antibodies (mabA, mabA_pH3, and mabA_NpH3) on bone mineral density (BMD) of lumbar spine in normal rats, as described in Example 8. Data represent mean+SE. : $p<0.01$, *: $p<0.001$ vs vehicle by Williams analysis. $$: $p<0.01$, $$$: $p<0.001$ vs vehicle by t-test analysis. ++: $p<0.01$, +++: $p<0.001$ vs same dosage of mabA_NpH3-SG2 by t-test analysis.
Figure 11B:
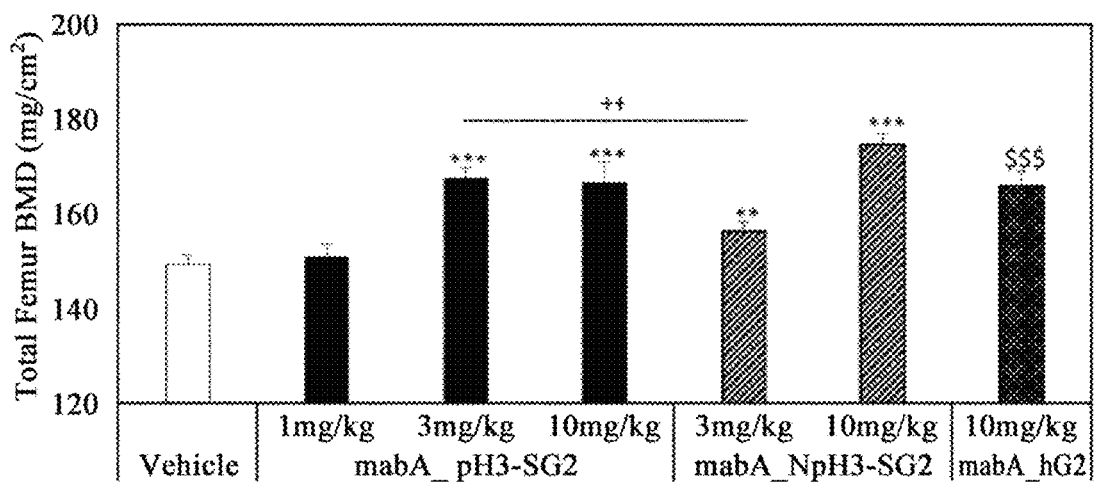
FIG. 11b illustrates in vivo efficacy of anti-sclerostin antibodies (mabA, mabA_pH3, and mabA_NpH3) on bone mineral density (BMD) of right femur in normal rats, as described in Example 8. Data represent mean+SE. : $p<0.01$, *: $p<0.001$ vs vehicle by Williams analysis. $$

The antibody mabA_pH3-SG2 significantly increased lumbar spine and total femur BMD at 3 and 10 mg/kg (FIGS. 11a and 11b). The antibody mabA_NpH3-SG2 increased lumbar BMD at 10 mg/kg, and femur BMD at 3 and 10 mg/kg. The antibody mabA-hG2 significantly increased lumbar and femur BMD at 10 mg/kg. The levels of lumbar and total femur BMD with mabA_pH3-SG2 at 3 mg/kg were significantly higher than those with mabA_NpH3-SG2 at 3 mg/kg.

These results indicated that anabolic effects of pH-dependent antibody mabA_pH3-SG2 on lumbar and femur BMD were better than Non-pH dependent antibody mabA_NpH3-SG2 in normal rats.

Example 9: In Vivo Efficacy of pH-Dependent Anti-Sclerostin Biparatopic Antibodies in SCID Mice In Vivo Test Using SCID Mice Efficacy of biparatopic anti-sclerostin sweeping antibody was evaluated in SCID mice. Conventional antibody mabA-hG2, pH dependent antibody mabA_pH3-SG2, and biparatopic sweeping antibody mabB//mabA_pH3-BSO1, at 2 and 10 mg/kg were administered intravenously (IV) into 8-week-old female SCID mice (Charles River Laboratories Japan, Inc.) by once weekly for 4 weeks. Plasma samples were obtained by collecting blood from the jugular vein once weekly before antibody administrations, and plasma levels of antibodies were measured by ELISA. After 4 weeks of administrations, mice were sacrificed, and lumbar spine was obtained. Bone mineral density (BMD) of lumbar spine was assessed by dual-energy X-ray absorptiometry (DXA) using a DCS-600EX (Aloka). Data are represented as the mean+/−SE and statistical significance was determined using JMP (Ver.11.2.1, SAS Institute Inc.). The Williams test or student t-test was performed to detect the significant differences in the antibody-treated groups compared with the vehicle group or other antibody group at the same dosage.

Measurement of Anti-Sclerostin Antibody Concentration in Plasma by ELISA

The concentration of anti-sclerostin antibody in mice plasma was measured by ELISA as described in Example 6. Plasma mouse samples were diluted 100 fold or more. The time course of plasma anti-sclerostin antibody concentration as measured by this method is shown in FIG. 12.

Measurement of Total Sclerostin Concentration in Plasma by Electrochemiluminescence (ECL)

The concentration of total sclerostin in mouse plasma was measured by ECL. For mouse plasma samples which did not contain an anti-sclerostin antibody, anti-sclerostin-immobilized plates were prepared by dispensing anti-sclerostin antibody SCL0122-SG110 onto a MULTI-ARRAY 96-well bare plate (Meso Scale Discovery) and allowed to stand overnight at 4 degrees C. Calibration curve samples and mouse plasma samples diluted 10-fold were prepared. Subsequently, the samples were added onto an anti-sclerostin-immobilized plate, and incubated at 30 degrees C. for 1 hour.

Next, SULFO TAG labelled mabA-hG2 was added and the plate was incubated at 30 degrees C. for 1 hour. Read Buffer T (×2) (Meso Scale Discovery) was immediately added to the plate and signal was detected by SECTOR Imager 2400 (Meso Scale Discovery). For mouse plasma samples which contained anti-sclerostin antibody, anti-sclerostin-immobilized plates were prepared by dispensing anti-sclerostin antibody SCL0800-rbIgG onto a MULTI-ARRAY 96-well bare plate (Meso Scale Discovery) and allowed to stand overnight at 4 degrees C. Calibration curve samples and mouse plasma samples diluted 500-fold were prepared. The samples were mixed in injected antibody solution (2 micro g/mL) to make all sclerostin complexes formed with the antibody and incubated at 37 degrees C. for 1 hour. Subsequently, the samples were added onto an anti-sclerostin-immobilized plate, and incubated at 30 degrees C. for 1 hour. Next, SULFO TAG labelled anti-human IgG antibody (SouthemBiotech) was added and the plate was incubated at 30 degrees C. for 1 hour. Read Buffer T (×2) (Meso Scale Discovery) was immediately added to the plate and signal was detected by SECTOR Imager 2400 (Meso Scale Discovery). The total sclerostin concentration was calculated based on the response of the calibration curve using the analytical software SOFTmax PRO (Molecular Devices). The time course of total sclerostin concentration in plasma measured by this method is shown in FIG. 13.

The antibody mabA-hG2 significantly increased lumbar spine BMD at 10 mg/kg (FIG. 14). The antibody mabA_pH3-SG2 increased lumbar BMD at 2 and 10 mg/kg. The antibody mabB//mabA_pH3-BSO1 significantly increased lumbar spine BMD at 2 and 10 mg/kg. The levels of lumbar BMD with mabB//mabA_pH3-BS01 at 10 mg/kg were significantly higher than those with mabA-hG2, and mabA_pH3-SG2 at the same dosage.

These results indicated that anabolic effects of biparatopic anti-sclerostin sweeping antibody mabB//mabA_pH3-BSO1 on BMD were superior to those of conventional antibody mabA-hG2 or pH dependent antibody mabA_pH3-SG2 in SCID mice.

Example 10: Identification of a Common Light Chain for mabA and mabB ("Each Residue Shuffling")

For therapeutic development, bispecific (biparatopic) antibodies need to be optimized by molecular engineering to enable their large-scale manufacturing at clinical grade, and a variety of molecular formats for bispecific antibodies have been studied, including single-chain diabody, tandem scFv, IgG-scFv, DVD-Ig, CrossMab, dual-binding Fab (Kontermann RE, mAbs 2012; 4: 182-197), and asymmetric bispecific IgG. Recombinant production of an asymmetric bispecific IgG antibody is more challenging than the other formats because it consists of two different heavy chains and two different light chains, which would result in the secretion of a mixture of ten different combinations of heavy and light chains (Klein C et al, mAbs 2012; 4: 653-663), and the purification of one desired bispecific antibody from a mixture of nine mispaired byproducts is nearly impossible. Engineering technologies to overcome this difficulty have been previously reported. First, identifying a common light chain by phage display technology to use as the partner of the two heavy chains can reduce the number of heavy and light combinations from ten to three: one heterodimeric bispecific antibody and two homodimeric monospecific antibodies (Merchant A M et al, Nat Biotechnol 1998; 16: 677-681). Second, engineering the CH3 domain to facilitate Fc heterodimerization can minimize the amount of homodimeric byproducts (Klein C et al, mAbs 2012; 4: 653-663, Merchant A M et al, Nat Biotechnol 1998; 16: 677-681).

A common light chain for two different heavy chains could be identified by CDR shuffling approach (Sampei et al, PLoS One 2013; 8: e57479). Therefore, we performed CDR shuffling to obtain an effective common light chain for mabA and mabB as illustrated in FIG. 15. The lights chains evaluated are as follows: Light chain A (SEQ ID NO: 15), Light chain B (SEQ ID NO: 27), A-A-B (SEQ ID NO: 92), A-B-A (SEQ ID NO: 93), A-B-B (SEQ ID NO: 94), B-A-A (SEQ ID NO: 95), B-A-B (SEQ ID NO: 96), and B-B-A (SEQ ID NO: 97). The amino acid sequences of the light chain variants are summarized in Table 6.

Each of these light chains was expressed with either of the mabA or mabB IgG1 heavy chain. The VH regions were combined with the human IgG CH, SG1 (SEQ ID NO: 78), and the VL regions were combined with the human CL, SK1 (SEQ ID NO: 82), respectively. FIG. 16 shows the binding activity to recombinant human SOST, measured by SPR analysis. None of the CDR shuffling light chain variants worked as an effective common light chain because they could not bind to the antigen strongly in both cases when combined with the mabA and mabB heavy chains.

Since no potent common light chain was identified by the CDR shuffling approach, we conducted a novel approach, named each residue shuffling. We constructed a set of mabA and mabB light chain variants, wherein the variants have a single amino acid mutation in CDRs, which substitutes an amino acid in a position in mabA (mabB) with the amino acid in the corresponding position in mabB (mabA) as illustrated in FIG. 17.

These mabA and mabB light chain variants were expressed with the mabA and mabB IgG1 heavy chains, respectively. The VH regions were combined with the human IgG CH, SG1 (SEQ ID NO: 78), and the VL regions were combined with the human CL, SK1 (SEQ ID NO: 82). Antigen-binding activity of these antibodies was examined to evaluate susceptibility and acceptability of the substitution in each position of the mabA and mabB light chgains. Based on the results of a pair of the mabA and mabB light chain variants having a single mutation at the same position, the better amino acid residue could be selected at each position and the "each residue-shuffling" variants were designed by combining the selected amino acid residues as illustrated in FIG. 18. The candidate light chain variants are as follows: abL063 (SEQ ID NO: 98), abL081 (SEQ ID NO: 99), and abL083 (SEQ ID NO: 100). The amino acid sequences of the light chain variants are summarized in Table 6.

Each of the light chain variants designed by the each residue shuffling approach was expressed with either of the mabA heavy chain or mabB heavy chain. FIG. 19 shows the binding activity to recombinant human SOST, measured by SPR analysis. These light chain variants worked as effective common light chains because they could bind to the antigen clearly when combined with any of the two heavy chains. Thus, this approach, each residue shuffling, is a novel effective approach to identify a potent common light chain when the CDR shuffling approach does not work well.

TABLE 6

Amino acid sequences of light chain variants

| | SEQ ID NO: | | | |
|---|---|---|---|---|
| Name | VL | HVR-L1 | HVR-L2 | HVR-L3 |
| A-A-B | 92 | 52 | 56 | 62 |
| A-B-A | 93 | 52 | 59 | 60 |
| A-B-B | 94 | 52 | 59 | 62 |
| B-A-A | 95 | 55 | 56 | 60 |
| B-A-B | 96 | 55 | 56 | 62 |
| B-B-A | 97 | 55 | 59 | 60 |
| abL063 | 98 | 109 | 112 | 60 |
| abL081 | 99 | 110 | 113 | 60 |
| abL083 | 100 | 110 | 114 | 60 |
| abL152 | 105 | 111 | 115 | 60 |

Example 11: pI Engineering of the Optimized Biparatopic Antibody

Having a common light chain reduces the number of pairs of heavy and light chains from ten to three, and engineering the CH3 domain enables preferential secretion of heterodimerized heavy chains. However, it is still difficult to completely prevent mispaired homodimerization in large-scale production. Therefore, a downstream purification process to remove homodimeric byproducts is essential for pharmaceutical development. Ion exchange (IEX) chromatography is the major purification process by which to remove impurities after the Protein A purification step. The retention of IgG antibodies by IEX chromatography is determined by the electrostatic charge of the antibody molecule, which can be measured as its pI. To facilitate the purification of the bispecific (biparatopic) antibody, pI engineering into the heavy chain variable regions was implemented to increase the pI difference between the bispecific antibody and the homodimeric byproducts in parallel with other optimizations for their stability and antigen binding activity, such as affinity, pH dependency, and cross-reactivity. After the optimization, cation exchange chromatography (CIEX) was performed and the separation between the bispecific (heterodimeric) antibody and the two homodimeric byproducts was observed. The chromatograms for the four selected antibodies (amH848/bsH638/abL152, amH848/bsH656/abL152, amH852/bsH638/abL152, and amH852/bsH656/abL152) are shown in FIGS. 20a-d. Herein, amH848 (SEQ ID NO: 101) and amH852 (SEQ ID NO: 102) are the mabA heavy chain variants, bsH638 (SEQ ID NO: 103) and bsH656 (SEQ ID NO: 104) are the mabB heavy chain variants, and abL152 (SEQ ID NO: 105) is the common light chain variant. The amino acid sequences of the heavy and light chain variants are summarized in Table 6 and 7. The homodimeric antibodies were produced using IgG1 constant region BS01b (SEQ ID NO: 80) for the mabA variants and BS01a (SEQ ID NO: 81) for the mabB variants, respectively. The bispeicific antibodies were produced using IgG1 constant region with the knobs-into-holes mutations, specifically SGlvl4k (SEQ ID NO: 106) for the mabA variants and SGlv14h (SEQ ID NO: 107) for the mabB variants. The results show that the optimized bispecific antibodies can be separated completely from the two homodimeric byproducts by CIEX, therefore, the purification of these bispecific antibodies in manufacturing is feasible.

TABLE 7

Amino acid sequences of mabA and mabB variants

| | SEQ ID NO: | | | |
|---|---|---|---|---|
| Name | VH | HVR-H1 | HVR-H2 | HVR-H3 |
| amH848 | 101 | 116 | 118 | 120 |
| amH852 | 102 | 31 | 118 | 120 |
| bsH638 | 103 | 117 | 119 | 121 |
| bsH656 | 104 | 117 | 37 | 121 |

In vitro neutralizing efficacy of the bispecific antibodies (amH848/bsH638/abL152, amH848/bsH656/abL152, amH852/bsH638/abL152, and amH852/bsH656/abL152) were measured using the same method as described in Example 4. As a result, those antibodies were found to show superior specific activity to mabB-hG4 (FIG. 21).

Example 12: Improvement of the Cross-Reactivity Between Human and Cynomolgus Monkey Antigens Antibody PK data and the effect on antigen concentration in primates such as cynomolgus monkeys are generally required before clinical trials. However, binding activity of mabB against the cynomolgus antigen was much weaker than that of the human antigen. Hence, together with affinity and pH dependency optimization, we screened mutations rationally or comprehensively that could improve the affinity of mabB against the cynomolgus antigen. We successfully generated mabB variants (bsH638/abL152 and bsH656/abL152) which bound to human and cynomolgus antigens quite similarly as shown in Table 8. FIGS. 22a-d shows the binding activity to recombinant human or cynomolgus SOST, measured by SPR analysis. The selected four bispecific (biparatopic) antibodies (amH848/bsH638/abL152, amH848/bsH656/abL152, amH852/bsH638/abL152, and amH852/bsH656/abL152) show very strong binding activity at pH 7.4 and rapidly dissociate from the antigen at pH 5.8 with the parameters shown in Table 8, and there is no significant difference between the human and cynomolgus antigens. Using the antibodies with the improved human/cynomolgus cross-reactivity, we could predict antibody PK, antigen concentration, and efficacy in human much more accurately based on results of studies in cynomolgus monkeys, which is strongly preferred before clinical trials.

TABLE 8

Kinetic parameters of anti-sclerostin (SOST) antibodies against human and cyno SOST at pH 7.4 and pH 5.8

| | Human SOST | | cyno SOST | |
|---|---|---|---|---|
| Antibody name | koff pI 7.4 | koff pH 7.4 >> 5.8 | koff pH 7.4 | koff pH 7.4 >> 5.8 |
| amH848/abL152 | 9.46E−03 | n.a.* | 8.54E−03 | n.a.* |
| amM852/abL152 | 2.57E−03 | 8.82E−02 | 1.90E−03 | 1.07E−01 |

TABLE 8-continued

Kinetic parameters of anti-sclerostin (SOST) antibodies against human and cyno SOST at pH 7.4 and pH 5.8

| Antibody name | Human SOST | | cyno SOST | |
| --- | --- | --- | --- | --- |
| | koff pI 7.4 | koff pH 7.4 >> 5.8 | koff pH 7.4 | koff pH 7.4 >> 5.8 |
| bsH638/abL152 | 9.30E−03 | n.a.* | 1.07E−02 | n.a.* |
| bsH656/abL152 | 1.04E−02 | n.a.* | 1.08E−02 | n.a.* |
| amM848/bsH638/abL152 | 5.96E−04 | 1.00E−01 | 6.06E−04 | 2.27E−01 |
| amH848/bsH656/abL152 | 5.15E−04 | 2.22E−01 | 6.06E−04 | 3.74E−01 |
| amH852/bsH638/abL152 | 4.18E−04 | 2.80E−02 | 3.87E−04 | 5.98E−02 |
| amH852/bsH656/abL152 | 4.19E−04 | 5.93E−02 | 4.05E−04 | 1.16E−01 |

*weak binder, koff pH 5.8 fitting not applicable

Example 13: Reducing the Immunogenicity of mabB

It was speculated that mabB might have a risk of developing anti-drug antibodies (ADAs) when administered in human even though this antibody was humanized. For clinical application, further reducing immunogenicity of the antibody was required. Since the amino acid sequence of mabB heavy chain (SEQ ID NO: 23) at position 27-30 (FPIK sequence) was found to be a non-human sequence, we aimed at substituting this region with a human germline sequence, which was considered to show lower immunogenicity. Together with other optimizations, we successfully substituted the region with the human germline sequence and reduced the potential immunogenicity of the antibody. The mabB heavy chain variants of the bispecific antibodies described in Example 12 have the human germline sequence at the region (position 27-30, YTLT).

Example 14: Improvement of the Chemical Stability

Sufficiently good pharmaceutical properties such as high solubility and stability are essential for a subcutaneously injectable liquid formulation and for manufacturability of therapeutic antibodies. Although liquid formulation is much more convenient for patients, monoclonal antibodies stored in aqueous solution often undergo deamidation of the asparagine residues into aspartic acid, and isomerization/succinimide formation of the aspartic acid residues in the CDRs, resulting in reduction of the biological activity of the antibody. Therefore, we substituted these residues having the potential of chemical degradation with other amino acids, in parallel with other optimizations. We successfully improved the stability of the bispecific antibodies with the mutations introduced: D31S, N52M, N53H, N60K, D98S, D99E in the mabA heavy chain, and D31H in the mabB heavy chain, and D28G, N31D, N34A (compared with the mabA light chain sequence) in the common light chain, as described in Example 12.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The sequences of SEQ ID NOs: 74, 128, and 130-132 are shown below:

```
<210>        SEQ ID NO: 74
<211>        5
<212>        PRT
<213>        Artificial sequence <220>
<223>        HVR-H1 consensus <220>
<221>        misc_feature
<222>        (1)..(1)
<223>        Xaa = Asp or His <220>
<221>        misc_feature
<222>        (2)..(2)
<223>        Xaa = Thr or His <400>        74
Xaa Xaa Phe Gln His
1                 5

<210>        SEQ ID NO: 128
<211>        5
<212>        PRT
<213>        Artificial sequence <220>
<223>        HVR-H1 consensus <220>
<221>        misc_feature
<222>        (1)..(1)
<223>        Xaa = Asp or His <220>
<221>        misc_feature
<222>        (2)..(2)
<223>        Xaa = Thr or His <220>
<221>        misc_feature
<222>        (4)..(4)
<223>        Xaa = Gln or Met <400>        128
Xaa Xaa Phe Xaa His
1                 5

<210>        SEQ ID NO: 130
<211>        11
<212>        PRT
<213>        Artificial sequence <220>
<223>        HVR-L1 consensus

<220>
```

-continued

```
<221>  misc_feature
<222>  (1)..(1)
<223>  Xaa = Arg or Lys

<220>
<221>  misc_feature
<222>  (4)..(4)
<223>  Xaa = Gln, His or Glu

<220>
<221>  misc_feature
<222>  (5)..(5)
<223>  Xaa = Asp or Gly

<220>
<221>  misc_feature
<222>  (6)..(6)
<223>  Xaa = Ile or Val

<220>
<221>  misc_feature
<222>  (7)..(7)
<223>  Xaa = Ser or His

<220>
<221>  misc_feature
<222>  (8)..(8)
<223>  Xaa = Asn, Thr or Asp

<220>
<221>  misc_feature
<222>  (9)..(9)
<223>  Xaa = Tyr or Ala

<220>
<221>  misc_feature
<222>  (10)..(10)
<223>  Xaa = Leu or Val

<220>
<221>  misc_feature
<222>  (11)..(11)
<223>  Xaa = Asn or Ala

<400>  130
Xaa Ala Ser Xaa Xaa Xaa Xaa Xaa Xaa Xaa Xaa
1               5                   10

<210>  SEQ ID NO: 131
<211>  7
<212>  PRT
<213>  Artificial sequence

<220>
<223>  HVR-L2 consensus

<220>
<221>  misc_feature
<222>  (1)..(1)
<223>  Xaa = Tyr, His or Trp

<220>
<221>  misc_feature
<222>  (2)..(2)
<223>  Xaa = Thr, His or Ala

<220>
<221>  misc_feature
```

-continued

```
<222>  (4)..(4)
<223>  Xaa = Arg or Thr

<220>
<221>  misc_feature
<222>  (5)..(5)
<223>  Xaa = Leu or Arg

<220>
<221>  misc_feature
<222>  (6)..(6)
<223>  Xaa = Leu, Trp or Glu

<220>
<221>  misc_feature
<222>  (7)..(7)
<223>  Xaa = Ser or Thr

<400>  131
Xaa Xaa Ser Xaa Xaa Xaa Xaa
1               5

<210>  SEQ ID NO: 132
<211>  9
<212>  PRT
<213>  Artificial sequence

<220>
<223>  HVR-L3 consensus

<220>
<221>  misc_feature
<222>  (1)..(1)
<223>  Xaa = Gln or His

<220>
<221>  misc_feature
<222>  (3)..(3)
<223>  Xaa = Gly or Tyr

<220>
<221>  misc_feature
<222>  (4)..(4)
<223>  Xaa = Asp, Ser or His

<220>
<221>  misc_feature
<222>  (5)..(5)
<223>  Xaa = Thr or Asp

<220>
<221>  misc_feature
<222>  (6)..(6)
<223>  Xaa = Leu or Tyr

<220>
<221>  misc_feature
<222>  (7)..(7)
<223>  Xaa = Pro or His

<220>
<221>  misc_feature
<222>  (8)..(8)
<223>  Xaa = Tyr or Trp

<400>  132
Xaa Gln Xaa Xaa Xaa Xaa Xaa Xaa Thr
1               5
```

SEQUENCE LISTING

```
Sequence total quantity: 135
SEQ ID NO: 1            moltype = AA   length = 213
FEATURE                 Location/Qualifiers
source                  1..213
                        mol_type = protein
                        organism = Homo sapiens
```

```
SEQUENCE: 1
MQLPLALCLV CLLVHTAFRV VEGQGWQAFK NDATEIIPEL GEYPEPPPEL ENNKTMNRAE    60
NGGRPPHHPF ETKDVSEYSC RELHFTRYVT DGPCRSAKPV TELVCSGQCG PARLLPNAIG   120
RGKWWRPSGP DFRCIPDRYR AQRVQLLCPG GEAPRARKVR LVASCKCKRL TRFHNQSELK   180
DFGTEAARPQ KGRKPRPRAR SAKANQAELE NAY                                213

SEQ ID NO: 2            moltype = AA  length = 213
FEATURE                 Location/Qualifiers
source                  1..213
                        mol_type = protein
                        organism = Macaca fascicularis
SEQUENCE: 2
MQLPLALCLV CLLVHAAFRV VEGQGWQAFK NDATEIIPEL GEYPEPPPEL ENNKTMNRAE    60
NGGRPPHHPF ETKDVSEYSC RELHFTRYVT DGQCRSAKPV TELVCSGQCG PARLLPNAIG   120
RGKWWRPSGP DFRCIPDRYR AQRVQLLCPG GAAPRARKVR LVASCKCKRL TRFHNQSELK   180
DFGPEAARPQ KGRKPRPRAR GAKANQAELE NAY                                213

SEQ ID NO: 3            moltype = AA  length = 213
FEATURE                 Location/Qualifiers
source                  1..213
                        mol_type = protein
                        organism = Rattus norvegicus
SEQUENCE: 3
MQLSLAPCLA CLLVHAAFVA VESQGWQAFK NDATEIIPGL REYPEPPPQEL ENNQTMNRAE   60
NGGRPPHHPY DTKDVSEYSC RELHYTRFVT DGPCRSAKPV TELVCSGQCG PARLLPNAIG   120
RVKWWRPNGP DFRCIPDRYR AQRVQLLCPG GAAPRSRKVR LVASCKCKRL TRFHNQSELK   180
DFGPETARPQ KGRKPRPRAR GAKANQAELE NAY                                213

SEQ ID NO: 4            moltype = AA  length = 211
FEATURE                 Location/Qualifiers
source                  1..211
                        mol_type = protein
                        organism = Mus musculus
SEQUENCE: 4
MQPSLAPCLI CLLVHAAFCA VEGQGWQAFR NDATEVIPGL GEYPEPPPEN NQTMNRAENG    60
GRPPHHPYDA KDVSEYSCRE LHYTRFLTDG PCRSAKPVTE LVCSGQCGPA RLLPNAIGRV   120
KWWRPNGPDF RCIPDRYRAQ RVQLLCPGGA APRSRKVRLV ASCKCKRLTR FHNQSELKDF   180
GPETARPQKG RKPRPGARGA KANQAELENA Y                                  211

SEQ ID NO: 5            moltype = DNA  length = 1113
FEATURE                 Location/Qualifiers
source                  1..1113
                        mol_type = unassigned DNA
                        organism = Homo sapiens
SEQUENCE: 5
atggggctct gggcgctgtt gcctggctgg gtttctgcta cgctgctgct ggcgctggcc    60
gctctgccca cagcccggc tgccaacagc agtggcgat ggtggggtat tgtgaacgta   120
gcctcctcca cgaacctgct tacagactcc aagagtctgc aactggtact cgagcccagt   180
ctgcagctgt tgagccgcaa acagcggcgt ctgatacgcc aaaatccggg gatcctgcac   240
agcgtgagtg gggggctgca gagtgccgtg cgcgagtgca gtggcagtt ccggaatcgc   300
cgctggaact gtcccactgc tccagggccc cacctcttcg gcaagatcgt caaccgggtg   360
tgtcgagaaa cggcgtttat cttcgctatc acctccgccg gggtcaccca ttcggtggcc   420
cgctcctgct cagaaggttc catcgaatcc tgcacgtgtg actaccggcg gcgcggcccc   480
ggggggcccc actggcactg ggggggctgc agcgacaaca ttgacttcgg ccgcctcttc   540
ggccgggagt tcgtggactc cggggagaag gggcgggacc tgcgcttcct catgaacctt   600
cacaacaacg aggcaggccg tacgaccgta ttctccgaga tgcgccagga gtgcaagtgc   660
cacgggatgt ccggctcatg cacggtgcgc acgtgctgga tgcggctgcc cacgctgcgc   720
gccgtggggc atgtgctgcg cgaccgcttc gacggcgcct cgcgcgtcct gtacggcaac   780
cgcggcagca accgcgcttc gcgggcggag ctgctgcgcc tggagccgga agaccggcc   840
cacaaaccgc cctccccca cgacctcgtc tacttcgaga aatcgcccaa ccttctgcag   900
tacagcggac gcctgggcac agcaggcacg gcagggcgcg cctgtaacag ctcgtcgccc   960
gcgctggacg gctgcgagct gctctgctgc ggcaggggcc accgcacgcg cacgcagcgc  1020
gtcaccgagc gctgcaactg caccttccac tggtgctgcc acgtcagctg ccgcaactgc  1080
acgcacacgc gcgtactgca cgagtgtctg tga                              1113

SEQ ID NO: 6            moltype = AA  length = 370
FEATURE                 Location/Qualifiers
source                  1..370
                        mol_type = protein
                        organism = Homo sapiens
SEQUENCE: 6
MGLWALLPGW VSATLLLALA ALPAALAANS SGRWWGIVNV ASSTNLLTDS KSLQLVLEPS    60
LQLLSRKQRR LIRQNPGILH SVSGGLQSAV RECKWQFRNR RWNCPTAPGP HLFGKIVNRG   120
CRETAFIFAI TSAGVTHSVA RSCSEGSIES CTCDYRRRGP GGPDWHWGGC SDNIDFGRLF   180
GREFVDSGEK GRDLRFLMNL HNNEAGRTTV FSEMRQECKC HGMSGSCTVR TCWMRLPTLR   240
AVGDVLRDRF DGASRVLYGN RGSNRASRAE LLRLEPEDPA HKPPSPHDLV YPEKSPNFCT   300
YSGRLGTAGT AGRACNSSSP ALDGCELLCC GRGHRTRTQR VTERCNCTFH WCCHVSCRNC   360
THTRVLHECL                                                          370
```

```
SEQ ID NO: 7                moltype = AA   length = 123
FEATURE                     Location/Qualifiers
REGION                      1..123
                            note = VH
source                      1..123
                            mol_type = protein
                            organism = synthetic construct
SEQUENCE: 7
EVQLVQSGAE VKKPGASVKV SCKASGYTFT DYNMHWVRQA PGQGLEWMGE INPNSGGAGY    60
NQKFKGRVTM TTDTSTSTAY MELRSLRSDD TAVYYCARLG YDDIYDDWYF DVWGQGTTVT   120
VSS                                                                 123

SEQ ID NO: 8                moltype = AA   length = 123
FEATURE                     Location/Qualifiers
REGION                      1..123
                            note = VH
source                      1..123
                            mol_type = protein
                            organism = synthetic construct
SEQUENCE: 8
EVQLVQSGAE VKKPGASVKV SCKASGYTFT DYNMHWVRQA PGQGLEWMGE INPNSGHAGY    60
NQKFKGRVTM TTDTSTSTAY MELRSLRSDD TAVYYCARLG YDDIYDDWYF DVWGQGTTVT   120
VSS                                                                 123

SEQ ID NO: 9                moltype = AA   length = 123
FEATURE                     Location/Qualifiers
REGION                      1..123
                            note = VH
source                      1..123
                            mol_type = protein
                            organism = synthetic construct
SEQUENCE: 9
EVQLVQSGAE VKKPGASVKV SCKASGYTFT DYNMHWVRQA PGQGLEWMGE INPNSGHAGY    60
NQKFKGRVTM TTDTSTSTAY MELRSLRSDD TAVYYCARLH YDHIYDDWYF DVWGQGTTVT   120
VSS                                                                 123

SEQ ID NO: 10               moltype = AA   length = 123
FEATURE                     Location/Qualifiers
REGION                      1..123
                            note = VH
source                      1..123
                            mol_type = protein
                            organism = synthetic construct
SEQUENCE: 10
EVQLVQSGAE VKKPGASVKV SCKASGYTFT DYNMHWVRQA PGQGLEWMGE INPHSGHAGY    60
NQKFKGRVTM TTDTSTSTAY MELRSLRSDD TAVYYCARLH YDDIHDDWYF DVWGQGTTVT   120
VSS                                                                 123

SEQ ID NO: 11               moltype = AA   length = 123
FEATURE                     Location/Qualifiers
REGION                      1..123
                            note = VH
source                      1..123
                            mol_type = protein
                            organism = synthetic construct
SEQUENCE: 11
EVQLVQSGAE VKKPGASVKV SCKASGYTFT DYNMHWVRQA PGQGLEWMGE INPHSGHAGY    60
NQKFKGRVTM TTDTSTSTAY MELRSLRSDD TAVYYCARLH YDDIHDDWYF DVWGQGTTVT   120
VSS                                                                 123

SEQ ID NO: 12               moltype = AA   length = 123
FEATURE                     Location/Qualifiers
REGION                      1..123
                            note = VH
source                      1..123
                            mol_type = protein
                            organism = synthetic construct
SEQUENCE: 12
EVQLVQSGAE VKKPGASVKV SCKASGYTFT DYNMHWVRQA PGQGLEWMGE INPNSGGAGY    60
NQKFKGRVTM TTDTSTSTAY MELRSLRSDD TAVYYCARLG YDDIYDDWYF HVWGQGTTVT   120
VSS                                                                 123

SEQ ID NO: 13               moltype = AA   length = 123
FEATURE                     Location/Qualifiers
REGION                      1..123
                            note = VH
source                      1..123
                            mol_type = protein
                            organism = synthetic construct
```

```
SEQUENCE: 13
EVQLVQSGAE VKKPGASVKV SCKASGYTFT DYNMHWVRQA PGQGLEWMGE INPNSGGAGY    60
NQKFKGRVTM TTDTSTSTAY MELRSLRSDD TAVYYCARLG YDDIYDDWYF DVWGQGTTVT   120
VSS                                                                123

SEQ ID NO: 14            moltype = AA  length = 123
FEATURE                  Location/Qualifiers
REGION                   1..123
                         note = VH
source                   1..123
                         mol_type = protein
                         organism = synthetic construct
SEQUENCE: 14
EVQLVQSGAE VKKPGASVKV SCKASGYTFT DYNMHWVRQA PGQGLEWMGE INPNSGGAGY    60
NQKFKGRVTM TTDTSTSTAY MELRSLRSDD TAVYYCARLG YDDIYDDWYF DVWGQGTTVT   120
VSS                                                                123

SEQ ID NO: 15            moltype = AA  length = 107
FEATURE                  Location/Qualifiers
REGION                   1..107
                         note = VL
source                   1..107
                         mol_type = protein
                         organism = synthetic construct
SEQUENCE: 15
DIQMTQSPSS LSASVGDRVT ITCRASQDIS NYLNWYQQKP GKAPKLLIYY TSRLLSGVPS    60
RFSGSGSGTD FTLTISSLQP EDFATYYCQQ GDTLPYTFGG GTKVEIK                107

SEQ ID NO: 16            moltype = AA  length = 107
FEATURE                  Location/Qualifiers
REGION                   1..107
                         note = VL
source                   1..107
                         mol_type = protein
                         organism = synthetic construct
SEQUENCE: 16
DIQMTQSPSS LSASVGDRVT ITCRASHDIS NYLNWYQQKP GKAPKLLIYY TSRLLSGVPS    60
RFSGSGSGTD FTLTISSLQP EDFATYYCQQ GDTLPYTFGG GTKVEIK                107

SEQ ID NO: 17            moltype = AA  length = 107
FEATURE                  Location/Qualifiers
REGION                   1..107
                         note = VL
source                   1..107
                         mol_type = protein
                         organism = synthetic construct
SEQUENCE: 17
DIQMTQSPSS LSASVGDRVT ITCRASHDIS NYLNWYQQKP GKAPKLLIYY TSRLLSGVPS    60
RFSGSGSGTD FTLTISSLQP EDFATYYCQQ GDTLPYTFGG GTKVEIK                107

SEQ ID NO: 18            moltype = AA  length = 107
FEATURE                  Location/Qualifiers
REGION                   1..107
                         note = VL
source                   1..107
                         mol_type = protein
                         organism = synthetic construct
SEQUENCE: 18
DIQMTQSPSS LSASVGDRVT ITCRASHDIS NYLNWYQQKP GKAPKLLIYY TSRLLSGVPS    60
RFSGSGSGTD FTLTISSLQP EDFATYYCQQ GDTLPYTFGG GTKVEIK                107

SEQ ID NO: 19            moltype = AA  length = 107
FEATURE                  Location/Qualifiers
REGION                   1..107
                         note = VL
source                   1..107
                         mol_type = protein
                         organism = synthetic construct
SEQUENCE: 19
DIQMTQSPSS LSASVGDRVT ITCRASHDIH NYLNWYQQKP GKAPKLLIYY TSRLLSGVPS    60
RFSGSGSGTD FTLTISSLQP EDFATYYCQQ GDTLPYTFGG GTKVEIK                107

SEQ ID NO: 20            moltype = AA  length = 107
FEATURE                  Location/Qualifiers
REGION                   1..107
                         note = VL
source                   1..107
                         mol_type = protein
                         organism = synthetic construct
```

```
SEQUENCE: 20
DIQMTQSPSS LSASVGDRVT ITCRASQDIS NYLNWYQQKP GKAPKLLIYH TSRLLSGVPS    60
RFSGSGSGTD FTLTISSLQP EDFATYYCQQ GDTLPYTFGG GTKVEIK                 107

SEQ ID NO: 21           moltype = AA  length = 107
FEATURE                 Location/Qualifiers
REGION                  1..107
                        note = VL
source                  1..107
                        mol_type = protein
                        organism = synthetic construct
SEQUENCE: 21
DIQMTQSPSS LSASVGDRVT ITCRASQDIS NYLNWYQQKP GKAPKLLIYH TSRLLSGVPS    60
RFSGSGSGTD FTLTISSLQP EDFATYYCQQ GDTLPYTFGG GTKVEIK                 107

SEQ ID NO: 22           moltype = AA  length = 107
FEATURE                 Location/Qualifiers
REGION                  1..107
                        note = VL
source                  1..107
                        mol_type = protein
                        organism = synthetic construct
SEQUENCE: 22
DIQMTQSPSS LSASVGDRVT ITCRASQDIS NYLNWYQQKP GKAPKLLIYY HSRLLSGVPS    60
RFSGSGSGTD FTLTISSLQP EDFATYYCHQ GDTLPYTFGG GTKVEIK                 107

SEQ ID NO: 23           moltype = AA  length = 118
FEATURE                 Location/Qualifiers
REGION                  1..118
                        note = VH
source                  1..118
                        mol_type = protein
                        organism = synthetic construct
SEQUENCE: 23
QVQLVQSGAE VKKPGASVKV SCKVSGFPIK DTFQHWVRQA PGKGLEWMGW SDPEIGDTEY    60
ASKFQGRVTM TEDTSTDTAY MELSSLRSED TAVYYCATGD TTYKFDFWGQ GTTVTVSS    118

SEQ ID NO: 24           moltype = AA  length = 118
FEATURE                 Location/Qualifiers
REGION                  1..118
                        note = VH
source                  1..118
                        mol_type = protein
                        organism = synthetic construct
SEQUENCE: 24
QVQLVQSGAE VKKPGASVKV SCKVSGFPIK HHFQHWVRQA PGKGLEWMGW SDPEIGDTEY    60
ASKFQGRVTM TEDTSTDTAY MELSSLRSED TAVYYCATGD TTYKFDFWGQ GTTVTVSS    118

SEQ ID NO: 25           moltype = AA  length = 118
FEATURE                 Location/Qualifiers
REGION                  1..118
                        note = VH
source                  1..118
                        mol_type = protein
                        organism = synthetic construct
SEQUENCE: 25
QVQLVQSGAE VKKPGASVKV SCKVSGFPIK HHFQHWVRQA PGKGLEWMGW SDPEIGDTEY    60
ASKFQGRVTM TEDTSTDTAY MELSSLRSED TAVYYCATGD TTYKFDFWGQ GTTVTVSS    118

SEQ ID NO: 26           moltype = AA  length = 118
FEATURE                 Location/Qualifiers
REGION                  1..118
                        note = VH
source                  1..118
                        mol_type = protein
                        organism = synthetic construct
SEQUENCE: 26
QVQLVQSGAE VKKPGASVKV SCKVSGFPIK HHFQHWVRQA PGKGLEWMGW SDPEIGDTEY    60
ASKFQGRVTM TEDTSTDTAY MELSSLRSED TAVYYCATGH TTYKFDFWGQ GTTVTVSS    118

SEQ ID NO: 27           moltype = AA  length = 107
FEATURE                 Location/Qualifiers
REGION                  1..107
                        note = VL
source                  1..107
                        mol_type = protein
                        organism = synthetic construct
SEQUENCE: 27
DIQMTQSPSS LSASVGDRVT ITCKASQDVH TAVAWYQQKP GKAPKLLIYW ASTRWTGVPS    60
```

```
RFSGSGSGTD FTLTISSLQP EDFATYYCQQ YSDYPWTFGG GTKVEIK           107

SEQ ID NO: 28           moltype = AA   length = 107
FEATURE                 Location/Qualifiers
REGION                  1..107
                        note = VL
source                  1..107
                        mol_type = protein
                        organism = synthetic construct
SEQUENCE: 28
DIQMTQSPSS LSASVGDRVT ITCKASQDVH TAVAWYQQKP GKAPKLLIYW ASTRWTGVPS    60
RFSGSGSGTD FTLTISSLQP EDFATYYCQQ YHDYPWTFGG GTKVEIK          107

SEQ ID NO: 29           moltype = AA   length = 107
FEATURE                 Location/Qualifiers
REGION                  1..107
                        note = VL
source                  1..107
                        mol_type = protein
                        organism = synthetic construct
SEQUENCE: 29
DIQMTQSPSS LSASVGDRVT ITCKASQDVH TAVAWYQQKP GKAPKLLIYW ASTRWTGVPS    60
RFSGSGSGTD FTLTISSLQP EDFATYYCQQ YSDYHWTFGG GTKVEIK          107

SEQ ID NO: 30           moltype = AA   length = 107
FEATURE                 Location/Qualifiers
REGION                  1..107
                        note = VL
source                  1..107
                        mol_type = protein
                        organism = synthetic construct
SEQUENCE: 30
DIQMTQSPSS LSASVGDRVT ITCKASQDVH TAVAWYQQKP GKAPKLLIYW ASTRWTGVPS    60
RFSGSGSGTD FTLTISSLQP EDFATYYCQQ YSDYHWTFGG GTKVEIK          107

SEQ ID NO: 31           moltype = AA   length = 5
FEATURE                 Location/Qualifiers
REGION                  1..5
                        note = HVR-H1
source                  1..5
                        mol_type = protein
                        organism = synthetic construct
SEQUENCE: 31
DYNMH                                                           5

SEQ ID NO: 32           moltype = AA   length = 5
FEATURE                 Location/Qualifiers
REGION                  1..5
                        note = HVR-H1
source                  1..5
                        mol_type = protein
                        organism = synthetic construct
SEQUENCE: 32
DTFQH                                                           5

SEQ ID NO: 33           moltype = AA   length = 5
FEATURE                 Location/Qualifiers
REGION                  1..5
                        note = HVR-H1
source                  1..5
                        mol_type = protein
                        organism = synthetic construct
SEQUENCE: 33
HHFQH                                                           5

SEQ ID NO: 34           moltype = AA   length = 17
FEATURE                 Location/Qualifiers
REGION                  1..17
                        note = HVR-H2
source                  1..17
                        mol_type = protein
                        organism = synthetic construct
SEQUENCE: 34
EINPNSGGAG YNQKFKG                                              17

SEQ ID NO: 35           moltype = AA   length = 17
FEATURE                 Location/Qualifiers
REGION                  1..17
                        note = HVR-H2
```

```
source                      1..17
                            mol_type = protein
                            organism = synthetic construct
SEQUENCE: 35
EINPNSGHAG YNQKFKG                                                              17

SEQ ID NO: 36               moltype = AA  length = 17
FEATURE                     Location/Qualifiers
REGION                      1..17
                            note = HVR-H2
source                      1..17
                            mol_type = protein
                            organism = synthetic construct
SEQUENCE: 36
EINPHSGHAG YNQKFKG                                                              17

SEQ ID NO: 37               moltype = AA  length = 17
FEATURE                     Location/Qualifiers
REGION                      1..17
                            note = HVR-H2
source                      1..17
                            mol_type = protein
                            organism = synthetic construct
SEQUENCE: 37
WSDPEIGDTE YASKFQG                                                              17

SEQ ID NO: 38               moltype = AA  length = 14
FEATURE                     Location/Qualifiers
REGION                      1..14
                            note = HVR-H3
source                      1..14
                            mol_type = protein
                            organism = synthetic construct
SEQUENCE: 38
LGYDDIYDDW YFDV                                                                 14

SEQ ID NO: 39               moltype = AA  length = 14
FEATURE                     Location/Qualifiers
REGION                      1..14
                            note = HVR-H3
source                      1..14
                            mol_type = protein
                            organism = synthetic construct
SEQUENCE: 39
LHYDDIYDDW YFDV                                                                 14

SEQ ID NO: 40               moltype = AA  length = 14
FEATURE                     Location/Qualifiers
REGION                      1..14
                            note = HVR-H3
source                      1..14
                            mol_type = protein
                            organism = synthetic construct
SEQUENCE: 40
LHYDHIYDDW YFDV                                                                 14

SEQ ID NO: 41               moltype = AA  length = 14
FEATURE                     Location/Qualifiers
REGION                      1..14
                            note = HVR-H3
source                      1..14
                            mol_type = protein
                            organism = synthetic construct
SEQUENCE: 41
LHYDDIHDDW YFDV                                                                 14

SEQ ID NO: 42               moltype = AA  length = 14
FEATURE                     Location/Qualifiers
REGION                      1..14
                            note = HVR-H3
source                      1..14
                            mol_type = protein
                            organism = synthetic construct
SEQUENCE: 42
LGYDDIYDDW YFHV                                                                 14

SEQ ID NO: 43               moltype = AA  length = 9
FEATURE                     Location/Qualifiers
REGION                      1..9
```

```
                        note = HVR-H3
source                  1..9
                        mol_type = protein
                        organism = synthetic construct
SEQUENCE: 43
GDTTYKFDF                                                                    9

SEQ ID NO: 44           moltype = AA   length = 9
FEATURE                 Location/Qualifiers
REGION                  1..9
                        note = HVR-H3
source                  1..9
                        mol_type = protein
                        organism = synthetic construct
SEQUENCE: 44
GHTTYKFDF                                                                    9

SEQ ID NO: 45           moltype = AA   length = 30
FEATURE                 Location/Qualifiers
REGION                  1..30
                        note = FR-H1
source                  1..30
                        mol_type = protein
                        organism = synthetic construct
SEQUENCE: 45
EVQLVQSGAE VKKPGASVKV SCKASGYTFT                                             30

SEQ ID NO: 46           moltype = AA   length = 30
FEATURE                 Location/Qualifiers
REGION                  1..30
                        note = FR-H1
source                  1..30
                        mol_type = protein
                        organism = synthetic construct
SEQUENCE: 46
QVQLVQSGAE VKKPGASVKV SCKVSGFPIK                                             30

SEQ ID NO: 47           moltype = AA   length = 14
FEATURE                 Location/Qualifiers
REGION                  1..14
                        note = FR-H2
source                  1..14
                        mol_type = protein
                        organism = synthetic construct
SEQUENCE: 47
WVRQAPGQGL EWMG                                                              14

SEQ ID NO: 48           moltype = AA   length = 14
FEATURE                 Location/Qualifiers
REGION                  1..14
                        note = FR-H2
source                  1..14
                        mol_type = protein
                        organism = synthetic construct
SEQUENCE: 48
WVRQAPGKGL EWMG                                                              14

SEQ ID NO: 49           moltype = AA   length = 32
FEATURE                 Location/Qualifiers
REGION                  1..32
                        note = FR-H3
source                  1..32
                        mol_type = protein
                        organism = synthetic construct
SEQUENCE: 49
RVTMTTDTST STAYMELRSL RSDDTAVYYC AR                                          32

SEQ ID NO: 50           moltype = AA   length = 32
FEATURE                 Location/Qualifiers
REGION                  1..32
                        note = FR-H3
source                  1..32
                        mol_type = protein
                        organism = synthetic construct
SEQUENCE: 50
RVTMTEDTST DTAYMELSSL RSEDTAVYYC AT                                          32

SEQ ID NO: 51           moltype = AA   length = 11
FEATURE                 Location/Qualifiers
```

```
REGION                  1..11
                        note = FR-H4
source                  1..11
                        mol_type = protein
                        organism = synthetic construct
SEQUENCE: 51
WGQGTTVTVS S                                                                    11

SEQ ID NO: 52           moltype = AA  length = 11
FEATURE                 Location/Qualifiers
REGION                  1..11
                        note = HVR-L1
source                  1..11
                        mol_type = protein
                        organism = synthetic construct
SEQUENCE: 52
RASQDISNYL N                                                                    11

SEQ ID NO: 53           moltype = AA  length = 11
FEATURE                 Location/Qualifiers
REGION                  1..11
                        note = HVR-L1
source                  1..11
                        mol_type = protein
                        organism = synthetic construct
SEQUENCE: 53
RASHDISNYL N                                                                    11

SEQ ID NO: 54           moltype = AA  length = 11
FEATURE                 Location/Qualifiers
REGION                  1..11
                        note = HVR-L1
source                  1..11
                        mol_type = protein
                        organism = synthetic construct
SEQUENCE: 54
RASHDIHNYL N                                                                    11

SEQ ID NO: 55           moltype = AA  length = 11
FEATURE                 Location/Qualifiers
REGION                  1..11
                        note = HVR-L1
source                  1..11
                        mol_type = protein
                        organism = synthetic construct
SEQUENCE: 55
KASQDVHTAV A                                                                    11

SEQ ID NO: 56           moltype = AA  length = 7
FEATURE                 Location/Qualifiers
REGION                  1..7
                        note = HVR-L2
source                  1..7
                        mol_type = protein
                        organism = synthetic construct
SEQUENCE: 56
YTSRLLS                                                                         7

SEQ ID NO: 57           moltype = AA  length = 7
FEATURE                 Location/Qualifiers
REGION                  1..7
                        note = HVR-L2
source                  1..7
                        mol_type = protein
                        organism = synthetic construct
SEQUENCE: 57
HTSRLLS                                                                         7

SEQ ID NO: 58           moltype = AA  length = 7
FEATURE                 Location/Qualifiers
REGION                  1..7
                        note = HVR-L2
source                  1..7
                        mol_type = protein
                        organism = synthetic construct
SEQUENCE: 58
YHSRLLS                                                                         7

SEQ ID NO: 59           moltype = AA  length = 7
```

```
FEATURE                 Location/Qualifiers
REGION                  1..7
                        note = HVR-L2
source                  1..7
                        mol_type = protein
                        organism = synthetic construct
SEQUENCE: 59
WASTRWT                                                                 7

SEQ ID NO: 60           moltype = AA  length = 9
FEATURE                 Location/Qualifiers
REGION                  1..9
                        note = HVR-L3
source                  1..9
                        mol_type = protein
                        organism = synthetic construct
SEQUENCE: 60
QQGDTLPYT                                                               9

SEQ ID NO: 61           moltype = AA  length = 9
FEATURE                 Location/Qualifiers
REGION                  1..9
                        note = HVR-L3
source                  1..9
                        mol_type = protein
                        organism = synthetic construct
SEQUENCE: 61
HQGDTLPYT                                                               9

SEQ ID NO: 62           moltype = AA  length = 9
FEATURE                 Location/Qualifiers
REGION                  1..9
                        note = HVR-L3
source                  1..9
                        mol_type = protein
                        organism = synthetic construct
SEQUENCE: 62
QQYSDYPWT                                                               9

SEQ ID NO: 63           moltype = AA  length = 9
FEATURE                 Location/Qualifiers
REGION                  1..9
                        note = HVR-L3
source                  1..9
                        mol_type = protein
                        organism = synthetic construct
SEQUENCE: 63
QQYHDYPWT                                                               9

SEQ ID NO: 64           moltype = AA  length = 9
FEATURE                 Location/Qualifiers
REGION                  1..9
                        note = HVR-L3
source                  1..9
                        mol_type = protein
                        organism = synthetic construct
SEQUENCE: 64
QQYSDYHWT                                                               9

SEQ ID NO: 65           moltype = AA  length = 23
FEATURE                 Location/Qualifiers
REGION                  1..23
                        note = FR-L1
source                  1..23
                        mol_type = protein
                        organism = synthetic construct
SEQUENCE: 65
DIQMTQSPSS LSASVGDRVT ITC                                              23

SEQ ID NO: 66           moltype = AA  length = 15
FEATURE                 Location/Qualifiers
REGION                  1..15
                        note = FR-L2
source                  1..15
                        mol_type = protein
                        organism = synthetic construct
SEQUENCE: 66
WYQQKPGKAP KLLIY                                                       15
```

```
SEQ ID NO: 67            moltype = AA  length = 32
FEATURE                  Location/Qualifiers
REGION                   1..32
                         note = FR-L3
source                   1..32
                         mol_type = protein
                         organism = synthetic construct
SEQUENCE: 67
GVPSRFSGSG SGTDFTLTIS SLQPEDFATY YC                                       32

SEQ ID NO: 68            moltype = AA  length = 10
FEATURE                  Location/Qualifiers
REGION                   1..10
                         note = FR-L4
source                   1..10
                         mol_type = protein
                         organism = synthetic construct
SEQUENCE: 68
FGGGTKVEIK                                                                10

SEQ ID NO: 69            moltype = AA  length = 17
FEATURE                  Location/Qualifiers
REGION                   1..17
                         note = HVR-H2 consensus
SITE                     5
                         note = misc_feature - X = Asn or His
SITE                     8
                         note = misc_feature - X = Gly or His
source                   1..17
                         mol_type = protein
                         organism = synthetic construct
SEQUENCE: 69
EINPXSGXAG YNQKFKG                                                        17

SEQ ID NO: 70            moltype = AA  length = 14
FEATURE                  Location/Qualifiers
REGION                   1..14
                         note = HVR-H3 consensus
SITE                     2
                         note = misc_feature - X = Gly or His
SITE                     5
                         note = misc_feature - X = Asp or His
SITE                     7
                         note = misc_feature - X = Tyr or His
SITE                     13
                         note = misc_feature - X = Asp or His
source                   1..14
                         mol_type = protein
                         organism = synthetic construct
SEQUENCE: 70
LXYDXIXDDW YFXV                                                           14

SEQ ID NO: 71            moltype = AA  length = 11
FEATURE                  Location/Qualifiers
REGION                   1..11
                         note = HVR-L1 consensus
SITE                     4
                         note = misc_feature - X = Gln or His
SITE                     7
                         note = misc_feature - X = Ser or His
source                   1..11
                         mol_type = protein
                         organism = synthetic construct
SEQUENCE: 71
RASXDIXNYL N                                                              11

SEQ ID NO: 72            moltype = AA  length = 7
FEATURE                  Location/Qualifiers
REGION                   1..7
                         note = HVR-L2 consensus
SITE                     1
                         note = misc_feature - X = Tyr or His
SITE                     2
                         note = misc_feature - X = Thr or His
source                   1..7
                         mol_type = protein
                         organism = synthetic construct
SEQUENCE: 72
XXSRLLS                                                                   7
```

```
SEQ ID NO: 73           moltype = AA  length = 9
FEATURE                 Location/Qualifiers
REGION                  1..9
                        note = HVR-L3 consensus
SITE                    1
                        note = misc_feature - X = Gln or His
source                  1..9
                        mol_type = protein
                        organism = synthetic construct
SEQUENCE: 73
XQGDTLPYT                                                                9

SEQ ID NO: 74           moltype =  length =
SEQUENCE: 74
000

SEQ ID NO: 75           moltype = AA  length = 9
FEATURE                 Location/Qualifiers
REGION                  1..9
                        note = HVR-H3 consensus
SITE                    2
                        note = misc_feature - X = Asp or His
source                  1..9
                        mol_type = protein
                        organism = synthetic construct
SEQUENCE: 75
GXTTYKFDF                                                                9

SEQ ID NO: 76           moltype = AA  length = 9
FEATURE                 Location/Qualifiers
REGION                  1..9
                        note = HVR-L3 consensus
SITE                    4
                        note = misc_feature - X = Ser or His
SITE                    7
                        note = misc_feature - X = Pro or His
source                  1..9
                        mol_type = protein
                        organism = synthetic construct
SEQUENCE: 76
QQYXDYXWT                                                                9

SEQ ID NO: 77           moltype = AA  length = 326
FEATURE                 Location/Qualifiers
REGION                  1..326
                        note = CH
source                  1..326
                        mol_type = protein
                        organism = synthetic construct
SEQUENCE: 77
ASTKGPSVFP LAPCSRSTSE STAALGCLVK DYFPEPVTVS WNSGALTSGV HTFPAVLQSS       60
GLYSLSSVVT VPSSNFGTQT YTCNVDHKPS NTKVDKTVER KCCVECPPCP APPVAGPSVF      120
LFPPKPKDTL MISRTPEVTC VVVDVSHEDP EVQFNWYVDG VEVHNAKTKP REEQFNSTFR      180
VVSVLTVVHQ DWLNGKEYKC KVSNKGLPAP IEKTISKTKG QPREPQVYTL PPSREEMTKN      240
QVSLTCLVKG FYPSDIAVEW ESNGQPENNY KTTPPMLDSD GSFFLYSKLT VDKSRWQQGN      300
VFSCSVMHEA LHNHYTQKSL SLSPGK                                          326

SEQ ID NO: 78           moltype = AA  length = 328
FEATURE                 Location/Qualifiers
REGION                  1..328
                        note = CH
source                  1..328
                        mol_type = protein
                        organism = synthetic construct
SEQUENCE: 78
ASTKGPSVFP LAPSSKSTSG GTAALGCLVK DYFPEPVTVS WNSGALTSGV HTFPAVLQSS       60
GLYSLSSVVT VPSSSLGTQT YICNVNHKPS NTKVDKKVEP KSCDKTHTCP PCPAPELLGG      120
PSVFLFPPKP KDTLMISRTP EVTCVVVDVS HEDPEVKFNW YVDGVEVHNA KTKPREEQYN      180
STYRVVSVLT VLHQDWLNGK EYKCKVSNKA LPAPIEKTIS KAKGQPREPQ VYTLPPSREE      240
MTKNQVSLTC LVKGFYPSDI AVEWESNGQP ENNYKTTPPV LDSDGSFFLY SKLTVDKSRW      300
QQGNVFSCSV MHEALHNHYT QKSLSLSP                                        328

SEQ ID NO: 79           moltype = AA  length = 324
FEATURE                 Location/Qualifiers
REGION                  1..324
                        note = CH
source                  1..324
                        mol_type = protein
```

```
                          organism = synthetic construct
SEQUENCE: 79
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVMHEA LHNHYTQKSL SLSP                                         324

SEQ ID NO: 80           moltype = AA  length = 328
FEATURE                 Location/Qualifiers
REGION                  1..328
                        note = CH
source                  1..328
                        mol_type = protein
                        organism = synthetic construct
SEQUENCE: 80
ASTKGPSVFP LAPSSRSTSE STAALGCLVK DYFPEPVTVS WNSGALTSGV HTFPAVLQSS    60
GLYSLSSVVT VPSSSLGTKT YTCNVDHKPS NTKVDKRVEP KSCDKTHTCP PCPAPELLGG   120
PSVFLFPPKP KDTLMISRTP EVTCVVVDVS QEDPEVQFNW YVDGVEVHNA KTKPREEQFN   180
STYRVVSVLT VLHQDWLNGK EYKCKVSNKG LPSSIEKTIS KAKGQPREPQ VYTLPPSRKE   240
MTKNQVSLTC LVKGFYPSDI AVEWESNGQP ENNYKTTPPY LDSDGSFFLY SKLTVDKSRW   300
QQGNVFSCSV MHEALHNHYT QKSLSLSP                                     328

SEQ ID NO: 81           moltype = AA  length = 328
FEATURE                 Location/Qualifiers
REGION                  1..328
                        note = CH
source                  1..328
                        mol_type = protein
                        organism = synthetic construct
SEQUENCE: 81
ASTKGPSVFP LAPSSRSTSE STAALGCLVK DYFPEPVTVS WNSGALTSGV HTFPAVLQSS    60
GLYSLSSVVT VPSSSLGTKT YTCNVDHKPS NTKVDKRVEP KSCDKTHTCP PCPAPELLGG   120
PSVFLFPPKP KDTLMISRTP EVTCVVVDVS QEDPEVQFNW YVDGVEVHNA KTKPREEQFN   180
STYRVVSVLT VLHQDWLNGK EYKCKVSNKG LPSSIEKTIS KAKGQPREPQ VYTLPPSREE   240
MTKNQVSLTC LVKGFYPSDI AVEWESNGQP ENNYKTTPPY LDSDGSFFLY SKLTVDKSRW   300
QQGNVFSCSV MHEALHNHYT QESLSLSP                                     328

SEQ ID NO: 82           moltype = AA  length = 107
FEATURE                 Location/Qualifiers
REGION                  1..107
                        note = CL
source                  1..107
                        mol_type = protein
                        organism = synthetic construct
SEQUENCE: 82
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 83           moltype = AA  length = 122
FEATURE                 Location/Qualifiers
REGION                  1..122
                        note = VH
source                  1..122
                        mol_type = protein
                        organism = synthetic construct
SEQUENCE: 83
QQQLEESGGG LVQPGGTLTL TCKASGFDFS SGYDMCWVRQ APGKGLEWIA YIYTGDGGTD    60
YANWAKGRFT ISKTSSTTVD LKMTSLTTAD TATYLCARGL YDGGNMSIQN LWGPGTLVTV   120
SS                                                                 122

SEQ ID NO: 84           moltype = AA  length = 110
FEATURE                 Location/Qualifiers
REGION                  1..110
                        note = VL
source                  1..110
                        mol_type = protein
                        organism = synthetic construct
SEQUENCE: 84
AYDMTQTPAS VEAAVGGTVT IKCQASQSIG SWLAWYQQKP GQRPKLLIYQ ASSLASGVPS    60
RFSGSGSGTQ FTLTINDLEC DDAATYYCQQ AYSINNIDNI FGGGTEVVVK              110

SEQ ID NO: 85           moltype = AA  length = 323
FEATURE                 Location/Qualifiers
REGION                  1..323
                        note = rbIgG
source                  1..323
                        mol_type = protein
```

```
                              organism = synthetic construct
SEQUENCE: 85
GQPKAPSVFP LAPCCGDTPS STVTLGCLVK GYLPEPVTVT WNSGTLTNGV RTFPSVRQSS      60
GLYSLSSVVS VTSSSQPVTC NVAHPATNTK VDKTVAPSTC SKPMCPPPEL LGGPSVFIFP     120
PKPKDTLMIS RTPEVTCVVV DVSQDDPEVQ FTWYINNEQV RTARPPLREQ QFNSTIRVVS     180
TLPIAHQDWL RGKEFKCKVH NKALPAPIEK TISKARGQPL EPKVYTMGPP REELSSRSVS     240
LTCMINGFYP SDISVEWEKN GKAEDNYKTT PTVLDSDGSY FLYSKLSVPT SEWQRGDVFT     300
CSVMHEALHN HYTQKSISRS PGK                                             323

SEQ ID NO: 86             moltype = AA  length = 104
FEATURE                   Location/Qualifiers
REGION                    1..104
                          note = rbIgk
source                    1..104
                          mol_type = protein
                          organism = synthetic construct
SEQUENCE: 86
GDPVAPTVLI FPPAADQVAT GTVTIVCVAN KYFPDVTVTW EVDGTTQTTG IENSKTPQNS      60
ADCTYNLSST LTLTSTQYNS HKEYTCKVTQ GTTSVVQSFN RGDC                      104

SEQ ID NO: 87             moltype = AA  length = 118
FEATURE                   Location/Qualifiers
REGION                    1..118
                          note = VH
source                    1..118
                          mol_type = protein
                          organism = synthetic construct
SEQUENCE: 87
QEQLVESGGG LVQPEASLTV TCTASGIDFN DYYYMCWVRQ APGKGLEWIG CIYTGVGSTY      60
YASWAKGRFT ISKTSSTTVT LQMTSLTAAD TAIYFCAREW AGNSYYLWGP GTLVTVSS      118

SEQ ID NO: 88             moltype = AA  length = 111
FEATURE                   Location/Qualifiers
REGION                    1..111
                          note = VL
source                    1..111
                          mol_type = protein
                          organism = synthetic construct
SEQUENCE: 88
ALVMTQTPSS VSAAVGGTVT ISCQASQSIY TNYLSWYQQK PGQPPKLLIY TASDLASGVP      60
SRFKGSGSGT QFALTISDLE CGDAATYYCA GYLSYSDDDF AFGGGTKVEI K              111

SEQ ID NO: 89             moltype = AA  length = 328
FEATURE                   Location/Qualifiers
REGION                    1..328
                          note = H chain constant region
source                    1..328
                          mol_type = protein
                          organism = synthetic construct
SEQUENCE: 89
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKKVEP KSCDKTHTCP PCPAPELLGG     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSRKE     240
MTKNQVSLTC LVKGFYPSDI AVEWESNGQP ENNYKTTPPY LDSDGSFFLY SKLTVDKSRW     300
QQGNVFSCSV MHEALHNHYT QKSLSLSP                                        328

SEQ ID NO: 90             moltype = AA  length = 125
FEATURE                   Location/Qualifiers
REGION                    1..125
                          note = VH
source                    1..125
                          mol_type = protein
                          organism = synthetic construct
SEQUENCE: 90
QSLEESGGRL VTPGTPLTLT CTVSGIDLSS YAMGWVRQAP GKGLEWIGII SGSGNTYYAN      60
WAKGRFTISK TSTTVDLKIT SPSTEDTATY FCARADGFYD SYGHAYATNS YFYLWGLGTL     120
VTVSS                                                                 125

SEQ ID NO: 91             moltype = AA  length = 110
FEATURE                   Location/Qualifiers
REGION                    1..110
                          note = VL
source                    1..110
                          mol_type = protein
                          organism = synthetic construct
SEQUENCE: 91
AIKMTQTPAS VSAAVGGTVT INCQASEDIV RYLAWYQQKP GQPPKLLIYD ASDLASGVPS      60
RFKGSGYGKQ FTLTISGVQC DDAATYYCQH GLYTTGSDIT FGGGTKVEIK                110
```

```
SEQ ID NO: 92              moltype = AA   length = 107
FEATURE                    Location/Qualifiers
REGION                     1..107
                           note = VL
source                     1..107
                           mol_type = protein
                           organism = synthetic construct
SEQUENCE: 92
DIQMTQSPSS LSASVGDRVT ITCRASQDIS NYLNWYQQKP GKAPKLLIYY TSRLLSGVPS    60
RFSGSGSGTD FTLTISSLQP EDFATYYCQQ YSDYPWTFGG GTKVEIK                 107

SEQ ID NO: 93              moltype = AA   length = 107
FEATURE                    Location/Qualifiers
REGION                     1..107
                           note = VL
source                     1..107
                           mol_type = protein
                           organism = synthetic construct
SEQUENCE: 93
DIQMTQSPSS LSASVGDRVT ITCRASQDIS NYLNWYQQKP GKAPKLLIYW ASTRWTGVPS    60
RFSGSGSGTD FTLTISSLQP EDFATYYCQQ GDTLPYTFGG GTKVEIK                 107

SEQ ID NO: 94              moltype = AA   length = 107
FEATURE                    Location/Qualifiers
REGION                     1..107
                           note = VL
source                     1..107
                           mol_type = protein
                           organism = synthetic construct
SEQUENCE: 94
DIQMTQSPSS LSASVGDRVT ITCRASQDIS NYLNWYQQKP GKAPKLLIYW ASTRWTGVPS    60
RFSGSGSGTD FTLTISSLQP EDFATYYCQQ YSDYPWTFGG GTKVEIK                 107

SEQ ID NO: 95              moltype = AA   length = 107
FEATURE                    Location/Qualifiers
REGION                     1..107
                           note = VL
source                     1..107
                           mol_type = protein
                           organism = synthetic construct
SEQUENCE: 95
DIQMTQSPSS LSASVGDRVT ITCKASQDVH TAVAWYQQKP GKAPKLLIYY TSRLLSGVPS    60
RFSGSGSGTD FTLTISSLQP EDFATYYCQQ GDTLPYTFGG GTKVEIK                 107

SEQ ID NO: 96              moltype = AA   length = 107
FEATURE                    Location/Qualifiers
REGION                     1..107
                           note = VL
source                     1..107
                           mol_type = protein
                           organism = synthetic construct
SEQUENCE: 96
DIQMTQSPSS LSASVGDRVT ITCKASQDVH TAVAWYQQKP GKAPKLLIYY TSRLLSGVPS    60
RFSGSGSGTD FTLTISSLQP EDFATYYCQQ YSDYPWTFGG GTKVEIK                 107

SEQ ID NO: 97              moltype = AA   length = 107
FEATURE                    Location/Qualifiers
REGION                     1..107
                           note = VL
source                     1..107
                           mol_type = protein
                           organism = synthetic construct
SEQUENCE: 97
DIQMTQSPSS LSASVGDRVT ITCKASQDVH TAVAWYQQKP GKAPKLLIYW ASTRWTGVPS    60
RFSGSGSGTD FTLTISSLQP EDFATYYCQQ GDTLPYTFGG GTKVEIK                 107

SEQ ID NO: 98              moltype = AA   length = 107
FEATURE                    Location/Qualifiers
REGION                     1..107
                           note = VL
source                     1..107
                           mol_type = protein
                           organism = synthetic construct
SEQUENCE: 98
DIQMTQSPSS LSASVGDRVT ITCRASQDIS TALAWYQQKP GKAPKLLIYW ASTLWSGVPS    60
RFSGSGSGTD FTLTISSLQP EDFATYYCQQ GDTLPYTFGG GTKVEIK                 107

SEQ ID NO: 99              moltype = AA   length = 107
```

```
FEATURE                 Location/Qualifiers
REGION                  1..107
                        note = VL
source                  1..107
                        mol_type = protein
                        organism = synthetic construct
SEQUENCE: 99
DIQMTQSPSS LSASVGDRVT ITCRASQDIH TYLAWYQQKP GKAPKLLIYW ASTRWSGVPS    60
RFSGSGSGTD FTLTISSLQP EDFATYYCQQ GDTLPYTFGG GTKVEIK                 107

SEQ ID NO: 100          moltype = AA   length = 107
FEATURE                 Location/Qualifiers
REGION                  1..107
                        note = VL
source                  1..107
                        mol_type = protein
                        organism = synthetic construct
SEQUENCE: 100
DIQMTQSPSS LSASVGDRVT ITCRASQDIH TYLAWYQQKP GKAPKLLIYW ASTRLSGVPS    60
RFSGSGSGTD FTLTISSLQP EDFATYYCQQ GDTLPYTFGG GTKVEIK                 107

SEQ ID NO: 101          moltype = AA   length = 123
FEATURE                 Location/Qualifiers
REGION                  1..123
                        note = VH
source                  1..123
                        mol_type = protein
                        organism = synthetic construct
SEQUENCE: 101
EVQLVQSGAE VKKPGASVKV SCKASGYTFT SYNMHWVRQA PGKGLEWMGE IMPHSGRYGL    60
KQKFKGRVTM TRDTSISTAY MELSRLRSDD TAVYYCARLE YSEIYDDWYF DVWGQGTTVT   120
VSS                                                                 123

SEQ ID NO: 102          moltype = AA   length = 123
FEATURE                 Location/Qualifiers
REGION                  1..123
                        note = VH
source                  1..123
                        mol_type = protein
                        organism = synthetic construct
SEQUENCE: 102
EVQLVQSGAE VKKPGASVKV SCKASGYTFT DYNMHWVRQA PGKGLEWMGE IMPHSGRYGL    60
KQKFKGRVTM TTDTSTSTAY MELRSLRSDD TAVYYCARLE YSEIYDDWYF DVWGQGTTVT   120
VSS                                                                 123

SEQ ID NO: 103          moltype = AA   length = 118
FEATURE                 Location/Qualifiers
REGION                  1..118
                        note = VH
source                  1..118
                        mol_type = protein
                        organism = synthetic construct
SEQUENCE: 103
QVQLVQSGAE VKKPGASVKV SCKVSGYTLT HTFMHWVRQA PGKGLEWMGW SDPEIGDHEY    60
ASKFQGRVTM TEDTSTDTAY MELSSLRSED TAVYYCATGD TTYKFDYWGQ GTLVTVSS    118

SEQ ID NO: 104          moltype = AA   length = 118
FEATURE                 Location/Qualifiers
REGION                  1..118
                        note = VH
source                  1..118
                        mol_type = protein
                        organism = synthetic construct
SEQUENCE: 104
QVQLVQSGAE VKKPGASVKV SCKVSGYTLT HTFMHWVRQA PGKGLEWMGW SDPEIGDTEY    60
ASKFQGRVTM TEDTSTDTAY MELSSLRSED TAVYYCATGD TTYKFDYWGQ GTLVTVSS    118

SEQ ID NO: 105          moltype = AA   length = 107
FEATURE                 Location/Qualifiers
REGION                  1..107
                        note = VL
source                  1..107
                        mol_type = protein
                        organism = synthetic construct
SEQUENCE: 105
DIQMTQSPSS LSASVGDRVT ITCRASEGIH DALAWYQQKP GKAPKLLIYW ASTLESGVPS    60
RFSGSGSGTD FTLTISSLQP EDFATYYCQQ GDTLPYTFGG GTKVEIK                 107

SEQ ID NO: 106          moltype = AA   length = 328
```

```
FEATURE                    Location/Qualifiers
REGION                     1..328
                           note = H chain constant region
source                     1..328
                           mol_type = protein
                           organism = synthetic construct
SEQUENCE: 106
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKTHTCP PCPAPELLGG             120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VCTLPPSREE   240
MTKNQVSLWC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 107             moltype = AA  length = 328
FEATURE                    Location/Qualifiers
REGION                     1..328
                           note = H chain constant region
source                     1..328
                           mol_type = protein
                           organism = synthetic construct
SEQUENCE: 107
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRCE   240
MTKNQVSLSC AVKGFYPSDI AVEWESNGQP ENNYKTTPPV LDSDGSFFLV SKLTVDKSRW   300
QQGNVFSCSV MHEALHNHYT QKSLSLSP                                     328

SEQ ID NO: 108             moltype = AA  length = 326
FEATURE                    Location/Qualifiers
REGION                     1..326
                           note = H chain constant region
source                     1..326
                           mol_type = protein
                           organism = synthetic construct
SEQUENCE: 108
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLG                                       326

SEQ ID NO: 109             moltype = AA  length = 11
FEATURE                    Location/Qualifiers
REGION                     1..11
                           note = HVR-L1
source                     1..11
                           mol_type = protein
                           organism = synthetic construct
SEQUENCE: 109
RASQDISTAL A                                                        11

SEQ ID NO: 110             moltype = AA  length = 11
FEATURE                    Location/Qualifiers
REGION                     1..11
                           note = HVR-L1
source                     1..11
                           mol_type = protein
                           organism = synthetic construct
SEQUENCE: 110
RASQDIHTYL A                                                        11

SEQ ID NO: 111             moltype = AA  length = 11
FEATURE                    Location/Qualifiers
REGION                     1..11
                           note = HVR-L1
source                     1..11
                           mol_type = protein
                           organism = synthetic construct
SEQUENCE: 111
RASEGIHDAL A                                                        11

SEQ ID NO: 112             moltype = AA  length = 7
FEATURE                    Location/Qualifiers
REGION                     1..7
                           note = HVR-L2
source                     1..7
```

```
                              mol_type = protein
                              organism = synthetic construct
SEQUENCE: 112
WASTLWS                                                                 7

SEQ ID NO: 113                moltype = AA   length = 7
FEATURE                       Location/Qualifiers
REGION                        1..7
                              note = HVR-L2
source                        1..7
                              mol_type = protein
                              organism = synthetic construct
SEQUENCE: 113
WASTRWS                                                                 7

SEQ ID NO: 114                moltype = AA   length = 7
FEATURE                       Location/Qualifiers
REGION                        1..7
                              note = HVR-L2
source                        1..7
                              mol_type = protein
                              organism = synthetic construct
SEQUENCE: 114
WASTRLS                                                                 7

SEQ ID NO: 115                moltype = AA   length = 7
FEATURE                       Location/Qualifiers
REGION                        1..7
                              note = HVR-L2
source                        1..7
                              mol_type = protein
                              organism = synthetic construct
SEQUENCE: 115
WASTLES                                                                 7

SEQ ID NO: 116                moltype = AA   length = 5
FEATURE                       Location/Qualifiers
REGION                        1..5
                              note = HVR-H1
source                        1..5
                              mol_type = protein
                              organism = synthetic construct
SEQUENCE: 116
SYNMH                                                                   5

SEQ ID NO: 117                moltype = AA   length = 5
FEATURE                       Location/Qualifiers
REGION                        1..5
                              note = HVR-H1
source                        1..5
                              mol_type = protein
                              organism = synthetic construct
SEQUENCE: 117
HTFMH                                                                   5

SEQ ID NO: 118                moltype = AA   length = 17
FEATURE                       Location/Qualifiers
REGION                        1..17
                              note = HVR-H2
source                        1..17
                              mol_type = protein
                              organism = synthetic construct
SEQUENCE: 118
EIMPHSGRYG LKQKFKG                                                     17

SEQ ID NO: 119                moltype = AA   length = 17
FEATURE                       Location/Qualifiers
REGION                        1..17
                              note = HVR-H2
source                        1..17
                              mol_type = protein
                              organism = synthetic construct
SEQUENCE: 119
WSDPEIGDHE YASKFQG                                                     17

SEQ ID NO: 120                moltype = AA   length = 14
FEATURE                       Location/Qualifiers
REGION                        1..14
                              note = HVR-H3
```

```
source                   1..14
                         mol_type = protein
                         organism = synthetic construct
SEQUENCE: 120
LEYSEIYDDW YFDV                                                          14

SEQ ID NO: 121           moltype = AA   length = 9
FEATURE                  Location/Qualifiers
REGION                   1..9
                         note = HVR-H3
source                   1..9
                         mol_type = protein
                         organism = synthetic construct
SEQUENCE: 121
GDTTYKFDY                                                                 9

SEQ ID NO: 122           moltype = AA   length = 11
FEATURE                  Location/Qualifiers
REGION                   1..11
                         note = common L HVR-L1 consensus
SITE                     4
                         note = misc_feature - X = Gln or Glu
SITE                     5
                         note = misc_feature - X = Asp or Gly
SITE                     7
                         note = misc_feature - X = Ser or His
SITE                     8
                         note = misc_feature - X = Thr or Asp
SITE                     9
                         note = misc_feature - X = Ala or Tyr
source                   1..11
                         mol_type = protein
                         organism = synthetic construct
SEQUENCE: 122
RASXXIXXXL A                                                             11

SEQ ID NO: 123           moltype = AA   length = 7
FEATURE                  Location/Qualifiers
REGION                   1..7
                         note = common L HVR-L2 consensus
SITE                     5
                         note = misc_feature - X = Leu or Arg
SITE                     6
                         note = misc_feature - X = Trp, Leu or Glu
source                   1..7
                         mol_type = protein
                         organism = synthetic construct
SEQUENCE: 123
WASTXXS                                                                   7

SEQ ID NO: 124           moltype = AA   length = 5
FEATURE                  Location/Qualifiers
REGION                   1..5
                         note = HVR-H1 consensus
SITE                     1
                         note = misc_feature - X = Asp or Ser
source                   1..5
                         mol_type = protein
                         organism = synthetic construct
SEQUENCE: 124
XYNMH                                                                     5

SEQ ID NO: 125           moltype = AA   length = 17
FEATURE                  Location/Qualifiers
REGION                   1..17
                         note = HVR-H2 consensus
SITE                     9
                         note = misc_feature - X = Thr or His
source                   1..17
                         mol_type = protein
                         organism = synthetic construct
SEQUENCE: 125
WSDPEIGDXE YASKFQG                                                       17

SEQ ID NO: 126           moltype = AA   length = 17
FEATURE                  Location/Qualifiers
REGION                   1..17
                         note = HVR-H2 consensus
SITE                     3
```

```
                        note = misc_feature - X = Asn or Met
SITE                    5
                        note = misc_feature - X = Asn or His
SITE                    8
                        note = misc_feature - X = Gly, His or Arg
SITE                    9
                        note = misc_feature - X = Ala or Tyr
SITE                    11
                        note = misc_feature - X = Tyr or Leu
SITE                    12
                        note = misc_feature - X = Asn or Lys
source                  1..17
                        mol_type = protein
                        organism = synthetic construct
SEQUENCE: 126
EIXPXSGXXG XXQKFKG                                                  17

SEQ ID NO: 127          moltype = AA  length = 14
FEATURE                 Location/Qualifiers
REGION                  1..14
                        note = HVR-H3 consensus
SITE                    2
                        note = misc_feature - X = Gly, His or Glu
SITE                    4
                        note = misc_feature - X = Asp or Ser
SITE                    5
                        note = misc_feature - X = Asp, His or Glu
SITE                    7
                        note = misc_feature - X = Tyr or His
SITE                    13
                        note = misc_feature - X = Asp or His
source                  1..14
                        mol_type = protein
                        organism = synthetic construct
SEQUENCE: 127
LXYXXIXDDW YFXV                                                     14

SEQ ID NO: 128          moltype =     length =
SEQUENCE: 128
000

SEQ ID NO: 129          moltype = AA  length = 9
FEATURE                 Location/Qualifiers
REGION                  1..9
                        note = HVR-H3 consensus
SITE                    2
                        note = misc_feature - X = Asp or His
SITE                    9
                        note = misc_feature - X = Phe or Tyr
source                  1..9
                        mol_type = protein
                        organism = synthetic construct
SEQUENCE: 129
GXTTYKFDX                                                           9

SEQ ID NO: 130          moltype =     length =
SEQUENCE: 130
000

SEQ ID NO: 131          moltype =     length =
SEQUENCE: 131
000

SEQ ID NO: 132          moltype =     length =
SEQUENCE: 132
000

SEQ ID NO: 133          moltype = AA  length = 30
FEATURE                 Location/Qualifiers
REGION                  1..30
                        note = FR-H1
source                  1..30
                        mol_type = protein
                        organism = synthetic construct
SEQUENCE: 133
QVQLVQSGAE VKKPGASVKV SCKVSGYTLT                                    30

SEQ ID NO: 134          moltype = AA  length = 32
FEATURE                 Location/Qualifiers
```

```
REGION              1..32
                    note = FR-H3
source              1..32
                    mol_type = protein
                    organism = synthetic construct
SEQUENCE: 134
RVTMTRDTSI STAYMELSRL RSDDTAVYYC AR                       32

SEQ ID NO: 135      moltype = AA   length = 11
FEATURE             Location/Qualifiers
REGION              1..11
                    note = FR-H4
source              1..11
                    mol_type = protein
                    organism = synthetic construct
SEQUENCE: 135
WGQGTLVTVS S                                              11
```

The invention claimed is:

1. A method of producing a common light-chain variable region (VL) shared between two different variable domains, the method comprising the steps of:
   (1) providing a first variable domain (V1) comprising a first heavy-chain variable region (VH1) and a first light-chain variable region (VL1), and a second variable domain (V2) comprising a second heavy-chain variable region (VH2) and a second light-chain variable region (VL2), wherein V1 binds to a first antigen (Ag1) and V2 binds to a second antigen (Ag2);
   (2) constructing a modified light-chain variable region (mVL) by replacing an amino acid residue at a position in hypervariable region (HVR)-L1, HVR-L2, or HVR-L3 of VL1 with an amino acid residue at the corresponding position in HVR-L1, HVR-L2, or HVR-L3 of VL2, wherein the amino acid residue position is according to Kabat numbering;
   (3) repeating step (2) for amino acid residues at different positions in HVR-L1, HVR-L2, or HVR-L3 of VL1 to construct different mVLs, each of the mVLs has a single amino acid residue replaced with the corresponding amino acid residue of VL2;
   (4) measuring the binding activity for each of the mVLs constructed in steps (2) and (3) to Ag1 and Ag2 when combined with VH1 or VH2, respectively;
   (5) selecting the amino acid residue at each of the positions based on the binding activity measured in step (4);
   if the mVL of step (4) binds to both Ag1 and Ag2, selecting the amino acid residue from the corresponding position of VL2 for constructing the common VL; and
   if the mVL of step (4) does not bind to both Ag1 and Ag2, selecting the amino acid residue located at the position in VL1 for constructing the common VL; and
   (6) constructing a novel VL (nVL) comprising the amino acid residues selected in step (5) at their corresponding positions in HVR-L1, HVR-L2, and HVR-L3 of VL1; and
   (7) measuring the binding activity of the nVL constructed in step (6) to Ag1 and Ag2 when combined with VH1 or VH2, respectively; and
   identifying the nVL that binds to both Ag1 and Ag2, when combined with VH1 or VH2, respectively, as the common light-chain variable region (VL) shared between two different variable domains.

2. The method of claim 1, wherein:
   step (3) comprises repeating step (2) until the amino acid residues at all positions in HVR-L1, HVR-L2, and HVR-L3 of VL1 are replaced; and
   steps (4) and (5) are repeated until the amino acid residues at all positions in HVR-L1, HVR-L2, and HVR-L3 of VL1 are selected.

3. The method of claim 1, wherein the length of the amino acid sequence of any one of HVRs selected from HVR-L1, HVR-L2, and HVR-L3 of VL1 is the same as that of the corresponding HVR of VL2.

4. The method of claim 1, wherein the length of the amino acid sequence of any one of the light-chain framework regions (FR-L) selected from FR-L1, FR-L2, FR-L3, and FR-L4 of VL1 is the same as that of the corresponding FR-L sequence of VL2.

5. The method of claim 1, wherein the amino acid sequence of any one of the light-chain framework regions (FR-L) selected from FR-L1, FR-L2, FR-L3, and FR-L4 of the nVL is selected from the corresponding FR-L sequence in VL1 and the corresponding FR-L sequence in VL2.

6. The method of claim 1, wherein the amino acid sequence of any one of the light-chain framework regions (FR-L) selected from FR-L1, FR-L2, FR-L3, and FR-L4 of VL1 comprises an amino acid sequence having at least 50% identity to the amino acid sequence of the corresponding FR-L of VL2.

7. The method of claim 1, wherein both VL1 and VL2 are variable regions derived from kappa light chain.

8. The method of claim 1, wherein both VL1 and VL2 are variable regions derived from lambda light chain.

* * * * *